(12) United States Patent
Wang et al.

(10) Patent No.: US 8,518,666 B2
(45) Date of Patent: Aug. 27, 2013

(54) SITE-SPECIFIC INCORPORATION OF AMINO ACIDS INTO MOLECULES

(75) Inventors: Pin Wang, Pasadena, CA (US); Inchan Kwon, Pasadena, CA (US); Soojin Son, Pasadena, CA (US); Yi Tang, San Gabriel, CA (US); David Tirrell, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1019 days.

(21) Appl. No.: 11/682,272

(22) Filed: Mar. 5, 2007

(65) Prior Publication Data

US 2008/0044854 A1 Feb. 21, 2008

Related U.S. Application Data

(60) Provisional application No. 60/779,375, filed on Mar. 3, 2006, provisional application No. 60/779,376, filed on Mar. 3, 2006.

(51) Int. Cl.
*C12N 15/67* (2006.01)
*C07H 21/00* (2006.01)
*C07K 2/00* (2006.01)

(52) U.S. Cl.
USPC .......................... 435/69.1; 435/183; 435/243

(58) Field of Classification Search
None
See application file for complete search history.

(56) References Cited

U.S. PATENT DOCUMENTS

| | | | |
|---|---|---|---|
| 6,269,312 B1 | 7/2001 | Mayo et al. | 702/19 |
| 7,045,337 B2 * | 5/2006 | Schultz et al. | 435/252.3 |
| 7,083,970 B2 * | 8/2006 | Schultz et al. | 435/252.3 |
| 7,139,665 B2 * | 11/2006 | Datta et al. | 702/19 |
| 2003/0108885 A1 | 6/2003 | Schultz et al. | 435/6 |
| 2006/0194256 A1 | 8/2006 | Miao et al. | 435/7.1 |
| 2006/0217289 A1 | 9/2006 | Miao et al. | 514/2 |

FOREIGN PATENT DOCUMENTS

| | | |
|---|---|---|
| WO | WO 92/16640 | 10/1992 |
| WO | WO 02/085923 | 10/2002 |
| WO | WO 2005/074546 | 8/2005 |
| WO | WO 2006/034410 | 3/2006 |
| WO | WO 2006/045116 | 4/2006 |
| WO | WO 2006/068802 | 6/2006 |
| WO | WO 2006/069246 | 6/2006 |
| WO | WO 2006/091231 | 8/2006 |
| WO | WO 2006/132969 | 12/2006 |
| WO | WO 2007/021297 | 2/2007 |
| WO | WO 2007/070659 | 6/2007 |
| WO | WO 2007/094916 | 8/2007 |

OTHER PUBLICATIONS

Kwon et al Breaking the Degeneracy of the -Genetic Code J. of the Am. Chem. Soc. (JACS), Jun. 25, 2003, vol. 123, No. 25, p. 7512-7513.*

Datta et al. A Designed Phenylalanyl-tRNA Synthetase Variant Allows Efficient in Vivo Incorporation of Aryl Ketone Functionality into Proteins J. Am. Chem. Soc. 2002, 124, 5652-5653.*
Bedoulle et al J. Bact. 1990, p. 3940-3945 Over-expression of Tyrosyl-tRNA Synthetase is Toxic to *Escherichia coli* a Genetic analysis.*
Bernstein et al., J. Mol. Biol. 112: 535-542, 1977.*
Kwon, "Protein Engineering Via Site-Specific Incorporation of Non-natural Amino Acids," Thesis, Degree of Doctor of Philosophy, California Institute of Technology, Pasadena, California, 2007, 233 pages.
Anderson et al., "Fluorescence Resonance Energy Transfer between Unnatural Amino Acids in a Structurally Modified Dihydrofolate Reductase," *J. Am. Chem. Soc.* 124:9674-9675, 2002.
Bain et al., "Ribosome-mediated incorporation of a non-standard amino acid into a peptide through expansion of the genetic code," *Nature* 356:537-539, 1992.
Bain et al., "Biosynthetic Site-Specific Incorporation of a Non-Natural Amino Acid into a Polypeptide," *J. Am. Chem. Soc.* 111:8013-8014, 1989.
Budisa et al., "High-level biosynthetic substitution of methionine in proteins by its analogs 2-aminohexanoic acid, selenomethionine, telluromethionine and ethionine in *Escherichia coli*," *Eur. J. Biochem.* 230:788-796, 1995.
Budisa, "Prolegomena to Future Experimental Efforts on Genetic Code Engineering by Expanding Its Amino Acid Repertoire," *Angew. Chem. Int. Ed.* 43:6426-6463, 2004.
Deming et al., "Biosynthetic Incorporation and Chemical Modification of Alkene Functionality in Genetically Engineered Polymers," *J. M.S.—Pure Appl. Chem.* A34:2143-2150, 1997.
Doctor et al., "Species Specificity of Amino Acid Acceptor Ribonucleic Acids and Aminoacyl Soluble Ribonucleic Acid Synthesis," *The Journal of Biological Chemistry* 238(11):3677-3681, 1963.
Döring et al., "Enlarging the Amino Acid Set of *Escherichia coli* by Infiltration of the Valine Coding Pathway," *Science* 292:501-504, 2001.
Duewel et al., "Incorporation of Trifluoromethionine into a Phage Lysozyme: Implications and a New Marker for Use in Protein $^{19}$F NMR," *Biochemistry* 36:3404-3416, 1997.
Furter, "Expansion of the genetic code: Site-directed *p*-fluorophenylalanine incorporation in *Escherichia coli*," *Protein Science* 7:419-426, 1998.
Giegé et al., "Aspartate identity of transfer RNAs," *Biochimie* 78:605-623, 1996.
Hohsaka et al., "Site-specific incorporation of photofunctional nonnatural amino acids into a polypeptide through in vitro protein biosynthesis," *FEBS Letters* 344:171-174, 1994.
Hohsaka et al., "Five-base codons for incorporation of nonnatural amino acids into proteins," *Nucleic Acids Research* 29(17):3646-3651, 2001.
Ibba et al., "Substrate Specificity is Determined by Amino Acid Binding Pocket Size in *Escherichia coli* Phenylalanyl-tRNA Synthetase," *Biochemistry* 33:7107-7112, 1994.

(Continued)

*Primary Examiner* — Kagnew H Gebreyesus
(74) *Attorney, Agent, or Firm* — Seed IP Law Group PLLC

(57) ABSTRACT

The invention provides certain embodiments relating to methods and compositions for incorporating non-natural amino acids into a polypeptide or protein by utilizing a mutant or modified aminoacyl-tRNA synthetase to charge the non-natural amino acid to a the corresponding tRNA. In certain embodiments, the tRNA is also modified such that the complex forms strict Watson-Crick base-pairing with a codon that normally forms wobble base-pairing with unmodified tRNA/ aminoacyl-tRNA synthetase pairs.

34 Claims, 20 Drawing Sheets

(56) References Cited

OTHER PUBLICATIONS

Kast et al., "Amino Acid Substrate Specificity of *Escherichia coli* Phenylalanyl-tRNA Synthetase Altered by Distinct Mutations," *J Mol. Biol.* 222:99-124, 1991.

Kirshenbaum et al., "Biosynthesis of Proteins Incorporating a Versatile Set of Phenylalanine Analogues," *ChemBioChem* 3(2-3):235-237, 2002.

Kowal et al., "Exploiting unassigned codons in *Micrococcus luteus* for tRNA-based amino acid mutagenesis," *Nucleic Acids Research* 25(22):4685-4689, 1997.

Kowal et al., "Twenty-first aminoacyl-tRNA synthetase-suppressor tRNA pairs for possible use in site-specific incorporation of amino acid analogues into proteins in eukaryotes and in eubacteria," *Proc. Natl. Acad. Sci.* 98(5):2268-2273, 2001.

Kwok et al., "Evolutionary relationship between *Halobacterium cutirubrum* and eukaryotes determined by use of aminoacyl-tRNA synthetases as phylogenetic probes," *Can. J. Biochem.* 58:213-218, 1980.

Kwon et al., "Breaking the Degeneracy of the Genetic Code," AIchE 2005 Annual Meeting, Nov. 2005, Abstract #299a, 1 page.

Kwon et al., "Design of a Bacterial Host for Site-Specific Incorporation of *p*-Bromophenylalanine into Recombinant Proteins," *J. Am. Chem. Soc.* 128:11778-11783, 2006.

Kwon et al., "Site-Specific Incorporation of Tryptophan Analogues into Recombinant Proteins in Bacterial Cells," *J. Am. Chem. Soc.* 129:10431-10437, 2007.

Link et al., "Discovery of aminoacyl-tRNA synthetase activity through cell-surface display of noncanonical amino acids," *Proc. Natl. Acad. Sci.* 103(27):10180-10185, 2006.

Link et al., "Non-canonical amino acids in protein engineering," *Current Opinion in Biotechnology* 14:603-609, 2003.

Liu et al., "Engineering a tRNA and aminoacyl-tRNA synthetase for the site-specific incorporation on unnatural amino acids into proteins in vivo," *Proc. Natl. Acad. Sci. USA* 94:10092-10097, 1997.

Liu et al., "Progress toward the evolution of an organism with an expanded genetic code," *Proc. Natl. Acad. Sci. USA* 96:4780-4785, 1999.

Noren et al., "A General Method for Site-Specific Incorporation of Unnatural Amino Acids into Proteins," *Science* 24:182-188, 1989.

Nowak et al., "In Vivo Incorporation of Unnatural Amino Acids into Ion Channels in *Xenopus* Oocyte Expression System," *Methods in Enzymology* 293:504-529, 1998.

Ohno et al., "Changing the Amino Acid Specificity of Yeast Tyrosyl-tRNA Synthetase by Genetic Engineering," *J. Biochem.* 130:417-423, 2001.

Pastrnak et al., "A New Orthogonal Suppressor tRNA/Aminoacyl-tRNA Synthetase Pair for Evolving an Organism with an Expanded Genetic Code," *Helvetica Chimica Acta* 83:2277-2286, 2000.

Sampson et al., "Biochemical and physical characterization of an unmodified yeast phenylalanine transfer RNA transcribed in vitro," *Proc. Natl. Acad. Sci. USA* 85:1033-1037, 1988.

Sharma et al., "Efficient introduction of aryl bromide functionality into proteins in vivo," *FEBS Letters* 467:37-40, 2000.

Tang et al., "Attenuation of the Editing Activity of the *Escherichia coli* Leucyl-tRNA Synthetase Allows Incorporation of Novel Amino Acids into Proteins in Vivo," *Biochemistry* 41:10635-10645, 2002.

van Hest et al., "Efficient introduction of alkene functionality into proteins in vivo," *FEBS Letters* 428:68-70, 1998.

Wang et al., "Expanding the Genetic Code of *Escherichia coli*," *Science* 292:498-500, 2001.

Wang et al., "Addition of the keto functional group to the genetic code of *Escherichia coli*," *Proc. Natl. Acad. Sci.* 100(1):56-61, 2003.

Whelihan et al., "Rescuing an essential enzyme-RNA complex with a non-essential appended domain," *The EMBO Journal* 16(10):2968-2974, 1997.

Wilson et al., "Incorporation of Modified Amino Acids Into Proteins In Vivo," *Biochimica et Biophysica Acta* 781:205-215, 1984.

Xie et al., "Adding amino acids to the genetic repertoire," *Current Opinion in Chemical Biology* 9:548-554, 2005.

International Preliminary Report on Patentability, for International Application No. PCT/US2007/005581, mailed Sep. 9, 2008, 10 pages.

International Search Report, for International Application No. PCT/US2007/005581, mailed Sep. 1, 2008, 10 pages.

Written Opinion, for International Application No. PCT/US2007/005581, mailed Sep. 1, 2008, 9 pages.

* cited by examiner

```
                        261          314
T. thermophilus:  RFQPVYFPFVEP...GFAFGLGVERLAMLRY
E. coli:          RFRPSTFPFTEP...GFAFGMGMERLTMLRY
S. cerevisiae:    RFKPTYNPYTEP...VLGMGLSLERPTMIKY
                        415          460
```

MRGSGIMVRPLNSIVAVSQNMGIG
     ⎧―――amber codon (tag)―――⎫
KNGDLPWPPLRNEZKYFQRMTTTS
  ―――――Peptide A――――  ――Peptide B――

SVEGKQNLVIMGRKTWFSIPEKNR

PLKDRINIVLSRELKEPPRGAHFL
           ―――――――――Peptide C―――――

AKSLDDALRLIEQPELASKVDMVW
―――

IVGGSSVYQEAMNQPGHLRLFVTR

IMQEFESDTFFPEIDLGKYKLLPE
                          ――――

YPGVLSEVQEEKGIKYKFEVYEKK
―――――――――――
  Peptide D
GSRSHHHHHHtaa  (ochre codon)

FIG. 3

>yeast_PheRS_alpha_mutation_sites_are_marked_with_NNN atgtctgact tccaattaga aattctaaag aaactagatg aattggatga gatcaagtcc
acactggcaa ctttccctca gcacggctct caagatgttc tttccgcttt gaactctttg
aaagcccaca acaagttaga gttttccaag gtcgacacgg ttacgtatga cttgaccaaa
gaaggtgctc aaattttgaa tgaaggttcg tacgaaatta aactagtcaa gctcatccaa
gagttgggtc aacttcaaat caaagatgtg atgtccaaac taggccctca agttggtaag
gtcggtcagg ctagagcttt caagaacggc tggatcgcca aaaacgcctc aaacgagctt
gaactctccg caaaattgca aataccgat ttaaatgagc ttactgatga aacgcaatct
attctagcgc aaatcaagaa caactcgcat ctggatagca ttgacgccaa gattttgaac
gacttgaaga aaagaaagtt aattgctcaa ggtaaaatca cagatttcag tgtcaccaaa
gggccagagt tctcgaccga cctcaccaaa ttggaaaccg atcttacctc cgacatggtc
tccaccaatg catacaagga cttgaagttc aagccttaca atttcaattc tcaaggtgtg
caaatatctt caggtgctct tcacccctta aacaaagtca gagaggaatt tagacaaatt
ttcttttcca tgggattcac agagatgccc tcgaaccaat acgtcgagac aggtttctgg
aacttcgatg cccttacgt cccacaacag catcctgctc gtgacctgca agacactttc
tacatcaagg acccactaac cgctgagttg cccgatgaca agacatacat ggacaatatc
aaagccgttc acgaacaggg gagattcggg tccatcggtt atcgttacaa ctggaagcca
gaagaatgtc aaaaattggt cttgagaact cactccacag ccatctctgc cagaatgctg
cacgatttgg ccaaagatcc aaagcccacc agattgtttt ctatcgaccg tgttttccgt
aacgaagcag ttgacgccac ccatttggcc gaattccacc aggtggaagg tgttcttgcc
gactacaaca ttactctggg tgacctgatc aagttcatgg aagagttttt cgaaagaatg
ggtgtcaccg gtttgagatt caagcctacc tacNNNcctt acNNNgagc aNNNatggaa
atcttttctt ggcacgaagg tttgcaaaaa tgggtcgaaa tcggtaacNNNggtatgttc
agaccagaaa tgctcgagtc catgggtcta ccaaaggatc taagagtcct tggttggggg
ttatccttgg aaagacctac catgatcaaa tataaggttc aaaacatcag agaactgtta
ggtcataaag tctctttgga ctttatcgaa accaatcctg ctgctagatt ggacgaagac
ttgtacgaat aa

|   | Name | 412 | 415 | 418 | 437 |
|---|------|-----|-----|-----|-----|
|   | T415G | AAT | GGC | TCA | TCT |
| 1 | 2Nal | GGG | GGG | TGT | TTT |
| 2 | 412_415 | GGG | GGC |   |   |
| 3 | 415_418 |   | GGC | TGT |   |
| 4 | 415_437 |   | GGC |   | TTT |
| 5 | 412_415_437 | GGG | GGC |   | TTT |
| 6 | 415_418_437 |   | GGC | TGT | TTT |
| 7 | 412_415_418 | GGG | GGC | TGT |   |

*FIG. 16*

SITE-SPECIFIC INCORPORATION OF AMINO ACIDS INTO MOLECULES

CROSS-REFERENCE TO RELATED APPLICATION

This application claims the benefit of the filing date of U.S. Provisional Application 60/779,375, filed on Mar. 3, 2006, and U.S. Provisional Application 60/779,376, filed on Mar. 3, 2006, the entire content of which are incorporated herein by reference.

STATEMENT OF GOVERNMENT INTEREST

This invention was made with federal government support under grant number GM62523, awarded by the NIH. The United States government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 110197_412d_SEQUENCE_LISTING.txt. The text file is 273 KB, was created on Jul. 4, 2013, and is being submitted electronically via EFS-Web.

BACKGROUND OF THE INVENTION

Protein engineering is a powerful tool for modification of the structural catalytic and binding properties of natural proteins and for the de novo design of artificial proteins. Protein engineering relies on an efficient recognition mechanism for incorporating mutant amino acids in the desired protein sequences. Though this process has been very useful for designing new macromolecules with precise control of composition and architecture, a major limitation is that the mutagenesis is restricted to the 20 naturally occurring amino acids. However, it is becoming increasingly clear that incorporation of unnatural amino acids can extend the scope and impact of protein engineering methods.

Non-natural amino acids carrying a wide variety of novel functional groups have been globally replaced for residue-specific replacement or incorporation into recombinant proteins. Biosynthetic assimilation of non-canonical amino acids into proteins has been achieved largely by exploiting the capacity of the wild type synthesis apparatus to utilize analogs of naturally occurring amino acids (Budisa 1995, *Eur. J. Biochem* 230: 788-796; Deming 1997, *J. Macromol. Sci. Pure Appl. Chem.* A34; 2143-2150; Duewel 1997, *Biochemistry* 36: 3404-3416; van Hest and Tirrell 1998, *FEBS Lett* 428(1-2): 68-70; Sharma et al., 2000, *FEBS Lett* 467(1): 37-40). However, there are situations in which single-site substitution or incorporation by non-natural amino acids is required. Such a methodology would enable the tailoring in a protein (the size, acidity, nucleophilicity, hydrogen-bonding or hydrophobic properties, etc. of amino acids) to fulfill a specific structural or functional property of interest. The ability to site-specifically incorporate such amino acid analogs into proteins would greatly expand our ability to rationally and systematically manipulate the structures of proteins, both to probe protein function and create proteins with new properties. For example, the ability to synthesize large quantities of proteins containing heavy atoms would facilitate protein structure determination, and the ability to site specifically substitute fluorophores or photo-cleavable groups into proteins in living cells would provide powerful tools for studying protein functions in vivo.

In recent years, several laboratories have pursued an expansion in the number of genetically encoded amino acids, by using either a nonsense suppressor or a frame-shift suppressor tRNA to incorporate non-canonical amino acids into proteins in response to amber or four-base codons, respectively (Bain et al., *J. Am. Chem. Soc.* 111: 8013, 1989; Noren et al., *Science* 244: 182, 1989; Furter, *Protein Sci.* 7: 419, 1998; Wang et al., *Proc. Natl. Acad. Sci. U.S.A.,* 100: 56, 2003; Hohsaka et al., *FEBS Lett.* 344: 171: 1994; Kowal and Oliver, *Nucleic Acids Res.* 25: 4685, 1997). Such methods insert non-canonical amino acids at codon positions that will normally terminate wild-type peptide synthesis (e.g., a stop codon or a frame-shift mutation). These methods have worked well for single-site insertion of novel amino acids. However, their utility in multisite position specific (versus residue specific) substitution or incorporation is limited by modest (20-60%) suppression efficiencies (Anderson et al., *J. Am. Chem. Soc.* 124: 9674, 2002; Bain et al., *Nature* 356: 537, 1992; Hohsaka et al., *Nucleic Acids Res.* 29: 3646, 2001). This is so partially because too high a stop codon suppression efficiency will interfere with the normal translation termination of some non-targeted proteins in the organism. On the other hand, a low suppression efficiency will likely be insufficient to suppress more than one nonsense or frame-shift mutation sites in the target protein, such that it becomes more and more difficult or impractical to synthesize a full-length target protein incorporating more and more non-canonical amino acids.

Efficient multisite incorporation has been accomplished by replacement of natural amino acids in auxotrophic *Escherichia coli* strains, for example, by using aminoacyl-tRNA synthetases with relaxed substrate specificity or altered editing activity (Wilson and Hatfield, *Biochim. Biophys. Acta* 781: 205, 1984; Kast and Hennecke, *J. Mol. Biol.* 222: 99, 1991; Ibba et al., *Biochemistry* 33: 7107, 1994; Sharma et al., *FEBS Lett.* 467: 37, 2000; Tang and Tirrell, *Biochemistry* 41: 10635, 2002; Datta et al., *J. Am. Chem. Soc.* 124: 5652, 2002; Doring et al., *Science* 292: 501, 2001). Although this method provides efficient incorporation of analogues at multiple sites, it suffers from the limitation that the novel amino acid must "share" codons with one of the natural amino acids. Thus for any given codon position where both natural and novel amino acids can be inserted, other than a probability of incorporation, there is relatively little control over which amino acid will end up being inserted. This may be undesirable, since for an engineered enzyme or protein, non-canonical amino acid incorporation at an unintended site may unexpectedly compromise the function of the protein, while missing incorporating the non-canonical amino acid at the designed site will fail to achieve the design goal.

In general, multisite substitution methods are relatively simple to carry out, but all sites corresponding to a particular natural amino acid throughout the protein are replaced. The extent of incorporation of the natural and non-natural amino acid may also vary. Furthermore, multisite incorporation of analogs often results in toxicity when cells are utilized, which makes it difficult to study the mutant protein in living cells. The present invention overcomes these hurdles by allowing for site-specific mutation of amino acids in proteins.

Certain embodiments disclosed herein provide a new technique for the incorporation of replacement amino acids, including naturally occurring amino acids, or non-standard or non-canonical amino acids into proteins that is based on breaking the degeneracy of the genetic code. Specifically, certain embodiments herein allow for high fidelity position-specific substitution or incorporation of non-natural amino acids into proteins.

BRIEF SUMMARY OF THE INVENTION

Certain embodiments disclosed herein provide for compositions of components used in protein biosynthetic machinery, which include external mutant aminoacyl tRNA molecules, external mutant aminoacyl-tRNA synthetase (AARS) molecules, or pairs of the same, as well as the individual components of the pairs.

Methods are also provided for generating and selecting external mutant tRNAs, external mutant aminoacyl-tRNA synthetases, and pairs thereof that are capable of incorporating amino acids, including non-natural amino acids, into polypeptides or proteins. Certain compositions of specific embodiments include novel external mutant tRNA or external mutant aminoacyl-tRNA synthetase pairs. The novel external mutant tRNA molecules, AARS molecules, or AARS-tRNA pairs can be used to incorporate an unnatural amino acid in a polypeptide in vitro and in vivo. Other embodiments of the invention include selecting external mutant pairs.

Some compositions of the present invention include an external mutant aminoacyl-tRNA synthetase, where the external mutant tRNA synthetase preferentially aminoacylates an external mutant tRNA with an unnatural amino acid, optionally, in vivo. In one embodiment, a nucleic acid or polynucleotide encoding an external mutant synthetase is provided, or a complementary nucleic acid sequence thereof.

Thus, certain embodiments include a composition comprising a first vector containing a polynucleotide encoding a modified aminoacyl tRNA synthetase (AARS), wherein said polynucleotide modified synthetase is mutated at one or more codons encoding the amino acid binding region necessary for interaction with the amino acid to be paired with a tRNA molecule, and wherein said modified synthetase is capable of charging a tRNA molecule with a non-natural amino acid. In some embodiments, the binding region comprises no more than 30, 20, 15, 10, or 5 contiguous amino acid residues. In at least one embodiment, the modified AARS is selected from the group consisting of a modified PheRS, a modified TrpRS, a modified TyrRS, and a modified MetRS. In some embodiments wherein the modified AARS is a modified PheRS, said PheRS is mutated at amino acid sequence positions selected from the group consisting of amino acid sequence position number 412, 415, 418, and 437. In at least one embodiment wherein said modified AARS is a modified TrpRS, the TrpRS is mutated at amino acid sequence positions selected from the group consisting of amino acid sequence position number 4, 5, 7, 132, 133, 141, and 143. In some embodiments wherein the modified AARS is a modified MetRS, the MetRS is mutated at amino acid sequence position number 13.

At least one embodiment further comprises a second vector containing a polynucleotide encoding a tRNA molecule. In at least one embodiment, said first and second vectors are the same vector. In other embodiments, said first and second vectors are different vectors.

In at least one embodiment, the tRNA is endogenous, and in at least one embodiment, the tRNA is modified. In at least one embodiment, the tRNA is modified such that it contains a mutated anticodon that base pairs with a corresponding wobble degenerate codon with an affinity greater than the affinity of the natural tRNA. In some embodiments, the AARS and the tRNA are from the same or different organisms. In at least one embodiment, the non-natural amino acid is selected from the group consisting of: azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindolyl)alanine, 3-(5-bromoindolyl)alanine, azidohomoalanine, and p-chlorophenylalanine.

Other embodiments disclosed herein include a polypeptide comprising a modified aminoacyl tRNA synthetase (AARS), wherein said modified synthetase is mutated at one or more codons in the amino acid binding region necessary for interaction with the amino acid to be paired with a tRNA molecule, and wherein said modified synthetase is capable of charging a tRNA molecule with a non-natural amino acid. In at least one embodiment, the binding region comprises no more than 30, 20, 15, 10, or 5 contiguous amino acid residues.

In at least one embodiment, the modified AARS is selected from the group consisting of a modified PheRS, a modified TrpRS, a modified TyrRS, and a modified MetRS. In some embodiments wherein the modified AARS is a modified PheRS, said PheRS is mutated at amino acid sequence positions selected from the group consisting of amino acid sequence position number 412, 415, 418, and 437. In at least one embodiment wherein said modified AARS is a modified TrpRS, the TrpRS is mutated at amino acid sequence positions selected from the group consisting of amino acid sequence position number 4, 5, 7, 132, 133, 141, and 143. In some embodiments wherein the modified AARS is a modified MetRS, the MetRS is mutated at amino acid sequence position number 13.

Certain embodiments include translation system comprising the polynucleotide encoding a modified aminoacyl tRNA synthetase (AARS), wherein said polynucleotide modified synthetase is mutated at one or more codons encoding the amino acid binding region necessary for interaction with the amino acid to be paired with a tRNA molecule, and wherein said modified synthetase is capable of charging a tRNA molecule with a non-natural amino acid. In at least one embodiment, the system comprises a host cell. In at least one embodiment, the modified aminoacyl tRNA synthetase is derived from an organism different than the host cell. In another embodiment, the translation system further comprises a polynucleotide encoding a modified tRNA molecule.

In certain embodiments, the modified tRNA molecule is derived from an organism different than the host cell. In certain embodiments, the modified tRNA molecule is derived from a eukaryotic cell and the host cell is a prokaryotic cell. In still other embodiments, the cell is an auxotroph.

In some embodiments, the translation system further comprises a culture media containing one or more non-natural amino acids. In still other embodiments, said one or more non-natural amino acids are selected from the group consisting of: azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindolyl)alanine, 3-(5-bromoindolyl)alanine, azidohomoalanine, and p-chlorophenylalanine. In still other embodiments, said modified AARS is selected from the group consisting of: a modified PheRS, a modified TrpRS, a modified TyrRS, and a modified MetRS.

Other embodiments relate to a method for incorporating a non-natural amino acid into a target polypeptide at one or more specified position(s), the method comprising the steps of:

(1) determining the structural change in the polypeptide for incorporation of a non-natural at one specific position in the polypeptide;

(2) providing a translation system;

(3) providing to the translation system a first polynucleotide of claim 1, or the modified AARS encoded thereby;

(4) providing to the translation system the non-natural amino acid;

(5) providing to the translation system a template polynucleotide encoding a polypeptide of interest, and, (6) allowing translation of the template polynucleotide, thereby incorporating the non-natural amino acid into the polypeptide of interest at the specified position(s), wherein steps (1)-(4) are effectuated in any order.

In certain embodiments, said translation system comprises a cell. In some embodiments, step (4) is effectuated by contacting said translation system with a solution containing the non-natural amino acid. In at least one embodiment, the specificity constant ($k_{cat}/K_M$) for activation of said non-natural amino acid by said modified AARS is at least 5-fold larger than that for said natural amino acid. In certain embodiments, the modified AARS mischarges a tRNA at a rate of no more than 1%, 2%, 3%, 4%, 5%, 6%, 7%, or 8%. In still other embodiments, the tRNA is a modified tRNA. In certain embodiments, said first polynucleotide or said second polynucleotide further comprises either a constitutively active or an inducible promoter sequence that controls the expression of the tRNA or AARS. In at least one embodiment, the method further comprises the step of screening for cells containing a modified AARS. In another embodiment, the method further comprises the step of verifying the incorporation of the non-natural amino acid. In another embodiment, the modified AARS is selected from the group consisting of: PheRS, TyrRS, TrpRS, and MetRS. Still other embodiments comprise a polypeptide made by the method disclosed.

Certain embodiments disclosed herein include a method for incorporating at least one non-natural amino acid into a target polypeptide at one or more specified location(s), the method comprising providing a translation system containing at least one non-natural amino acid; providing to the translation system one or more modified AARS selected from the group consisting of: modified PheRS, TrpRS, TyrRS, and MetRS; providing to the translation system a polynucleotide encoding a target polypeptide of interest; and allowing translation of interest, thereby incorporating at least one non-natural amino acid into the target polypeptide. Certain embodiments include a polypeptide made by this method.

BRIEF DESCRIPTION OF THE SEVERAL VIEWS OF THE DRAWINGS

FIG. 1 shows a sequence alignment of PheRS variants from conserved sequences of Thermus thermophilus, SEQ ID NOs:105 and 106), Escherichia coli(SEQ ID NOs:107 and 108), and Saccharomyces cerevisiae(SEQ ID NOs:109 and 110) (FIG. 1A).

FIG. 3 shows the amino acid sequence for an exemplary polypeptide used for some embodiments disclosed herein, dihydrofolate reductase (DHFR; SEQ ID NO:111). Four proteolytic peptide fragments (labeled Peptide A (SEQ ID NO:5), Peptide B, (SEQ ID NO:112), Peptide C (SEQ ID NO:113) and Peptide D (SEQ ID NO:114) were used for MALDI and liquid chromatography-Mass Spectrum/Mass Spectrum (LC-MS/MS) analyses as underscored.

FIG. 16 illustrates exemplary mutations made in a yeast phenylalanine tRNA synthetase SEQ ID NO:3).

DETAILED DESCRIPTION OF THE INVENTION

Figures 1A, 1B:
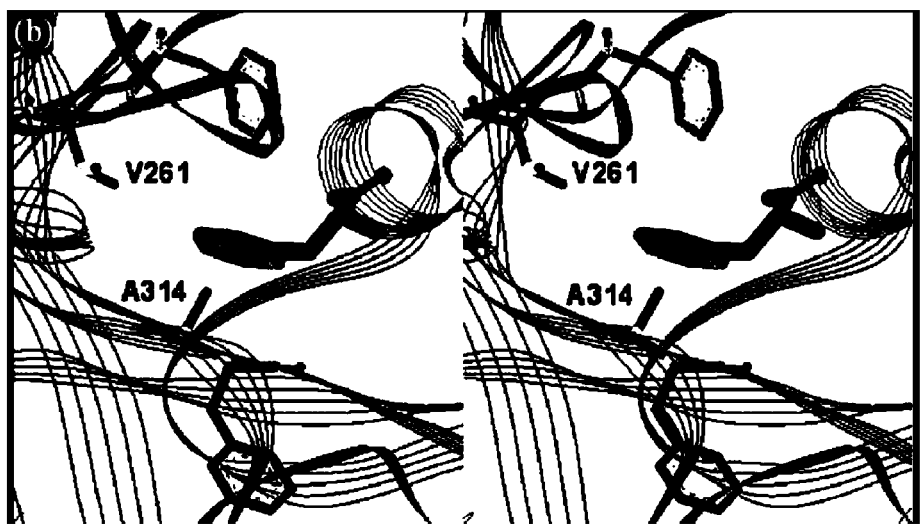
FIG. 1B provides a stereoscopic view of the amino acid binding pocket of ePheRS. Amino acid residues V261 and A314 are indicated.

Proteins are at the crossroads of virtually every biological process, from photosynthesis and vision to signal transduction and the immune response. Modifying proteins or polypeptides to include non-natural amino acids has great potential for use in human therapeutics, agriculture, biofuel, and other areas.

Aminoacyl-tRNA synthetases catalyze the aminoacylation reaction for incorporation of amino acids into proteins via the corresponding transfer RNA molecules. Precise manipulation of synthetase activity can alter the aminoacylation specificity to stably attach non-canonical amino acids into the intended tRNA. Then, through codon-anticodon interaction between message RNA (mRNA) and tRNA, the amino acid analogs can be delivered into a growing polypeptide chain. Thus, incorporation of non-natural amino acids into proteins relies on the manipulation of amino acid specificity of aminoacyl tRNA synthetases (AARS).

Aminoacyl-tRNA synthetases function to transform the genetic code sequences into biologically functional proteins through a two-step aminoacylation reaction. As an initial step, the cognate amino acid is activated by AARS in the presence of ATP to form the amino acid adenylate; subsequently AARS catalyzes the esterification reaction to join the amino acid to 2'- or 3'-OH of the terminal ribonucleotide of its cognate tRNA. Once the aminoacylation reaction occurs, the amino acid is directed into the growing polypeptide chain by the charged tRNA.

Certain embodiments disclosed herein relate to mutant or modified aminoacyl tRNA synthetase (AARS or RS) molecules that have been mutated or modified such that the enzymes are capable of charging a tRNA molecule with a replacement amino acid, preferably a non-natural amino acid due to disruption of between the synthetase and the corresponding natural amino acid.

For example, the disruption may be due to interfering with Watson-Crick base pairing, interfering with wobble base pairing, or creation of novel wobble or other base pairing.

Some embodiments relate to a polynucleotide encoding a mutant or modified tRNA of a tRNA for a natural amino acid, wherein the natural amino acid is encoded by one or more wobble degenerate codon(s), the modified tRNA comprises a modified anticodon sequence that forms Watson-Crick base-pairing with one of the wobble degenerate codon(s). Preferably, the modified tRNA is not or only inefficiently charged by an endogenous aminoacyl-tRNA synthetase (AARS) for the natural amino acid. In one embodiment, multiple modified AARS molecules may be used with one or more tRNA molecules. In one embodiment, one or more modified or mutated AARS molecule can be used with one or more native tRNA molecule, while in another embodiment a modified or mutated AARS can be used with a modified or mutated tRNA molecule. In certain embodiments, one or more pairs of modified AARS/tRNA molecules may be utilized. In certain embodiments, heterologous pairs may be used. In certain embodiments, one or more modified or mutant AARS and/or tRNA may be derived from the same or a different organism.

In some exemplary embodiments, a particular AARS may utilize several methods for incorporation of a replacement amino acid (including a non-natural amino acid) into a polypeptide or protein. For example, a single AARS may utilize a nonsense codon (such as an amber stop codon) for incorporation of a replacement amino acid (such as a non-natural amino acid) at a particular location in the polypeptide. In addition or instead of this, a wobble codon (such as UUU) could be used for incorporation of the replacement amino acid at the wobble codon site (in this example, using a modified PheRS).

In other exemplary embodiments, multiple replacement amino acids (such as two different non-natural amino acids) may be incorporated into a polypeptide or protein through the use of various methods. For example, one non-natural amino acid may be incorporated at a wobble site, while a different non-natural amino acid may be incorporated at an amber stop codon. In some exemplary embodiments, incorporation of multiple replacement amino acids (including non-natural amino acids) includes utilizing one AARS for multiple different amino acid analogs of any amino acid, or multiple different amino acid analogs all of a particular naturally occurring amino acid. Thus, for example, a modified PheRS may be used to incorporate multiple different phenylalanine analogs, such as bromophenylalanine and/or p-idiophenylalanine, in the same polypeptide or protein.

A similar approach involves using a heterologous synthetase and a mutant initiator tRNA of the same organism or a related organism as a tRNA molecule. (See, for example, Kowal, et al., *PNAS,* 98, 2268 (2001)).

In certain embodiments, the modified or mutated RS interacts with the desired amino acid replacement (whether naturally occurring or non-natural amino acid) with an altered binding specificity and/or altered catalytic event of the enzyme toward the amino acid replacement when compared to the wild type RS enzyme or wild type corresponding amino acid.

In enzyme kinetics, $k_{cat}$ is a first-order rate constant corresponding to the slowest step or steps in the overall catalytic pathway. The $k_{cat}$ represents the maximum number of molecules of substrate which can be converted into product per enzyme molecule per unit time (which occurs if the enzyme is "saturated" with substrate), and thus is often referred to as the turnover number. The $K_m$ is an apparent dissociation constant and is related to the enzyme's affinity for the substrate; it is the product of all the dissociation and equilibrium constants prior to the first irreversible step in the pathway. Often, it is a close measure of the enzyme-substrate dissociation constant. The $k_{cat}/K_m$ is a second-order rate constant which refers to the free enzyme (not enzyme-substrate complex) and is also a measure of the overall efficiency of the enzyme catalysis and is also referred to as the specificity constant.

In certain embodiments, the external mutant synthetase has improved or enhanced enzymatic properties, e.g., the $K_m$ is higher or lower, the $k_{cat}$ is higher or lower, the value of $k_{cat}/K_m$ is higher or lower or the like, for the unnatural amino acid compared to a naturally occurring amino acid, e.g., one of the 20 known amino acids. The Km of the mutant or modified AARS is preferably equal or lower for the non-natural amino acid than for the corresponding wild type natural amino acid.

In certain embodiments, the $k_{cat}/K_m$ values of the RS variant may range from 3-fold, 5-fold, 10-fold, 25-fold, 50-fold, 100-fold, 150-fold, 200-fold, 250-fold, 300-fold, 350-fold, 385-fold, 400-fold higher than for the naturally occurring amino acid.

In certain embodiments, the modified tRNA interacts with the wobble degenerate codon with an affinity at 37° C. of at least about 1.0 kcal/mole, 1.5 kcal/mole, 2.0 kcal/mole, 2.5 kcal/mole, 3.0 kcal/mole, 3.5 kcal/mole, 4.0 kcal/mole, 4.5 kcal/mole, 5.0 kcal/mole or greater (or any value therebetween) favorably than the interaction between its unmodified version and the wobble degenerate codon.

For example, phenylalanine (Phe) is encoded by two codons, UUC and UUU. Both codons are read by a single tRNA, which is equipped with the anticodon sequence GAA. The UUC codon is therefore recognized through standard Watson-Crick base-pairing between codon and anticodon; UUU is read through a G-U wobble base-pair at the first position of the anticodon (Crick, *J. Mol. Biol.* 19: 548, 1966; Soll and RajBhandary, *J. Mol. Biol.* 29: 113, 1967). Thermal denaturation of RNA duplexes has yielded estimates of the Gibbs free energies of melting of G-U, G-C, A-U, and A-C basepairs as 4.1, 6.5, 6.3, and 2.6 kcal/mol, respectively, at 37° C. Thus the wobble basepair, G-U, is less stable than the Watson-Crick basepair, A-U. A modified tRNA$^{Phe}$ outfitted with the AAA anticodon (tRNA$^{Phe}_{AAA}$) was engineered to read the UUU codon, and was predicted to read such codons faster than wild-type tRNA$^{Phe}_{GAA}$.

In some embodiments, the binding pocket of the RS is modified such that the modified RS exhibits a preference for the non-natural amino acid over the corresponding naturally occurring amino acid. In preferred embodiments, the RS is modified at one or more codon necessary for structural contact between the RS and the amino acid being charged to the tRNA. In certain embodiments, the one or more codon selected for mutation or modification are selected by way of computer modeling. While any RS can be modified according to the present disclosure, certain embodiments relate to phenylalanyl-tRNA synthetase (PheRS), or tryptophan tRNA synthetase (TrpRS). In some embodiments, the modified RS is from *Saccharomyces cerevisiae*, or another eukaryotic cell. In other embodiments, the modified RS is from *E. coli* or another prokaryotic cell. In certain embodiments wherein the RS is a PheRS, the enzyme has a point mutation (N412G), (T415G), (T415A), (S418C), or (S437F) in the alpha subunit of the enzyme, or mutations at equivalent locations or positions in a homologous protein of another species or organism. The point mutations (for example, the T to G or A mutation at position 415, or S to C mutation at position 418, or N to G mutation at position 412, or S to F mutation at position 437) are located in the binding pocket region of the aminoacyl-tRNA synthetase (RS).

In some exemplary embodiments, typical Km values for different analogs with AARS may range from approximately 15 microM, 20 microM, 30 microM, 50 microM, 75 microM, 100 microM, 150 microM, 200 microM, 300 microM, 400 microM, 440 microM, 500 microM, 1000 microM, 1500 microM, 2000 microM, 3000 microM, 4000 microM, 5000 microM, 6000 microM, or greater or any value therebetween.

Likewise, the $k_{cat}$ values of the mutant AARS is preferably equal to or higher for the amino acid analog than for the natural amino acid. For example, $k_{cat}$ values for different analogs with the corresponding AARS may range from approximately 0.002 sec$^{-1}$, 0.0018 sec$^{-1}$, 0.0015 sec$^{-1}$, 0.014 sec$^{-1}$, 0.1 sec$^{-1}$, 0.3 sec$^{-1}$, 1 sec$^{-1}$, 3 sec$^{-1}$, 5 sec$^{-1}$, 8 sec$^{-1}$, 10 sec$^{-1}$, 13.3 sec$^{-1}$, 15 sec$^{-1}$, or higher.

Thus, the $k_{cat}$/Km of the mutant AARS is optimally equal to or higher for the amino acid analog than for the natural wild type amino acid. Typical $k_{cat}$/Km values may range from approximately 0.0001 M$^{-1}$ s$^{-1}$, 0.0003 M$^{-1}$ s$^{-1}$, 0.005 M$^{-1}$ s$^{-1}$, 0.05 M$^{-1}$ s$^{-1}$, 0.5 M$^{-1}$ s$^{-1}$, 0.547 M$^{-1}$ s$^{-1}$, 1 M$^{-1}$ s$^{-1}$, 5 M$^{-1}$ s$^{-1}$, 10 M$^{-1}$ s$^{-1}$, 20 M$^{-1}$ s$^{-1}$, 30 M$^{-1}$ s$^{-1}$, 32 M$^{-1}$ s$^{-1}$, 500 M$^{-1}$ s$^{-1}$, 600 M$^{-1}$ s$^{-1}$, 1000 M$^{-1}$ s$^{-1}$, 5000 M$^{-1}$ s$^{-1}$, 11000 M$^{-1}$ s$^{-1}$.

While the point mutations of a mutated AARS typically relate to the binding pocket, the amino acids of the AARS selected for mutation may be altered to any amino acid that allows for aminoacylation of the corresponding tRNA (and thus allows for incorporation of the non-natural amino acid into the target polypeptide or protein).

In certain embodiments, the AARS point mutations may be altered to any amino acid, depending on the characteristics of the non-natural amino acid desired for incorporation into the test protein/polypeptide. In certain embodiments, an amino acid in the binding pocket of the AARS may be mutated to a codon for an amino acid with a small side chain, an amino acid with an aliphatic side chain, a cyclic amino acid, an amino acid with hydroxyl or sulfur containing side chains, an aromatic amino acid, a basic amino acid, an acidic amino acid (or amide). Selection of the amino acid for mutating the AARS at a particular point is routine, depending on the desired outcome and desired non-natural amino acid to be incorporated into the target or test polypeptide/protein. For example, if the goal is to enlarge the binding pocket of the AARS molecule, then an amino acid with an aliphatic side chain, or a small side chain, could be chosen for mutating the AARS. In other instances, if a binding pocket is desired that harbors a charged pocket, then a basic or acidic amino acid may be selected for point mutation of the AARS.

Certain embodiments disclosed herein include any modified RS molecule in which the binding pocket region has been mutated by at least one point mutation. In certain embodiments, the point mutation are located at one or more positions at which the RS contacts the amino acid for which the RS aminoacylates, or charges, a tRNA molecule. In certain embodiments, multiple point mutations comprise multiple positions at which the RS contacts an amino acid. That is, in certain embodiments multiple or every codon of the entire binding pocket region of an RS may be mutated or modified, or one, two, three, four, or more codons of the binding pocket region of the RS may be mutated or modified. In certain other embodiments, each codon that represents a structural binding point between the particular RS and an amino acid may be mutated or modified. As disclosed herein, multiple different RS molecules have been modified or mutated from various species at the binding point, and guidance is provided for methods that allow one of skill in the art to predictably mutate or modify other RS homolog molecules in the same manner. Certain embodiments provided herein would enable modification and/or mutation of the binding points of the homologous RS molecules in a similar way. Accordingly, such mutation or modification of other RS molecules would be routine experimentation in light of the guidance provided herein.

In some embodiments, the modified RS may be used in a translation system, including an auxotrophic host cell or prototrophic host cell along with a suppressor tRNA in order to enable the assignment of a stop codon (such as an amber, ochre or opal nonsense codon, a stop codon that is not present in a particular organism, any nonsense codon, a four or five base pair codon, or another natural amino acid that is not present in significant levels in the protein, such as methionine) to incorporate another amino acid, including an amino acid analog. Thus, the RS enzymes can be "reprogrammed" for promiscuous substrate specificity in order to facilitate incorporation of a non-natural amino acid into a polypeptide in a site-specific manner. In particular embodiments, any aromatic non-natural amino acid may be utilized with the modified PheRS or TrpRS. This reprogramming allows for high fidelity incorporation of an amino acid, including non-natural amino acids, into polypeptides or proteins with or without the use of auxotrophic host cells.

Reprogramming an AARS enzyme may involve structural or biochemical analysis, including computer modeling or sequence alignment. As there is sequence information available for many AARS molecules, for example at GenBank, comparing sequence alignments is a routine procedure once the particular sequence region of interest is determined.

The use of auxotrophic host cells may increase the level of incorporation of the non-natural amino acid, or decrease the level of misincorporation of another amino acid rather than the desired non-natural amino acid. For example, after enhancing the cellular aminoacylation reactivity by expression of wild type AARS in the host, we surprisingly found that some of the sluggish amino acid analogs could also be introduced into proteins even in the absence of an auxotrophic host cell.

In certain embodiments, the expression of one or more modified or mutant AARS molecules, one or more modified or mutant tRNA molecules, or both, may be regulated by a constitutive or inducible promoter or other inducible expression system.

Certain embodiments disclosed herein relate to allowing for site-selective insertion of one or more unnatural amino acids at any desired position of any protein, (ii) is applicable to both prokaryotic and eukaryotic cells, and enables in vivo studies of mutant proteins in addition to the generation of large quantities of purified mutant proteins. In addition, certain embodiments relate to adapting to incorporate any of a large variety of unnatural amino acids, into proteins in vivo. Thus, in a specific polypeptide sequence a number of different site-selective insertions of unnatural amino acids is possible. Such insertions are optionally all of the same type (e.g., multiple examples of one type of unnatural amino acid inserted at multiple points in a polypeptide) or are optionally of diverse types (e.g., different unnatural amino acid types are inserted at multiple points in a polypeptide).

One surprising result disclosed herein shows that the re-design of the synthetic site of an AARS enzyme can expand the ability to introduce replacement amino acids (including non-natural amino acids) into polypeptides or proteins. In some embodiments, the compositions and methods of modifying or mutating an AARS may optionally include altering the editing function of the modified or mutant AARS. In some embodiments, the editing or proofreading ability of the modified or mutant AARS is approximately equal to that of the wild type (unaltered) AARS. In other embodiments, the editing or proofreading ability of the modified or mutant AARS is reduced. In still other embodiments, the editing or proofreading ability of the modified or mutant AARS is eliminated. In some certain embodiments, the alteration of the AARS' editing or proofreading function is inherent to modification of the AARS in order to accommodate a replacement amino acid (for example modification to the binding pocket of the AARS). In other embodiments, the alteration to the editing or proofreading function may be performed in addition to the modification of the AARS in order to accommodate a replacement amino acid. In still other embodiments, the editing or proofreading function of the AARS is unaltered. Thus, in addition to modification or alteration of the binding pocket of an AARS, the proofreading or editing domain of the modified AARS may also be altered in order to allow for increased specificity of aminoacylating the replacement amino acid (including non-natural amino acid) to a tRNA (whether endogenous or external mutant tRNA), while optionally hydrolyzing the wild type amino acid(s)-adenylate that may form and resulting in greater fidelity or specificity of incorporation of the replacement amino acid (including a non-natural amino acid) into the polypeptide or protein.

In some embodiments, the incorporation rates of a non-natural amino acid were approximately 65% or greater, 70% or greater, 75% or greater, 80% or greater, 85% or greater, 90% or greater, 91% or greater, 92% or greater, 93% or greater, 94% or greater, 95% or greater, 96% or greater, 97% or greater, 98% or greater, or 99% or greater utilizing a modified RS.

As disclosed herein inter alia, the crystal structure of the exact RS to be modified, or the crystal structure of a homologous RS can be used for molecular modeling of the enzyme-amino acid interaction in order to determine the contact points between the RS and the corresponding naturally occurring amino acid, and/or the contact points between the RS and the selected non-natural amino acid desired to be incorporated into a polypeptide. For example, in certain embodiments herein, the crystal structure of *Thermus thermophilus* PheRS complexed with phenylalanine was used for the molecular modeling design of a *Saccharomyces cerevisiae* PheRS, due to the sequence identity of approximately 40% in the active site region of the synthetases. Mutation of the Threonine at position 415 to *Glycine* or Alanine (T415G or T415A, respectively) enlarged the active site and enabled accommodation of larger phenylalanine analogs. Mutations such as this that disrupt the Watson-Crick base pairing with the naturally occurring amino acid designated for a particular RS allow for increased specificity for incorporation of a non-natural amino acid and decreased misincorporation of another amino acid. As set forth in the Examples and Figures, the (T415A) yeast phenylalanine aminoacyl tRNA synthetase (PheRS) revealed a 5-fold preference for bromophenylalanine than for naturally occurring phenylalanine. Thus, it is possible to alter an aminoacyl tRNA synthetase molecule (RS) to preferentially incorporate a desired amino acid at 2-fold, 3-fold, 4-fold, 5-fold, 6-fold, 7-fold, 8-fold, 9-fold, 10-fold, or greater, depending on the properties of the particular RS and desired amino acid (including non-natural amino acid).

In another particular embodiment, the TrpRS (tryptophan aminoacyl tRNA synthetase) active site generally accommodates bulky non-natural amino acids, other specific point mutations may allow for further specificity with regard to amino acid incorporation. For example, the point mutation of the D at position 132 of the TrpRS may be altered to a hydrophobic amino acid, which allows for incorporation of bulky non-natural amino acids (such as phenylalanine-derived amino acids). Further mutations at other particular positions in the binding site at locations where recognition occurs for special functional groups of non-natural amino acids may allow for increased specificity and/or higher fidelity of incorporation of the desired amino acid (including non-natural amino acids).

In one particular embodiment, it was found that the space around the para position of the aryl ring of bound Phe could be slightly reduced to exclude other aromatic amino acids, such as Trp, while still accommodating a non-natural amino acid, such as pBrF. Thus, one embodiment discloses incorporation of an aryl bromide functional group into a polypeptide at a programmed position by providing a chemoselective ligation via palladium catalyzed cross-coupling with ethyne or acetylene reaction partners. While such reprogrammed or modified RSs may be used in any number of host cells, including auxotrophic host cells, the high level of efficiency of incorporation of the desired amino acid (or analog) of the modified RSs of certain embodiments, as well as high yields of protein production, render the use of auxotrophic host cells unnecessary.

As the active site region for almost all amino acid synthetases is known or readily deduced, such an exemplary technique may be applied to other AARSs in an effort to reprogram the amino acid specificity from a naturally occurring amino acid to a non-natural amino acid with an expectation of success and without undue experimentation.

As an illustrative example, the threonine at position 415 in yeast PheRS is the equivalent to threonine 251 in *E. coli* PheRS. Thus, mutation of the yeast PheRS (T415G) allowed for activation of a variety of Phe analogs. (See Examples, herein). Further point mutations and/or use of an auxotrophic host cell allowed for decreased misincorporation in the T415G yeast PheRS variant.

In another particular embodiment disclosed herein, a mutant yeast transfer RNA (ytRNA$^{Phe}_{CUA}$) of which a Watson-Crick base pairing between nucleotides encoding amino acid position 30 and amino acid position 40, was disrupted was charged with p-bromo-phenylalanine (pBrF) by a co-expressed yeast phenylalanine tRNA synthetase. In certain embodiments, the amino acid binding pocket of the AARS constitutes approximately 200, approximately 100, approximately 75, approximately 50, approximately 25, approximately 10, approximately 5 or more or less amino acids. In some embodiments, the amino acids to be mutated in the active or binding site are contiguous stretches of amino acids. In other embodiments, the amino acids to be mutated are located within a close proximity to each other but are not contiguous.

In certain embodiments, the natural amino acid is encoded by two or more genetic codes (thus encoded by degenerate genetic codes). In most, if not all cases, this includes 18 of the 20 natural amino acids, except Met and Trp. In these circumstances, to recognize all the degenerate genetic codes for the natural amino acid, the anticodon loop of the wild-type tRNA (s) relies on both wobble base-pairing and pure Watson-Crick base-pairing. The subject modified tRNA contains at least one modification in its anticodon loop, such that the modified anticodon loop now forms Watson-Crick base-pairing to one of the degenerate genetic codes, which the tRNA previously bind only through wobble base-pairing.

Since Watson-Crick base pairing is invariably stronger and more stable than wobble base pairing, the subject modified tRNA will preferentially bind to a previous wobble base-pairing genetic code (now through Watson-Crick base-pairing), over a previous Watson-Crick base-pairing (now through wobble base-pairing). Thus an analog may be incorporated at the subject codon, if the modified tRNA is charged with an analog of a natural amino acid, which may or may not be the same as the natural amino acid encoded by the codon in question.

Thus in certain embodiments, if it is desirable to incorporate certain amino acid analogs at codons for Met or Trp, a tRNA for a natural amino acid (e.g., a Met tRNA, a Trp tRNA, or even a Phe tRNA, etc.) may be modified to recognize the Met or Trp codon. Under this type of unique situation, both the modified tRNA and the natural tRNA compete to bind the same (single) genetic code through Watson-Crick base-pairing. Some, but not all such codons will accept their natural amino acids, while others may accept amino acid analogs carried by the modified tRNA. Other factors, such as the abundance of the natural amino acid vs. that of the analog, may affect the final outcome. (See Examples disclosed herein).

In certain preferred embodiments, the modified tRNA is not charged or only inefficiently charged by an endogenous aminoacyl-tRNA synthetase (AARS) for any natural amino acid, such that the modified tRNA largely (if not exclusively) carries an amino acid analog, but not a natural amino acid. Although a subject modified tRNA may still be useful if it can be charged by the endogenous AARS with a natural amino acid.

In certain embodiments, the modified tRNA charged with an amino acid analog has such an overall shape and size that the analog-tRNA is a ribosomally acceptable complex, that is, the tRNA-analog complex can be accepted by the prokaryotic or eukaryotic ribosomes in an in vivo or in vitro translation system.

Preferably, the modified AARS specifically or preferentially charges the analog to the modified tRNA over any natural amino acid. In a preferred embodiment, the specificity constant for activation of the analog by the modified AARS (defined as $k_{cat}/K_M$) is equal to or greater than at least about 2-fold larger than that for the natural amino acid, preferably about 3-fold, 4-fold, 5-fold, 6 fold, 7 fold, 8 fold, 9 fold, 10 fold or more than that for the natural amino acid.

In certain embodiments, the modified tRNA further comprises a mutation at the fourth, extended anticodon site for increase translational efficiency.

The use of extended codons is based on frameshift suppression of translation. Four base codons have the potential for insertion of multiple non-natural amino acids into the same protein. For example, the quadruplet UAGA can be decoded by a tRNA$^{Leu}$ with a UCUA anticodon with an efficiency of 13 to 26%. (See, for example, Moore, et al., *J. Mol. Biol.*, 298: 195 (2000)). The use of extended codons alone has potential problems, such as in-frame readthrough of the first three bases as a triplet in the extended codon competes with the overall frameshift suppression. In some cases, extended codons based on rare codons or nonsense codons may reduce missense readthrough and frameshift suppression at other undesired sites. These problems may be overcome, however, with the use of an extended codon/anticodon and a modified AARS and/or tRNA as indicated in some embodiments disclosed herein.

Thus, to summarize, specific codons are reserved for use in methods disclosed herein by the mutant or modified AARS and/or modified or mutant tRNA for incorporation of a replacement amino acid (including a naturally occurring or non-natural amino acid). Such methods may include use of amber (ochre, umber, or other suppressor tRNA) decoding that reads stop (TAG) codons, bias decoding that exploits unused tRNAs responsible for codon bias, wobble decoding, that creates new tRNAs that read wobble codons, and extended (4-5 base or more) codons that use mutant "suppressor" tRNAs that use 4 base or 5 base (or more) anticodons.

At least one other embodiment provides a method for incorporating an amino acid analog into a target protein at one or more specified positions, the method comprising: (1) providing to an environment a first subject polynucleotide for a modified tRNA, or a subject modified tRNA; (2) providing to the environment a second subject polynucleotide encoding a modified AARS, wherein the modified AARS is capable of charging the modified tRNA with the analog; (3) providing to the environment the analog; (4) providing a template polynucleotide encoding the target protein, wherein the codon on the template polynucleotide for the specified position only forms Watson-Crick base-pairing with the modified tRNA; and, (5) allowing translation of the template polynucleotide to proceed, thereby incorporating the analog into the target protein at the specified position, wherein steps (1)-(4) are effectuated in any order.

In certain embodiments, the method further comprises verifying the incorporation of the analog by, for example, mass spectrometry, protein sequencing, amino acid tagging such as by fluorescence, radioactivity, etc., ELISA, or other antibody screening, functional assays or screenings, or other methods.

In certain embodiments, the method incorporates the analog into the position at an efficiency of at least about 50%, or 60%, 70%, 80%, 90%, 95%, 99% or nearly 100%.

Definitions

Before describing certain embodiments in detail, it is to be understood that this invention is not limited to particular compositions or biological systems, which can, of course, vary. It is also to be understood that the terminology used herein is for the purpose of describing particular illustrative embodiments only, and is not intended to be limiting. As used in this specification and the appended claims, the singular forms "a," "an," and "the" include plural referents unless the content clearly dictates otherwise. Thus, for example, reference to "a molecule" optionally includes a combination of two or more such molecules, and the like.

Unless specifically defined below, the terms used in this specification generally have their ordinary meanings in the art, within the general context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used.

"About" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

"Amino acid analog," "non-canonical amino acid," or "non-standard amino acid," "non-natural amino acid," "unnatural amino acid," and the like may all be used interchangeably, and is meant to include all amino acid-like compounds that are similar in structure and/or overall shape to one or more of the twenty L-amino acids commonly found in naturally occurring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y, as defined and listed in WIPO Standard ST.25 (1998), Appendix 2, Table 3). Amino acid analog can also be natural amino acids with modified side chains or backbones. Amino acids can also be naturally occurring amino acids in D-, rather than L-form. Preferably, these analogs usually are not "substrates" for the aminoacyl tRNA synthetases (AARSs) because of the normally high specificity of the AARSs. Although occasionally, certain analogs with structures or shapes sufficiently close to those of natural amino acids may be erroneously incorporated into proteins by AARSs, especially modified AARSs with relaxed substrate specificity. In a preferred embodiment, the analogs share backbone structures, and/or even the most side chain structures of one or more natural amino acids, with the only difference(s) being containing one or more modified groups in the molecule. Such modification may include, without limitation, substitution of an atom (such as N) for a related atom (such as S), addition of a group (such as methyl, or hydroxyl group, etc.) or an atom (such as Cl or Br, etc.), deletion of a group (supra), substitution of a covalent bond (single bond for double bond, etc.), or combinations thereof. Amino acid analogs may include α-hydroxy acids, and β-amino acids, and can also be referred to as "modified amino acids," or "unnatural AARS substrates."

The amino acid analogs may either be naturally occurring or non-natural (e.g., synthesized). As will be appreciated by those in the art, any structure for which a set of rotamers is known or can be generated can be used as an amino acid analog. The side chains may be in either the (R) or the (S) configuration (or D- or L-configuration). In a preferred embodiment, the amino acids are in the (S) or L-configuration.

Preferably, the overall shape and size of the amino acid analogs are such that, upon being charged to (natural or modified or re-designed) tRNAs by (natural or re-designed) AARS, the analog-tRNA is a ribosomally accepted complex, i.e., the tRNA-analog complex can be accepted by the prokaryotic or eukaryotic ribosomes in an in vivo or in vitro translation system.

"Achor residues" are residue positions in AARS that maintain critical interactions between the AARS and the natural amino acid backbone.

"Backbone," or "template" includes the backbone atoms and any fixed side chains (such as the anchor residue side chains) of the protein (e.g., AARS). For calculation purposes, the backbone of an analog is treated as part of the AARS backbone.

"Protein backbone structure" or grammatical equivalents herein is meant the three dimensional coordinates that define the three dimensional structure of a particular protein. The structures which comprise a protein backbone structure (of a naturally occurring protein) are the nitrogen, the carbonyl carbon, the α-carbon, and the carbonyl oxygen, along with the direction of the vector from the α-carbon to the β-carbon.

The protein backbone structure that is input into a computer for computational molecular structural or interaction prediction, can either include the coordinates for both the backbone and the amino acid side chains, or just the backbone, i.e., with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogen atoms attached to the nitrogen and α-carbon).

Optionally, the protein backbone structure may be altered prior to the analysis outlined below. In this embodiment, the representation of the starting protein backbone structure is reduced to a description of the spatial arrangement of its secondary structural elements. The relative positions of the secondary structural elements are defined by a set of parameters called supersecondary structure parameters. These parameters are assigned values that can be systematically or randomly varied to alter the arrangement of the secondary structure elements to introduce explicit backbone flexibility. The atomic coordinates of the backbone are then changed to reflect the altered supersecondary structural parameters, and these new coordinates are input into the system for use in the subsequent protein design automation. For details, see U.S. Pat. No. 6,269,312, the entire content incorporated herein by reference.

"Conformational energy" refers generally to the energy associated with a particular "conformation", or three-dimensional structure, of a macromolecule, such as the energy associated with the conformation of a particular protein. Interactions that tend to stabilize a protein have energies that are represented as negative energy values, whereas interactions that destabilize a protein have positive energy values. Thus, the conformational energy for any stable protein is quantitatively represented by a negative conformational energy value. Generally, the conformational energy for a particular protein will be related to that protein's stability. In particular, molecules that have a lower (i.e., more negative) conformational energy are typically more stable, e.g., at higher temperatures (i.e., they have greater "thermal stability"). Accordingly, the conformational energy of a protein may also be referred to as the "stabilization energy."

Typically, the conformational energy is calculated using an energy "force-field" that calculates or estimates the energy contribution from various interactions which depend upon the conformation of a molecule. The force-field is comprised of terms that include the conformational energy of the alpha-carbon backbone, side chain-backbone interactions, and side chain-side chain interactions. Typically, interactions with the backbone or side chain include terms for bond rotation, bond torsion, and bond length. The backbone-side chain and side chain-side chain interactions include van der Waals interactions, hydrogen-bonding, electrostatics and salvation terms. Electrostatic interactions may include Coulombic interactions, dipole interactions and quadrapole interactions). Other similar terms may also be included. Force-fields that may be used to determine the conformational energy for a polymer are well known in the art and include the CHARMM (see. Brooks et al, *J. Comp. Chem.* 1983, 4:187-217; MacKerell et al., in *The Encyclopedia of Computational Chemistry*, Vol. 1:271-277, John Wiley & Sons, Chichester, 1998), AMBER (see, Cornell et al., *J. Amer. Chem. Soc.* 1995, 117:5179; Woods et al., *J. Phys. Chem.* 1995, 99:3832-3846; Weiner et al., *J. Comp. Chem.* 1986, 7:230; and Weiner et al., *J. Amer. Chem. Soc.* 1984, 106:765) and DREIDING (Mayo et al., *J. Phys. Chem.* 1990, 94-:8897) force-fields, to name but a few.

In a preferred implementation, the hydrogen bonding and electrostatics terms are as described in Dahiyat & Mayo (*Science* 1997 278:82). The force field can also be described to include atomic conformational terms (bond angles, bond lengths, torsions), as in other references. See e.g., Nielsen, et al. *Prot. Eng.,* 12: 657662 (1999); Stikoff, et al., *Biophys. J.,* 67: 2251-2260 (1994); Hendsch, et al., *Prot. Sci.,* 3: 211-226 (1994); Schneider, et al., *J. Am. Chem. Soc.,* 119: 5742-5743 (1997); Sidelar, et al., *Prot. Sci.,* 7: 1898-1914 (1998). Solvation terms could also be included. See e.g., Jackson, et al., *Biochemistry,* 32: 11259-11269 (1993); Eisenberg, et al., *Nature,* 319: 199-203 (1986); Street A G and Mayo S L, *Folding & Design,* 3: 253-258 (1998); Eisenberg and Wesson, *Prot. Sci.,* 1: 227-235 (1992); Gordon & Mayo, supra.

"Coupled residues" are residues in a molecule that interact, through any mechanism. The interaction between the two residues is therefore referred to as a "coupling interaction." Coupled residues generally contribute to polymer fitness through the coupling interaction. Typically, the coupling interaction is a physical or chemical interaction, such as an electrostatic interaction, a van der Waals interaction, a hydrogen bonding interaction, or a combination thereof. As a result of the coupling interaction, changing the identity of either residue will affect the "fitness" of the molecule, particularly if the change disrupts the coupling interaction between the two residues. Coupling interaction may also be described by a distance parameter between residues in a molecule. If the residues are within a certain cutoff distance, they are considered interacting.

"Fitness" is used to denote the level or degree to which a particular property or a particular combination of properties for a molecule, e.g., a protein, are optimized. In certain embodiments of the invention, the fitness of a protein is preferably determined by properties which a user wishes to improve. Thus, for example, the fitness of a protein may refer to the protein's thermal stability, catalytic activity, binding affinity, solubility (e.g., in aqueous or organic solvent), and the like. Other examples of fitness properties include enantioselectivity, activity towards unnatural substrates, and alternative catalytic mechanisms. Coupling interactions can be modeled as a way of evaluating or predicting fitness (stability). Fitness can be determined or evaluated experimentally or theoretically, e.g., computationally.

Preferably, the fitness is quantitated so that each molecule, e.g., each amino acid will have a particular "fitness value". For example, the fitness of a protein may be the rate at which the protein catalyzes a particular chemical reaction, or the protein's binding affinity for a ligand. In a particularly preferred embodiment, the fitness of a protein refers to the conformational energy of the polymer and is calculated, e.g., using any method known in the art. See, e.g., Brooks, et al., *J. Comp. Chem.,* 4: 187-217 (1983); Mayo, et al., *J. Phys. Chem.,* 94: 8897-8909 (1990); Pabo, et al., *Biochemistry,* 25: 5987-5991 (1986), Lazar, et al., *Prot Sci.,* 6: 1167-1178 (1997); Lee, et al., *Nature,* 352: 448-451 (1991); Colombo, et al., *J. Am. Chem. Soc.,* 121: 6895-6903 (1999); Weiner, et al., *J. Am. Chem. Soc.,* 106: 765-784 (1984). Generally, the fitness of a protein is quantitated so that the fitness value increases as the property or combination of properties is optimized. For example, in embodiments where the thermal stability of a protein is to be optimized (conformational energy is preferably decreased), the fitness value may be the negative conformational energy; i.e., $F=-E$.

The "fitness contribution" of a protein residue refers to the level or extent $f(i_a)$ to which the residue $i_a$, having an identity a, contributes to the total fitness of the protein. Thus, for example, if changing or mutating a particular amino acid residue will greatly decrease the protein's fitness, that residue is said to have a high fitness contribution to the polymer. By contrast, typically some residues $i_a$ in a protein may have a variety of possible identities a without affecting the protein's fitness. Such residues, therefore have a low contribution to the protein fitness.

"Dead-end elimination" (DEE) is a deterministic search algorithm that seeks to systematically eliminate bad rotamers and combinations of rotamers until a single solution remains. For example, amino acid residues can be modeled as rotamers that interact with a fixed backbone. The theoretical basis for DEE provides that, if the DEE search converges, the solution is the global minimum energy conformation (GMEC) with no uncertainty (Desmet et al., 1992).

Dead end elimination is based on the following concept. Consider two rotamers, $i_r$ and $i_t$, at residue i, and the set of all other rotamer configurations $\{S\}$ at all residues excluding i (of which rotamer $j_s$ is a member). If the pairwise energy contributed between $i_r$ and $j_s$ higher than the pairwise energy between $i_t$ and $j_s$ for all $\{S\}$, then rotamer $i_r$ cannot exist in the global minimum energy conformation, and can be eliminated. This notion is expressed mathematically by the inequality.

$$E(i_r) + \sum_{j \neq i}^{N} E(i_r, j_s) > E(i_t) + \sum_{j \neq i}^{N} E(i_t, j_s)\{S\} \quad \text{(Equation A)}$$

If this expression is true, the single rotamer $i_r$ can be eliminated (Desmet et al., 1992).

In this form, Equation A is not computationally tractable because, to make an elimination, it is required that the entire sequence (rotamer) space be enumerated. To simplify the problem, bounds implied by Equation A can be utilized:

$$E(i_r) + \sum_{j \neq i}^{N} \min(s)E(i_r, j_s) > E(i_t) + \sum_{j \neq i}^{N} \max(s)E(i_t, j_s)\{S\} \quad \text{(Equation B)}$$

Using an analogous argument, Equation B can be extended to the elimination of pairs of rotamers inconsistent with the GMEC. This is done by determining that a pair of rotamers $i_r$ at residue i and $j_s$ at residue j, always contribute higher energies than rotamers $i_u$ and $j_v$ with all possible rotamer combinations $\{L\}$. Similar to Equation B, the strict bound of this statement is given by:

$$\varepsilon(i_r, j_s) + \sum_{k \neq i,j}^{N} \min(t)\varepsilon(i_r, j_s, k_t) > \quad \text{(Equation C)}$$

$$\varepsilon(i_u, j_v) + \sum_{k \neq i,j}^{N} \max(t)\varepsilon(i_u, j_v, k_i)$$

where $\varepsilon$ is the combined energies for rotamer pairs $$\epsilon(i_r, j_s) = E(i_r) + E(j_s) + E(i_r, j_s) \quad \text{(Equation D)},$$

and $$\epsilon(i_r, j_s, k_t) = E(i_r, k_t) + E(j_s, k_t) \quad \text{(Equation E)}.$$

This leads to the doubles elimination of the pair of rotamers $i_r$ and $j_s$, but does not eliminate the individual rotamers completely as either could exist independently in the GMEC. The doubles elimination step reduces the number of possible pairs (reduces S) that need to be evaluated in the right-hand side of Equation 6, allowing more rotamers to be individually eliminated.

The singles and doubles criteria presented by Desmet et al. fail to discover special conditions that lead to the determination of more dead-ending rotamers. For instance, it is possible that the energy contribution of rotamer $i_t$ is always lower than $i_r$ without the maximum of $i_t$ being below the minimum of $i_r$. To address this problem, Goldstein 1994 presented a modification of the criteria that determines if the energy profiles of two rotamers cross. If they do not, the higher energy rotamer can be determined to be dead-ending. The doubles calculation uses significantly more computational time than the singles calculation. To accelerate the process, other computational methods have been developed to predict the doubles calculations that will be the most productive (Gordon & Mayo, 1998). These kinds of modifications, collectively referred to as fast doubles, significantly improved the speed and effectiveness of DEE.

Several other modifications also enhance DEE. Rotamers from multiple residues can be combined into so-called superrotamers to prompt further eliminations (Desmet et al., 1994; Goldstein, 1994). This has the advantage of eliminating multiple rotamers in a single step. In addition, it has been shown that "splitting" the conformational space between rotamers improves the efficiency of DEE (Pierce et al., 2000). Splitting handles the following special case. Consider rotamer $i_r$. If a rotamer $i_{t1}$ contributes a lower energy than $i_r$ for a portion of the conformational space, and a rotamer $i_{t2}$ has a lower energy than $i_r$ for the remaining fraction, then $i_r$ can be eliminated. This case would not be detected by the less sensitive Desmet or Goldstein criteria. In the preferred implementations as described herein, all of the described enhancements to DEE were used.

For further discussion of these methods see, Goldstein, *Biophysical Journal* 66, 1335-1340 (1994); Desmet, et al., *Nature* 356, 539-542 (1992); Desmet, et al., *The Protein Folding Problem and Tertiary Structure Prediction* (Jr., K. M. & Grand, S. L., eds.), pp. 307-337 (Birkhauser, Boston, 1994); De Maeyer, et al., *Folding & Design* 2, 53-66 (1997), Gordon, and Mayo, *J. Comp. Chem.* 19, 1505-1514 (1998); Pierce, et al., *J. Comp. Chem.* 21, 999-1009 (2000).

Another calculation, dubbed SCREAM (Side-Chain Rotamer Energy Analysis Method), may be used. SCREAM enables examination of the mechanism of discrimination against non-cognate amino acids, by calculating the relative binding energies of the 20 natural amino acids to a particular AARS. (See, for example, McClendon, et al., *Prot Eng. Design & Select.* 19: 195-203 (2006)).

As a first step, the rotamer energy spectrum is calculated for a single amino acid in an empty backbone, with no other moveable sidechains. Next, starting with the lowest rotamers from the empty backbone, fill in the sidechains but eliminate clashes. For example, place sidechains at every site, estimating the energies of low lying excitations from the empty backbone spectrum and calculate pairwise interactions, eliminating configurations having clashes. Thus, $E_{tot}(A, B) = E_{self}(A) + E_{self}(B) + E_{int}(A,B) = E_{self}(A,B)$ and $E_{tot}(A,B,C) = E_{self}(A) + E_{self}(B) + E_{self}(C) + E_{int}(A,B) + E_{int}(A,C) + E_{int}(B,C) = E_{self}(AB) + E_{self}(C) + E_{int}(A,C) + E_{int}(B,C) = E_{self}(A,B) + E_{self}(C) + E_{int}(AB,C)$ establishes the recursive relation. Next, all low lying sidechain excitations must be analyzed until the energy distribution of rotamer energies in the empty backbone ceases to increase. Briefly, the ground state energy for all residues is evaluated, followed by a set of rotamers with the lowest linear sum energy, and finally the next lowest linear sum energy and so forth. Furthermore, electrostatic interactions must be addressed as the charges polarize the environment to shield the charges and reduce the desired amino acid interaction. Since molecular dynamics' modeling methods don't usually account for polarization, the bias is in favor of salt bridges. In order to overcome this, the residues are neutralized and parameters evaluated again according to DREIDING parameterization.

For DREIDING parameterization, the lost charged-charged and charged-dipole interactions are compensated by introducing hydrogen bond term. This can be done in conjunction with other programs, including CHARMM, as described herein. Thus, using a crystallographic structure from a particular AARS, or homologous AARS from another organism, we can use a program such as SCREAM, and HierDock, or others, to predict the binding conformation and binding energy of each of the 20 natural amino acids in the binding site in the best-binding mode and the activating mode, by ordering calculations according to which amino acids compete for binding to a particular AARS.

In particular, selective binding is first run, which provides the amino acid and the molecule of ATP to bind to the active site of the AARS. This sometimes leads to a conformational change. Next, selective activation of the AARS to catalyze the formation of a covalent bond between the amino acid and the ATP, forms an aminoacyl adenylate complexed with the AARS and removes inorganic pyrophosphate. Third, if misactivation of a non-cognate amino acid occurs, the AARS may hydrolytically cleave the aminoacyl adenylate complex (as pre-transfer proofreading). Finally, if a non-cognate aminoacyl adenylate has survived, the AARS may hydrolytically cleave the aminoacyl-tRNA complex (post-transfer proofreading).

Thus, such computational programs allow for reliable prediction of the likelihood of the natural amino acids that complete to bind and aminoacylation by wild-type or mutant AARS enzymes. Utilizing multiple programs (such as SCREAM and HierDock together) reduce the misincorporation rate and allow for greater predictability in selecting amino acid locations that specifically bind the amino acid.

Still other computer modeling programs include SCAP (Side Chain Amino Acid Prediction Program) (Xiang and Honig, *J. Mol. Biol.* 311, 421-430 (2001)), and SCWRL (Side Chain Replacement With a Rotamer Library), which is useful for adding sidechains to a protein backbone based on the backbone-dependent rotamer library. The SCWRL library provides lists of chi1-chi2-chi3-chi4 values and their relative probabilities for residues at given phi-psi values, and explores these conformations to minimize sidechain-backbone clashes and sidechain-sidechain clashes. (See, for example, Bower, et al., *J. Mol. Biol.*, 267, 1268-1282 (1997)).

The computational predictability is due, in large part, to utilize known nucleic acid and/or amino acid sequences of AARS enzymes. For example, the catalytic domain is conserved across all members of a particular class of AARS enzyme. (O'Donoghue and Luthey-Schulten, *Microbiol. And Mol. Biol. Rev.*: 550-573 (2003); Diaz-Lazcoz, et al., *Mol. Biol. Evol.* 15(11): 1548-1561 (1998); Wang, et al., *Chem. Commun.* 1-11 (2002)).

"Expression system" means a host cell, or cellular components and compatible vector under suitable conditions, e.g., for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, *Drosophila* cells (Schneider cells) and expression systems, and mammalian host cells and vectors.

"Host cell" means any cell of any organism that is selected, modified, transformed, grown or used or manipulated in any way for the production of a substance by the cell. A host cell may be auxotrophic, that is unable to synthesize at least one particular organic compound required for its maintenance or growth and must obtain the compound from another source, such as its environment or culture media. In addition, an auxotrophic host cell may have single, double, triple, quadruple or more levels of auxotrophy, such that it is unable to synthesize one, two, three, four or more organic compounds necessary for its growth or maintenance, respectively. For example, a host cell may be one that is manipulated to express a particular gene, a DNA or RNA sequence, a protein or an enzyme. Host cells may be cultured in vitro or one or more cells in a non-human animal (e.g., a transgenic animal or a transiently transfected animal).

Certain embodiments disclosed herein expressly utilize only a cell-free expression or translation system and not a host cell. Certain other embodiments expressly utilize only an auxotrophic host cell. Still certain other embodiments expressly utilize only a non-auxotrophic host cell, or a prototrophic host cell.

Sequence similarity may be relevant to certain embodiments as they may include steps of comparing sequences to each other, including wild-type sequence to one or more mutants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, "-", or "Δ") in the polymer sequence not containing the inserted or deleted residue.

"Homologous", in all its grammatical forms and spelling variations, refers to the relationship between two molecules (e.g., proteins, tRNAs, nucleic acids) that possess a "common evolutionary origin", including proteins from superfamilies in the same species of organism, as well as homologous proteins from different species of organism. Such proteins (and their encoding nucleic acids) have sequence and/or structural homology, as reflected by their sequence similarity, whether in terms of percent identity or by the presence of specific residues or motifs and conserved positions. Homologous molecules frequently also share similar or even identical functions.

In some aspects, homologous may include a sequence that is at least 50% homologous, but that presents a homologous structure in three dimensions, i.e., includes a substantially similar surface charge or presentation of hydrophobic groups. Since hydrogen bonds, van der Waals forces and hydrophobic interactions may function to bind an amino acid to the binding pocket of an AARS, manipulation of a structure of the AARS may also alter one or more of these forces.

Thus, as used herein, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

The term "sequence similarity", in all its grammatical forms, refers to the degree of identity or correspondence between nucleic acid or amino acid sequences that may or may not share a common evolutionary origin (see, Reeck et al., supra). However, in common usage and in the instant application, the term "homologous", when modified with an adverb such as "highly", may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is a 0.15M NaCl, 0.015M Na-citrate. Hybridization requires that the two nucleic acids contain complementary stretches of genetic or amino acid sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base hybridization conditions for oligonucleotides include washing in 6×SSC/0.05% sodium pyrophosphate, or other conditions that afford equivalent levels of hybridization.

"Polypeptide," "peptide" or "protein" are used interchangeably to describe a chain of amino acids that are linked together by chemical bonds called "peptide bonds." A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Rotamer" is defined as a set of possible conformers for each amino acid or analog side chain. See Ponder, et al., Acad. Press Inc. (London) Ltd. pp. 775-791 (1987); Dunbrack, et al., *Struc. Biol.* 1(5):334-340 (1994); Desmet, et al., *Nature* 356:539-542 (1992). A "rotamer library" is a collection of a set of possible/allowable rotameric conformations for a given set of amino acids or analogs. There are two general types of rotamer libraries: "backbone dependent" and "backbone independent." A backbone dependent rotamer library allows different rotamers depending on the position of the residue in the backbone; thus for example, certain leucine rotamers are allowed if the position is within an α helix, and different leucine rotamers are allowed if the position is not in an α-helix. A backbone independent rotamer library utilizes all rotamers of an amino acid at every position. In general, a backbone independent library is preferred in the consideration of core residues, since flexibility in the core is important. However, backbone independent libraries are computationally more expensive, and thus for surface and boundary positions, a backbone dependent library is preferred. However, either type of library can be used at any position.

"Variable residue position" herein is meant an amino acid position of the protein to be designed that is not fixed in the design method as a specific residue or rotamer, generally the wild-type residue or rotamer. It should be noted that even if a position is chosen as a variable position, it is possible that certain methods disclosed herein will optimize the sequence in such a way as to select the wild type residue at the variable position. This generally occurs more frequently for core residues, and less regularly for surface residues. In addition, it is possible to fix residues as non-wild type amino acids as well.

"Fixed residue position" means that the residue identified in the three dimensional structure as being in a set conformation. In some embodiments, a fixed position is left in its original conformation (which may or may not correlate to a specific rotamer of the rotamer library being used). Alternatively, residues may be fixed as a non-wild type residue depending on design needs; for example, when known site-directed mutagenesis techniques have shown that a particular residue is desirable (for example, to eliminate a proteolytic site or alter the substrate specificity of an AARS), the residue may be fixed as a particular amino acid. Residues which can be fixed include, but are not limited to, structurally or biologically functional residues, for example, the anchor residues.

In certain embodiments, a fixed position may be "floated"; the amino acid or analog at that position is fixed, but different rotamers of that amino acid or analog are tested. In this embodiment, the variable residues may be at least one, or anywhere from 0.1% to 99.9% of the total number of residues. Thus, for example, it may be possible to change only a few (or one) residues, or most of the residues, with all possibilities in between.

As used herein, the term "external mutant" refers to a modified molecule (e.g., an external mutant tRNA and/or an external mutant aminoacyl tRNA synthetase) that exhibits a reduced efficiency (as compared to wild-type or endogenous) for aminoacylation with the corresponding wild type amino acid. "External mutant" refers to the inability or reduced efficiency, e.g., less than 20% efficient, less than 10% efficient, less than 5% efficient, or, e.g., less than 1% efficient, of a tRNA and/or RS to function with the corresponding naturally occurring amino acid in the translation system of interest. For example, an external mutant RS in a translation system of interest aminoacylates any endogenous tRNA of a translation system of interest with the wild type amino acid at reduced or even zero efficiency, when compared to aminoacylation of an endogenous tRNA by the endogenous RS.

It should be noted, however, that an external mutant RS aminoacylates an endogenous tRNA with a replacement amino acid (whether naturally occurring or non-natural) with an increased efficiency compared with the ability of the endogenous RS to aminoacylate an endogenous tRNA with a replacement amino acid. Likewise, an external mutant tRNA functions at a higher efficiency toward the replacement amino acid (whether non-natural or other naturally occurring amino acid) than toward the corresponding wild type amino acid.

"Wobble degenerate codon" refers to a codon encoding a natural amino acid, which codon, when present in mRNA, is recognized by a natural tRNA anticodon through at least one non-Watson-Crick, or wobble base-pairing (e.g., A-C or G-U base-pairing). Watson-Crick base-pairing refers to either the G-C or A-U (RNA or DNA/RNA hybrid) or A-T (DNA) base-pairing. When used in the context of mRNA codon—tRNA anticodon base-pairing, Watson-Crick base-pairing means all codon-anticodon base-pairings are mediated through either G-C or A-U pairings.

The term "preferentially aminoacylates" refers to an efficiency, e.g., about 20%, about 30%, about 40%, about 50%, about 60%, about 70%, about 75%, about 85%, about 90%, about 95%, about 99% or more efficient. The efficiency may be measured by which a modified or external mutant aminoacyl tRNA synthetase aminoacylates a tRNA with a replacement amino acid, whether an unnatural amino acid or another naturally occurring amino acid when compared to the corresponding natural amino acid assigned to the particular tRNA, AARS, or both. The term "preferentially aminoacylates" further may refer to the efficiency of the modified or external mutant aminoacyl tRNA synthetase to aminoacylate or charge a tRNA with any amino acid other than the corresponding natural amino acid assigned to the particular tRNA, AARS, or both. The term "preferentially aminoacylates" further may refer to the efficiency of the modified or external mutant aminoacyl tRNA synthetase to aminoacylate a tRNA with a non-natural amino acid compared with the non-modified or naturally occurring AARS.

It should be noted that the efficiency of aminoacylation of the tRNA by the AARS may be correlated to the efficiency of specificity, or fidelity of incorporation of the non-natural amino acid in the target polypeptide or protein. This is due to the function of the protein synthesis machinery in that once a tRNA is aminoacylated with an amino acid (whether the wild type amino acid, or a non-natural amino acid), the charged tRNA is released from the AARS enzyme and the amino acid is incorporated into the target polypeptide. When the proofreading ability of the AARS is altered, the enzyme will allow the replacement amino acid to charge the tRNA and be released for incorporation into the target protein. Thus, the efficiency of aminoacylation by the AARS directly correlates to the fidelity or specificity of incorporation of the non-natural amino acid into the target polypeptide.

The replacement (whether non-natural or naturally occurring) amino acid is then incorporated into a growing polypeptide chain with high fidelity, e.g., at greater than about 20%, 30%, 40%, 50%, 60%, 75%, 80%, 90%, 95%, or greater than about 99% efficiency for a particular codon.

The term "complementary" refers to components of an external mutant pair, the external mutant tRNA and external mutant synthetase that can function together, e.g., the external mutant synthetase aminoacylates the external mutant tRNA.

The term "derived from" refers to a component that is isolated from an organism or isolated and modified, or generated, e.g., chemically synthesized, using information of the component from the organism.

The term "translation system" refers to the components necessary to incorporate a naturally occurring or unnatural amino acid into a growing polypeptide chain (protein). For example, components can include ribosomes, tRNA(s), synthetas(es), mRNA and the like. The components disclosed herein can be added to a translation system, in vivo or in vitro. An in vivo translation system may be a cell (eukaryotic or prokaryotic cell). An in vitro translation system may be a cell-free system, such as reconstituted one with components from different organisms (purified or recombinantly produced). In certain embodiments, the translation system does not comprise a cell. In certain embodiments, the translation system does not comprise an auxotrophic cell. If the translation system does not comprise an auxotrophic cell, it may comprise another cell or cellular components.

The term "inactive RS" refers to a synthetase that has been mutated so that it no longer can aminoacylate its cognate tRNA with any amino acid, whether naturally occurring or non-natural. The term "modified RS" refers to a synthetase that has been mutated so that it no longer can aminoacylate its cognate tRNA with the corresponding naturally occurring amino acid, but may be able to aminoacylate its cognate tRNA with another amino acid, preferably a non-natural amino acid.

The term "selection agent" refers to an agent that when present allows for a selection of certain components from a population, e.g., an antibiotic, wavelength of light, an antibody, a nutrient or the like. The selection agent can be varied, e.g., such as concentration, intensity, etc.

The term "positive selection marker" refers to a marker than when present, e.g., expressed, activated or the like, results in identification of an organism with the positive selection marker from those without the positive selection marker.

The term "negative selection marker" refers to a marker than when present, e.g., expressed, activated or the like, allows identification of an organism that does not possess the desired property (e.g., as compared to an organism which does possess the desired property).

The term "reporter" refers to a component that can be used to select components described in the disclosure. For example, a reporter can include a green fluorescent protein, a firefly luciferase protein, or genes such as β-gal/lacZ (β-galactosidase), Adh (alcohol dehydrogenase) or the like.

The term "not efficiently recognized" refers to an efficiency, e.g., less than about 10%, less than about 5%, or less than about 1%, at which a RS from one organism aminoacylates an external mutant tRNA. In certain embodiments, the RS may be from the same or a different organism than the external mutant tRNA. In some embodiments, the RS has been modified to aminoacylate a tRNA with a particular amino acid, preferably a non-natural amino acid.

The term "eukaryote" refers to organisms belonging to the phylogenetic domain Eucarya such as animals (e.g., mammals, insects, reptiles, birds, etc.), ciliates, plants, fungi (e.g., yeasts, etc.), flagellates, microsporidia, protists, etc. Additionally, the term "prokaryote" refers to non-eukaryotic organisms belonging to the Eubacteria (e.g., *Escherichia coli, Thermus thermophilus*, etc.) and Archaea (e.g., *Methanococcus jannaschii, Methanobacterium thermoautotrophicum, Halobacterium* such as *Haloferax volcanii* and *Halobacterium* species NRC-1, *A. fulgidus, P. firiosus, P. horikoshii, A. pernix*, etc.) phylogenetic domains.

The Genetic Code, Host Cells, and the Degenerate Codons

The standard genetic code most cells use is listed below.

| | The Genetic Code Middle | | | | |
|---|---|---|---|---|---|
| First | U | C | A | G | Last |
| U | Phe | Ser | Tyr | Cys | U |
| | Phe | Ser | Tyr | Cys | C |
| | Leu | Ser | Stop (Ochre) | | A |
| | Leu (Umber) Stop (Amber) | Ser | Stop | | |
| | Leu | Ser | Stop | | |
| | Trp | G | | | |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

The genetic code is degenerate, in that the protein biosynthetic machinery utilizes 61 mRNA sense codons to direct the templated polymerization of the 20 natural amino acid monomers. (Crick et al., Nature 192: 1227, 1961). Just two amino acids, i.e., methionine and tryptophan, are encoded by unique mRNA triplets.

The standard genetic code applies to most, but not all, cases. Exceptions have been found in the mitochondrial DNA of many organisms and in the nuclear DNA of a few lower organisms. Some examples are given in the following table.

| Examples of non-standard genetic codes. | | |
|---|---|---|
| Mitochondria | Vertebrates | UGA→ Trp; AGA, AGG → STOP |
| | Invertebrates | UGA→ Trp; AGA, AGG → Ser |
| | Yeasts | UGA→ Trp; CUN → Thr |
| | Protista | UGA→ Trp; |
| Nucleus | Bacteria | GUG, UUG, AUU, CUG → initiation |
| | Yeasts | CUG → Ser |
| | Ciliates | UAA, UAG → Gln |

*Plant cells use the standard genetic code in both mitochondria and the nucleus.

The NCBI (National Center for Biotechnology Information) maintains a detailed list of the standard genetic code, and genetic codes used in various organisms, including the vertebrate mitochondrial code; the yeast mitochondrial code; the mold, protozoan, and coelenterate mitochondrial code and the mycoplasma/spiroplasma code; the invertebrate mitochondrial code; the ciliate, dasycladacean and hexamita nuclear code; the echinoderm and flatworm mitochondrial code; the euplotid nuclear code; the bacterial and plant plastid code; the alternative yeast nuclear code; the ascidian mitochondrial code; the alternative flatworm mitochondrial code; blepharisma nuclear code; chlorophycean mitochondrial code; trematode mitochondrial code; scenedesmus obliquus mitochondrial code; thraustochytrium mitochondrial code (all incorporated herein by reference). These are primarily based on the reviews by Osawa et al., *Microbiol. Rev.* 56: 229-264, 1992, and Jukes and Osawa, *Comp. Biochem. Physiol.* 106B: 489-494, 1993.

Host Cells

Some methods disclosed herein can be practiced within a cell, which enables production levels of proteins to be made for practical purposes. In preferred embodiments, the cells used are culturable cells (i.e., cells that can be grown under laboratory conditions). Suitable cells include mammalian cells (human or non-human mammals), bacterial cells, and insect cells, etc.

One example includes PFENEX™ technology, which is a cell line using *Pseudomonas fluorescens*-based cell line that increase cellular expression while maintaining certain solubility and activity characteristics due to its use of different pathways in the metabolism of certain sugars compared to *E. coli*.

In addition, other auxotrophic host cell lines include K10 based Phe ausotrophic strain (AF), Phe/Trp double auxotrophic strains (AFW), Phe/Trp/Lys triple auxotrophic strains (AFWK), a Met auxotroph (M15MA on M15 background), as well as DH10B based AF strain.

Cells that may be used to practice certain embodiments disclosed herein include auxotrophic host cells (whether prokaryotic or eukaryotic). Auxotrophic cells may exhibit single, double, triple, quadruple, or greater levels of auxotrophy (each level of auxotrophy indicating a particular organic compound of which the organism is unable to synthesize and must be supplied to the cell). Certain embodiments disclosed herein expressly do not utilize an auxotrophic host cell. Insofar as an auxotrophic host cell is not used, another cell or cell components may still be used to practice certain embodiments disclosed herein. Other embodiments may use one, two, three, or more different auxotrophic host cells that may be from the same or different strains or organisms.

Host cells are genetically engineered (e.g., transformed, transduced or transfected) with the vectors of this disclosure, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *PNAS*. USA 82, 5824 (1985)), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods.

The engineered host cells can be cultured in conventional nutrient media modified as appropriate for such activities as, for example, screening steps, activating promoters or selecting transformants. These cells can optionally be cultured into transgenic organisms.

Certain embodiments disclosed herein further include methods of screening modified AARSs and/or modified tRNAs. For example, in one embodiment, a yeast PheRS library is subjected to double sieve screening in order to detect high levels of incorporation of a non-natural amino acid or misincorporation of natural amino acids other than Phe will lead to severe misfolding or unfolding of GFP. The yeast PheRS library cells are thus subjected to high-throughput screening based on flow cytometry analysis (FACS). First, the yeast PheRS library cells are expressed in the presence of 2NaI and low fluorescent cells indicating higher incorporation of either 2NaI or other natural amino acids are collected by FACS. Next, the yeast PheRS library cells are expressed without 2NaI. Bright cells are collected in order to eliminate yeast PheRS variants that can misincorporate other natural amino acids. In on exemplary embodiment, two cycles of screening yielded a mutant yeast PheRS with mutations in N412G, S418C, T415G and S437F, which had low fluorescence in the presence of 2NaI and high fluorescence in the absence of 2NaI. This technique allows for incorporation of 2NaI at UUU codon, increasing to around 90%.

Other useful references, e.g., for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture; Fundamental Methods* Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into bacterial cells are available, any of which can be used in certain embodiments disclosed herein. These include: fusion of the recipient cells with bacterial protoplasts containing the DNA, electroporation, projectile bombardment, and infection with viral vectors, etc. Bacterial cells can be used to amplify the number of plasmids containing DNA constructs of certain embodiments disclosed herein. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EASYPREP™, FLEXIPREP™, both from Pharmacia Biotech; STRATA-CLEAN™, from Stratagene; and, QIAPREP™ from Qiagen). The isolated and purified plasmids are then further manipulated to produce other plasmids, used to transfect cells or incorporated into related vectors to infect organisms.

Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA* $2^{nd}$ Edition Scientific American Books, NY.

Degenerate Codon Selection

As described above, all amino acids, with the exception of methionine and tryptophan are encoded by more than one codon. According to some methods disclosed herein, a codon in the genome that is normally used to encode a natural amino acid is reprogrammed, in part by the transcriptional or translational machinery to instead encode an amino acid analog. An amino acid analog can be a naturally occurring or canonical amino acid analog. In a preferred embodiment, the amino acid analog is not a canonically encoded amino acid.

The thermodynamic stability of a codon-anticodon pair can be predicted or determined experimentally. According to some embodiments, it is preferable that the external mutant tRNA interacts with the degenerate codon with an affinity (at 37° C.) of at least about 1.0 kcal/mol more strongly, even more preferably 1.5 kcal/mole more strongly, and even more preferably more than 2.0 kcal/mol more strongly than a natural tRNA in the cell would recognize the same sequence. These values are known to one of skill in the art and can be determined by thermal denaturation experiments (see, e.g., Meroueh and Chow, *Nucleic Acids Res.* 27: 1118, 1999).

The following table lists some of the known anti-codon sequences for *E. coli*. In general, for any organism, tRNA anticodon sequence can be routinely determined using art-recognized technologies. For example, any tRNA gene can be amplified by, for example, PCR. Sequencing can be performed to determine the exact sequences of the anti-codon loop. Alternatively, biochemical binding assay may be used to determine the binding affinity of a purified tRNA to one of the 2-6 possible codons. The codon that binds the tRNA with the highest specificity/affinity presumably has pure Watson-Crick match at all three codon positions, thus determining the sequence of the anti-codon loop.

In general, the wobble base in the anti-codon loop tends to be G or U (rather than A or C).

| The Degenerate Codons for *E. coli* | | | | | | | |
|---|---|---|---|---|---|---|---|
| Amino Acid | Anti-codon | Base-paring at $3^{rd}$ base | Codon | Amino Acid | Anti-codon | Base-paring | Codon |
| Ala | GGC | W/C[1] | GCC | His | GUG | W/C | CAC |
|  |  | Wobble[2] | GCU |  |  | Wobble | CAU |
|  | UGC | W/C | GCA | Ile | GAU | W/C | AUC |
|  |  | Wobble | GCG |  |  | Wobble | AUU, AUA |
| Asp | GUC | W/C | GAC | Leu | GAG | W/C | CUC, CUA, CUG, UUC, UUG |
|  |  | Wobble | GAU |  |  | Wobble | CUU |
| Asn | GUU | W/C | AAC | Lys | UUU | W/C | AAA |
|  |  | Wobble | AAU |  |  | Wobble | AAG |
| Cys | GCA | W/C | UGC | Phe | GAA | W/C | UUC |
|  |  | Wobble | UGU |  |  | Wobble | UUU |
| Glu | UUC | W/C | GAA | Ser | GGA | W/C | UUC, AGU |
|  |  | Wobble | GAG |  |  | Wobble | UCU, AGC, UCA, UCG |

-continued

The Degenerate Codons for *E. coli*

| Amino Acid | Anti-codon | Base-paring at 3rd base | Codon | Amino Acid | Anti-codon | Base-paring | Codon |
|---|---|---|---|---|---|---|---|
| Gly | GCC | W/C | GGC, GGA, GGG | Tyr | GUA | W/C | UAC |
|  |  | Wobble | GGU |  |  | Wobble | UAU |
| Met |  | W/C | AUG | Thr |  | W/C | ACC, ACA, ACG |
| Gln |  | W/C | CAA, CAG |  |  | Wobble | ACU |
| Arg |  | W/C | AGA, AGG, CGU, CGG | Pro |  | W/C | CCC, CCA, CCG |
|  |  | Wobble | CGC, CGA | Trp |  | Wobble | CCU |
|  |  |  |  |  |  | W/C | UGG |
| STOP |  | W/C | UGA, UAA | Val |  | W/C | GUC, GUA |
|  |  | Wobble | UAG |  |  | Wobble | GUU, GUG |

[1] Watson-Crick base pairing
[2] Wobble base pairing

When a single tRNA recognizes a codon through a perfect complementary interaction between the anticodon of the tRNA and one codon, it is called Watson-Crick base pairing. When a single tRNA recognizes a second, degenerate codon, it is called a wobble or other non-standard base pairing. In certain embodiments disclosed herein, a new tRNA can be constructed having an anticodon sequence that is perfectly complementary to a degenerate codon or a codon for a non-natural amino acid, thus utilizing wobble or Watson-Crick base pairing. Likewise, a new AARS can be constructed that utilizes a replacement amino acid (other than wild type—may be another naturally occurring amino acid or a non-natural amino acid) to aminoacylate the corresponding tRNA. This may be in addition to or instead of modifying a tRNA molecule for incorporation of a replacement amino acid.

The modified AARS may be altered such that the binding efficiency to the non-natural amino acid, or another selected naturally occurring amino acid, is greater than the binding efficiency of the modified AARS to the corresponding naturally occurring amino acid. In this way, a modified AARS may preferentially bind a non-natural amino acid in order to charge a tRNA even in the presence of the naturally occurring amino acid that corresponds to the AARS in its unmodified state. This "reprogramming" of an aminoacyl tRNA synthetase allows for incorporation of a non-natural amino acid into a polypeptide with lower levels of mis-incorporation of other amino acids into the desired site.

The "reprogramming" further may allow for use of the modified or external mutant synthetase with high levels of incorporation in standard host cells, without the need for auxotrophic host cells, and with or without depleting the media of the corresponding naturally occurring amino acid. Thus, while certain embodiments disclosed herein may be practiced by using an auxotrophic host cell, certain other embodiments may be practiced without using an auxotrophic host cell. In the event of not using an auxotrophic host cell to practice certain embodiments, another host cell may be used, cellular components may be used, or an entirely cell-free system may be used.

When the cell has multiple tRNA molecules for a particular amino acid, and one tRNA has an anticodon sequence that is perfectly complementary to the degenerate codon selected, the gene encoding the tRNA can be disabled through any means available to one of skill in the art including, for example, site-directed mutagenesis or deletion of either the gene or the promoter sequence of the gene. Expression of the gene also can be disable through any antisense or RNA interference techniques.

Unnatural or Non-Natural Amino Acids

The first step in the protein engineering process is usually to select a set of unnatural or non-natural amino acids that have the desired chemical properties. The selection of non-natural amino acids depends on pre-determined chemical properties one would like to have, and the modifications one would like to make in the target protein. Unnatural amino acids, once selected, can either be purchased from vendors, or chemically synthesized.

A wide variety of unnatural or non-natural amino acids can be used in the methods disclosed herein. The unnatural amino acid can be chosen based on desired characteristics of the unnatural amino acid, e.g., function of the unnatural amino acid, such as modifying protein biological properties such as toxicity, biodistribution, immunogenicity, or half life, structural properties, spectroscopic properties, chemical and/or photochemical properties, catalytic properties, ability to react with other molecules (either covalently or noncovalently), or the like.

As used herein an "unnatural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

Formula I

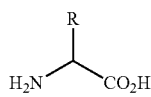

An unnatural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the unnatural amino acids disclosed herein may be naturally occurring compounds other than the twenty alpha-amino acids above. Because the unnatural amino acids disclosed herein typically differ from the natural amino acids in side chain only, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thioether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Aryl substitutions may occur at various positions, e.g. ortho, meta, para, and with one or more functional groups placed on the aryl ring. Other unnatural amino acids of interest include, but are not limited to, amino acids comprising a photoactivatable cross-linker, spin-labeled amino acids, dye-labeled amino acids, fluorescent amino acids, metal binding amino acids, metal-containing amino acids, radioactive amino acids, amino acids with novel functional groups, amino acids with altered hydrophilicity, hydrophobicity, polarity, or ability to hydrogen bond, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or a polyether, a polyalcohol, or a polysaccharide, amino acids that can undergo metathesis, amino acids that can undergo cycloadditions, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, amino acids containing a drug moiety, and amino acids comprising one or more toxic moieties.

In addition to unnatural amino acids that contain novel side chains, unnatural amino acids also optionally comprise modified backbone structures, e.g., as illustrated by the structures of Formula II and III:

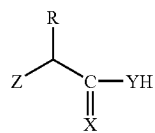

Formula II

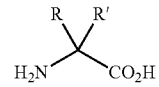

Formula III wherein Z typically comprises OH, NH$_2$, SH, NH$_2$O—, NH—R', R'NH—, R'S—, or S—R'—; X and Y, which may be the same or different, typically comprise S, N, or O, and R and R', which are optionally the same or different, are typically selected from the same list of constituents for the R group described above for the unnatural amino acids having Formula I as well as hydrogen or (CH$_2$)$_x$ or the natural amino acid side chains. For example, unnatural amino acids disclosed herein optionally comprise substitutions in the amino or carboxyl group as illustrated by Formulas II and III. Unnatural amino acids of this type include, but are not limited to, α-hydroxy acids, α-thioacids α-aminothiocarboxylates, or α-α-disubstituted amino acids, with side chains corresponding e.g. to the twenty natural amino acids or to unnatural side chains. They also include but are not limited to β-amino acids or γ-amino acids, such as substituted β-alanine and γ-amino butyric acid. In addition, substitutions or modifications at the α-carbon optionally include L or D isomers, such as D-glutamate, D-alanine, D-methyl-O-tyrosine, aminobutyric acid, and the like. Other structural alternatives include cyclic amino acids, such as proline analogs as well as 3-, 4-, 6-, 7-, 8-, and 9-membered ring proline analogs. Some non-natural amino acids, such as aryl halides (p-bromo-phenylalanine, p-iodophenylalanine, provide versatile palladium catalyzed cross-coupling reactions with ethyne or acetylene reactions that allow for formation of carbon-carbon, carbon-nitrogen and carbon-oxygen bonds between aryl halides and a wide variety of coupling partners.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, β-substituted derivatives, cyclic derivatives, and amide substituted glutamine derivatives. Exemplary phenylalanine analogs include, but are not limited to, meta-substituted phenylalanines, wherein the substituent comprises a hydroxy group, a methoxy group, a methyl group, an allyl group, an acetyl group, or the like.

Specific examples of unnatural amino acids include, but are not limited to, o, m and/or p forms of amino acids or amino acid analogs (non-natural amino acids), including homoallylglycine, cis- or trans-crotylglycine, 6,6,6-trifluoro-2-aminohexanoic acid, 2-aminoheptanoic acid, norvaline, norleucine, O-methyl-L-tyrosine, o-, m-, or p-methyl-phenylalanine, O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azidophenylalanine, a p-acyl-L-phenylalanine, a p-benzoyl-L-phenylalanine, an L-phosphoserine, a phosphonoserine, a phosphonotyrosine, a p-iodo-phenylalanine, o-, m-, or p-bromophenylalanine, 2-, 3-, or 4-pyridylalanine, p-idiophenylalanine, diaminobutyric acid, aminobutyric acid, benzofuranylalanine, 3-bromo-tyrosine, 3-(6-chloroindolyl)alanine, 3-(6-bromoindolyl)alanine, 3-(5-bromoindolyl)alanine, p-chlorophenylalanine, p-ethynyl-phenylalanine, p-propargly-oxy-phenylalanine, m-ethynyl-phenylalanine, 6-ethynyl-tryptophan, 5-ethynyl-tryptophan, (R)-2-amino-3-(4-ethynyl-1H-pyrol-3-yl)propanoic acid, azidonorleucine, azidohomoalanine, p-acetylphenylalanine, p-amino-L-phenylalanine, homopropargylglycine, p-ethyl-phenylalanine, p-ethynyl-phenylalanine, p-propargly-oxy-phenylalanine, isopropyl-L-phenylalanine, an 3-(2-naphthyl)alanine, 3-(1-naphthyl)alanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homopropargylglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine, 4-, 5-, or 6-fluoro-tryptophan, 4-aminotryptophan, 5-hydroxytryptophan, biocytin, aminooxyacetic acid, m-hydroxyphenylalanine, m-allyl phenylalanine, m-methoxyphenylalanine group, β-GlcNAc-serine, α-GalNAc-threonine, p-acetoacetylphenylalanine, para-halo-phenylalanine, seleno-methionine, ethionine, S-nitroso-homocysteine, thia-proline, 3-thienyl-alanine, homo-allyl-glycine, trifluoroisoleucine, trans and cis-2-amino-4-hexenoic acid, 2-butynyl-glycine, allyl-glycine, para-azido-phenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, β-2-thienyl-L-alanine, β-(2-thiazolyl)-DL-alanine, homopropargylglycine (HPG) and azidohomoalanine (AHA) and the like. The structures of a variety of non-limiting unnatural amino acids are provided in the figures, e.g., FIGS. 29, 30, and 31 of US 2003/0108885 A1, the entire content of which is incorporated herein by reference.

Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, β-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like.

Additionally, other examples optionally include (but are not limited to) an unnatural analog of a tyrosine amino acid; an unnatural analog of a glutamine amino acid; an unnatural analog of a phenylalanine amino acid; an unnatural analog of a serine amino acid; an unnatural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analog containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid.

Typically, the unnatural amino acids utilized herein for certain embodiments may be selected or designed to provide additional characteristics unavailable in the twenty natural amino acids. For example, unnatural amino acid are optionally designed or selected to modify the biological properties of a protein, e.g., into which they are incorporated. For example, the following properties are optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Other examples of amino acid analogs optionally include (but are not limited to) an unnatural analog of a tyrosine amino acid; an unnatural analog of a glutamine amino acid; an unnatural analog of a phenylalanine amino acid; an unnatural analog of a serine amino acid; an unnatural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

Aminoacyl-tRNA Synthetases

The aminoacyl-tRNA synthetase (used interchangeably herein with AARS, RS or "synthetase") used in certain methods disclosed herein can be a naturally occurring synthetase derived from an organism, whether the same (homologous) or different (heterologous), a mutated or modified synthetase, or a designed synthetase.

The synthetase used can recognize the desired (unnatural) amino acid analog selectively over related amino acids available. For example, when the amino acid analog to be used is structurally related to a naturally occurring amino acid, the synthetase should charge the external mutant tRNA molecule with the desired amino acid analog with an efficiency at least substantially equivalent to that of, and more preferably at least about twice, 3 times, 4 times, 5 times or more than that of the naturally occurring amino acid. However, in cases in which a well-defined protein product is not necessary, the synthetase can have relaxed specificity for charging amino acids. In such an embodiment, a mixture of external mutant tRNAs could be produced, with various amino acids or analogs.

In certain embodiments, it is preferable that the synthetase has activity both for the amino acid analog and for the amino acid that is encoded by the corresponding codon of the tRNA molecule.

A synthetase can be obtained by a variety of techniques known to one of skill in the art, including combinations of such techniques as, for example, computational methods, selection methods, and incorporation of synthetases from other organisms (see below).

In certain embodiments, synthetases can be used or developed that efficiently charge tRNA molecules that are not charged by synthetases of the host cell. For example, suitable pairs may be generally developed through modification of synthetases from organisms distinct from the host cell. In certain embodiments, the synthetase can be developed by selection procedures. In certain embodiments, the synthetase can be designed using computational techniques such as those described in Datta et al., *J. Am. Chem. Soc.* 124: 5652-5653, 2002, and in U.S. Pat. No. 7,139,665, hereby incorporated by reference.

Computational Design of AARS

Specifically, in one embodiment, the subject method partly depends on the design and engineering of natural AARS to a modified form that has relaxed substrate specificity, such that it can uptake non-canonical amino acid analogs as a substrate, and charge a modified tRNA (with its anticodon changed) with such a non-canonical amino acid. The following sections briefly describe a method for the generation of such modified AARS, which method is described in more detail in U.S. Pat. No. 7,139,665, the entire contents of which are incorporated herein by reference.

Briefly, the methods of some embodiments described therein relate to computational tools for modifying the substrate specificity of an AminoAcyl tRNA Synthetases (AARSs) through mutation to enable the enzyme to more efficiently utilize amino acid analog(s) in protein translation systems, either in vitro, in whole cells, or in other translation systems. A feature of some embodiments includes systematically redesigning the substrate binding site of an AARS enzyme to facilitate the use of unnatural substrates in the peptide or protein translation reaction the enzyme catalyzes.

According to one method, a rotamer library for the artificial amino acid is built by varying its torsional angles to create rotamers that would fit in the binding pocket for the natural substrate. The geometric orientation of the backbone of the amino acid analog is specified by the crystallographic orientation of the backbone of the natural substrate in the crystal structure. The crystallographic structure of the organism-specific amino acid synthetase may be used, or a homologous structure from another organism may be used, depending on structural similarity. Amino acids in the binding pocket of the synthetase that interact with the side chain on the analog are allowed to vary in identity and rotameric conformation in the subsequent protein design calculations.

One such protocol also employs a computational method to enhance the interactions between the substrate and the protein positions. This is done by scaling up the pair-wise energies between the substrate and the amino acids allowed at the design positions on the protein in the energy calculations. In an optimization calculation where the protein-substrate interactions are scaled up compared to the intra-protein interactions, sequence selection is biased toward selecting amino acids to be those that have favorable interaction with the substrate.

The described method helped to construct a new modified form of the *E. coli* phenylalanyl-tRNA synthetase, based on the known structure of the related *Thermus thermophilus* PheRS (tPheRS). The new modified form of the *E. coli* phenylalanyl-tRNA synthetase (ePheRS) allows efficient in vivo incorporation of reactive aryl ketone functionality into recombinant proteins. In addition, a modified tryptophanyl-tRNA synthetase was modified in a similar manner and has demonstrated the ability to incorporate non-natural amino acid analogs in polypeptides in place of naturally occurring tryptophan. The results described therein also demonstrate the general power of computational protein design in the development of aminoacyl-tRNA synthetases for activation and charging of non-natural amino acids.

A. Available Sequence and Structural Information for tRNA Synthetases

Protein translation from an mRNA template is carried out by ribosomes. During the translation process, each tRNA is matched with its amino acid long before it reaches the ribosome. The match is made by a collection of enzymes known as the aminoacyl-tRNA synthetases (AARS). These enzymes charge each tRNA with the proper amino acid, thus allowing each tRNA to make the proper translation from the genetic code of DNA (and the mRNA transcribed from the DNA) into the amino acid code of proteins.

Most cells make twenty different aminoacyl-tRNA synthetases, one for each type of amino acid. These twenty enzymes are each optimized for function with its own particular amino acid and the set of tRNA molecules appropriate to that amino acid. Aminoacyl-tRNA synthetases must perform their tasks with high accuracy. Many of these enzymes recognize their tRNA molecules using the anticodon. These enzymes make about one mistake in 10,000. For most amino acids, this level of accuracy is not too difficult to achieve, since most of the amino acids are quite different from one another.

In the subject method, an accurate description of the AARS binding pocket for tRNA is important for the computational design approach, since it depends on the crystal structure for the protein backbone descriptions, although in many cases it is perfectly acceptable to use crystal structure of a homologous protein (for example, a homolog from a related species) or even a conserved domain to substitute the crystallographic binding pocket structure description. The crystal structure also defines the orientation of the natural substrate amino acid in the binding pocket of a synthetase, as well as the relative position of the amino acid substrate to the synthetase residues, especially those residues in and around the binding pocket. To design the binding pocket for the analogs, it is preferred that these analogs bind to the synthetase in the same orientation as the natural substrate amino acid, since this orientation may be important for the adenylation step.

The AARSs may be from any organism, including prokaryotes and eukaryotes, with enzymes from bacteria, fungi, extremeophiles such as the archebacteria, worm, insects, fish, amphibian, birds, animals (particularly mammals and particularly human) and plants all possible.

As described above, most cells make twenty different aminoacyl-tRNA synthetases, one for each type of amino acid. Some suitable synthetases are known, including: yeast phenylalanyl-tRNA synthetase (Kwon et al., *J. Am. Chem. Soc.* 125: 7512-7513, 2003); *Methonococcus jannaschii* tyrosyl-tRNA synthetase (Wang et al., *Science* 292, 498-500, 2001); and yeast tyrosyl-tRNA synthetase (Ohno et al., *J. Biochem.* 130, 417-423, 2001). In fact, the crystal structures of nearly all 20 different AARS enzymes are currently available in the Brookhaven Protein Data Bank (PDB, see Bernstein et al., *J. Mol. Biol.* 112: 535-542, 1977). A list of all the AARSs with solved crystal structures as of April 2001 is available on the PDB website. For example, the crystal structure of *Thermus Aquaticus* Phenylalanyl tRNA Synthetase complexed with Phenylalanine has a resolution of 2.7 Å, and its PDB ID is 1B70.

The structure database or Molecular Modeling DataBase (MMDB) contains experimental data from crystallographic and NMR structure determinations. The data for MMDB are obtained from the Protein Data Bank (PDB). The NCBI (National Center for Biotechnology Information) has cross-linked structural data to bibliographic information, to the sequence databases, and to the NCBI taxonomy. Cn3D, the NCBI 3D structure viewer, can be used for easy interactive visualization of molecular structures from Entrez.

The Entrez 3D Domains database contains protein domains from the NCBI Conserved Domain Database (CDD). Computational biologists define conserved domains based on recurring sequence patterns or motifs. CDD currently contains domains derived from two popular collections, Smart and Pfam, plus contributions from colleagues at NCBI, such as COG. The source databases also provide descriptions and links to citations. Since conserved domains correspond to compact structural units, CDs contain links to 3D-structure via Cn3D whenever possible.

To identify conserved domains in a protein sequence, the CD-Search service employs the reverse position-specific BLAST algorithm. The query sequence is compared to a position-specific score matrix prepared from the underlying conserved domain alignment. Hits may be displayed as a pairwise alignment of the query sequence with a representative domain sequence, or as a multiple alignment. CD-Search now is run by default in parallel with protein BLAST searches. While the user waits for the BLAST queue to further process the request, the domain architecture of the query may already be studied. In addition, CDART, the Conserved Domain Architecture Retrieval Tool allows user to search for proteins with similar domain architectures. CDART uses pre-computed CD-search results to quickly identify proteins with a set of domains similar to that of the query. For more details, see Marchler-Bauer et al., *Nucleic Acids Research* 31: 383-387, 2003; and Marchler-Bauer et al., *Nucleic Acids Research* 30: 281-283, 2002.

In addition, a database of known aminoacyl tRNA synthetases has been published by Maciej Szymanski, Marzanna A. Deniziak and Jan Barciszewski, in *Nucleic Acids Res.* 29:288-290, 2001 (titled "Aminoacyl-tRNA synthetases database"). A corresponding website (rose.man.poznan.pl/aars/seq_main.html) provides details about all known AARSs from different species. For example, according to the database, the Isoleucyl-tRNA Synthetase for the radioresistant bacteria *Deinococcus radiodurans* (Accession No. AAF10907) has 1078 amino acids, and was published by White et al. in *Science* 286:1571-1577 (1999); the Valyl-tRNA Synthetase for mouse (*Mus musculus*) has 1263 amino acids (Accession No. AAD26531), and was published by Snoek M. and van Vugt H. in *Immunogenetics* 49: 468-470 (1999); and the Phenylalanyl-tRNA Synthetase sequences for human, *Drosophila, S. pombe, S. cerevisiae,* Candida albicans, *E. coli,* and mumerous other bacteria including *Thermus aquaticus* ssp. *thermophilus* are also available. The database was last updated in November, 2006. Similar information for other newly identified AARSs can be obtained, for example, by conducting a BLAST search using any of the known sequences in the AARS database as query against the available public (such as the non-redundant database at NCBI, or "nr") or proprietary private databases.

Alternatively, in certain embodiments, if the exact crystal structure of a particular AARS is not known, but its protein sequence is similar or homologous to a known AARS sequence with a known crystal structure. In such instances, it is expected that the conformation of the AARS in question will be similar to the known crystal structure of the homologous AARS. The known structure may, therefore, be used as the structure for the AARS of interest, or more preferably, may be used to predict the structure of the AARS of interest (i.e., in "homology modeling" or "molecular modeling"). As a particular example, the Molecular Modeling Database (MMDB) described above (see, Wang et al., *Nucl. Acids Res.* 2000, 28:243-245; Marchler-Bauer et al., *Nucl. Acids Res.* 1999, 27:240-243) provides search engines that may be used to identify proteins and/or nucleic acids that are similar or homologous to a protein sequence (referred to as "neighboring" sequences in the MMDB), including neighboring sequences whose three-dimensional structures are known. The database further provides links to the known structures along with alignment and visualization tools, such as Cn3D (developed by NCBI), RasMol, etc., whereby the homologous and parent sequences may be compared and a structure may be obtained for the parent sequence based on such sequence alignments and known structures.

The homologous AARS sequence with known 3D-structure is preferably at least about 60%, or at least about 70%, or at least about 80%, or at least about 90%, or at least about 95% identical, or at least about 98% identical to the AARS of interest in the active site region or the pocket region for amino acid substrate binding. Such active site or pocket site may not be continuous in the primary amino acid sequence of the AARS since distant amino acids may come together in the 3D-structure. In this case, sequence homology or identity can be calculated using, for example, the NCBI standard BLASTp programs for protein using default conditions, in regions aligned together (without insertions or deletions in either of the two sequences being compared) and including residues known to be involved in substrate amino acid binding. For example, the *Thermus Aquaticus* phenylalanyl tRNA synthetase catalytic (alpha) subunit appears to have an "insert" region from residues 156 to 165 when compared to its homologs from other species. This region can be disregarded in calculating sequence identity. Alternatively, the homologous AARS is preferably about 35%, or 40%, or 45%, or 50%, or 55% identical overall to the AARS of interest. The *E. coli* phenylalanyl tRNA synthetase alpha subunit is about 45% identical overall, and about 80% identical in the active site region to the *Thermus Aquaticus* phenylalanyl tRNA synthetase. The human phenylalanyl tRNA synthetase alpha subunits is about 62%, 60%, 54%, 50% identical overall to its *Drosophila*, worm (*C. elegans*), plant (*Arabidopsis thaliana*), yeast (*S. cerevisiae*) counterparts, respectively.

In the few cases where the structure for a particular AARS sequence may not be known or available, it is possible to determine the structure using routine experimental techniques (for example, X-ray crystallography and Nuclear Magnetic Resonance (NMR) spectroscopy) and without undue experimentation. See, e.g., *NMR of Macromolecules: A Practical Approach*, G. C. K. Roberts, Ed., Oxford University Press Inc., New York (1993); Ishima and Torchia, *Nat. Struct. Biol.* 7: 740-743, 2000; Gardner and Kay, *Annu. Rev. Bioph. Biom.* 27: 357-406, 1998; Kay, *Biochem. Cell. Biol.* 75: 1-15, 1997; Dayie et al., *Annu. Rev. Phys. Chem.* 47: 243-282, 1996; Wuthrich, *Acta Cyrstallogr. D* 51: 249-270, 1995; Kahn et al., *J. Synchrotron Radiat.* 7: 131-138, 2000; Oakley and Wilce, *Clin. Exp. Pharmacol. P.* 27: 145-151, 2000; Fourme et al., *J. Synchrotron Radiat.* 6: 834-844, 1999.

Alternatively, the three-dimensional structure of a AARS sequence may be calculated from the sequence itself and using ab initio molecular modeling techniques already known in the art. See e.g., Smith et al., *J. Comput. Biol.* 4: 217-225, 1997; Eisenhaber et al., *Proteins* 24: 169-179, 1996; Bohm, *Biophys Chem.* 59: 1-32, 1996; Fetrow and Bryant, *BioTechnol.* 11: 479-484, 1993; Swindells and Thorton, *Curr. Opin. Biotech.* 2: 512-519, 1991; Levitt et al., *Annu. Rev. Biochem.* 66: 549-579, 1997; Eisenhaber et al., *Crit. Rev. Biochem. Mol.* 30: 1-94, 1995; Xia et al., *J. Mol. Biol.* 300: 171-185, 2000; Jones, *Curr. Opin. Struc. Biol.* 10: 371-379, 2000. Three-dimensional structures obtained from ab initio modeling are typically less reliable than structures obtained using empirical (e.g., NMR spectroscopy or X-ray crystallography) or semi-empirical (e.g., homology modeling) techniques. However, such structures will generally be of sufficient quality, although less preferred, for use in some methods disclosed herein.

B. Methods for Predicting 3D Structure Based on Sequence Homology

For AARS proteins that have not been crystallized or been the focus of other structural determinations, a computer-generated molecular model of the AARS and its binding site can nevertheless be generated using any of a number of techniques available in the art. For example, the Cα-carbon positions of the target AARS sequence can be mapped to a particular coordinate pattern of an AARS enzyme ("known AARS") having a similar sequence and deduced structure using homology modeling techniques, and the structure of the target protein and velocities of each atom calculated at a simulation temperature (To) at which a docking simulation with an amino acid analog is to be determined. Typically, such a protocol involves primarily the prediction of side-chain conformations in the modeled target AARS protein, while assuming a main-chain trace taken from a tertiary structure, such as provided by the known AARS protein. Computer programs for performing energy minimization routines are commonly used to generate molecular models. For example, both the CHARMM (Brooks et al. (1983) *J Comput Chem* 4:187-217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488). At the heart of these programs is a set of subroutines that, given the position of every atom in the model, calculate the total potential energy of the system and the force on each atom. These programs may utilize a starting set of atomic coordinates, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input coordinate data and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject AARS proteins.

In general, energy minimization methods can be carried out for a given temperature, Ti, which may be different than the docking simulation temperature, To. Upon energy minimization of the molecule at Ti, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode. In this regard, the low frequency vibrations will often dominate the motion of the molecule.

After the molecular model has been energy minimized at Ti, the system is "heated" or "cooled" to the simulation temperature, To, by carrying out an equilibration run where the velocities of the atoms are scaled in a step-wise manner until the desired temperature, To, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J. Comput. Phys.* 23:327; and Van Gunsteren et al. (1977) *Mol. Phys.* 34:1311) is easy to implement and scales as O(N) as the number of constraints increases. Therefore, the method is applicable to macromolecules such as AARS proteins. An alternative method, RATTLE (Anderson (1983) *J. Comput. Phys.* 52:24) is based on the velocity version of the Verlet algorithm. Like SHAKE, RATTLE is an iterative algorithm and can be used to energy minimize the model of a subject AARS protein.

C. Alternative Methods

In other embodiments, rather than holding the identity of the amino acid analog constant and varying the AARS structure (by modeling several different mutant structures), the subject method is carried out using the molecular model(s) for a single modified AARS (e.g., in which one more non-anchor amino acid residues are changed) and sampling a variety of different amino acid analogs or potential fragments thereof, to identify analogs which are likely to interact with, and be substrates for the modified AARS enzyme. This approach can make use of coordinate libraries for amino acid analogs (including rotamer variants) or libraries of functional groups and spacers that can be joined to form the side-chain of an amino acid analog.

Using such approaches as described above, e.g., homology modeling, a coordinate set for the binding site for the modified AARS can be derived.

There are a variety of computational methods that can be readily adapted for identifying the structure of amino acid analogs that would have appropriate steric and electronic properties to interact with the substrate binding site of a modified AARS. See, for example, Cohen et al. (1990) *J. Med. Cam.* 33: 883-894; Kuntz et al. (1982) *J. Mol. Biol.* 161: 269-288; DesJarlais (1988) *J. Med. Cam.* 31: 722-729; Bartlett et al. (1989) (*Spec. Publ., Roy. Soc. Chem.*) 78: 182-196; Goodford et al. (1985) *J. Med. Cam.* 28: 849-857; DesJarlais et al. *J. Med. Cam.* 29: 2149-2153). Directed methods generally fall into two categories: (1) design by analogy in which 3-D structures of known molecules (such as from a crystallographic database) are docked to the AARS binding site structure and scored for goodness-of-fit; and (2) de novo design, in which the amino acid analog model is constructed piece-wise in the AARS binding site. The latter approach, in particular, can facilitate the development of novel molecules, uniquely designed to bind to the subject modified AARS binding site.

In an illustrative embodiment, the design of potential amino acid analogs that may function with a particular modified AARS begins from the general perspective of shape complimentary for the substrate binding site of the enzyme, and a search algorithm is employed which is capable of scanning a database of small molecules of known three-dimensional structure for candidates which fit geometrically into the substrate binding site. Such libraries can be general small molecule libraries, or can be libraries directed to amino acid analogs or small molecules which can be used to create amino acid analogs. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the substrate binding site. Most algorithms of this type provide a method for finding a wide assortment of chemical structures that may be complementary to the shape of the AARS substrate binding site.

For instance, each of a set of small molecules from a particular data-base, such as the Cambridge Crystallographic Data Bank (CCDB) (Allen et al. (1973) *J. Chem. Doc.* 13: 119), is individually docked to the binding site of the modified AARS in a number of geometrically permissible orientations with use of a docking algorithm. In a preferred embodiment, a set of computer algorithms called DOCK, can be used to characterize the shape of invaginations and grooves that form the binding site. See, for example, Kuntz et al. (1982) *J. Mol. Biol* 161: 269-288. The program can also search a database of small molecules for templates whose shapes are complementary to particular binding site of the modified AARS. Exemplary algorithms that can be adapted for this purpose are described in, for example, DesJarlais et al. (1988) *J. Med. Chem.* 31:722-729.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor or enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

In certain embodiments, the subject method can utilize an algorithm described by Goodford (1985, *J. Med. Chem.* 28:849-857) and Boobbyer et al. (1989, *J. Med. Chem.* 32:1083-1094). Those papers describe a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated amino acid analog that is believed to be important for binding. Goodsell and Olson (1990, *Proteins: Struct. Funct Genet.* 8:195-202) have used the Metropolis (simulated annealing) algorithm to dock a single known ligand into a target protein, and their approach can be adapted for identifying suitable amino acid analogs for docking with the AARS binding site. This algorithm can allow torsional flexibility in the amino acid side-chain and use GRID interaction energy maps as rapid lookup tables for computing approximate interaction energies.

Yet a further embodiment utilizes a computer algorithm such as CLIX which searches such databases as CCDB for small molecules which can be oriented in the substrate binding site of the AARS in a way that is both sterically acceptable and has a high likelihood of achieving favorable chemical interactions between the candidate molecule and the surrounding amino acid residues. The method is based on characterizing the substrate binding site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding. Again, the starting library can be of amino acid analogs or of molecules which can be used to generate the side-chain of an amino acid analog.

The algorithmic details of CLIX is described in Lawerence et al. (1992) Proteins 12:31-41, and the CLIX algorithm can be summarized as follows. The GRID program is used to determine discrete favorable interaction positions (termed target sites) in the binding site of the AARS protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the binding site of the modified AARS, describe an energy minimum for the molecule, albeit a local one.

A further assumption implicit in CLIX is that the potential ligand, when introduced into the substrate binding site of the modified AARS, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying amino acid analogs that may be utilized by a predetermined modified AARS comprises the de novo synthesis of potential inhibitors by algorithmic connection of small molecular fragments that will exhibit the desired structural and electrostatic complementarity with the substrate binding site of the enzyme. The methodology employs a large template set of small molecules with are iteratively pieced together in a model of the AARS' substrate binding site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In yet another embodiment, potential amino acid analogs can be determined using a method based on an energy minimization-quenched molecular dynamics algorithm for determining energetically favorable positions of functional groups in the substrate binding site of a modified AARS enzyme. The method can aid in the design of molecules that incorporate such functional groups by modification of known amino acid and amino acid analogs or through de novo synthesis.

For example, the multiple copy simultaneous search method (MCSS) described by Miranker et al. (1991) Proteins 11: 29-34 can be adapted for use in the subject method. To determine and characterize a local minima of a functional group in the force field of the protein, multiple copies of selected functional groups are first distributed in a binding site of interest on the AARS protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the force field of the protein.

Implementation of the MCSS algorithm requires a choice of functional groups and a molecular mechanics model for each of them. Groups must be simple enough to be easily characterized and manipulated (3-6 atoms, few or no dihedral degrees of freedom), yet complex enough to approximate the steric and electrostatic interactions that the functional group would have in substrate binding to the site of the AARS protein. A preferred set is, for example, one in which most organic molecules can be described as a collection of such groups (*Patai's Guide to the Chemistry of Functional Groups*, ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000-5,000 groups at random inside a sphere centered on the binding site; only the space not occupied by the protein needs to be considered. If the interaction energy of a particular group at a certain location with the protein is more positive than a given cut-off (e.g., 5.0 kcal/mole) the group is discarded from that site. Given the set of starting positions, all the fragments are minimized simultaneously by use of the TDH approximation (Elber et al. (1990) *J. Am. Chem. Soc.* 112: 9161-9175). In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, e.g., 100, of the randomly placed groups. After a certain number of step intervals, such as 1,000 intervals, the results can be examined to eliminate groups converging to the same minimum. This process is repeated until minimization is complete (e.g., RMS gradient of 0.01 kcal/mole/Å). Thus the resulting energy minimized set of molecules comprises what amounts to a set of disconnected fragments in three dimensions representing potential side-chains for amino acid analogs.

The next step then is to connect the pieces with spacers assembled from small chemical entities (atoms, chains, or ring moieties) to form amino acid analogs, e.g., each of the disconnected can be linked in space to generate a single molecule using such computer programs as, for example, NEWLEAD (Tschinke et al. (1993) *J. Med. Chem.* 36: 3863, 3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is single molecule. Such a program can use for example, three types of spacers: library spacers, single-atom spacers, and fuse-ring spacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In addition, the order in which the steps of this method are performed is purely illustrative in nature. In fact, the steps can be performed in any order or in parallel, unless otherwise indicated by the present disclosure.

Furthermore, the methods disclosed herein may be performed in either hardware, software, or any combination thereof, as those terms are currently known in the art. In particular, the present method may be carried out by software, firmware, or microcode operating on a computer or computers of any type. Additionally, software may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, certain embodiments are not limited to any particular platform, unless specifically stated otherwise in the present disclosure.

Exemplary computer hardware means suitable for carrying out certain embodiments can be a Silicon Graphics Power Challenge server with 10 R10000 processors running in parallel. Suitable software development environment includes CERIUS2 by Biosym/Molecular Simulations (San Diego, Calif.), or other equivalents.

The computational method described above has been effectively used in modifying enzymes of the protein synthesis machinery (e.g., AARS) to allow incorporation of unnatural amino acids. The same suite of computational tools can also be leveraged to design the final products (e.g., monoclonal antibodies or other therapeutics) in which the unnatural amino acids would be incorporated so as to enhance or modify their structural or functional properties.

While particular embodiments disclosed herein have been shown and described, it will be apparent to those skilled in the art that changes and modifications may be made without departing from the broader aspect and, therefore, the appended claims are to encompass within their scope all such changes and modifications as fall within the true spirit of this invention.

Adoption of AARS from Different Organisms

A second strategy for generating an external mutant tRNA, modified or external mutant RS, or modified tRNA/RS pair involves importing a tRNA and/or synthetase from another organism into the translation system of interest, such as *Escherichia coli*. In this particular example, the properties of the heterologous synthetase candidate include, e.g., that it does not charge *Escherichia coli* tRNA reasonably well (preferably not at all), and the properties of the heterologous tRNA candidate include, e.g., that it is not acylated by *Escherichia coli* synthetase to a reasonable extent (preferably not at all).

Schimmel et al. reported that *Escherichia coli* GlnRS (EcGlnRS) does not acylate *Saccharomyces cerevisiae* tRNAGln (EcGlnRS lacks an N-terminal RNA-binding domain possessed by *Saccharomyces cerevisiae* GlnRS (ScGlnRS)). See, E. F. Whelihan and P. Schimmel, *EMBO J.*, 16:2968 (1997). For example, the *Saccharomyces cerevisiae* amber suppressor tRNAGln (SctRNAGlnCUA) was analyzed to determine whether it is also not a substrate for EcGlnRS. In vitro aminoacylation assays showed this to be the case; and in vitro suppression studies show that the SctRNAGlnCUA is competent in translation. See, e.g., Liu and Schultz, *PNAS. USA*, 96:4780 (1999). It was further shown that ScGlnRS does not acylate any *Escherichia coli* tRNA, only the SctRNAGlnCUA in vitro. The degree to which ScGlnRS is able to aminoacylate the SctRNAGlnCUA in *Escherichia coli* was also evaluated using an in vivo complementation assay. An amber nonsense mutation was introduced at a permissive site in the β-lactamase gene. Suppression of the mutation by an amber suppressor tRNA should produce full-length β-lactamase and confer ampicillin resistance to the cell. When only SctRNAGlnCUA is expressed, cells exhibit an $IC_{50}$ of 20 μg/mL ampicillin, indicating virtually no acylation by endogenous *Escherichia coli* synthetases; when SctRNAGlnCUA is coexpressed with ScGlnRS, cells acquire an $IC_{50}$ of about 500 μg/mL ampicillin, demonstrating that ScGlnRS acylates SctRNAGlnCUA efficiently in *Escherichia coli*. See, Liu and Schultz, *PNAS, USA*, 96:4780 (1999).

As another example, *Saccharomyces cerevisiae* $tRNA^{Asp}$ is known to be an external mutant to *Escherichia coli* synthetases. See, e.g., Doctor and Mudd, *J. Biol. Chem.*, 238: 3677 (1963); and, Kwok and Wong, *Can. J. Biochem.*, 58:213 (1980). It was demonstrated that an amber suppressor tRNA derived from it ($SctRNA^{Asp}_{CUA}$) is also an external mutant in *Escherichia coli* using the in vivo β-lactamase assay described above. However, the anticodon of $tRNA^{Asp}$ is a critical recognition element of AspRS, see, e.g., Giege, et al, *Biochimie*, 78:605 (1996), and mutation of the anticodon to CUA results in a loss of affinity of the suppressor for AspRS. An *Escherichia coli* AspRS E93K mutant has been shown to recognize *Escherichia coli* amber suppressor $tRNA^{Asp}_{CUA}$ about an order of magnitude better than wt AspRS. See, e.g., Martin, 'Thesis', Universite Louis Pasteur, Strasbourg, France, 1995. It was speculated that introduction of the related mutation in *Saccharomyces cerevisiae* AspRS (E188K) might restore its affinity for $SctRNA^{Asp}_{CUA}$. It was determined that the *Saccharomyces cerevisiae* AspRS (E188K) mutant does not acylate *Escherichia coli* tRNAs, but charges $SctRNA^{Asp}_{CUA}$ with moderate efficiency as shown by in vitro aminoacylation experiments. See, e.g., Pastrnak, et al., *Helv. Chim. Acta*, 83:2277 (2000).

A similar approach involves the use of a heterologous synthetase as the external mutant synthetase and a mutant initiator tRNA of the same organism or a related organism as the modified tRNA. RajBhandary and coworkers found that an amber mutant of human initiator $tRNA^{fMet}$ is acylated by *Escherichia coli* GlnRS and acts as an amber suppressor in yeast cells only when EcGlnRS is coexpressed. See, Kowal, et al., *PNAS USA*, 98:2268 (2001). This pair thus represents an external mutant pair for use in yeast. Also, an *Escherichia coli* initiator $tRNA^{fMet}$ amber mutant was found that is inactive toward any *Escherichia coli* synthetases. A mutant yeast TyrRS was selected that charges this mutant tRNA, resulting in an external mutant pair in *Escherichia coli*.

Using the methods disclosed herein, the pairs and components of pairs desired above are evolved to generate external mutant tRNA and/or RS that possess desired characteristic, e.g., that can preferentially aminoacylate an O-tRNA with an unnatural amino acid.

In certain embodiments, the modified tRNA and the modified RS can be derived by mutation of a naturally occurring tRNA and RS from a variety of organisms. In one embodiment, the modified tRNA and/or modified RS are derived from at least one organism, where the organism is a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the modified tRNA is derived by mutation of a naturally occurring tRNA from a first organism and the modified RS is derived by mutation of a naturally occurring RS from a second organism. In one embodiment, the modified tRNA and modified RS can be derived from a mutated tRNA and mutated RS. In certain embodiments, the modified RS and/or modified tRNA from a first organism is provided to a translational system of a second organism, which optionally has non-functional endogenous RS and/or tRNA with respect to the codons recognized by the modified tRNA or modified RS.

The external mutant tRNA and/or the external mutant tRNA synthetase also can optionally be isolated from a variety of organisms. In one embodiment, the external mutant tRNA and/or external mutant synthetase are isolated from at least one organism, where the organism is a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the external tRNA is isolated from a naturally occurring tRNA from a first organism and the external mutant synthetase is isolated from a naturally occurring RS from a second organism. In one embodiment, the external mutant tRNA and/or external mutant tRNA synthetase can be isolated from one or more library (which optionally comprises one or more tRNA and/or RS from one or more organism (including those comprising prokaryotes and/or eukaryotes).)

Methods for selecting an external mutant tRNA and/or tRNA synthetase pair for use in any translation system are also disclosed herein. The methods include: introducing a marker gene, a tRNA and/or an aminoacyl-tRNA synthetase (RS) isolated or derived from a first organism into a first set of cells from the second organism; introducing the marker gene and the tRNA or RS into a duplicate cell set from the second organism; and, selecting for surviving cells in the first set that fail to survive in the duplicate cell set, where the first set and the duplicate cell set are grown in the presence of a selection agent, and where the surviving cells comprise the external mutant tRNA and/or RS for use in the in a translation system. In one embodiment, comparing and selecting includes an in vivo complementation assay. In another embodiment, the concentration of the selection agent is varied. The same assay may also be conducted in an in vitro or in vivo system based on the second organism.

Generation of AARS by Mutagenesis and Selection/Screening

The mutation or modification of an AARS to be used for incorporation of a non-natural amino acid into a target polypeptide or protein can be performed by using directed mutagenesis once the desired contact amino acid residues have been identified. Identification of the contact amino acids can be performed using any method that allows analysis of the structure of the AARS, including crystallographic analysis, computer modeling, nuclear magnetic resonance (NMR) spectroscopy, library screening, or a combination of any of these or other methods.

A number of AARS molecules have been sequenced, and provide guidance as to which amino acids are important for binding the amino acid with which to charge the corresponding tRNA. See, for example, SEQ ID Nos. 48-103.

In certain embodiments, the AARS capable of charging a particular external mutant tRNA with a particular unnatural amino acid can be obtained by mutagenesis of the AARS to generate a library of candidates, followed by screening and/or selection of the candidate AARS's capable of their desired function. Such external mutant AARSs and external mutant tRNAs may be used for in vitro/in vivo production of desired proteins with modified unnatural amino acids.

Thus methods for generating components of the protein biosynthetic machinery, such as the external mutant RSs, external mutant tRNAs, and/or external mutant tRNA/RS pairs that can be used to incorporate an unnatural amino acid are provided in certain embodiments disclosed herein.

In one embodiment, methods for producing at least one recombinant external mutant aminoacyl-tRNA synthetase comprise: (a) generating a library of (optionally mutant) RSs derived from at least one aminoacyl-tRNA synthetase (RS) from a first organism, e.g., a eukaryotic organism (such as a yeast), or a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like; (b) selecting (and/or screening) the library of RSs (optionally mutant RSs) for members that aminoacylate an external mutant tRNA in the presence of an unnatural amino acid and a natural amino acid, thereby providing a pool of active (optionally mutant) RSs; and/or, (c) selecting (optionally through negative selection) the pool for active RSs (e.g., mutant RSs) that preferentially aminoacylate the O-tRNA in the absence of the unnatural amino acid, thereby providing the at least one recombinant external mutant synthetase, wherein the at least one recombinant external mutant synthetase preferentially aminoacylates the external mutant tRNA with the unnatural amino acid. Recombinant external mutant synthetases produced by the methods are also included in certain embodiments disclosed herein.

In one embodiment, the RS is an inactive RS, which may have been generated from mutating an active RS. For example, the inactive RS can be generated by mutating at least about 1, at least about 2, at least about 3, at least about 4, at least about 5, at least about 6, or at least about 10 or more amino acids to different amino acids, e.g., alanine.

Libraries of mutant RSs can be generated using various mutagenesis techniques known in the art. For example, the mutant RSs can be generated by site-specific mutations, random mutations, diversity generating recombination mutations, chimeric constructs, and by other methods described herein or known in the art.

In one embodiment, selecting (and/or screening) the library of RSs (optionally mutant RSs) for members that are active, e.g., that aminoacylate an external mutant tRNA in the presence of an unnatural amino acid and a natural amino acid, includes: introducing a positive selection or screening marker, e.g., an antibiotic resistance gene, or the like, and the library of (optionally mutant) RSs into a plurality of cells, wherein the positive selection and/or screening marker comprises at least one codon, whose translation (optionally conditionally) depends on the ability of a candidate RSs to charge the external mutant tRNA (with either a natural and/or a unnatural amino acid); growing the plurality of cells in the presence of a selection agent; identifying cells that survive (or show a specific response) in the presence of the selection and/or screening agent by successfully translate the codon in the positive selection or screening marker, thereby providing a subset of positively selected cells that contains the pool of active (optionally mutant) RSs. Optionally, the selection and/or screening agent concentration can be varied. In certain embodiments, the cells do not contain a functional endogenous tRNA, RS or tRNA-RS pair that can help to translate the codon. The endogenous tRNA/RS pair may be disabled by gene deletion and/or RS inhibitors.

Since many essential genes of the cell likely also contain such codon that depends on the ability of the external mutant synthetase to charge the modified tRNA at the absence of functional endogenous RS/tRNA pair, in one embodiment, no extra positive selection markers are needed for the positive selection process—the survival of the cell can be used as a readout of the positive selection process.

In one aspect, the positive selection marker is a chloramphenicol acetyltransferase (CAT) gene. Optionally, the positive selection marker is a β-lactamase gene. In another aspect the positive screening marker comprises a fluorescent or luminescent screening marker or an affinity based screening marker (e.g., a cell surface marker).

In a similar embodiment, a cell-free in vitro system may be used to test the ability of the external mutant synthetase to charge the modified tRNA in a positive screening. For example, the ability of the in vitro system to translate a positive screening gene, such as a fluorescent marker gene, may depend on the ability of the external mutant synthetase to charge modified tRNA to read through a codon of the marker gene.

In one embodiment, negatively selecting or screening the pool for active RSs (optionally mutants) that preferentially aminoacylate the mutant tRNA in the absence of the unnatural amino acid includes: introducing a negative selection or screening marker with the pool of active (optionally mutant) RSs from the positive selection or screening into a plurality of translational system, wherein the negative selection or screening marker comprises at least one codon (e.g., codon for a toxic marker gene, e.g., a ribonuclease barnase gene), whose translation depends on the ability of a candidate RS to charge the external mutant tRNA (with a natural amino acid); and, identifying the translation system that shows a specific screening response in a first media supplemented with the unnatural amino acid and a screening or selection agent, but fail to show the specific response in a second media supplemented with the natural amino acid and the selection or screening agent, thereby providing surviving cells or screened cells with the at least one recombinant RS.

In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a *eubacterium*, a plant, an insect, a protist, etc. In other embodiments, the screening marker comprises a fluorescent or luminescent screening marker (such as green fluorescent protein) or an affinity based screening marker.

Also, some aspects include wherein the negative selection marker comprises a ribonuclease barnase gene (which comprises at least one said codon). Other aspects include wherein the screening marker optionally comprises a fluorescent or luminescent screening marker or an affinity based screening marker. In the embodiments herein, the screenings and/or selections optionally include variation of the screening and/or selection stringency.

In one aspect, the second set of mutated RS derived from at least one recombinant RS can be generated by mutagenesis, e.g., random mutagenesis, site-specific mutagenesis, recombination or a combination thereof.

The methods embodied herein optionally comprise wherein the unnatural amino acid is selected from, e.g.: an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine. A recombinant RS produced by the methods herein is also included in the embodiments disclosed herein.

In a related aspect, methods for producing a recombinant external mutant tRNA include: (a) generating a library of mutant tRNAs derived from at least one tRNA, from a first organism; (b) selecting (e.g., negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced external mutant RS, thereby providing at least one recombinant tRNA; wherein the at least one recombinant tRNA recognizes a non-natural amino acid codon and is not efficiency recognized by the RS from the second organism and is preferentially aminoacylated by the external mutant RS.

The various methods disclosed herein optionally comprise wherein selecting or screening comprises one or more positive or negative selection or screening, e.g., a change in amino acid permeability, a change in translation efficiency, and a change in translational fidelity. Additionally, the one or more change is optionally based upon a mutation in one or more gene in an organism in which an external mutant tRNA-tRNA synthetase pair are used to produce such protein. Selecting and/or screening herein optionally comprises wherein at least 2 codons within one or more selection gene or within one or more screening gene are used. Such multiple codons are optionally within the same gene or within different screening/selection genes. Additionally, the optional multiple codons are optionally different codons or comprise the same type of codons.

Kits are an additional feature of certain embodiments disclosed herein. For example, the kits can include one or more translation system as noted above (e.g., a cell), one or more tRNA (including modified or mutated tRNA), one or more AARS (including modified or mutated AARS), one or more unnatural amino acid, e.g., with appropriate packaging material, containers for holding the components of the kit, instructional materials for practicing the methods herein and/or the like. If one or more AARS and/or one or more tRNA are provided in a kit, they may be supplied as nucleic acids, or proteins and may be part of a single vector or contained in separate vectors. Similarly, products of the translation systems (e.g., proteins such as EPO analogues comprising unnatural amino acids) can be provided in kit form, e.g., with containers for holding the components of the kit, instructional materials for practicing the methods herein and/or the like.

Exemplary Uses

Well over 100 non-coded amino acids (all ribosomally acceptable) have been reportedly introduced into proteins using other methods (see, for example, Schultz et al., *J. Am. Chem. Soc.*, 103: 1563-1567, 1981; Hinsberg et al., *J. Am. Chem. Soc.*, 104: 766-773, 1982; Pollack et al., *Science*, 242: 1038-1040, 1988; Nowak et al., *Science*, 268: 439-442, 1995) all these analogs may be used in the subject methods for efficient incorporation of these analogs into protein products.

In another preferred embodiment, two or more analogs may be used in the same in vitro or in vivo translation system, each with its external mutant tRNA or external mutant synthetase pairs. This is more easily accomplished when a natural amino acid is encoded by four or more codons (such as six for Leu and Arg). However, for amino acids encoded by only two codons, one can be reserved for the natural amino acid, while the other "shared" by one or more amino acid analog(s). These analogs may resemble only one natural amino acid (for example, different Phe analogs), or resemble different amino acids (for example, analogs of Phe and Tyr).

In certain embodiments, a first nucleic acid encoding an external mutant/modified tRNA molecule that is not charged efficiently by an endogenous aminoacyl-tRNA synthetase in the cell/in vitro translation system (IVT), or the external mutant/modified tRNA itself. According to some embodiments, a second nucleic acid encoding an external mutant/modified aminoacyl tRNA synthetase (AARS) is also introduced into the cell/IVT. The external mutant/modified AARS is capable of charging the external mutant/modified tRNA with a chosen amino acid analog. The amino acid analog can then be provided to the cell so that it can be incorporated into one or more proteins within the cell or IVT.

In other embodiments, the environment is a cell. A variety of cells (or lysates thereof suitable for IVT) can be used in certain methods, including, for example, a bacterial cell, a fungal cell, an insect cell, and a mammalian cell (e.g., a human cell or a non-human mammal cell). In one embodiment, the cell is an *E. coli* cell, in another embodiment, the cell is a *Pseudomonas* cell.

In certain embodiments, the amino acid analog can be provided by directly contacting the cell or IVT with the analog, for example, by applying a solution of the analog to the cell in culture, or by directly adding the analog to the IVT. The analog can also be provided by introducing one or more additional nucleic acid construct(s) into the cell/IVT, wherein the additional nucleic acid construct(s) encodes one or more amino acid analog synthesis proteins that are necessary for synthesis of the desired analog.

Certain embodiments further involve introducing a template nucleic acid construct into the cell/IVT, the template encoding a protein, wherein the nucleic acid construct contains at least one degenerate codon sequence. The nucleic acids introduced into the cell/IVT can be introduced as one construct or as a plurality of constructs. In certain embodiments, the various nucleic acids are included in the same construct. For example, the nucleic acids can be introduced in any suitable vectors capable of expressing the encoded tRNA and/or proteins in the cell/IVT. In one embodiment, the first and second nucleic acid sequences are provided in one or more plasmids. In another embodiment, the vector or vectors used are viral vectors, including, for example, adenoviral and lentiviral vectors. The sequences can be introduced with an appropriate promoter sequence for the cell/IVT, or multiple sequences that can be inducible for controlling the expression of the sequences.

For in vitro use, one or more external mutant synthetase can be recombinantly produced and supplied to any the available in vitro translation systems (such as the commercially available Wheat Germ Lysate-based PROTEINscript-PRO™, Ambion®'s *E. coli* system for coupled in vitro transcription/translation; or the rabbit reticulocyte lysate-based Retic Lysate IVT™ Kit from Ambion®). Optionally, the in vitro translation system can be selectively depleted of one or more natural AARSs (by, for example, immunodepletion using immobilized antibodies against natural AARS) and/or natural amino acids so that enhanced incorporation of the analog can be achieved. Alternatively, nucleic acids encoding the re-designed external mutant synthetases may be supplied in place of recombinantly produced AARSs. The in vitro translation system is also supplied with the analogs to be incorporated into mature protein products.

Although in vitro protein synthesis usually cannot be carried out on the same scale as in vivo synthesis, in vitro methods can yield hundreds of micrograms of purified protein containing amino acid analogs. Such proteins have been produced in quantities sufficient for their characterization using circular dichroism (CD), nuclear magnetic resonance (NMR) spectrometry, and X-ray crystallography. This methodology can also be used to investigate the role of hydrophobicity, packing, side chain entropy and hydrogen bonding in determining protein stability and folding. It can also be used to probe catalytic mechanism, signal transduction and electron transfer in proteins. In addition, the properties of proteins can be modified using this methodology. For example, photocaged proteins can be generated that can be activated by photolysis, and novel chemical handles have been introduced into proteins for the site specific incorporation of optical and other spectroscopic probes.

The development of a general approach for the incorporation of amino acid analogs into proteins in vivo, directly from the growth media, would greatly enhance the power of unnatural amino acid mutagenesis. For example, the ability to synthesize large quantities of proteins containing heavy atoms would facilitate protein structure determination, and the ability to site-specifically substitute fluorophores or photocleavable groups into proteins in living cells would provide powerful tools for studying protein function in vivo. Alternatively, one might be able to enhance the properties of proteins by providing building blocks with new functional groups, such as a keto-containing amino acid.

For in vivo use, one or more AARS can be supplied to a host cell (prokaryotic or eukaryotic) as genetic materials, such as coding sequences on plasmids or viral vectors, which may optionally integrate into the host genome and constitutively or inducibly express the re-designed AARSs. A heterologous or endogenous protein of interest can be expressed in such a host cell, at the presence of supplied amino acid analogs. The protein products can then be purified using any art-recognized protein purification techniques, or techniques specially designed for the protein of interest.

These are a few possible means for generating a transcript which encodes a polypeptide. In general, any means known in the art for generating transcripts can be employed to synthesize proteins with amino acid analogs. For example, any in vitro transcription system or coupled transcription/translation systems can be used for generate a transcript of interest, which then serves as a template for protein synthesis. Alternatively, any cell, engineered cell/cell line, or functional components (lysates, membrane fractions, etc.) that is capable of expressing proteins from genetic materials can be used to generate a transcript. These means for generating a transcript will typically include such components as RNA polymerase (T7, SP6, etc.) and co-factors, nucleotides (ATP, CTP, GTP, UTP), necessary transcription factors, and appropriate buffer conditions, as well as at least one suitable DNA template, but other components may also added for optimized reaction condition. A skilled artisan would readily envision other embodiments similar to those described herein.

Chemical Moieties

In certain embodiments, the unnatural amino acid(s) and/or the therapeutic molecule comprises a chemically reactive moiety. The moiety may be strongly electrophilic or nucleophilic and thereby be available for reacting directly with the therapeutic molecule or the antibody or fragment thereof. Alternatively, the moiety may be a weaker electrophile or nucleophile and therefore require activation prior to the conjugation with the therapeutic molecule or the antibody or fragment thereof. This alternative would be desirable where it is necessary to delay activation of the chemically reactive moiety until an agent is added to the molecule in order to prevent the reaction of the agent with the moiety. In either scenario, the moiety is chemically reactive, the scenarios differ (in the reacting with antibody scenario) by whether following addition of an agent, the moiety is reacted directly with an antibody or fragment thereof or is reacted first with one or more chemicals to render the moiety capable of reacting with an antibody or fragment thereof. In certain embodiments, the chemically reactive moiety includes an amino group, a sulfhydryl group, a hydroxyl group, a carbonyl-containing group, or an alkyl leaving group.

Certain embodiments may employ click chemistry, which include, but is not limited to, Huisgen 1, 3-dipolar cycloaddition, in particular the Cu(I)-catalyzed stepwise variant, Diels-Alder reaction, nucleophilic substitution especially to small strained rings like epoxy and aziridine compounds, carbonyl-chemistry-like formation of ureas and amides, addition reactions to carbon-carbon double bonds like epoxidation and dihydroxylation.

Thus, in addition to or instead of glycosylation of polypeptides of the embodiments disclosed herein, other chemical moieties (including poly(ethylene) glycol) may be added, linked, joined, or otherwise conjugated or incorporated into the modified polypeptides. PEGylation is a process to covalently attach oligosaccharides and synthetic polymers such as polyethylene glycol (PEG) site-specifically onto therapeutic protein molecules. PEGylation can significantly enhance protein half-life by shielding the polypeptide from proteolytic enzymes and increasing the apparent size of the protein, thus reducing clearance rates. Moreover, PEG conjugates can enhance protein solubility and have beneficial effects on biodistribution. The physical and pharmacological properties of PEGylated proteins are affected by the number and the size of PEG chains attached to the polypeptide, the location of the PEG sites, and the chemistry used for PEGylation.

Examples of PEG conjugation to proteins include reactions of N-hydroxysuccinimidyl ester derivatized PEGs with lysine, 1,4-addition reactions of maleimide and vinylsulfone derivatized PEGs with cysteine, and condensation of hydrazide containing PEGs with aldehydes generated by oxidation of glycoproteins. When more than one reactive site is present in a protein (e.g., multiple amino or thiol groups) or reactive electrophiles are used, nonselective attachment of one or multiple PEG molecules can occur, leading to the generation of a heterogeneous mixture that is difficult to separate. The lack of selectivity and positional control in the attachment of PEG chains can lead to significant losses in biological activity and possibly enhanced immunogenicity of the conjugated protein. In fact, historically, loss of biological activity and product heterogeneity have been the two most common problems encountered in the development of long-acting protein pharmaceuticals using standard PEGylation techniques. Modification of proteins with amine-reactive PEGs typically results in drastic loss of biological activity due to modification of lysine residues located in regions of the protein important for biological activity. In certain situations, bioactivity of growth hormones may be reduced 400-fold or more. For example, bioactivity of GCSF is reduced 1,000-fold when the proteins are modified using conventional amine-PEGylation technologies (Clark et al., *J. Biol. Chem.* 271: 21969, 1996; Bowen et al., *Exp. Hematol.* 27, 425, 1999). Thus there is a need for a method that allows for the completely site-specific and irreversible attachment of PEG chains to proteins.

It would be advantageous to use advanced protein engineering technologies to create long-acting, "patient friendly" human protein pharmaceuticals, by, for example, incorporating unnatural amino acids into a drug protein, such that the engineered drug protein may achieve longer half life and/or sustained or even enhanced biological activity. Towards this end, certain embodiments disclosed herein may be used to overcome problems such as heterogeneity and loss of activity inherent in standard amine-PEGylation techniques. Incorporating unnatural amino acids will provide unique, pre-determined sites away from the binding or the catalytic site on the target protein where PEG molecules can be site-specifically conjugated. In addition, PEG molecules may be attached to unnatural amino acids through techniques other than amine-PEGylation, thus sparing the primary amine groups of lysines from undesirable PEGylation. These techniques may be used to enhance the half-life, efficacy, and/or safety of bio-pharmaceuticals in all areas, including the specific field of cancer, endocrinology, infectious disease, and inflammation, etc.

As an illustrative example, Click Chemistry or cycloaddition may be used to form a triazole linkage. One particular example of cycloaddition is a copper-mediated Huisgen [3+2]cycloaddition (Tornoe et al., *J. Org. Chem.* 67: 3057, 2002; Rostovtsev et al., *Angew. Chem., Int. Ed.* 41: 596, 2002; and Wang et al., *J. Am. Chem. Soc.* 125: 3192, 2003) of an azide and an alkyne is external mutant to all functional groups found in proteins, and forms a stable triazole linkage, this reaction can be used for the selective PEGylation of proteins. For example, Deiters et al. (*Bioorg. Med. Chem. Lett.* 14(23): 5743-5745, 2004) report a generally applicable PEGylation methodology based on the site-specific incorporation of para-azidophenylalanine into proteins in yeast. The azido group was used in a mild [3+2]cycloaddition reaction with an alkyne derivatized PEG reagent to afford selectively PEGylated protein. This strategy should be useful for the generation of selectively PEGylated proteins for therapeutic applications.

In certain embodiments, the polypeptide is a therapeutic, diagnostic, or other protein selected from: Alpha-1 antitrypsin, Angiostatin, Antihemolytic factor, antibodies (including an antibody or a functional fragment or derivative thereof selected from: Fab, Fab', F(ab)2, Fd, Fv, ScFv, diabody, tribody, tetrabody, dimmer, trimer or minibody), angiogenic molecules, angiostatic molecules, Apolipoprotein, Apoprotein, Atrial natriuretic factor, Atrial natriuretic polypeptide, Asparaginase, Adenosine deaminase, Hirudin, Ciliary Neurotrophic factor, bone morphogenic factor (any and all BMPs), Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, calcitonin, C-kit ligand, collagen, Colony stimulating factor (CSF), C-type natriuretic peptide (CNP), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), deoxyribonucleic acids, Epidermal Growth Factor (EGF), Erythropoietin, Exfoliating toxins A and B, Factor IX, Factor VII, Factor VIII, Factor X, Fibroblast Growth Factor (FGF), Fibrinogen, Fibronectin, granulocyte-colony stimulating factor (G-CSF), granulocyte macrophage colony stimulating factor (GM-CSF), follitropin, Glucocerebrosidase, Gonadotropin, glucagons, GLP-1, growth factors, Hedgehog proteins (e.g., Sonic, Indian, Desert), Human Growth Hormone, Hemoglobin, Hepatocyte Growth Factor (HGF), Hepatitis viruses, Hirudin, Human serum albumin, Insulin, Insulin-like Growth Factor (IGF), interferons (e.g., IFN-α, IFN-β, IFN-γ, IFN-ε, IFN-ζ, IFN-η, IFN-κ, IFN-λ, IFN-τ, IFN-ς, IFN-ω), interleukins (e.g., IL-1, IL-2, IL-3, IL-4, IL-5, IL-6, IL-7, IL-8, IL-9, IL-10, IL-11, IL-12, IL-13, IL-14, IL-15, etc.), Keratinocyte Growth Factor (KGF), Lactoferrin, leukemia inhibitory factor, Luciferase, Luteinizing hormone, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Phenylalanine hydroxylase, Parathormone (PTH), Prolactin, Pyrogenic exotoxins A, B, and C, Relaxin, Renin, ribonucleic acids, SCF, Soluble complement receptor I, Soluble I-CAM 1, Soluble interleukin receptors (IL-1, IL-2, IL-3, IL-4, IL-5, IL-6, IL-7, IL-9, IL-10, IL-11, IL-12, IL-13, IL-14, IL-15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Tumor necrosis factor related apoptosis-inducing ligand (TRAIL), Vascular Endothelial Growth Factor (VEGEF), Urokinase; a transcriptional modulator that modulates cell growth, differentiation, or regulation, wherein the transcriptional modulator is from prokaryotes, viruses, or eukaryotes, including fungi, plants, yeasts, insects, and animals, including mammals; expression activator selected from cytokines, inflammatory molecules, growth factors, their receptors, oncogene products, interleukins (e.g., IL-1, IL-2, IL-8, etc.), interferons, FGF, IGF-I, IGF-II, FGF, PDGF, TNF, TGF-α, TGF-β, EGF, KGF, SCF/ c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; transcriptional activators and suppressors, e.g., p53, Tat, Fos, Myc, Jun, Myb, Rel; steroid hormone receptors selected from receptors for estrogen, progesterone, testosterone, aldosterone, LDL, or corticosterone; or an enzyme selected from: amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, or nucleases.

In the event that the protein or molecule of interest to be modified is an antibody or antibody fragment, the non-natural amino acid residue(s) may be placed at any location or position in the antibody structure, depending on the desired goal. For example, the non-natural amino acid residue may be placed in the Fab variable region, the Fc region, or in another location that interacts with the Fc region of the antibody. In other embodiments, the non-natural amino acid residue may be placed in the binding interface of the antibody, or the $V_H$ region. In certain embodiments, the modified antibody exhibits an increase or decrease in its ability to kill one or more targets. In particular, an antibody with increased ability to kill one or more targets, or with reduced side effects may be desired.

In other embodiments, the non-natural amino acid(s) confer enhanced binding affinity to an Fc-receptor and/or to C1q of the complement system. In particular, a modified antibody may have an altered (e.g., enhanced) affinity and/or specificity for an antigen or a protein binding partner (e.g., C1q of the complement and/or the Fc receptor on macrophages, etc.). For example, modification of a molecule may increase or decrease its antibody-dependent cell-mediated cytotoxicity (ADCC) function, or complement fixation activity. In other examples, modification of a particular molecule may increase or decrease its ability to bind another molecule of natural counter structure (such as an antibody).

Glycosylation Through Unnatural Amino Acids

The post-translational modification of proteins by glycosylation can affect protein folding and stability, modify the intrinsic activity of proteins, and modulate their interactions with other biomolecules. See, e.g., Varki, *Glycobiology* 3: 97-130, 1993. Natural glycoproteins are often present as a population of many different glycoforms, which makes analysis of glycan structure and the study of glycosylation effects on protein structure and function difficult. Therefore, methods for the synthesis of natural and unnatural homogeneously glycosylated proteins are needed for the systematic understanding of glycan function, and for the development of improved glycoprotein therapeutics.

One previously known approach for making proteins having desired glycosylation patterns makes use of glycosidases to convert a heterogeneous natural glycoprotein to a simple homogenous core, onto which saccharides can then be grafted sequentially with glycosyl transferases. See, e.g., Witte et al., *J. Am. Chem. Soc.* 119: 2114-2118, 1997. A limitation of this approach is that the primary glycosylation sites are predetermined by the cell line in which the protein is expressed. Alternatively, a glycopeptide containing the desired glycan structure can be synthesized by solid phase peptide synthesis. This glycopeptide can be coupled to other peptides or recombinant protein fragments to afford a larger glycoprotein by native chemical ligation (see, e.g., Shin et al., *J. Am. Chem. Soc.* 121: 11684-11689, 1999), expressed protein ligation (see, e.g., Tolbert and Wong, *J. Am. Chem. Soc.* 122: 5421-5428, 2000), or with engineered proteases (see, e.g., Witte et al., *J. Am. Chem. Soc.* 120: 1979-1989, 1998). Both native chemical ligation and expressed protein ligation are most effective with small proteins, and necessitate a cysteine residue at the N-terminus of the glycopeptide.

When a protease is used to ligate peptides together, the ligation site must be placed far away from the glycosylation site for good coupling yields. See, e.g., Witte et al., *J. Am. Chem. Soc.* 120: 1979-1989, 1998. A third approach is to modify proteins with saccharides directly using chemical methods. Good selectivity can be achieved with haloacetamide saccharide derivatives, which are coupled to the thiol group of cysteine (see, e.g., Davis and Flitsch, *Tetrahedron Lett.* 32: 6793-6796, 1991; and Macmillan et al., *Org. Lett.* 4: 1467-1470, 2002). But this method can become problematic with proteins that have more than one cysteine residue.

Certain embodiments provided herein disclose methods for synthesis of glycoproteins. These methods involve, in some embodiments, incorporating into a protein an unnatural amino acid that comprises a first reactive group; and contacting the protein with a saccharide moiety that comprises a second reactive group, wherein the first reactive group reacts with the second reactive group, thereby forming a covalent bond that attaches the saccharide moiety to the unnatural amino acid of the protein. Glycoproteins produced by these methods are also included in certain embodiments.

The first reactive group is, in some embodiments, an electrophilic moiety (e.g., a keto moiety, an aldehyde moiety, and/or the like), and the second reactive group is a nucleophilic moiety. In some embodiments, the first reactive group is a nucleophilic moiety and the second reactive group is an electrophilic moiety (e.g., a keto moiety, an aldehyde moiety, and/or the like). For example, an electrophilic moiety is attached to the saccharide moiety and the nucleophilic moiety is attached to the unnatural amino acid. The saccharide moiety can include a single carbohydrate moiety, or the saccharide moiety can include two or more carbohydrate moieties.

In some embodiments, the methods further involve contacting the saccharide moiety with a glycosyl transferase, a sugar donor moiety, and other reactants required for glycosyl transferase activity for a sufficient time and under appropriate conditions to transfer a sugar from the sugar donor moiety to the saccharide moiety. The product of this reaction can, if desired, be contacted by at least a second glycosyl transferase, together with the appropriate sugar donor moiety.

In certain embodiments, the method further comprises contacting the saccharide moiety with one or more of a β1-4N-acetylglucosaminyl transferase, an α1,3-fucosyl transferase, an α1,2-fucosyl transferase, an α1,4-fucosyl transferase, a β1-4-galactosyl transferase, a sialyl transferase, and/or the like, to form a biantennary or triantennary oligosaccharide structure. In one embodiment, the saccharide moiety comprises a terminal GlcNAc, the sugar donor moiety is UDP-Gal and the glycosyl transferase is a β-1,4-galactosyl transferase.

In one embodiment, the saccharide moiety comprises a terminal GlcNAc, the sugar donor moiety is UDP-GlcNAc and the glycosyl transferase is a β1-4N-acetylglucosaminyl transferase.

Optionally, the some methods further comprise contacting the product of the N-acetylglucosaminyl transferase reaction with a β1-4-mannosyl transferase and GDP-mannose to form a saccharide moiety that comprises Manβ1-4GlcNAcβ1-4GlcNAc-. Optionally, the method further comprises contacting the Manβ1-4GlcNAcβ1-4GlcNAc-moiety with an α1-3mannosyl transferase and GDP-mannose to form a saccharide moiety that comprises Manα1-3Manβ1-4GlcNAcβ1-4GlcNAc-. Optionally, the method further comprises contacting the Manα1-3Manβ1-4GlcNAcβ1-4GlcNAc-moiety with an α1-6 mannosyl transferase and GDP-mannose to form a saccharide moiety that comprises Manα1-6(Manα1-3)Manβ1-4GlcNAcβ1-4GlcNAc-.

Optionally, the method further comprises contacting the Manα1-6(Manα1-3)Manβ1-4GlcNAcβ1-4GlcNAc-moiety with a β1-2N-acetylglucosaminyl transferase and UDP-GlcNAc to form a saccharide moiety that comprises Manα1-6(GlcNAcβ1-2Manα1-3)Manβ1-4GlcNAcβ1-4GlcNAc-.

Optionally, the method further comprises contacting the Manα1-6(GlcNAcβ1-2Manα1-3)Manβ1-4GlcNAcβ1-4GlcNAc-moiety with a β1-2N-acetylglucosaminyl transferase and UDP-GlcNAc to form a saccharide moiety that comprises GlcNAcβ1-2Manα1-6(GlcNAcβ1-2Manα1-3)Manβ1-4GlcNAcβ1-4GlcNAc-.

The step of incorporating into a protein an unnatural amino acid that comprises a first reactive group, in some embodiments, comprises using an external mutant tRNA, an external mutant RS, or an external mutant tRNA/RS pair. In such cases, the external mutant tRNA preferentially recognizes a degenerate codon for wild-type tRNA, and incorporates the unnatural amino acid into the protein in response to the degenerate codon, and wherein the external mutant synthetase preferentially aminoacylates the external mutant tRNA with the unnatural amino acid. In some embodiments, the unnatural amino acid is incorporated into the polypeptide in vivo.

A wide variety of suitable reactive groups are known to those of skill in the art. Such suitable reactive groups can include, for example, amino, hydroxyl, carboxyl, carboxylate, carbonyl, alkenyl, alkynyl, aldehyde, ester, ether (e.g., thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

In some embodiments, one of the reactive groups is an electrophilic moiety, and the second reactive group is a nucleophilic moiety. Either the nucleophilic moiety or the electrophilic moiety can be attached to the side-chain of the unnatural amino acid; the corresponding group is then attached to the saccharide moiety.

Suitable electrophilic moieties that react with nucleophilic moieties to form a covalent bond are known to those of skill in the art. In certain embodiments, such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

Suitable nucleophilic moieties that can react with electrophilic moiety are known to those of skill in the art. In certain embodiments, such nucleophiles include, for example, aliphatic or aromatic amines, such as ethylenediamine. In certain embodiments, the nucleophilic moieties include, but are not limited to, e.g., —NR1-NH$_2$ (hydrazide), —NR1(C=O)NR2NH$_2$ (semicarbazide), —NR1(C=S)NR2NH$_2$ (thiosemicarbazide), —(C=O)NR1NH$_2$ (carbonylhydrazide), —(C=S)NR1NH$_2$ (thiocarbonylhydrazide), —(SO$_2$)NR1NH$_2$ (sulfonylhydrazide), —NR1NR2(C=O)NR3NH$_2$ (carbazide), NR1NR2(C=S)NR3NH$_2$ (thiocarbazide), —O—NH$_2$ (hydroxylamine), and the like, where each R1, R2, and R3 is independently H, or alkyl having 1-6 carbons, preferably H. In certain embodiments, the reactive group is a hydrazide, hydroxylamine, semicarbazide, carbohydrazide, a sulfonylhydrazide, or the like.

The product of the reaction between the nucleophile and the electrophilic moiety typically incorporates the atoms originally present in the nucleophilic moiety. Typical linkages obtained by reacting the aldehydes or ketones with the nucleophilic moieties include reaction products such as an oxime, an amide, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

These methods can further involve contacting the saccharide moiety with a glycosyl transferase, a sugar donor moiety, and other reactants required for glycosyl transferase activity for a sufficient time and under appropriate conditions to transfer a sugar from the sugar donor moiety to the saccharide moiety. In certain embodiments, the method further comprises contacting the product of the glycosyl transferase reaction with at least a second glycosyl transferase and a second sugar donor moiety. In other words, certain embodiments disclosed herein provide methods in which an amino acid-linked saccharide moiety or an unnatural amino acid that includes a saccharide moiety is further glycosylated. These glycosylation steps are preferably (though not necessarily) carried out enzymatically using, for example, a glycosyltransferase, glycosidase, or other enzyme known to those of skill in the art. In some embodiments, a plurality of enzymatic steps are carried out in a single reaction mixture that contains two or more different glycosyl transferases. For example, one can conduct a galactosylating and a sialylating step simultaneously by including both sialyl transferase and galactosyl transferase in the reaction mixture.

For enzymatic saccharide syntheses that involve glycosyl transferase reactions, the recombinant cells optionally contain at least one heterologous gene that encodes a glycosyl transferase. Many glycosyl transferases are known, as are their polynucleotide sequences. See, e.g., "The WWW Guide To Cloned Glycosyl transferases," (available on the World Wide Web). Glycosyl transferase amino acid sequences and nucleotide sequences encoding glycosyl transferases from which the amino acid sequences can be deduced are also found in various publicly available databases, including GenBank, Swiss-Prot, EMBL, and others.

In certain embodiments, a glycosyl transferase includes, but is not limited to, e.g., a galactosyl transferase, a fucosyl transferase, a glucosyl transferase, an N-acetylgalactosaminyl transferase, an N-acetylglucosaminyl transferase, a glucuronyl transferase, a sialyl transferase, a mannosyl transferase, a glucuronic acid transferase, a galacturonic acid transferase, an oligosaccharyl transferase, and the like. Suitable glycosyl transferases include those obtained from eukaryotes or prokaryotes.

An acceptor for the glycosyl transferases will be present on the glycoprotein to be modified by methods disclosed herein. Suitable acceptors, include, for example, galactosyl acceptors such as Galβ1,4GalNAc-; Galβ1,3GalNAc-; lacto-N-tetraose-; Galβ1,3GlcNAc-; Galβ1,4GlcNAc-; Galβ1,3Ara-; Galβ1,6GlcNAc-; and Galβ1,4Glc-(lactose). Other acceptors known to those of skill in the art (see, e.g., Paulson et al., *J. Biol. Chem.* 253: 5617-5624, 1978). Typically, the acceptors form part of a saccharide moiety chain that is attached to the glycoprotein.

In one embodiment, the saccharide moiety comprises a terminal GlcNAc, the sugar donor moiety is UDP-GlcNAc and the glycosyl transferase is a β1-4N-acetylglucosaminyl transferase. In another embodiment, the saccharide moiety comprises a terminal GlcNAc, the sugar donor moiety is UDP-Gal and the glycosyl transferase is a β1-4-galactosyl transferase. Additional sugars can be added as well.

The glycosylation reactions include, in addition to the appropriate glycosyl transferase and acceptor, an activated nucleotide sugar that acts as a sugar donor for the glycosyl transferase. The reactions can also include other ingredients that facilitate glycosyl transferase activity. These ingredients can include a divalent cation (e.g., $Mg^{2+}$ or $Mn^{2+}$), materials necessary for ATP regeneration, phosphate ions, and organic solvents. The concentrations or amounts of the various reactants used in the processes depend upon numerous factors including reaction conditions such as temperature and pH value, and the choice and amount of acceptor saccharides to be glycosylated. The reaction medium may also comprise solubilizing detergents (e.g., Triton or SDS) and organic solvents such as methanol or ethanol, if necessary.

Also provided by certain embodiments for modifying a glycoprotein are compositions that include a translation system which may or may not include a host cell, an external mutant tRNA, an external mutant RS, or any or all of these.

As used herein, the term "saccharide moiety" refers to natural and unnatural sugar moieties (i.e., a unnaturally occurring sugar moiety, e.g., a sugar moiety that is modified, e.g., at one or more hydroxyl or amino positions, e.g., dehydroxylated, deaminated, esterified, etc., e.g., 2-deoxyGal is an example of an unnatural sugar moiety).

The term "carbohydrate" has the general formula $(CH_2O)_n$, and includes, but is not limited to, e.g., monosaccharides, disaccharides, oligosaccharides and polysaccharides. Oligosaccharides are chains composed of saccharide units, which are alternatively known as sugars. Saccharide units can be arranged in any order and the linkage between two saccharide units can occur in any of approximately ten different ways. The following abbreviations are used herein: Ara=arabinosyl; Fru=fructosyl; Fuc=fucosyl; Gal=galactosyl; GalNAc=N-acetylgalactosaminyl; Glc=glucosyl; GlcNAc=N-acetylglucosaminyl; Man=mannosyl; and NeuAc=sialyl (typically N-acetyl-neuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3; 2→3; 2-3; or (2,3). Natural and unnatural linkages (e.g., 1-2; 1-3; 1-4; 1-6; 2-3; 2-4; 2-6; etc.) between two sugars are included in certain embodiments. Each saccharide is a pyranose.

The term "sialic acid" (abbreviated "Sia") refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid) (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al., *J. Biol. Chem.* 261: 11550-11557, 1986; Kanamori et al., *J. Biol. Chem.* 265: 21811-21819, 1990). Also included are 9-substituted sialic acids such as a 9-O—C1-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40, 1992; Sialic Acids: Chemistry, Metabolism and Function, R. Schauer, Ed. (Springer-Verlag, New York (1992). The synthesis and use of sialic acid compounds in a silylation procedure is described in, for example, international application WO 92/16640 (entire contents incorporated herein by reference).

Donor substrates for glycosyl transferases are activated nucleotide sugars. Such activated sugars generally consist of uridine and guanosine diphosphate, and cytidine monophosphate, derivatives of the sugars in which the nucleoside diphosphate or monophosphate serves as a leaving group. Bacterial, plant, and fungal systems can sometimes use other activated nucleotide sugars.

The incorporation of an unnatural amino acid, e.g., an unnatural amino acid comprising a moiety where a saccharide moiety can be attached, or an unnatural amino acid that includes a saccharide moiety, can be done to, e.g., tailor changes in protein structure and/or function, e.g., to change size, acidity, nucleophilicity, hydrogen bonding, hydrophobicity, accessibility of protease target sites, target access to a protein moiety, etc. Proteins that include an unnatural amino acid, e.g., an unnatural amino acid comprising a moiety where a saccharide moiety can be attached, or an unnatural amino acid that includes a saccharide moiety, can have enhanced, or even entirely new, catalytic or physical properties.

For example, the following properties are optionally modified by inclusion of an unnatural amino acid, e.g., an unnatural amino acid comprising a moiety where a saccharide moiety can be attached, or an unnatural amino acid that includes a saccharide moiety into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid, e.g., an unnatural amino acid comprising a moiety where a saccharide moiety can be attached, or an unnatural amino acid that includes a saccharide moiety are useful for, e.g., novel therapeutics, diagnostics, catalytic enzymes, industrial enzymes, binding proteins (e.g., antibodies), and e.g., the study of protein structure and function. See, e.g., Dougherty, Curr. Opin. in Chem. Biol., 4:645-652 (2000).

In one aspect, a composition includes at least one protein with at least one, e.g., at least about two, three, four, five, six, seven, eight, nine, or at least about ten or more unnatural amino acids, e.g., an unnatural amino acid comprising a moiety where a saccharide moiety can be attached, or an unnatural amino acid that includes a saccharide moiety, and/or which include another unnatural amino acid. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the unnatural amino acid, e.g., an unnatural amino acid comprising a moiety where a saccharide moiety can be attached, or an unnatural amino acid that includes a saccharide moiety. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different, or a combination of multiple unnatural amino acids of the same kind with at least one different unnatural amino acid.

Essentially any protein (or portion thereof that includes an unnatural amino acid, e.g., an unnatural amino acid comprising a moiety where a saccharide moiety is attached, such as an aldehyde- or keto-derivatized amino acid, or an unnatural amino acid that includes a saccharide moiety (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate degenerate codons in a relevant translation system. Common sequence repositories for known proteins include GenBank EMBL, DDBJ and the NCBI. Other repositories can easily be identified by searching the internet.

Typically, the proteins are, e.g., at least about 60%, 70%, 75%, 80%, 90%, 95%, or at least about 99% or more identical to any available protein (e.g., a therapeutic protein, a diagnostic protein, an industrial enzyme, or portion thereof, and the like), and they comprise one or more unnatural amino acid.

In addition to modifying one or more amino acid residues of the protein, the protein's carbohydrate composition may be modified, i.e., through glycosylation. The post-translational modification of proteins by glycosylation can affect protein folding and stability, modify the intrinsic activity of proteins, and modulate their interactions with other biomolecules. See, e.g., Varki, *Glycobiology* 3: 97-130, 1993, hereby incorporated by reference in its entirety. Natural glycoproteins are often present as a population of many different glycoforms, which makes analysis of glycan structure and the study of glycosylation effects on protein structure and function difficult. Therefore, methods for the synthesis of natural and unnatural homogeneously glycosylated proteins are needed for the systematic understanding of glycan function, and for the development of improved glycoprotein therapeutics.

One class of proteins that can be made using certain compositions and methods disclosed herein includes transcriptional modulators, enzymes, or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Some examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Some of the polypeptides that can be modified according to certain embodiments disclosed herein are commercially available (see, e.g., the Sigma BioSciences catalogue and price list), and the corresponding protein sequences and genes and, typically, many variants thereof, are well-known (see, e.g., Genbank).

Examples of therapeutically relevant properties that may be manipulated or modified by any of the embodiments disclosed herein (including glycosylation and/or pegylation, and/or incorporation of non-natural amino acids) include serum half-life, shelf half-life, stability, immunogenicity, therapeutic activity, detectability (e.g., by the inclusion of reporter groups (e.g., labels or label binding sites) in the unnatural amino acids, specificity, reduction of LD50 or other side effects, ability to enter the body through the gastric tract (e.g., oral availability), or the like. Examples of relevant diagnostic properties include shelf half-life, stability, diagnostic activity, detectability, specificity, or the like. Examples of relevant enzymatic properties include shelf half-life, stability, specificity, enzymatic activity, production capability, or the like.

A variety of other proteins can also be modified to include one or more unnatural amino acids according to certain embodiments disclosed herein. For example, the proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g., polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for modification by certain embodiments disclosed herein.

In certain embodiments, the protein or polypeptide of interest (or portion thereof in the methods and/or compositions disclosed herein is encoded by a nucleic acid. Typically, the nucleic acid comprises at least one degenerate codon, at least about two, three, four, five, six, seven, eight, nine, or at least about ten or more degenerate codons.

Thus the above-described artificial (e.g., man-made, and not naturally occurring) polypeptides and polynucleotides are also features of certain embodiments disclosed herein. An artificial polynucleotide may include, e.g., (a) a polynucleotide comprising a nucleotide sequence encoding an artificial polypeptide; (b) a polynucleotide that is complementary to or that encodes a polynucleotide sequence of (a); (c) a nucleic acid that hybridizes to a polynucleotide of (a) or (b) under stringent conditions over substantially the entire length of the nucleic acid; (d) a polynucleotide that is at least about 95%, preferably at least about 98% identical to a polynucleotide of (a), (b), or (c); and, (e) a polynucleotide comprising a conservative variation of (a), (b), (c), or (d).

Unnatural amino acids are generally described above. Of particular interest for making glycoproteins as described herein are unnatural amino acids in which R in Formula I includes a moiety that can react with a reactive group that is attached to a saccharide moiety, to link the saccharide moiety to a protein that includes the unnatural amino acid. Suitable R groups include, for example, keto-, azido-, hydroxyl-, hydrazine, cyano-, halo-, aminooxy-, alkenyl, alkynyl, carbonyl, ether, thiol, seleno-, sulfonyl-, borate, boronate, phospho, phosphono, phosphine, heterocyclic, enone, imine, aldehyde, ester, thioacid, thioester, hindered ester, hydroxylamine, amine, and the like, or any combination thereof. In some embodiments, the unnatural amino acids have a photoactivatable cross-linker.

In addition to unnatural amino acids that contain novel side chains, unnatural amino acids also optionally comprise modified backbone structures, e.g., as illustrated by the structures of Formula II and III:

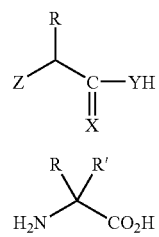

Formula II

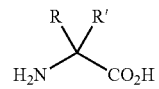

Formula III wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids disclosed herein are optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3-, 4-, 6-, 7-, 8-, and 9-membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, γ-substituted derivatives, cyclic derivatives, and amide substituted glutamine derivatives. Example phenylalanine analogs include, but are not limited to, meta-substituted, ortho-substituted, and/or para-substituted phenylalanines, wherein the substituent comprises a hydroxy group, a methoxy group, a methyl group, an allyl group, an aldehyde or keto group, or the like.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Unnatural amino acids suitable for use in some methods disclosed herein also include those that have a saccharide moiety attached to the amino acid side chain. In one embodiment, an unnatural amino acid with a saccharide moiety includes a serine or threonine amino acid with a Man, GalNAc, Glc, Fuc, or Gal moiety. Examples of unnatural amino acids that include a saccharide moiety include, but are not limited to, e.g., a tri-O-acetyl-GlcNAcβ-serine, a β-O-GlcNAc-L-serine, a tri-O-acetyl-GalNAc-α-threonine, an α-GalNAc-L-threonine, an O-Man-L-serine, a tetra-acetyl-O-Man-L-serine, an O-GalNAc-L-serine, a tri-acetyl-O-GalNAc-L-serine, a Glc-L-serine, a tetraacetyl-Glc-L-serine, a fuc-L-serine, a tri-acetyl-fuc-L-serine, an O-Gal-L-serine, a tetra-acetyl-O-Gal-L-serine, a beta-O-GlcNAc-L-threonine, a tri-acetyl-beta-GlcNAc-L-threonine, an O-Man-L-threonine, a tetra-acetyl-O-Man-L-threonine, an O-GalNAc-L-threonine, a tri-acetyl-O-GalNAc-L-threonine, a Glc-L-threonine, a tetraacetyl-Glc-L-threonine, a fuc-L-threonine, a tri-acetyl-fuc-L-threonine, an O-Gal-L-threonine, a tetra-acetyl-O-Gal-L-serine, and the like. Certain embodiments also include unprotected and acetylated forms of the above.

In some embodiments, the design of unnatural amino acids is biased by known information about the active sites of synthetases, e.g., external mutant tRNA synthetases used to aminoacylate an external mutant tRNA. For example, three classes of glutamine analogs are provided, including derivatives substituted at the nitrogen of amide (1), a methyl group at the γ-position (2), and a N—Cγ-cyclic derivative (3). Based upon the x-ray crystal structure of E. coli GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the Cγ position of Gln.

For example, N-phthaloyl-L-glutamic 1,5-anhydride (compound number 4 in FIG. 23 of WO 02/085923) is optionally used to synthesize glutamine analogs with substituents at the nitrogen of the amide. See, e.g., King and Kidd, J. Chem. Soc., 3315-3319, 1949; Friedman and Chatterrji, J. Am. Chem. Soc. 81, 3750-3752, 1959; Craig et al., J. Org. Chem. 53, 1167-1170, 1988; and Azoulay et al., Eur. J. Med. Chem. 26, 201-5, 1991. The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the γ-position is typically accomplished via alkylation of glutamic acid. See, e.g., Koskinen and Rapoport, J. Org. Chem. 54, 1859-1866, 1989. A protected amino acid, e.g., as illustrated by compound number 5 in FIG. 24 of WO 02/085923, is optionally prepared by first alkylation of the amino moiety with 9-bromo-9-phenylfluorene (PhflBr) (see, e.g., Christie and Rapoport, J. Org. Chem. 1989, 1859-1866, 1985) and then esterification of the acid moiety using O-tert-butyl-N,N'-diisopropylisourea. Addition of KN(Si(CH$_3$)$_3$)$_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24 of WO 02/085923).

Certain other embodiments include an immunoconjugate comprising an antibody (or its functional fragment) specific for a target (e.g., a target cell), the antibody (or fragment or functional equivalent thereof conjugated, at specific, pre-determined positions, with two or more therapeutic molecules, wherein each of the positions comprise an unnatural amino acid. In certain embodiments, the antibody fragments are F(ab')$_2$, Fab', Fab, or Fv fragments.

In certain embodiments, the two or more therapeutic molecules are the same. In certain embodiments, the two or more therapeutic molecules are different. In certain embodiments, the therapeutic molecules are conjugated to the same unnatural amino acids. In certain embodiments, the therapeutic molecules are conjugated to different unnatural amino acids.

In certain embodiments, the nature or chemistry of the unnatural amino acid/therapeutic molecule linkage allows cleavage of the linkage under certain conditions, such as mild or weak acidic conditions (e.g., about pH 4-6, preferably about pH5), reductive environment (e.g., the presence of a reducing agent), or divalent cations, and is optionally accelerated by heat.

In certain embodiments, the therapeutic molecule is conjugated to an antibody through a linker/spacer (e.g., one or more repeats of methylene (—CH$_2$—), methyleneoxy (—CH$_2$—O—), methylenecarbonyl (—CH$_2$—CO—), amino acids, or combinations thereof.

Multiprotein Complexes

Unnatural amino acids can also be used to join two or more proteins or protein sub-units with unique functionalities. For example, bispecific antibodies may be generated by linking two antibodies (or functional parts thereof or derivatives thereof, such as Fab, Fab', Fd, Fv, scFv fragments, etc.) through unnatural amino acids incorporated therein.

Thus certain embodiments herein provide methods for synthesis of multi-protein conjugates. These methods involve, in some embodiments, incorporating into a first protein (e.g., a first antibody) a first unnatural amino acid that comprises a first reactive group; and contacting the first protein with a second protein (e.g., a second antibody) comprising a second unnatural amino acid that comprises a second reactive group, wherein the first reactive group reacts with the second reactive group, thereby forming a covalent bond that attaches the second protein to the first protein.

The first reactive group is, in some embodiments, an electrophilic moiety (e.g., a keto moiety, an aldehyde moiety, and/or the like), and the second reactive group is a nucleophilic moiety. In some embodiments, the first reactive group is a nucleophilic moiety and the second reactive group is an electrophilic moiety (e.g., a keto moiety, an aldehyde moiety, and/or the like). For example, an electrophilic moiety is attached to the unnatural amino acid of the first Ab, and the nucleophilic moiety is attached to the unnatural amino acid of the second Ab.

Different functional domains of different proteins may be linked together through similar fashion to create novel proteins with novel functions (e.g., novel transcription factors with unique combination of DNA binding and transcription activation domains; novel enzymes with novel regulatory domains, etc.).

pH-Sensitive Binding

Many protein interactions are pH-sensitive, in the sense that binding affinity of one protein for its usual binding partner may change as environmental pH changes. For example, many ligands (such as insulin, interferons, growth hormone, etc.) bind their respective cell-surface receptors to elicit signal transduction. The ligand-receptor complex will then be internalized by receptor-mediated endocytosis, and go through a successive series of more and more acidic endosomes. Eventually, the ligand-receptor interaction is weakened at a certain acidic pH (e.g., about pH 5.0), and the ligand dissociates from the receptor. Some receptors (and perhaps some ligands) may be recycled back to cell surface. There, they may be able to bind their respective normal binding partners.

If the pH-sensitive binding can be modulated such that the ligand-receptor complex can be dissociated at a relatively higher pH, then certain ligands may be dissociated earlier from their receptors, and become preferentially recycled to cell surface rather than be degraded. This will result in an increased in vivo half-life of such ligands, which might be desirable since less insulin may be needed for the same (or better) efficacy in diabetes patients. In other situations, it might be desirable to modulate the pH-sensitive binding by favoring binding at a lower pH.

For example, monoclonal antibodies are generally very specific for their targets. However, in many applications, such as in cancer therapy, they tend to elicit certain side effects by, for example, binding to non-tumor tissues. One reason could be that the tumor targets against which monoclonal antibodies are raised are not specifically expressed on tumor cells, but are also expressed (although may be in smaller numbers) on some healthy cells. Such side effects are generally undesirable, and there is a need for antibodies with an improved specificity.

The pH of human blood is highly regulated and maintained in the range of about 7.6-7.8. On the other hand, tumor cells have an extracellular pH of 6.3-6.5, due to the accumulation of metabolic acids that are inefficiently cleared because of poor tumor vascularization. If the interaction between a tumor antigen and its therapeutic antibody can be modulated such that at low pH, the binding is favored, the tumor-antibody may have an added specificity/affinity/selectivity for those tumor antigens, even though the same tumor antigens are also occasionally found on normal tissues.

In fact, such modified antibodies may be desirable not only for cancer therapy, but also desirable for any antigen-antibody binding that may occur at a lower-than-normal level of pH.

General Techniques

The practice of the embodiments disclosed herein will employ, unless otherwise indicated, conventional techniques of molecular biology, cell biology, cell culture, microbiology and recombinant DNA, which are within the skill of the art. Such techniques are explained fully in the literature. See, for example, *Molecular Cloning: A Laboratory Manual*, $2^{nd}$ Ed., ed. By Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987).

Furthermore, general texts disclosing general cloning, mutation, cell culture and the like, include Berger and Kimmel, *Guide to Molecular Cloning Techniques, Methods in Enzymology* vol. 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) are all hereby incorporated by reference in their entireties. These texts describe mutagenesis, the use of vectors, promoters and many other relevant topics related to, e.g., the generation of external mutant tRNA, external mutant synthetases, and pairs thereof.

Various types of mutagenesis are used in certain embodiments, e.g., to produce novel synthetases or tRNAs. They include but are not limited to site-directed (such as through use of Amber, Ochre, Umber or other stop codon), via wobble codon mutagenesis, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included in certain embodiments. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications and references cited within: Sieber, et al., *Nature Biotechnology*, 19:456-460 (2001); Ling et al., *Approaches to DNA mutagenesis: an overview, Anal. Biochem.* 254(2): 157-178 (1997); Dale et al., *Methods Mol. Biol.* 57:369-374 (1996); I. A. Lorimer, I. Pastan, *Nucleic Acids Res.* 23, 3067-8 (1995); W. P. C. Stemmer, *Nature* 370, 389-91 (1994); Arnold, *Curr. Opin. in Biotech.* 4:450-455 (1993); Bass et al., *Science* 242: 240-245 (1988); Fritz et al., *Nucl. Acids Res.* 16: 6987-6999 (1988); Kramer et al., *Nucl. Acids Res.* 16: 7207 (1988); Sakamar and Khorana, *Nucl. Acids Res.* 14: 6361-6372 (1988); Sayers et al., *Nucl. Acids Res.* 16:791-802 (1988); Sayers et al., *Nucl. Acids Res.* 16: 803-814 (1988); Carter, *Methods in Enzymol.* 154: 382-403 (1987); Kramer & Fritz *Methods in Enzymol.* 154:350-367 (1987); Kunkel, *Nucleic Acids & Mol. Biol.* (Eckstein, F. and Lilley, D. M. J. eds., Springer Verlag, Berlin)) (1987); Kunkel et al., *Methods in Enzymol.* 154, 367-382 (1987); Zoller & Smith, *Methods in Enzymol.* 154:329-350 (1987); Carter, *Biochem. J.* 237:1-7 (1986); Eghtedarzadeh & Henikoff, *Nucl. Acids Res.* 14: 5115 (1986); Mandecki, *PNAS*, USA, 83:7177-7181 (1986); Nakamaye & Eckstein, *Nucl. Acids Res.* 14: 9679-9698 (1986); Wells et al., *Phil. Trans. R. Soc. Lond.* A 317: 415-423 (1986); Botstein & Shortle, *Science* 229:1193-1201 (1985) Carter et al., *Nucl. Acids Res.* 13: 4431-4443 (1985); Grundstöm et al., *Nucl. Acids Res.* 13: 3305-3316 (1985); Kunkel, *PNAS*, USA 82:488-492 (1985); Smith, *Ann. Rev. Genet.* 19:423-462 (1985); Taylor et al., *Nucl. Acids Res.* 13: 8749-8764 (1985); Taylor et al., *Nucl. Acids Res.* 13: 8765-8787 (1985); Wells et al., *Gene* 34:315-323 (1985); Kramer et al., *Nucl. Acids Res.* 12: 9441-9456 (1984); Kramer et al., *Cell* 38:879-887 (1984); Nambiar et al., *Science* 223: 1299-1301 (1984); Zoller & Smith, *Methods in Enzymol.* 100:468-500 (1983); and Zoller & Smith, *Nucl Acids Res.* 10:6487-6500 (1982). Additional details on many of the above methods can be found in Methods in Enzymology Volume 154, which also describes useful controls for trouble-shooting problems with various mutagenesis methods.

Oligonucleotides, e.g., for use in mutagenesis in certain embodiments, e.g., mutating libraries of synthetases, or altering tRNAs, are typically synthesized chemically according to the solid phase phosphoramidite triester method described by Beaucage and Caruthers, *Tetrahedron Letts.* 22(20):1859-1862, (1981) e.g., using an automated synthesizer, as described in Needham-VanDevanter et al., *Nucl Acids Res.*, 12:6159-6168 (1984).

In addition, essentially any nucleic acid can be custom or standard ordered from any of a variety of commercial sources, such as The Midland Certified Reagent Company, The Great American Gene Company, ExpressGen Inc., Operon Technologies Inc. (Alameda, Calif.) and many others.

All embodiments described herein are intended to be able to be combined with one or more other embodiments, even for those described under different sections of the disclosure.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

EXAMPLES

These examples illustrate the incorporation of an amino acid analog in proteins at positions encoded by codons which normally specifically encode phenylalanine (Phe) or specifically encode tryptophan (Trp). A schematic diagram is shown in FIG. 1. Similar approaches can be used for any other analogs.

Phe is encoded by two codons, UUC and UUU. Both codons are read by a single tRNA, which is equipped with the anticodon sequence GAA. The UUC codon is therefore recognized through standard Watson-Crick base-pairing between codon and anticodon; UUU is read through a G-U wobble base-pair at the first position of the anticodon (Crick, *J. Mol. Biol.* 19: 548, 1966; Soll and RajBhandary, *J. Mol. Biol.* 29: 113, 1967). Thermal denaturation of RNA duplexes has yielded estimates of the Gibbs free energies of melting of G-U, G-C, A-U, and A-C basepairs as 4.1, 6.5, 6.3, and 2.6 kcal/mol, respectively, at 37° C. Thus the wobble basepair, G-U, is less stable than the Watson-Crick basepair, A-U. A modified tRNA$^{Phe}$ outfitted with the AAA anticodon (tRNA$^{Phe}_{AAA}$) was engineered to read the UUU codon, and was predicted to read such codons faster than wild-type tRNA$^{Phe}_{GAA}$.

Murine dihydrofolate reductase (mDHFR), which contains nine Phe residues, was chosen as the test protein. The expression plasmid pQE16 encodes mDHFR under control of a bacteriophage T5 promoter; the protein is outfitted with a C-terminal hexahistidine (HIS$_6$) tag to facilitate purification via immobilized metal affinity chromatography.

The modified yeast PheRS (mu-yPheRS) was prepared by introduction of a Thr415Gly or Thr415Ala mutation in the α-subunit of the synthetase (Datta et al., *J. Am. Chem. Soc.* 124: 5652, 2002). The kinetics of activation of NaI and Phe by mu-yPheRS were analyzed in vitro via the adenosine triphosphate-pyrophosphate exchange assay. The specificity constant ($k_{cat}/K_M$) for activation of NaI by mu-yPheRS was found to be $1.55 \times 10^{-3}$ (s$^{-1}$ M$^{-1}$), 8-fold larger than that for Phe. Therefore, when the ratio of NaI to Phe in the culture medium is high, ytRNA$^{Phe}_{AAA}$ should be charged predominantly with NaI. In addition, the T415G mutant was generated by four-primer mutagenesis.

Both *E. coli* and yeast synthetases are α$_2$β$_2$ hetero-tetramers and the molecular weights for each subunit are rather different α(ePheRS)=37 kDA; α(yPheRS)=57 kDa; β(ePheRS)=87 kDa; and β(yPheRS)=67.5, all approximately.

Thus, the following examples are provided as way of illustration and not by way of limitation.

Example 1

In order to alter the capability of a yeast aminoacyl tRNA synthetase, the yPheRS gene was amplified from template plasmid pUC-ASab2 encoding alpha and beta subunits of the PheRS gene. The amplification was conducted with a 14 base pair intergenic sequence containing a translational reinitiation site upstream of the ATG start code of the beta subunit gene.

The following oligo primers were used for the PCR: 5'-CGA TTT TCA CAC AGG ATC CAG ACC ATG ATT CTA G-3' (SEQ ID NO:7) (primer 1 with restriction site BamHI) and 5'-GAC GGC CAG TGA ATT CGA GCT CGG TAC-3' (SEQ ID NO: 8) (primer 2 with restriction site KpnI). The resulting DNA product was introduced into the BamHI and KpnI sites of pQE32 to give pQE32-yFRS. The mutant yPheRS polynucleotide was generated by using primer mutagenesis by standard techniques.

Briefly, two complementary oligonucleotides: 5'-CTA CCT ACA ATC CTT ACG GCG AGC CAT CAA TGG AAA TC-3' (SEQ ID NO:9) (primer 3) and 5'-GAT TTC CAT TGA TGG CTC GCC GTA AGG ATT GTA GGT AG-3' (SEQ ID NO: 10) (primer 4) were synthesized to carry the specific mutation at position 415 of the alpha subunit of the yPheRS polynucleotide.

Example 2

The plasmid pQE32-yFRS, and pQE32-T415G, pQE32-T415A were each transformed into *E. coli* host cell strain BLR (from NOVAGEN®) to form expression strains BLR (pQE32-yFRS_ and BLR(pQE32-T415G). Cells were grown in LB media, to a concentration of 0.6 at OD 600. Expression was then induced with 1 mM IPTG for 4 hours. Cells were harvested and polypeptides were purified by way of a nickel-nitrilotriacetic acid affinity column under native conditions according to the manufacturer's protocol (QIAGEN®). The imidazole in the elution buffer was removed by desalting column, and polypeptides were eluted into a buffer containing 50 mM Tris-HCl (pH=7.5), 1 mM DTT. Aliquots of polypeptides were stored in −80° C. with 50% glycerol.

Example 3

The amino acid dependent ATP-PP$_i$ exchange reaction was used to evaluate the activation of non-natural amino acids by yPheRS. The assay was performed in 200 microliters of reaction buffer containing 50 mM HEPES (pH=7.6), 20 mM MgCl$_2$, 1 mM DTT, 2 mM ATP and 2 mM [$^{32}$P]-PP$_i$ with specific activity of 0.2-0.5 TBq/mol. Depending on the activity of the various non-natural amino acids with the synthetase, the amino acid concentration varied from 10 microM to 5 mM and enzyme concentration varied from 10 nM to 100 nM. Aliquots of 20 microliters were removed from the reaction solution at various time points and quenched into 500 microliters of buffer solution containing 200 mM NaPP$_i$, 7% w/v HClO$_4$ and 3% w/v activated charcoal. The charcoal was spun down and washed twice with 500 microliters of 10 mM NaPP$_i$ and 0.5% HclO$_4$ solution. The radio-labeled ATP absorbed into the charcoal was quantified via liquid scintillation methods. The specificity constants were calculated by nonlinear regression fit of the data to a Michaelis Menten model. The kinetic parameters for the ATP-PPi exchange of amino acids by the yPheRS (T415G), wild type yPheRS, and yPheR-S_naph variant are shown in the table below.

| Amino Acid | Enzyme | Km (μM) | Kcat (s$^{-1}$) | Kcat/Km (M$^{-1}$s$^{-1}$) | Kcat/Km (relative) |
|---|---|---|---|---|---|
| Phe | T415G | 55 +/− 14 | 0.202 +/− 0.11 | 3512 +/− 1134 | 1[a] |
| Trp | T415G | 2.83 +/− 1.6 | 0.153 +/− 0.003 | 63190 +/− 34590 | 18[a] |
| 2Nal | T415G | 7.03 +/− 0.14 | 0.208 +/− 0.04 | 29535 +/− 5848 | 8.4[a] |
| Phe | wild type | 3.85 +/− 0.99 | 0.181 +/− 0.011 | 50994 +/− 22655 | 15[a] |
| Phe | naph | 11010 +/− 2688 | 0.0095 +/− 0.0021 | 0.855 +/− 0.007 | 1[b] |
| Trp | naph | 1424 +/− 597 | 0.0035 +/− 0.0009 | 2.52 +/− 0.44 | 2.9[b] |
| 2Nal | naph | 2030 +/− 691 | 0.030 +/− 0.018 | 14.54 +/− 4.22 | 17[b] |

Example 4

The expression plasmid, pQE16 (QIAGEN®) was used with marker polypeptide murine dihydrofolate reductase (mDHFR) with a C-terminal hexa-histidine tag gene under the control of a bacteriophage T5 promoter and $t_0$ terminator.

An Amber codon (TAG) was placed at the 38$^{th}$ position of mDHFR using a QUICK-CHANGE® mutagenesis kit. Two complementary oligo primers (5'-CCG CTC AGG AAC GAG TAG AAG TAC TTC CAA AGA ATG-3' (SEQ ID NO: 11) and 5'-CAT TCT TTG GAA GTA CTT CTA CTC GTT CCT GAG CGG-3' (SEQ ID NO: 12)) were used to produce pQE16am. The mutant yPheRS gene T415G was amplified from pQE32-T415G and a constitutive tac promoter with an abolished lac repressor binding site was added upstream from the start codon of the gene.

The entire expression cassette of T415G was inserted into PvuII site of pQE16 to yield pQE16 am-T415G. The mutant yeast suppressor tRNA (mutRNA$^{Phe}$(CUA)) was constitutively expressed under control of lpp promoter. The expression cassette of mutRNA$^{Phe}$(CUA) was inserted into repressor plasmid pREP4 to form pREP4-tRNA using known methods.

A phenylalanine (Phe) auxotrophic bacterial strain, AF (K10, Hfr(Cavalli) pheS13rel-1 tonA22 thi T2$^R$ pheA18) was used as a host strain. A Phe/Trp double auxotrophic strain, AFW (K10, Hfr(Cavalli) pheS13rel-1 tonA22 thi T2$^R$ pheA18, trpB114) and a Phe/Trp/Lys triple auxotrophic strain AFWK (K10, Hfr(Cavalli) pheS13rel-1 tonA2$^R$ thi T2R pheA18, trpB114, lysA) were prepared by P1 phage-mediated transduction with trpB::Tn10 and lysA::Tn10 transposons.

Example 5

The auxotrophic host cell strains AF, AFW, and AFWK were each transformed with plasmid pQE16am-T415G and pREP4-tRNA to yield expression strains AF[pQE16am-T415G/pREP4-tRNA] and AWF[pQE16am-T415G/pREP4-tRNA], respectively. The cells were grown in M9 minimal medium supplemented with glucose, thiamin, MgSO$_4$, CaCl$_2$, 20 amino acids (20 mg/L), antibiotics (kanamycin and ampicillin). When cells reached an OD600 reading of 1.0, they were sedimented by centrifugation, washed twice with cold 0.9% NaCl, and shifted to supplemented M9 medium containing 17 amino acids (20 mg/L), 3 mM non-natural amino acid of interest, and the indicated concentrations of Phe, Trp, and Lys. Protein expression was induced by adding IPTG (1 mM). After 4 hours, cells were pelleted and the protein was purified by way of a C-terminal hexa-Histidine tag and a Nickel-NTA spin column according to manufacturer's directions. (QIAGEN®).

Example 6

Mutant mDHFR was purified under denaturing conditions and eluted with standard buffer (8 M urea, 100 mM NaH$_2$PO$_4$, 10 mM Tris, pH 4.5). The polypeptides were trypsin digested with 10 microliters of the solution diluted into 90 microliters of 75 mM (NH$_4$)$_2$CO$_3$ and the pH was adjusted to 8. Two microliters of modified trypsin (0.2 micrograms/microliter) was added and the sample was incubated at room temperature overnight. The polypeptides were endoproteinase digested with Lys-C, 10 microliters of solution diluted in 90 microliters of 25 mM Tris-HCl, pH 8 and 1 mM EDTA. Next, 2 microliters of Lys-C (0.2 micrograms/microliter; CALBIOCHEM®) was added and the reaction was incubated at 37° for 10 hours. The digestion reaction was stopped by adding 2 microliters of trifluoroacetic acid (TFA). The solution was purified by way of ZIPTIP$_{C18}$® (MILLIPORE®) and the digested peptides were eluted with 3 microliters of 50% CH$_3$CN, 0.1% TFA. One microliter was used for matrix-assisted laser desorption ionization mass spectrometry (MALDI-MS) analysis with alpha-cyano-4-hydroxycinnamic acid and 2,5-dihydroxybenzoic acid as the matrix. The analysis was performed using a PERSEPTIVE BIOSYSTEMS® Voyager DE PRO MALDI-TOF mass spectrometer in linear and positive ion modes.

LC-MS/MS analysis of protease-digested peptides was conducted on FINNIGAN® LCQ ion trap mass spectrometry with HPLC pump and ESI probe. Tandem mass sequencing was carried out by fragmentation of the precursor ion with m/z corresponding to protease-digested fragment including the residue at position 38 of mutant mDHFR.

Example 7

Plasmids were constructed for wild type yPheRS and yPheRS (T415G) as described in Example 1 herein. In addition, the E. coli lysS gene was amplified by PCR from template plasmid pXLLysKS1, using the following primers: 5'-GCA CTG ACC ATG GCT GAA CAA CAC GCA CAG-3' (SEQ ID NO: 13) (with NcoI restriction site) and 5'-GGA CTT CGG ATC CTT TCT GTG GGC GCA TCG C-3' (SEQ ID NO: 14) (with BamHI restriction site). The resulting DNA was introduced into the NcoI and BamHI sites of pQE60 to yield pQE60-eLysS. The cloned enzymes contain N-terminal or C-terminal hexaHistidine tags to facilitate protein purification.

At the first two reactions, (primer 1 and primer 4) and (primer 2 and primer 3) were added into individual tubes and two DNA fragments were generated from these two PCR reactions. With the mixture of two reaction products and additional outside primers, a 3400 bp DNA fragment was obtained. The fragment was purified by standard methods and digested with BamHI and KpnI and inserted into pQE32 to produce pQE32-T415G. The cloned PheRS enzymes contained an N-terminal known hexa-histidine sequence tag for purification. The entire yPheRS gene was DNA sequenced for verification.

Example 8

The plasmid PQE32-T415A, and pQE60-eLysS were individually co-transformed with a repressor plasmid pREP4 into an *E. coli* strain BLR to form expression strains BLR (pQE32-yFRS), BLR (pQE32-T415G), BLR (pQE32-T415A) and BLR (pQE60-eLysS). Overexpression was conducted in 2×YT media with 100 micrograms/mL of ampicillin and 35 micrograms/mL of kanamycin. At OD 600=0.6, expression of yPheRS variants and *E. coli* lysyl-tRNA synthetase encoded by the lysS gene (eLysS) were induced with 1 mM IPTG. After 4 hour expression, cells were harvested and proteins were purified over a nickel-nitrilotriacetic acid affinity column under native conditions according to the manufacturer's protocol (QIAGEN®). The imidazole in the elution buffer was removed by desalting column and polypeptides were eluted into a buffer containing 50 mM Tris-HCl (pH 7.5), 1 mM DTT. Aliquots of polypeptides were stored in −80° C. with 50% glycerol. Concentrations of yPheRS variants and eLysS were determined by UV absorbance at 280 nm.

Example 9

Figure 9:
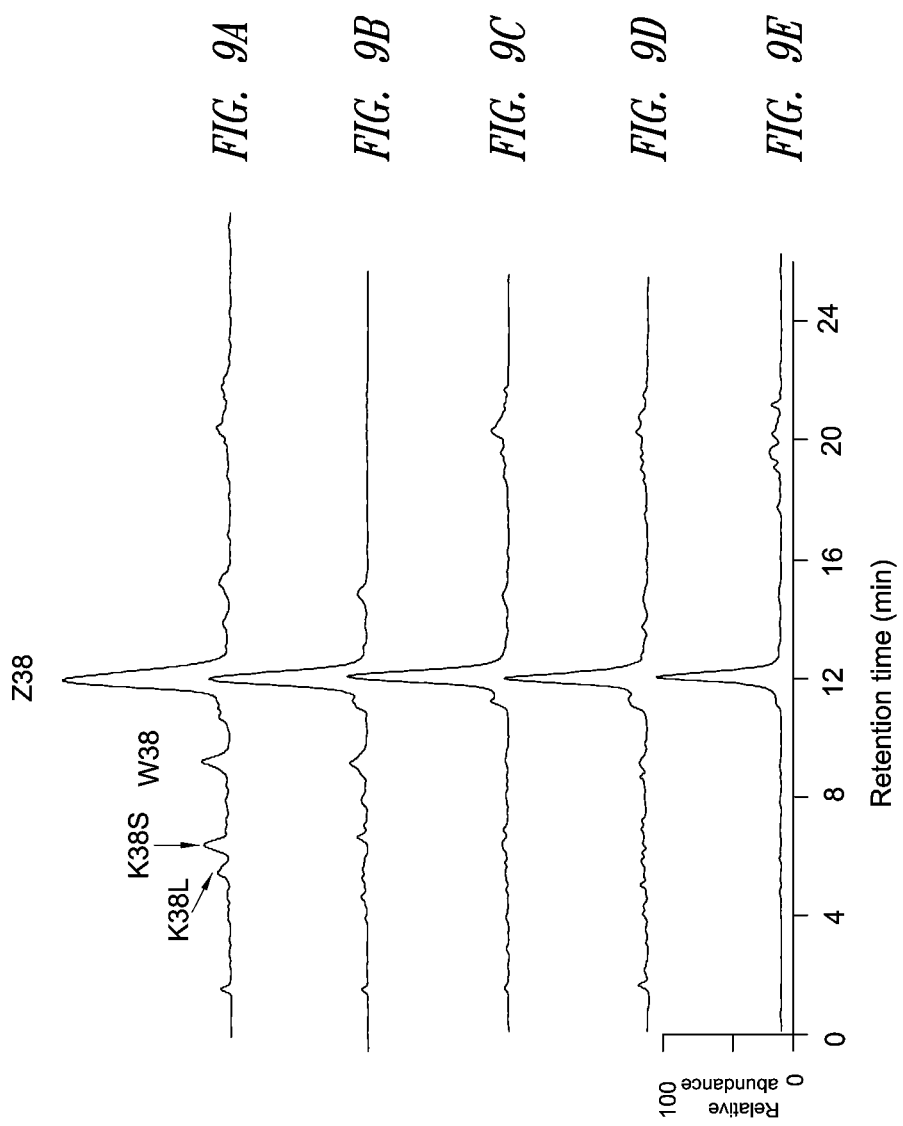
FIG. 9 shows LC-MS chromatograms of tryptic digests of the mDHFR polypeptides
Figure 10:
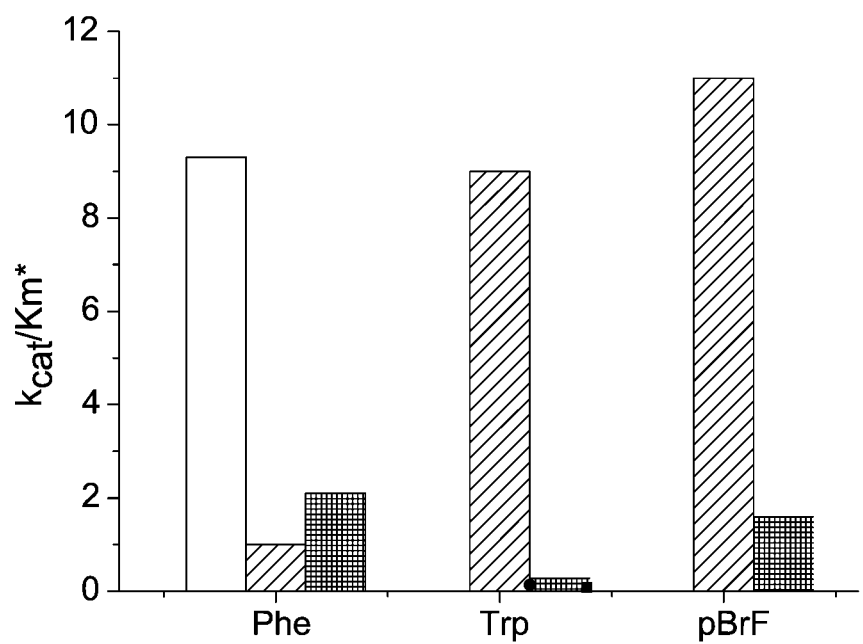
FIG. 10 shows ATP-PPi exchange rates for phenylalanine, tryptophan and p-bromophenylalanine by wild type yeast PheRS and external mutant yeast PheRS T415G or external mutant yeast PheRS T415A.
Figure 11A:
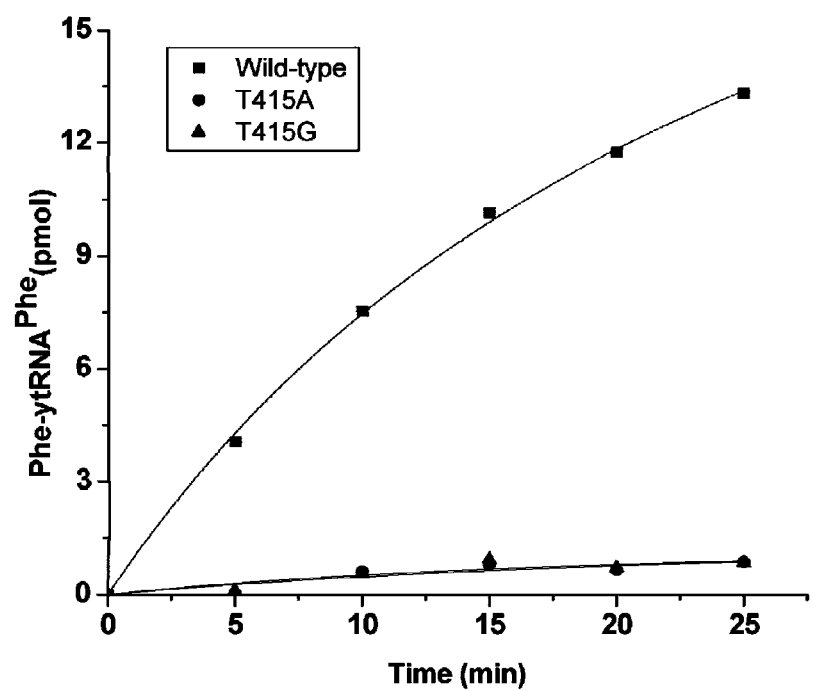
FIG. 11 shows aminoacylation of phenylalanine (FIG. 11A) and tryptophan (FIG. 11B) by wild type aminoacyl tRNA synthetase or external mutant tRNA synthetase (T415G or T415A).
Figure 11B:
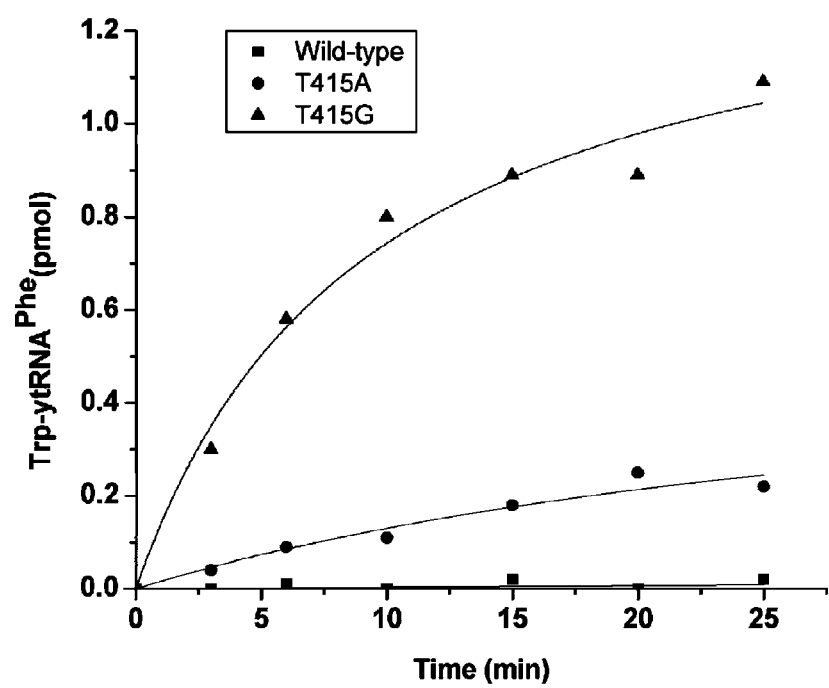

The peptide38 (residues 26-39; NGDLPWPPLRNEamber codonK) (SEQ ID NO: 15) contains the amber codon at position number 38. Peptides (K38S, K38L), Peptide W38 and Peptide pBrF (Z)38 were separated and detected by MS. Polypeptides were synthesized in triple auxotrophic host cells with (a) tRNA$^{Phe}_{CUA}$ and yPheRS (T415G); (b) tRNA$^{Phe}_{CUA\_UG}$ and yPheRS (T415G); (c) tRNA$^{Phe}_{CUA}$ and yPheRS (T415A); (d) tRNA$^{Phe}_{CUA\_UG}$ and yPheRS (T415A) or (e) in a single auxotrophic strain with tRNA$^{Phe}_{CUA\_UG}$ and yPheRS (T415A). The expression minimal media were supplemented with 6.0 mM pBrF, 0.01 mM Trp, 1.0 mM Lys, 0.03 mM Phe (a and b) or 0.01 mM Phe (c, d and e) and 25 mg/L of 17 amino acids, results are shown in FIG. 9.

Example 10

The amino acid-dependent ATP-PP$_i$ exchange reaction was used to evaluate the activation of amino acid analogs by yPheRS as described in the above Examples. Briefly, a 200 microliter aliquot of reaction buffer contains 50 mM HEPES (pH 7.6), 20 nM MgCl$_2$, 1 mM DTT, 2 mM ATP, and 2 mM $^{32}$P-pyrophosphate (PPi) with specific activity of 10-50 Ci/mol. Depending on the activity of analogs by the synthetase, the amino acid concentration varied from 10 microM to 2.5 mM and enzyme concentration varied from 10 nM to 100 nM. Aliquots of 20 microliters were removed from the reaction solution at various time points and quenched into 500 microliters of buffer solution containing 200 mN NaPP$_i$, 7% w/v HclO$_4$, and 3% w/v activated charcoal. The charcoal was spun down and washed twice with 500 microliters of 10 mM NaPP$_i$ and 0.5% HClO$_4$ solution. The radio-labeled ATP absorbed into the charcoal was quantified via liquid scintillation methods. The specificity constants were calculated by non linear regression fit for the data to a Michaelis Menten model.

The results of the kinetic parameters are shown in Table I. Substitution at the indole ring (especially at the 6$^{th}$ position) was highly favorable for some analogs (8-10).

TABLE I

Kinetic Parameters for ATP-PPi exchange of exemplary amino acids (1-11) by the external mutant yeast PheRS.

Figure 2:
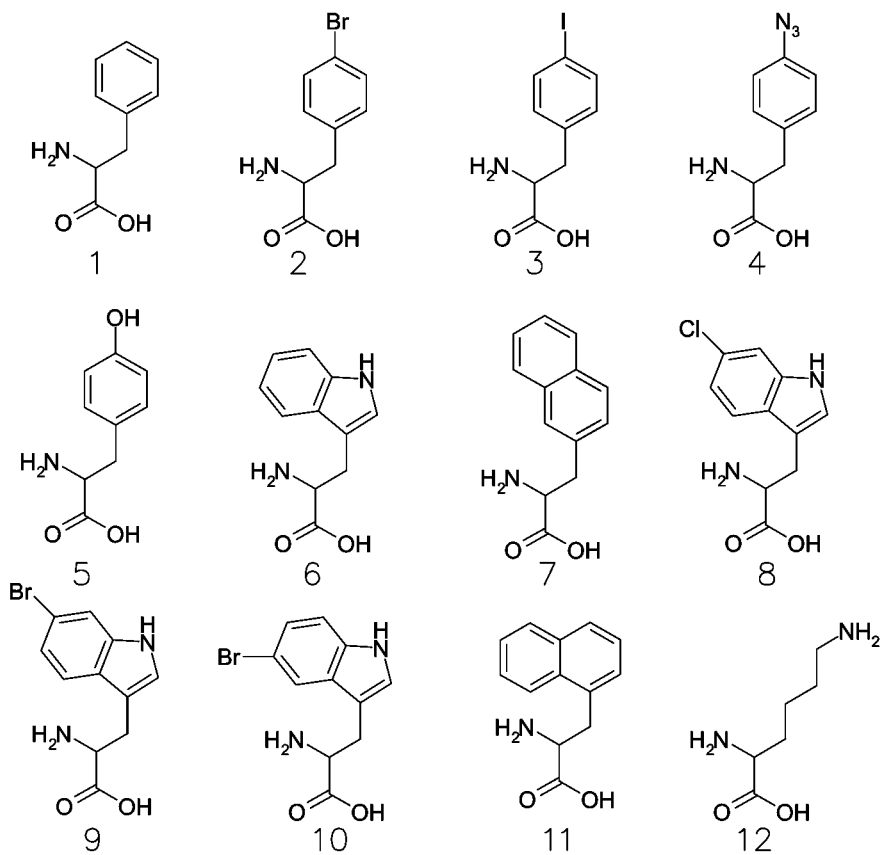
FIG. 2 shows several exemplary amino acids (naturally occurring or non-natural) used for some embodiments disclosed herein.
Figure 4A:
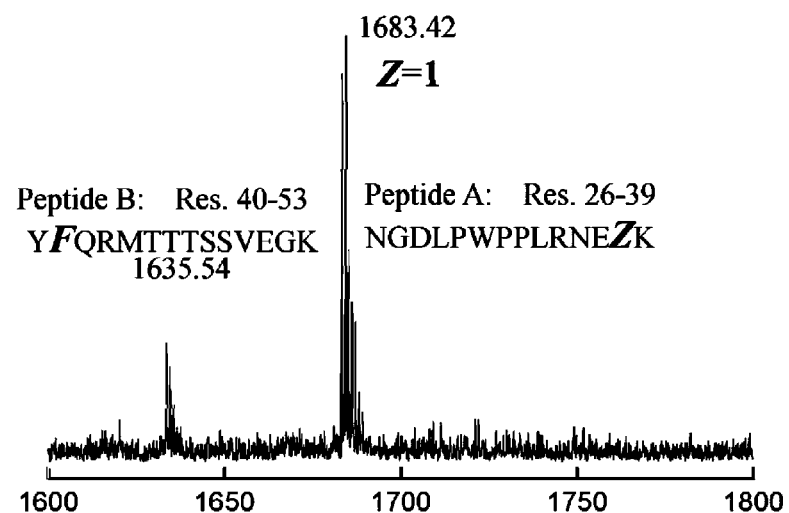
FIG. 4 shows a MALDI-MS of proteolytic peptide fragments derived from mDHFR expressed in media supplemented with amino acid 1 (3 mM) (FIG. 4A); amino acid 7 (3 mM) and 1 (0.03 mM) (FIG. 4B); amino acid 2 (3 mM) and 1 (0.03) (FIG. 4C); amino acid 2 (3 mM) and 1 (0.03 mM) (FIG. 4D). No tryptophan is supplemented during induction, except that 1 mM of tryptophan is supplemented in media at (c). Peptide B (SEQ ID NO:112), containing one Phe codon, is the control. Peptide A (SEQ ID NO:5) contains an amber codon (Z), the amino acid for which is assigned based on the mass units for Peptide A at different expression conditions. Due to lysine incorporation with Peptide A (FIG. 4C), C-terminal lysine was cleaved to produce a shorter Peptide A (NGDLPWPPLRNEK) (SEQ ID NO: 4).
Figure 4B:
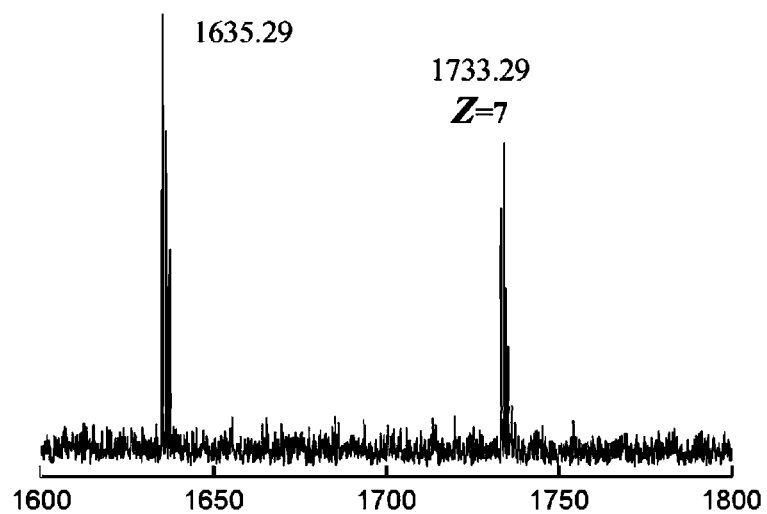
Figure 4C:
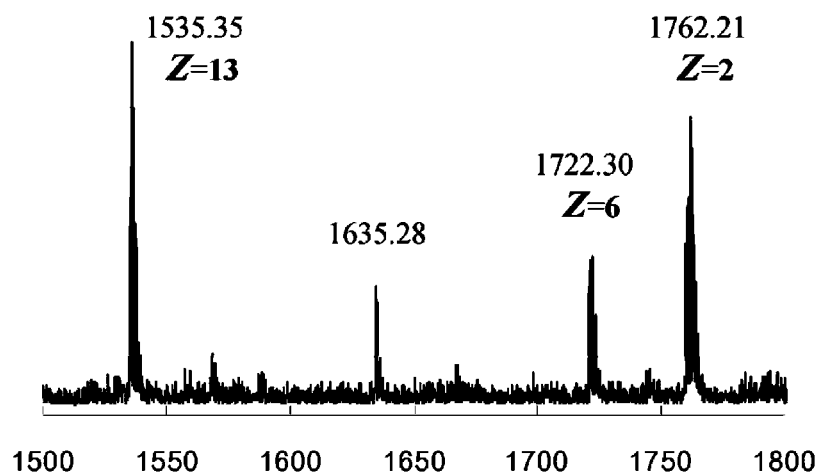
Figure 4D:
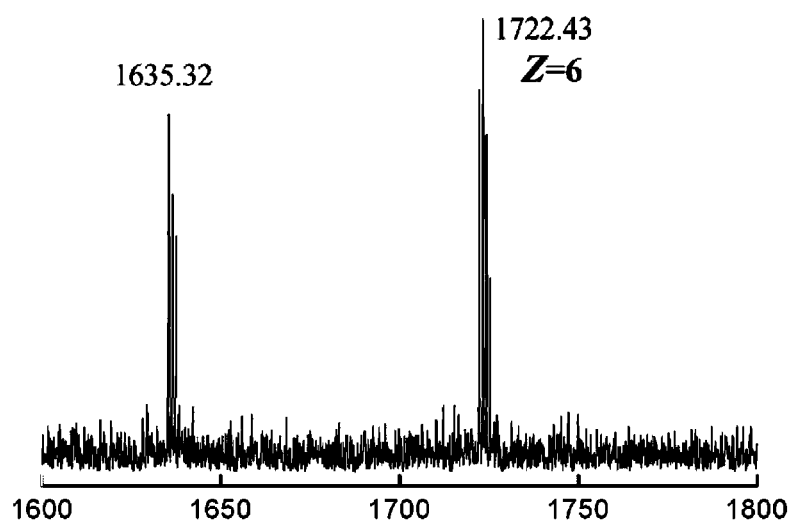
Figure 5:
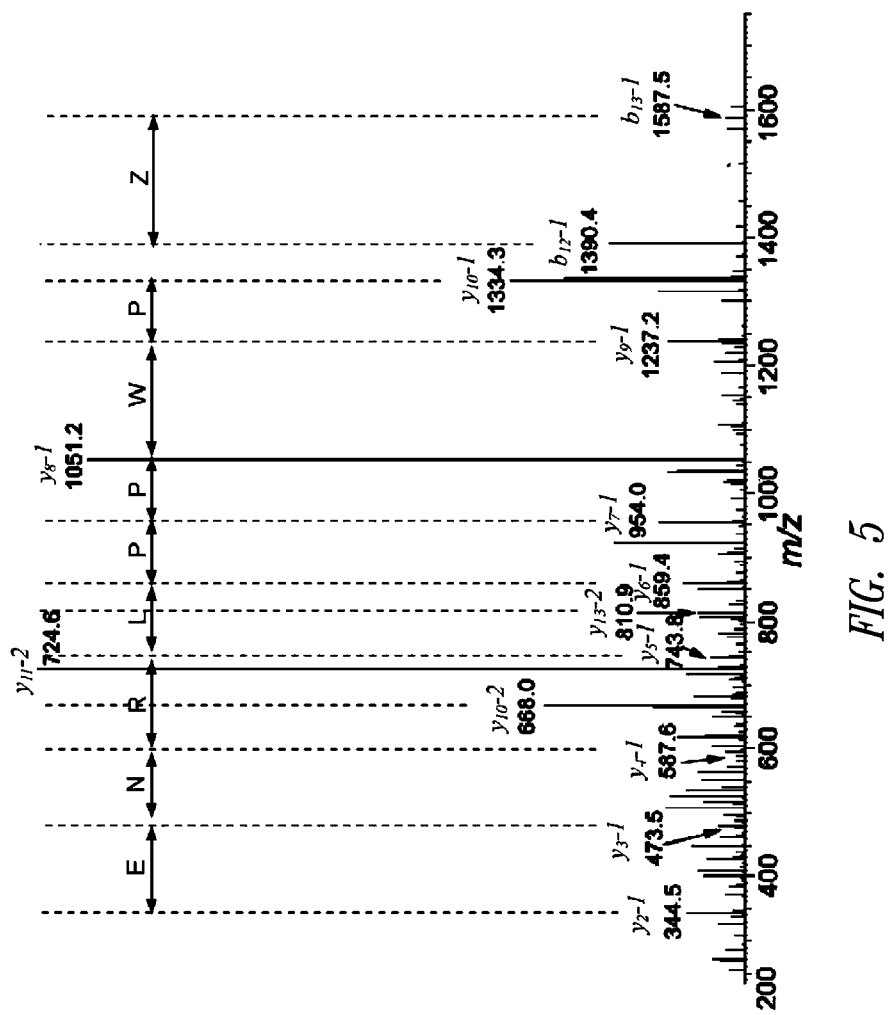
FIG. 5 Tandem mass spectrum of Peptide A (NGDLPWPPLRNEZK) (SEQ ID NO: 5) derived from DHFR expressed in media supplemented with amino acid 7 (3 mM) and amino acid 1 (0.03 mM). Partial sequence of PWPPLRNE (SEQ ID NO: 6) and residue Z (corresponding to amino acid 7) of Peptide A can be assigned from the annotated y and b ion series, respectively.
Figure 6A:
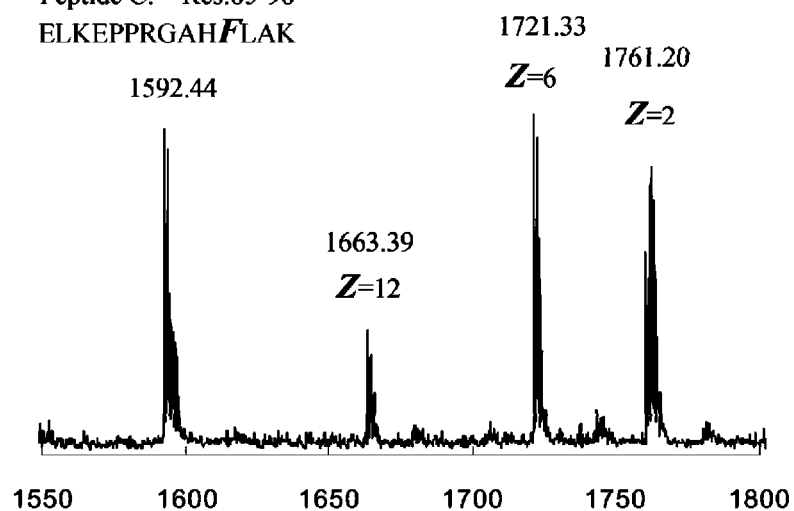
FIG. 6 shows MALDI-MS of proteolytic peptide fragments derived from mDHFR (Peptide A;SEQ ID NO:5) expressed in media supplemented with amino acid 2 (3 mM) and amino acid 6 (3 mM) and amino acid 1 (0.03 mM) and amino acid 13 (0.2 mM) (FIG. 6A); amino acid 2 (3 mM) and amino acid 6 (0.01 mM) and amino acid 1 (0.03 mM) and amino acid 13 (0.2 mM) (FIG. 6B); amino acid 3 (3 mM) and amino acid 6 (0.01 mM) and amino acid 1 (0.03 mM) and amino acid 13 (0.01 mM) (FIG, 6C). Peptide C (SEQ ID NO:113), with one Phe codon, is the control.
Figure 6B:
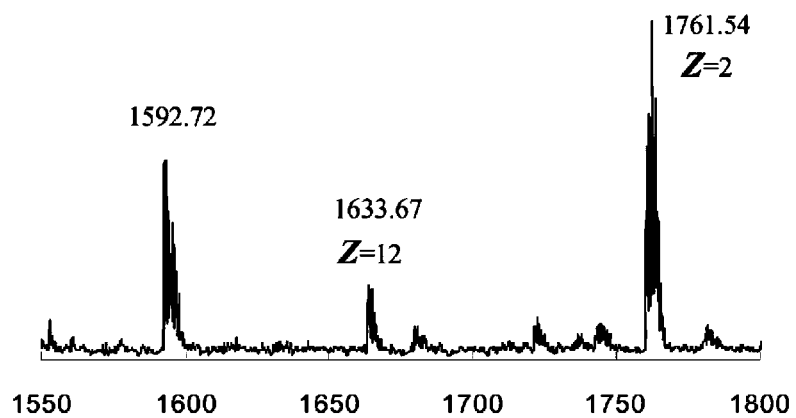
Figure 6C:
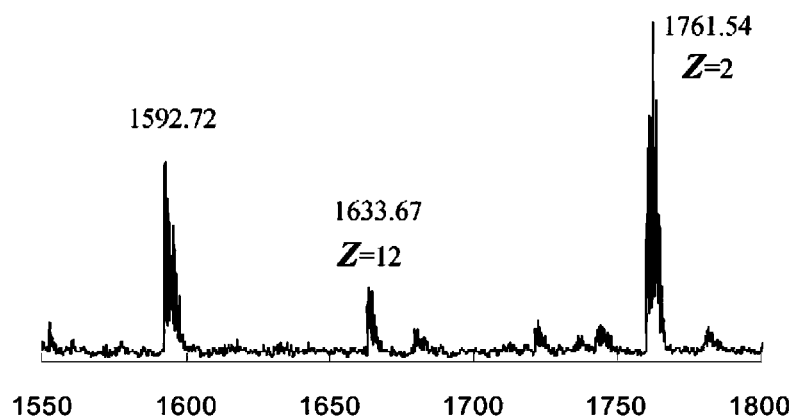
Figure 6D:
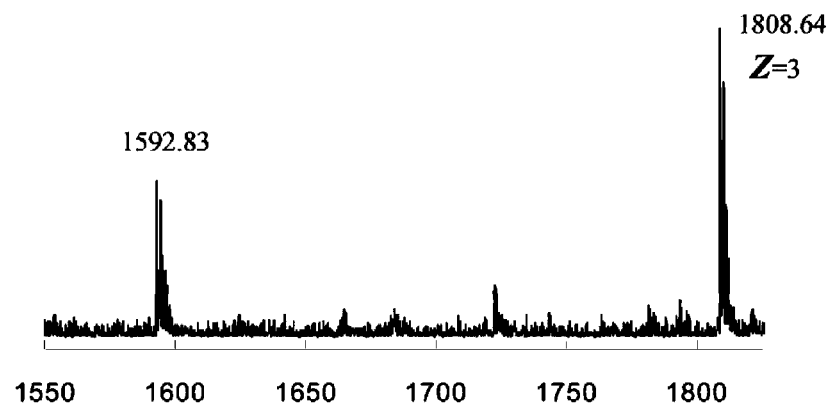
Figure 7A:
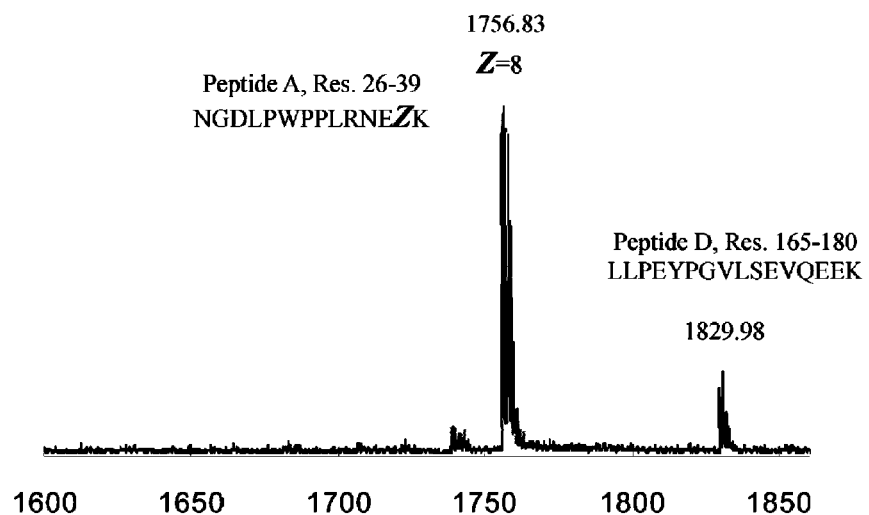
FIG. 7 shows MALDI-MS results of proteolytic peptide fragments derived from mDHFR (Peptide A;SEQ ID NO:5) expressed in media supplemented with amino acid 9 (3 mM) and amino acid 6 (0.03 mM) and amino acid 1 (0.01 mM) (FIG. 7A); amino acid 10 (3 mM) and amino acid 6 (0.03 mM) and amino acid 1 (0.03 mM) )(FIG. 7B); amino acid 11 (3 mM) and amino acid 6 (0.01 mM) and amino acid 1 (0.03 mM) )(FIG. 7C). Peptide D (SEQ ID NO:114) was the control.
Figure 7B:
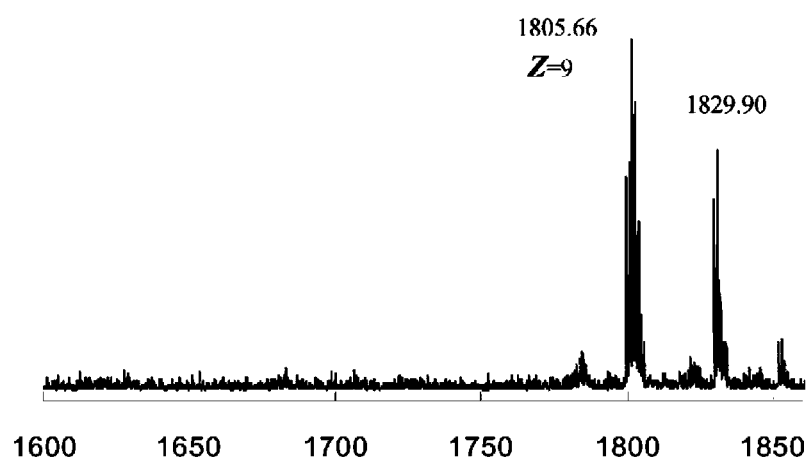
Figure 7C:
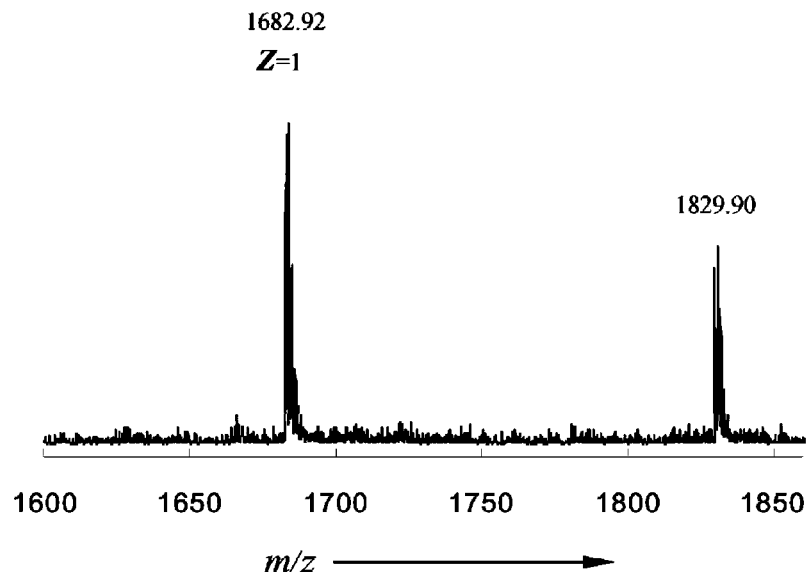
Figure 8:
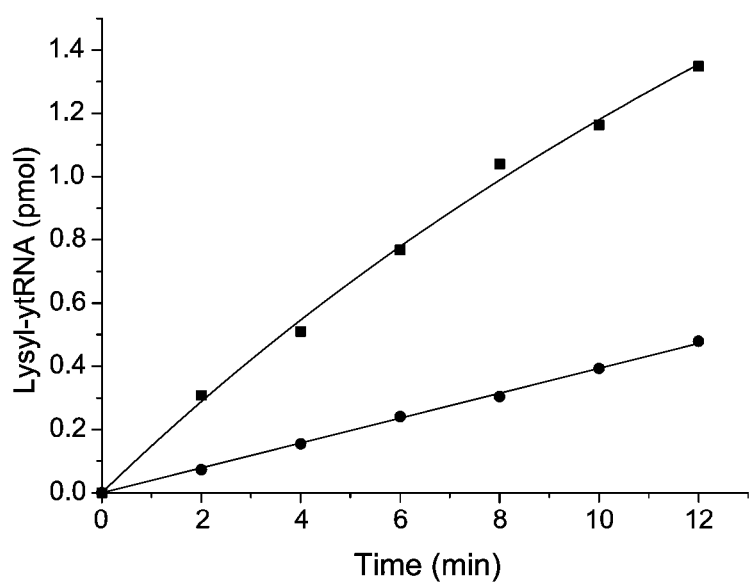
FIG. 8 shows the aminoacylation of yeast tRNA$^{Phe}_{CUA}$ (square) and tRNA$^{Phe}_{CUA\_UG}$ (circle) with lysine by eLysS.

| Amino Acid | Enzyme | Km (μM) | Kcat (s$^{-1}$) | Kcat/Km (M$^{-1}$s$^{-1}$) | Kcat/Km (relative)* |
|---|---|---|---|---|---|
| 1 | T415G | 264 +/− 42 | 0.05 +/− 0.002 | 184 +/− 30 | 1 |
| 2 | T415G | 22 +/− 3 | 0.03 +/− 0.001 | 1,538 +/− 228 | 8 |
| 3 | T415G | 12 +/− 2 | 0.05 +/− 0.001 | 4,365 +/− 797 | 24 |
| 4 | T415G | 11 +/− 3 | 0.05 +/− 0.002 | 4,558 +/− 1,186 | 25 |
| 5 | T415G | 757 +/− 149 | 0.4 +/− 0.003 | 48 +/− 10 | 1\4 |
| 6 | T415G | 20 +/− 5 | 0.30 +/− 0.006 | 15,000 +/− 4,063 | 82 |
| 7 | T415G | 27 +/− 2 | 0.04 +/− 0.001 | 1,550 +/− 125 | 8 |
| 8 | T415G | 20 +/− 8 | 0.20 +/− 0.018 | 10,256 +/− 4,562 | 56 |
| 9 | T415G | 8 +/− 4 | 0.55 +/− 0.097 | 70,876 +/− 34,843 | 385 |
| 10 | T415G | 31 +/− 18 | 0.06 +/− 0.005 | 1,939 +/− 1,149 | 10 |
| 11 | T415G | 94 +/− 50 | 0.05 +/− 0.006 | 533 +/− 293 | 3 |
| 1 | T415G | 68 +/− 20 | 0.52 +/− 0.093 | 7,627 +/− 2,664 | 41 |

Where the amino acids are indicated as in FIG. 2.

Example 11

The mutant yeast amber suppressor tRNA (ytRNA$^{Phe}_{CUA}$) was constitutively expressed under control of lpp promoter. The expression cassette of ytRNA$^{Phe}_{CUA}$ was inserted into repressor plasmid pREP4 to form pREP4-ytRNA as previously described in the Examples herein. The mutant yeast suppressor ytRNA$^{Phe}_{CUA}$_30U40G (ytRNA$^{Phe}_{CUA\_UG}$) was constructed from ytRNA$^{Phe}_{CUA}$ by use of a QUICK-CHANGE® mutagenesis kit. Two complementary oligonucleotides, designated as primer UG-f (5'-GAA CAC AGG ACC TCC ACA TTT AGA GTA TGG CGC TCT CCC-3') (SEQ ID NO: 16) for the forward primer and primer UG-r (5'-GGG AGA GCG CCA TAC TCT AAA TGT GGA GGT CCT GTG TTC-3') (SEQ ID NO: 17) for the reverse primer were synthesized to carry the specific mutation at either position 30 or position 40 of mutant yeast suppressor tRNA. The resulting plasmid carrying the gene encoding ytRNA$^{Phe}_{CUA\_UG}$ is designated as pREP4-ytRNA_UG. In order to construct the plasmids for in vitro transcription of ytRNA$^{Phe}$, the ytR- NA$^{Phe}_{CUA}$ and ytRNA$^{Phe}_{CUA\_UG}$ genes were amplified from template plasmid pREP4-ytRNA and pREP4-ytRNA_UG, respectively. At the end of the tRNA sequence, a BstNI site was inserted to produce accurate transcript of ytRNA$^{Phe}$. A T7 promoter sequence was added for in vitro transcription of ytRNA$^{Phe}$ by a T7 RNA polymerase. The following primers were used for the PCR: 5'-CTG GGT AAG CTT CGC TAA GGA TCT GCC CTG GTG CGA ACT CTG-3' (SEQ ID NO: 18) (with restriction sites HindIII and BstNI) and 5'-GAT TAC GGA TTC CTA ATA CGA CTC ACT ATA GCG GAC TTA GCT C-3' (SEQ ID NO: 19) (with EcoRI restriction site and a T7 promoter sequence). The resulting DNA was introduced into the HindIII and EcoRI sites of pUC18 to yield pUC18-ytRNA$^{Phe}_{CUA}$ and pUC18-ytRNA$^{Phe}_{CUA\_UG}$.

In order to facilitate DNA handling, one BstNI cleavage site close to the T7 promoter sequence of pUC18-ytRNA$^{Phe}_{CUA}$ was removed to increase the size of the DNA fragment containing the ytRNA$^{Phe}_{CUA}$ gene from 180 bp to 500 bp after BstNI digestion. Two complementary oligonucleotides, 5'-CGG AAG CAG AAA GTG TAA AGA GCG GGG TGC CTA ATG AGT G-3' (SEQ ID NO: 20) for the forward primer and 5'-CAC TCA TTA GGC ACC CCG CTC TTT ACA CTT TAT GCT TCC G-3' (SEQ ID NO: 21) for the reverse primer, were synthesized to carry the specific mutation.

Example 12

Linearized DNA was prepared by BstNI digestion of pUC18-ytRNA$^{Phe}_{CUA}$ and pUC18-ytRNA$^{Phe}_{CUA\_UG}$ as described previously (See Sampson, Uhlenbeck, PNAS USA 85: 1033-1037 (1988)). In vitro transcription of linearized DNA templates and purification of transcripts were performed as described previously (See Nowak, et al., Ion Channels pt. B 293: 504-529 (1998)). The in vitro transcription of linearized DNA to produce 76mer tRNA transcripts was performed with the AMBION® T7-MEGASHORTSCRIPT® kit. Transcripts were isolated with a 25:24:1 phenol:CHCl$_3$:isoamyl alcohol (PCI) extraction. The organic layer was re-extracted with water and a 24:1 CHCl$_3$:isoamyl alcohol (CI) was performed on the aqueous layers. The water layer was then mixed with an equal volume of isopropanol, precipitated overnight at −20° C., pelleted, dried, and re-dissolved in water. Unreacted nucleotides in the tRNA solution were eliminated using CHROMA SPIN-30® DEPC-H$_2$O (BD Bioscience®). Concentrations of the transcripts were determined by UV absorbance at 260 nm.

The aminoacylation of wild-type ytRNA$^{Phe}_{GAA}$ with Phe and Trp by yPheRS variants was performed as described previously (See Sampson, Uhlenbeck, PNAS USA 85: 1033-1037 (1988)). Aminoacylation reactions were carried out in the buffer containing 30 mM HEPES (pH 7.45), 15 mM MgCl$_2$, 4 mM DTT, 25 mM KCl, and 2 mM ATP at 30° C., in 100 microliter reaction volumes. Purified yeast total tRNA was used in the assay at final concentration of 4 mg/mL (ytRNA$^{Phe}_{GAA}$ concentration approximately 2.24 microM). For aminoacylation of Phe, 13.3 microM [$^3$H]-Phe (5.3 Ci/mmol) and 80 nM yPheRS variants were used; for aminoacylation of Trp, 3.3 microM [$^3$H]-Trp (30.0 Ci/mmol) and 160 nM yPheRS variants were used. Aminoacylation of ytRNA$^{Phe}$ transcripts was performed in 100 microliter reaction volumes in buffer containing 100 mM potassium-HEPES (pH 7.4), 10 mM MgCl$_2$, 1 mM DTT, 0.2 mM EDTA, 2 mM ATP, and 4 units/mL yeast inorganic pyrophosphatase at 37° C. for eLysS. For aminoacylation of Lys, 4 microM of ytRNA$^{Phe}$ transcript, 1.1 microM [$^3$H]-Lys (91 Ci/mmol) and 80 nM eLysS were used. The tRNAs were annealed before use by heating up to 85° C. for 4 minutes in the annealing buffer (60 mM Tris, pH 7.8, 2 mM MgCl$_2$) followed by slow cooling down to room temperature. Reactions were initiated by adding the enzyme and 10 microliter aliquots were quenched by spotting on Whatman filter disks soaked with 5% TCA. The filters were washed for three 10 minute periods in ice-cold 5% TCA, washed in ice-cold 95% ethanol, and counted via liquid scintillation methods.

Example 13

Plasmid construction for in vivo incorporation of a non-natural amino acid was performed in a Phe/Trp double auxotrophic strain, AFW, and a Phe/Trp/Lys triple auxotrophic strain, AFWK. The auxotrophic strains were constructed from a Phe auxotrophic strain, AF (K10, Hfr(Cavalli) pheS13rel-1 tonA22 thi T2R pheA18, trpB114) (See Furter, Prot. Sci, 7:419-426 (1998)) by P1 phage-mediated transposon transduction. A pQE16 vector (QIAGEN®) was chosen as the expression plasmid, which encodes a marker protein murine dihydrofolate reductase (mDHFR) with C-terminal hexa-histidine tag gene under control of a bacteriophage T5 promoter and t$_o$ terminator. Quick-change mutagenesis kit was used to place an amber codon (TAG) at the 38$^{th}$ position of mDHFR with two complementary oligonucleotides (5'-CCG CTC AGG AAC GAG TAG AAG TAC TTC CAA AGA ATG-3' (SEQ ID NO: 11); 5'-CAT TCT TTG GAA GTA CTT CTA CTC GTT CCT GAG CGG-3') (SEQ ID NO: 12) to yield pQE16am. The mutant yPheRS genes T415G and T415A were amplified from pQE32-T415G and pQE32-T415A and a constitutive tac promoter with an abolished lac repressor binding site was added into the upstream of the start codon of the gene. The entire expression cassette of T415G and T415A were inserted into PvuII site of pQE16am-T415G and pQE16am-T415A.

Example 14

The auxotrophic bacterial strains AF, AFW, and AFWK were transformed with plasmid pQE16am containing yPheRS variants and pREP4-ytRNA vectors containing ytRNA variants to investigate pBrF incorporation. The E. coli expression strains were grown in M9 minimal medium supplemented with glucose, thiamin, MgSO$_4$, CaCl$_2$, 20 amino acids (at 25 mg/L) antibiotics (35 micrograms/mL of kanamycin and 100 micrograms/mL of ampicillin). When cells reached an OD$_{600}$ of 0.8-1.0, they were sedimented by centrifugation, washed twice with cold 0.9% NaCl, and shifted to expression media supplemented with 17 amino acids (at 20 mg/L), 6 mM of pBrF (p-bromo-phenylanine) or plodoF(p-iodo-phenylalanine), and the indicated concentrations of phenylalanine, tryptophan, and lysine. Protein expression was induced by the addition of 1 mM IPTG. After four hours expression, cells were pelleted by centrifugation, and the protein was purified by virtue of C-terminal hexa-histidine tag through a nickel-NTA spin column according to manufacturer's directions (QIAGEN®). After purification, expression levels of mDHFR were determined by UV absorbance at 280 nm.

Example 15

Figure 12:
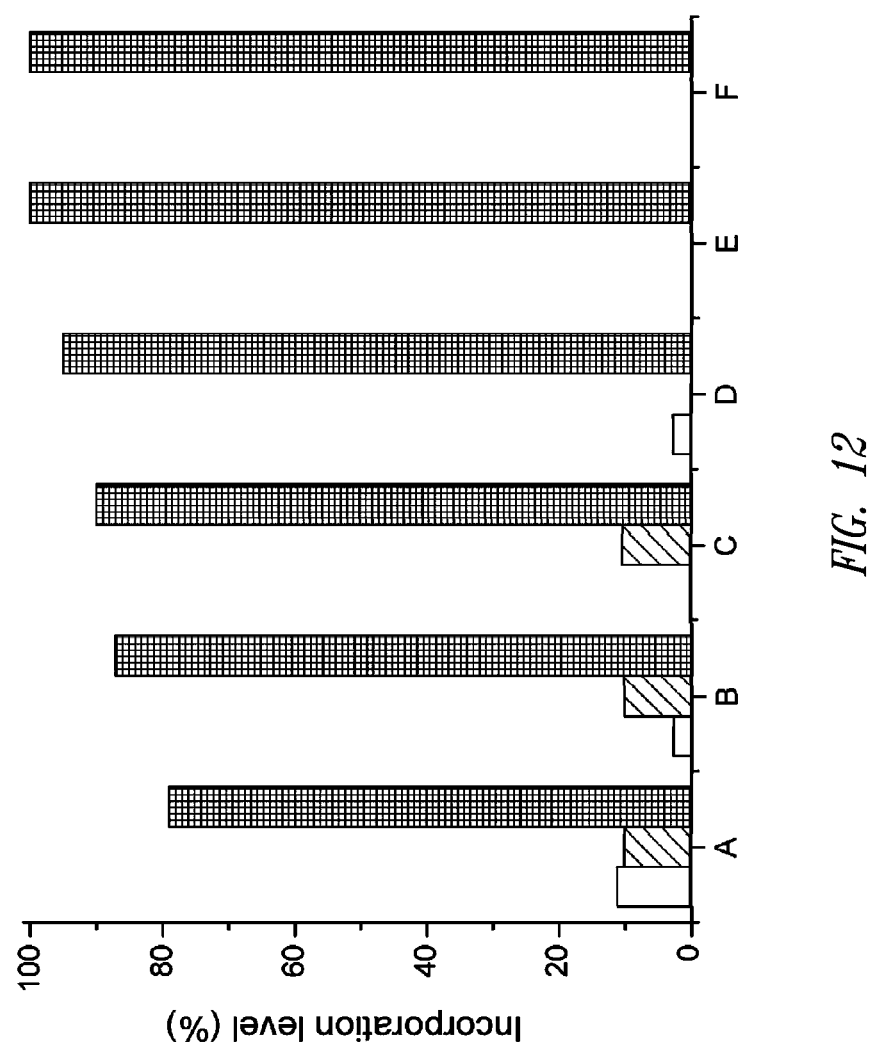
FIG. 12 shows incorporation of lysine (open square), tryptophan (cross-hatch) or p-bromophenylalanine (checker board).

LC-MS/MS analysis of tryptic digests of mDHFR was conducted on a Finnigan LCQ ion trap mass spectrometer with HPLC pump and ESI probe. Mutant mDHFR purified under denaturing conditions was in elution buffer (8 M urea, 100 mM NaH$_2$PO$_4$, 10 mM Tris, pH 4.5). For trypsin digestion, 10 microL of the solution was diluted into 90 microL of 75 mM $(NH_4)_2CO_3$. One microliter of modified trypsin (0.2 micrograms/microliter) was added. The sample was incubated at 37° C. for 2 to 6 hours. The digestion reaction was stopped by addition of 12 microL of 5% TFA solution. Digested peptide solution was subjected to desalting with C18 Vydac Microspin column (the Nest group) and eluted with 50 microL of 80% of acetonitrile and 20% of 0.1% w/v formic acid. Digested peptide solution eluted form Microspin column was dried, redissolved in 10% acetronitrile and 90% of 0.1% TFA solution, and injected into HPLC pump. Peptides were separated by Magic C18 column (Michrom, 300 Å, 0.3×150 mm) and eluted at a flow rate of 30 microL/min using a gradient of 10-95% of solvent A (90% of acetonitrile and 10% of 0.1 M acetic acid solution) and solvent B (2% of acetonitrile and 98% of 0.1 M acetic acid solution) for 30 minutes. The column eluent flow to the electrospray source and each signal of tryptic digest was detected. Tandem mass sequencing was carried out simultaneously by fragmentation of the precursor ion with m/z corresponding to protease-digested fragment including the residue at position 38 of mutant mDHFR. Thus, DHFR polypeptides were synthesized in a triple auxotrophic host cell with (a), (b) yeast $tRNA^{Phe}_{CUA}$ and yeast PheRS (T415G); (c) yeast $tRNA^{Phe}_{CUA\_UG}$ and yeast PheRS (T415G); (d) yeast $tRNA^{Phe}_{CUA}$ and yeast PheRS (T415A); (e) yeast $tRNA^{Phe}_{CUA\_UG}$ and yeast PheRS (T415A) or (f) in a single auxotrophic strain with yeast $tRNA^{Phe}_{CUA\_UG}$ and yeast PheRS (T415A), the results of which are shown in FIG. 12.

Example 16

The binding pocket of TrpRS from *Bacillus sterothermophillus* was mutated in order to incorporate non-natural amino acids into polypeptides. Candidate sites for mutational analysis include amino acid sequence position number 4 (F), 5 (F), 7 (N), 132 (D), 133 (I), 141 (V) and 143 (V) which lie in a region recognized as the hydrophobic amino acid binding pocket.

TrpRS Kinetic Data for F5Y Substitution:

| TrpRS | Electrostatics (kcal/mol) | VDW (kcal/mol) | Total |
| --- | --- | --- | --- |
| Wild type | −53.94 +/− 5.32 | −25.78 +/− 0.35 | −79.75 +/− 5.08 |
| F5Y | −63.04 +/− 2.47 | −25.26 +/− 0.43 | −88.32 +/− 2.59 |
| Difference | −9.1 | +0.5 | −8.6 |

The fused ring of tryptophan gears the recognition site toward the second aromatic ring. As it is more "meta" than "para" in conformation, a mutation of position 132 (D to G) was tested. Briefly, molecular modeling revealed that the 6-ethynyl indole clashes with the Phe5 backbone which inhibited movement. Without backbone movement, the amino acid (analog) will not fit into the binding pocket. As the amino acid at position 132 (D) is highly conserved, we predicted that its modification may disrupt a hydrogen bond network within the TrpRS. Thus, 5-ethynyl tryptophan was computationally modeled in the binding site since it did not clash with the amino acid at location 132. In order to accommodate this analog, the amino acid sequence position 143 was mutated (to A and G, respectively). The binding differentiation was found to be 5.8 kcal/mol (V143A) and 4.4 kcal/mol (V143G) for the binding of 5-ethynyl tryptophan, which distinguish tryptophan from the analog.

Additionally, mutating the amino acid sequence position number 132 to other amino acids was tested. The kinetic data are shown in the table below:

TrpRS Kinetic Data for Mutations in Binding Site:

| Tryptophan | Km (μM) | Kcat ($s^{-1}$) |
| --- | --- | --- |
| Wild type | 1.6 +/− 0.1 | 1.1 +/− 0.03 |
| D132N | 12.1 +/− 1.6 | 0.0067 +/− 0.0003 |
| D132S | 17.8 +/− 2.3 | 0.055 +/− 0.004 |
| D132T | 8.6 +/− 1.4 | 0.011 +/− 0.0008 |

Example 17

Figure 13:
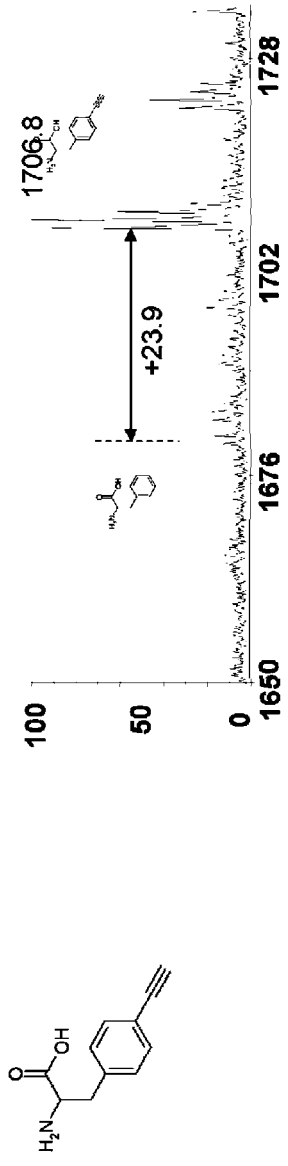
FIG. 13 shows mass spectra of p-ethynylphenylalanine incorporated into a polypeptide using a modified tRNA synthetase (T415G) and tRNA$^{Phe}$ with an amber suppressor in a host cell.

A yeast PheRS library (using green fluorescent protein or GFP) was screened to identify PheRS mutations that enable the incorporation of NaI. Specific amino acid sequence positions that were mutated include residue numbers 412, 415, 418, and 437, which are located in the binding site and contact the amino acid. As indicated in FIG. 13, p-ethynyl-phenylalanine was incorporated into a test protein using the modified yeast PheRS.

Briefly, GFP was ligated into a vector containing the mutant T415G or wild type yeast PheRS gene according to standard procedures. The mutant yeast amber suppressor tRNA ($ytRNA^{Phe}_{AAA}$) was constitutively expressed under control of lpp promoter and transformed into a Phe/Trp double *E. coli* auxotrophic strain AFW. Cells were grown in M9 minimal medium supplemented with glucose, thiamin, $MgSO_4$, $CaCl_2$, 20 amino acids (at 25 mg/L), antibiotics (35 μg/mL of kanamycin and 100 μg/mL of ampicillin). When cells reached an $OD_{600}$ of 0.8-1.0, cells were pelleted and washed twice by ice-cold 0.9% NaCl and shifted to expression media supplemented with 18 amino acids (at 20 mg/L) and various concentrations of phenylalanine, tryptophan and 2NaI. Protein expression was induced by IPTG.

Example 18

Mutagenesis of the four amino acid residues selected (N412, T145, S418, and S437) were conducted by two step PCR mutation. Briefly, a series of PCR mutagenesis were performed at $GFP_{UV}$ gene in a $pQE9\_GFP_{UV}$ plasmid (STRATAGENE®), using four complementary pairs of primers (F64LS65T_f: 5'-CTT GTC ACT ACT CTG ACC TAT GGT GTT CAA TGC TTC TCC CGT-3' (SEQ ID NO: 22); F64LS65T_r: 5'-ACG GGA GAA GCA TTG AAC ACC ATA GGT CAG AGT AGT GAC AAG-3' (SEQ ID NO: 23); S99F_f: 5'-GTA CAG GAA CGC ACT ATA TTC TTC AAA GAT GAC GGG AAC-3' (SEQ ID NO: 24); S99F_r: 5'-GTT CCC GTC ATC TTT GAA GAA TAT AGT GCG TTC CTG TAC-3' (SEQ ID NO: 25); T153M_f: 5'-CAC AAT GTA TAC ATC ATG GCA GAC AAA CAA AAG AAT GGA-3' (SEQ ID NO: 26); T153M_r: 5'-TCC ATT CTT TTG TTT GTC TGC CAT GAT GTA TAC ATT GTG-3' (SEQ ID NO: 27)).

The GFP mutants were generated as described herein. Briefly, a GFP3 has 12 Phe residues of which five are encoded by Phe wobble codons (UUU). A GFP5 and a GFP6 variant were prepared by replacing UUC codons with UUU codons using two-step PCR reactions followed by ligation. A GFP5 was prepared by replacing four UUC codons and one Leu codon at F8, L64, F84, F99 and F165 residues with UUU codons using twelve primers (1: 5'-GTG CCA CCT GAC GTC TAA GAA ACC ATT ATT ATC ATG ACA TTA ACC-3' (SEQ ID NO: 28) 2: 5'-GAG TAA AGG AGA AGA ACT TTT TAC TGG AGT TGT CCC AAT TC-3' (SEQ ID NO: 29) 3: 5'-GAA TTG GGA CAA CTC CAG TAA AAA GTT CTT CTC CTT TAC TC-3' (SEQ ID NO: 30) 4: 5'-GGC CAA CAC TTG TCA CTA CTT TTA CCT ATG GTG TTC AAT GCT T-3' (SEQ ID NO: 31) 5: 5'-AAG CAT TGA ACA CCA TAG GTA AAA GTA GTG ACA AGT GTT GGC C-3' (SEQ ID NO: 32) 6: 5'-CAT ATG AAA CGG CAT GAC TTT TTT AAG AGT GCC ATG CCC GAA G-3' (SEQ ID NO:33) 7: 5'-CTT CGG GCA TGG CAC TCT TAA AAA AGT CAT GCC GTT TCA TAT G (SEQ ID NO: 34) 8: 5'-GTT ATG TAC AGG AAC GCA CTA TAT TTT TCA AAG ATG ACG GGA ACT ACA A-3' (SEQ ID NO: 35) 9: 5'-TTG TAG TTC CCG TCA TCT TTG AAA AAT ATA GTG CGT TCC TGT ACA TAA C-3' (SEQ ID NO: 36) 10: 5'-ACA AAA GAA TGG AAT CAA AGC TAA CTT TAA AAT TCG CCA CAA CAT TGA AGA TG-3' (SEQ ID NO: 37) 11: 5'-CAT CTT CAA TGT TGT GGC GAA TTT TAA AGT TAG CTT TGA TTC CAT TCT TTT GT-3' (SEQ ID NO: 38); 12: 5'-CGC CAA GCT AGC TTG GAT TCT CAC CAA TAA AAA ACG CCC-3' (SEQ ID NO: 39) Five partially overlapping fragments of GFP3 expression cassettes were obtained by five PCR reactions with five sets of primers (1 and 3; 2 and 5; 4 and 7; 6 and 9; 8 and 10).

These PCR products were purified by agarose gel electrophoresis followed by gel extraction. A GFP6 of which all Phe residues are encoded by UUU was prepared by replacing two Phe codons (F71 and F99) of GFP5 with UUU codons using six primers. (1 and 12 are the same as above; 13: 5'-TAC CTA TGG TGT TCA ATG CTT TTC CCG TTA TCC GGA TCA TAT G-3' (SEQ ID NO: 40); 14: 5'-CAT ATG ATC CGG ATA ACG GGA AAA GCA TTG AAC ACC ATA GGT A-3' (SEQ ID NO: 41); 15: 5'-GTT ATG TAC AGG AAC GCA CTA TAT TTT TTA AAG ATG ACG GGA ACT ACA AG-3' (SEQ ID NO: 42); 16: 5'-CTT GTA GTT CCC GTC ATC TTT AAA AAA TAT AGT GCG TTC CTG TAC ATA AC-3' (SEQ ID NO: 43)).

Example 19

Library construction was performed in two steps as well. Briefly, saturation mutagenesis in four residues (N412, T415, S418 and S437) was accomplished with two step PCR mutagenesis. First, degenerate codons were introduced into S437 by PCR mutagenesis with two complementary primers (437_f: 5'-GTC GAA ATC GGT AAC NNK GGT ATG TTC AGA CCA GAA ATG CTC G-3' (SEQ ID NO: 44); 437_r: 5'-C GAG CAT TTC TGG TCT GAA CAT ACC MNN GTT AC C GAT TTC GAC-3' (SEQ ID NO: 45)). After 1 hr digestion of PCR product with DpnI, PCR product was transformed into XL-1 blue cloning host. The plasmids of the 437th position were saturated and isolated and used as a template for 2nd PCR mutagenesis to introduce mutation at residues N412, T415 and S418. The 2nd PCR mutagenesis was performed with another complementary primer pair (412_418_f: 5'-C AAG CCT ACC TAC NNK CCT TAC NNK GAG CCA NNK ATG GAA ATC TTT T-3' (SEQ ID NO: 46); 412_418_r: 5'-A AAA GAT TTC CAT MNN TGG CTC MNN GTA AGG MN N GTA GG T AGG CTT G-3' (SEQ ID NO: 47)). Following PCR, the products were digested with DpnI for 1 hr, it was cleaned and concentrated by spin column. Elute was electroporated into ElectroTen-Blue electrocompetent cell (Stratagene) according to manufacturer's protocol. Eight million transformants were obtained. The library plasmid was expanded in culture and digested with NsiI and BglII. After purification of these inserts, they was ligated with large fragments of pQE9_GFP6_yPheRS (T415G) and pQE9_GFP9_yPheRS (T415G) obtained by digestion with NsiI and BglII.

The library was transformed into chemical-competent AFW and DHF E. coli cells. These cells were then inoculated into 2×YT media with kanamycin and grown overnight. When cells reached an $OD_{600}$ of 0.8, cells were pelleted and resuspended in distilled water. Glycerol stocks of the library were expressed as is standard in the art.

Figure 14A:
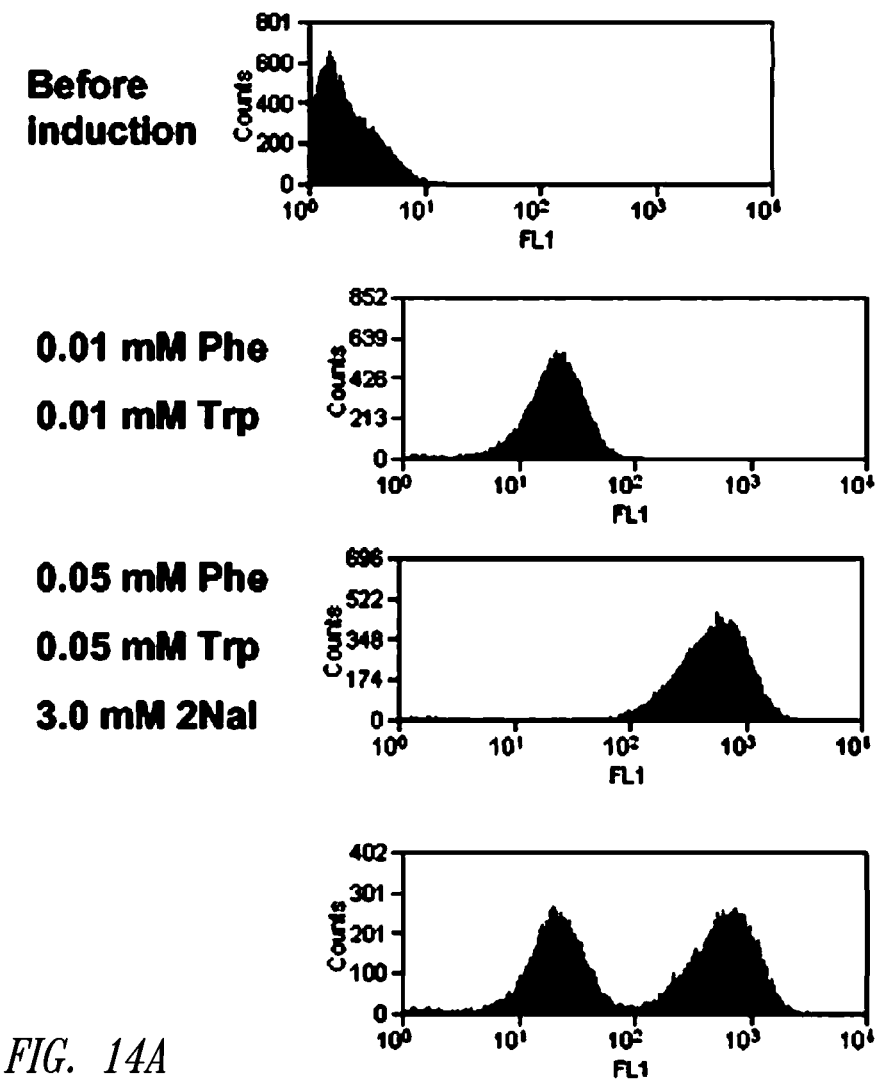
FIGS. 14A and 14B show FACS of green fluorescent protein (GFP) incorporation of amino acids using amber suppression codon in a test protein.
Figure 14B:
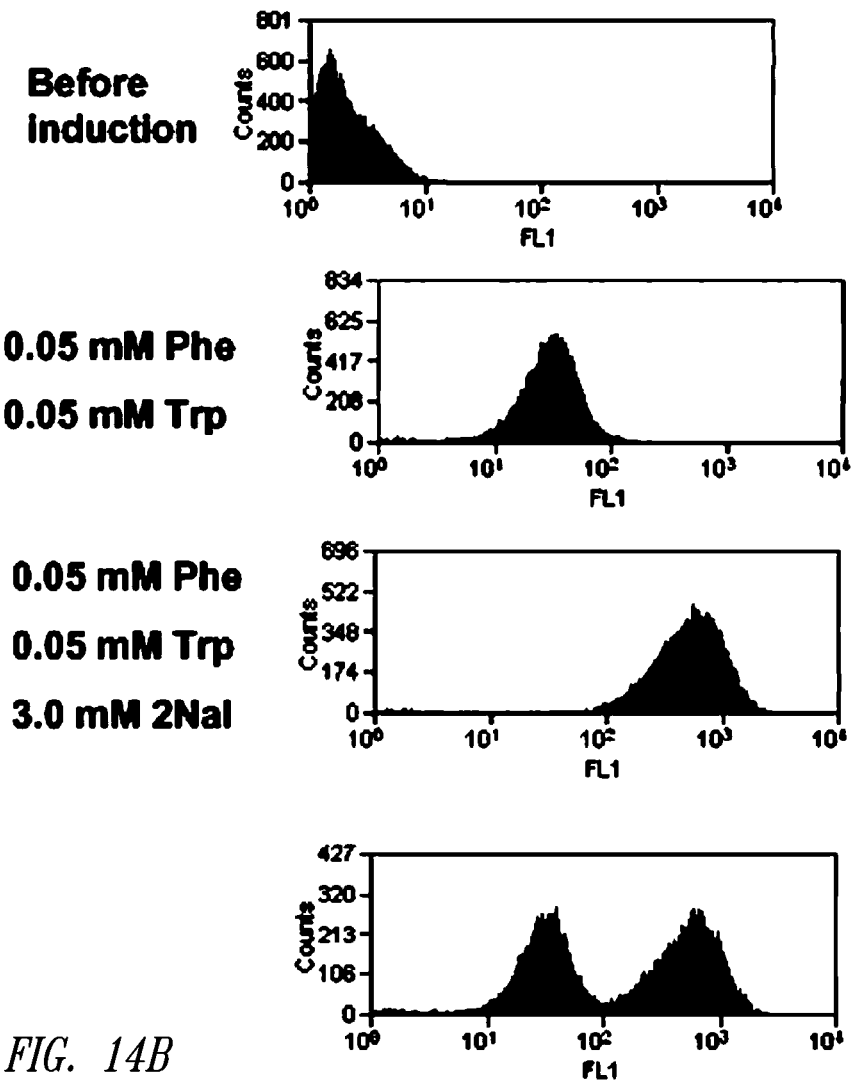
Figure 15:
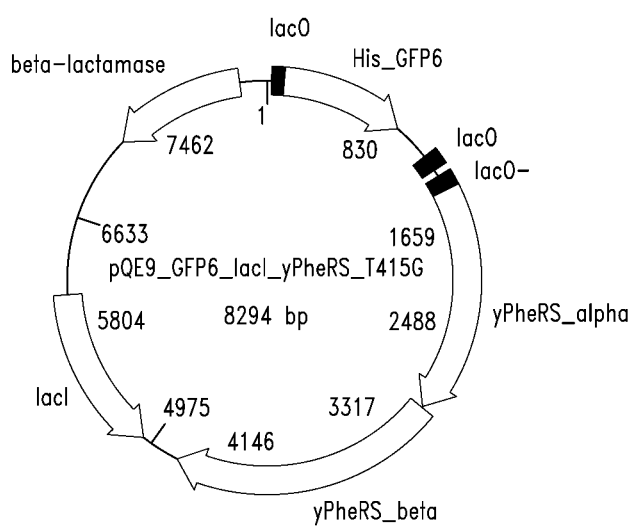
FIG. 15 illustrates an exemplary plasmid mapping of a mutant aminoacyl tRNA synthetase (T415G).

After expression of GFP for 3 hours, 1 mL of cells (based on $OD_{600}$ of 1.0) were washed with PBS and diluted in distilled water, then subjected to flow cytometric analysis (Mo-Flo Cell Sorter®, DakoCytomation, Fort Collins, Colo.), using an excitation wavelength of 488 nm, emission of 525 nm, and a cut-off filter of 495 nm. At least 20,000 events were collected in each measurement. Data were analyzed with Summit software (DakoCytomation). Library screening was done both positively and negatively, that is the yPheRS variants that enable the high incorporation of 2NaI or any other natural amino acids except Phe at UUU codons will unfold GFP and are less bright, and so low fluorescence cells are collected. The yPheRS variants that do not allow incorporation of any other natural amino acids except Phe at UUU codons will not affect GFP folding and are bright. Thus, bright cells are collected. FIG. 14 illustrates histograms of GFP yPheRS library screening.

Example 20

A modified MetRS from E. coli that was mutated at amino acid sequence position 13 (L→G) to incorporate azidonorleucine into a test protein (DHFR) in plasmid pQE-80, according to the methods described herein for other Examples, and at SEQ ID NO:1. In this particular exemplary embodiment, the DHFR and MetRS genes are located in the same plasmid vector.

Example 21

Interferon-beta molecule was used as a test molecule to mutate three out of four methionine residues to other replacement amino acids (including non-natural amino acids). Methionine residues at amino acid positions 36, 62 and 117 were mutated to other amino acids via side chain rotamer excitation analysis. Structures were optimized using molecular dynamics software and the energy calculations of the mutated structures, including salvation. Next, comparisons were made of the energy calculations of the wild type interferon beta molecule with the modified interferon beta molecule in order to determine the overall stability of the modified molecule. Results of energy calculations with the various point mutations are shown in the tables below:

Mutation at Position 36 of Human Interferon Beta:

| Mutation | Energy |
|---|---|
| M→H | −0.2 kcal/mol |
| M→C | −0.2 kcal/mol |
| M→I | +1.0 kcal/mol |
| M→T | +1.4 kcal/mol |
| M→V | +1.6 kcal/mol |
| M→A | +4 kcal/mol |

Mutation at Position 62 of Human Interferon Beta:

| Mutant | Energy (kcal/mol) |
|---|---|
| H | +1.1 |
| G | 0 |
| Y | −2.2 |
| S | −4.7 |
| Q | −4.8 |
| A | −5.0 |
| N | −5.7 |
| F | −7.4 |
| T | −8.8 |
| Wild type | −11.6 |

Mutation at Position 117 of Human Interferon Beta:

| Mutation | Energy |
|---|---|
| M→I | −1.2 kcal/mol |
| M→L | −1.0 kcal/mol |
| M→V | −0.1 kcal/mol |
| M→T | +3 kcal/mol |
| M→Y | +3 kcal/mol |
| M→S | +4 kcal/mol |
| M→G | +5.9 kcal/mol |

All of the above U.S. patents, U.S. patent application publications, U.S. patent applications, foreign patents, foreign patent applications, and non-patent publications referred to in this specification and/or listed in the Application Data Sheet, are herein incorporated by reference in their entireties.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Equivalents

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The invention claimed is:

1. A composition comprising a first vector containing a polynucleotide encoding a modified phenylalanyl-tRNA synthetase (PheRS), wherein said modified PheRS is mutated at amino acid sequence position 415 and one or more amino acids selected from the group consisting of amino acid sequence positions 412, 418, and 437 of the polypeptide encoded by the polynucleotide of SEQ ID NO:3, and wherein said modified PheRS is capable of charging a tRNA molecule with a non-natural amino acid.

2. The composition of claim 1, wherein said modified PheRS is mutated at amino acid sequence positions selected from the group consisting of: (i) the amino acid sequence position numbers 412 and 415; (ii) the amino acid sequence position numbers 415 and 418; (iii) the amino acid sequence position numbers 415 and 437; (iv) the amino acid sequence position numbers 412, 415 and 437; (v) the amino acid sequence position numbers 415, 418 and 437; (vi) the amino acid sequence position numbers 412, 415 and 418; and (vii) the amino acid sequence position numbers 412, 415, 418 and 437.

3. The composition of claim 1, further comprising a second vector containing a polynucleotide encoding a modified tRNA molecule.

4. The composition of claim 3 wherein said first and second vectors are the same vector.

5. The composition of claim 3 wherein said first and second vectors are different vectors.

6. The composition of claim 3, wherein said modified tRNA is modified such that it contains a mutated anticodon that base pairs with a corresponding wobble degenerate codon with an affinity greater than the affinity of the natural tRNA.

7. The composition of claim 1 wherein said non-natural amino acid is selected from the group consisting of: azido-norleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-iodophenylalanine, p-azidophenylalanine, p-acetylphenylalanine, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

8. A polypeptide comprising a modified phenylalanyl-tRNA synthetase (PheRS), wherein said modified PheRS is mutated at amino acid sequence position 415 and one or more amino acids selected from the group consisting of amino acid sequence positions 412, 418, and 437 of the polypeptide encoded by the polynucleotide of SEQ ID NO:3, and wherein said modified AARS is capable of charging a tRNA molecule with a non-natural amino acid.

9. The polypeptide of claim 8, wherein said PheRS is mutated at amino acid sequence positions selected from the group consisting of: (i) the amino acid sequence position numbers 412 and 415; (ii) the amino acid sequence position numbers 415 and 418; (iii) the amino acid sequence position numbers 415 and 437; (iv) the amino acid sequence position numbers 412, 415 and 437; (v) the amino acid sequence position numbers 415, 418 and 437; (vi) the amino acid sequence position numbers 412, 415 and 418; and (vii) the amino acid sequence position numbers 412, 415, 418 and 437.

10. A translation system comprising a polynucleotide encoding a modified phenylalanyl-tRNA synthetase (PheRS), wherein said modified PheRS is mutated at amino acid sequence position 415 and one or more amino acids selected from the group consisting of amino acid sequence positions 412, 418, and 437 of the polypeptide encoded by the polynucleotide of SEQ ID NO:3, and wherein said modified PheRS is capable of charging a tRNA molecule with a non-natural amino acid.

11. The translation system of claim 10 wherein said system comprises a host cell.

12. The translation system of claim 10 further comprising a polynucleotide encoding a modified tRNA molecule.

13. The translation system of claim 12, wherein said modified tRNA molecule comprises a mutated anticodon that base pairs with a corresponding wobble degenerate codon with an affinity greater than the affinity of the natural tRNA molecule.

14. The translation system of claim 12 wherein said modified tRNA molecule is derived from a eukaryotic cell and the host cell is a prokaryotic cell.

15. The translation system of claim 11 wherein the host cell is a phenylalanine auxotroph.

16. The translation system of claim 11 further comprising a culture media containing one or more non-natural amino acids.

17. The translation system of claim 10 wherein said one or more non-natural amino acids are selected from the group consisting of: azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-iodophenylalanine, p-azidophenylalanine, p-acetylphenylananine, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

18. A method for incorporating at least one non-natural amino acid into a target polypeptide at one or more specified location(s), the method comprising: providing a translation system containing at least one non-natural amino acid; providing to the translation system one or more modified phenylalanyl-tRNA synthetase (PheRS), wherein said modified PheRS is mutated at amino acid sequence position 415 and one or more amino acids selected from the group consisting of amino acid sequence positions 412, 418, and 437 of the polypeptide encoded by the polynucleotide of SEQ ID NO:3, and wherein said modified PheRS is capable of charging a tRNA molecule with a non-natural amino acid; providing to the translation system a polynucleotide encoding the target polypeptide; and allowing translation of the target polypeptide, thereby incorporating at least one non-natural amino acid into the target polypeptide.

19. A polypeptide made by the method of claim 18.

20. The method of claim 18 wherein said polypeptide is human growth hormone.

21. The method of claim 18, wherein said translation system comprises a cell, and the cell is a phenylalanine auxotroph.

22. The method of claim 18, wherein the translation system comprises a cell is selected from the group consisting of: yeast cell, eubacterial cell, eukaryotic cell; fungal cell, mammalian cell, insect cell, plant cell, and *Pseudomonas* cell.

23. The method of claim 18, wherein said target polypeptide is human growth hormone.

24. The composition of claim 6, wherein said modified tRNA is tRNA$^{Phe}$ outfitted with the AAA anticodon.

25. The translation system of claim 13, wherein said modified tRNA is tRNA$^{Phe}$ outfitted with the AAA anticodon.

26. The translation system of claim 10, wherein said modified PheRS is mutated at amino acid sequence positions selected from the group consisting of: (i) the amino acid sequence position numbers 412 and 415; (ii) the amino acid sequence position numbers 415 and 418; (iii) the amino acid sequence position numbers 415 and 437; (iv) the amino acid sequence position numbers 412, 415 and 437; (v) the amino acid sequence position numbers 415, 418 and 437; (vi) the amino acid sequence position numbers 412, 415 and 418; and (vii) the amino acid sequence position numbers 412, 415, 418 and 437.

27. The translation system of claim 26, wherein said PheRS is mutated at the amino acid sequence position numbers 412, 415, 418 and 437.

28. The method of claim 18, wherein said modified PheRS is mutated at amino acid sequence positions selected from the group consisting of: (i) the amino acid sequence position numbers 412 and 415; (ii) the amino acid sequence position numbers 415 and 418; (iii) the amino acid sequence position numbers 415 and 437; (iv) the amino acid sequence position numbers 412, 415 and 437; (v) the amino acid sequence position numbers 415, 418 and 437; (vi) the amino acid sequence position numbers 412, 415 and 418; and (vii) the amino acid sequence position numbers 412, 415, 418 and 437.

29. The method of claim 28, wherein said PheRS is mutated at the amino acid sequence position numbers 412, 415, 418 and 437.

30. The method of claim 18, wherein said tRNA molecule is modified such that it contains a mutated anticodon that base pairs with a corresponding wobble degenerate codon with an affinity greater than the affinity of the natural tRNA.

31. The method of claim 18, wherein said translation system comprises a host cell and a modified tRNA, wherein said modified tRNA is modified such that it contains a mutated anticodon that base pairs with a corresponding wobble degenerate codon with an affinity greater than the affinity of the natural tRNA, and wherein said modified PheRS and/or said modified tRNA is derived from an organism different than the host cell.

32. The method of claim 31, wherein said modified tRNA is tRNA$^{Phe}$ outfitted with the AAA anticodon.

33. The composition of claim 2, wherein said modified PheRS is mutated at the amino acid sequence position numbers 412, 415, 418 and 437.

34. The polypeptide of claim 9, wherein said PheRS is mutated at the amino acid sequence position numbers 412, 415, 418 and 437.

* * * * *

SEQUENCE LISTING

```
<160> NUMBER OF SEQ ID NOS: 115

<210> SEQ ID NO 1
<211> LENGTH: 7790
<212> TYPE: DNA
<213> ORGANISM: Artificial Sequence
<220> FEATURE:
<223> OTHER INFORMATION: Modified mouse, dihydrofolate reductase gene
      and E. coli MetRs gene

<400> SEQUENCE: 1
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc ggcatcatgg ttcgaccatt gaactcgatc     180
gtcgccgtgt cccaaaatat ggggattggc aagaacggag acctaccctg gcctccgctc     240
aggaacgagt tcaagtactt ccaaagaatg accacaacct cttcagtgga aggtaaacag     300
aatctggtga ttatgggtag gaaaacctgg ttctccattc ctgagaagaa tcgaccttta     360
aaggacagaa ttaatatagt tctcagtaga gaactcaaag aaccaccacg aggagctcat     420
tttcttgcca aaagtttgga tgatgcctta agacttattg aacaaccgga attggcaagt     480
aaagtagaca tggtttggat agtcggaggc agttctgttt accaggaagc catgaatcaa     540
ccaggccacc ttagactctt tgtgacaagg atcatgcagg aatttgaaag tgacacgttt     600
ttcccagaaa ttgatttggg gaaatataaa cttctcccag aatacccagg cgtcctctct     660
gaggtccagg aggaaaaagg catcaagtat aagtttgaag tctacgagaa gaaaggttgg     720
aagatcttaa gcttaattag ctgagcttgg actcctgttg atagatccag taatgacctc     780
agaactccat ctggatttgt tcagaacgct cggttgccgc cgggcgtttt ttattggtga     840
gaatccaagc tagctctaga gacgtccggc cggagctcca ccgcggtggc ggccgctcta     900
gagtcactta cttaacattt tcccatttgg tactatctaa ccccttttca ctattaagaa     960
```

```
gtaatgccta ctatgactca agtcgcgaag aaaattctgg tgacgtgcgc actgccgtac   1020
gctaacggct caatccacct cggccatatg ctggagcaca tccaggctga tgtctgggtc   1080
cgttaccagc gaatgcgcgg ccacgaggtc aacttcatct gcgccgacga tgcccacggt   1140
acaccgatca tgctgaaagc tcagcagctt ggtatcaccc cggagcagat gattggcgaa   1200
atgagtcagg agcatcagac tgatttcgca ggctttaaca tcagctatga caactatcac   1260
tcgacgcaca gcgaagagaa ccgccagttg tcagaactta tctactctcg cctgaaagaa   1320
aacggtttta ttaaaaaccg caccatctct cagctgtacg atccggaaaa aggcatgttc   1380
ctgccggacc gttttgtgaa aggcacctgc ccgaaatgta atccccggga tcaatacggc   1440
gataactgcg aagtctgcgg cgcgacctac agcccgactg aactgatcga gccgaaatcg   1500
gtggtttctg cgctacgccg gtaatgcgt gattctgaac acttcttctt tgatctgccc   1560
tctttcagcg aaatgttgca ggcatggacc cgcagcggtg cgttgcagga gcaggtggca   1620
aataaaatgc aggagtggtt tgaatctggc ctgcaacagt gggatatctc ccgcgacgcc   1680
ccttacttcg gttttgaaat tccgaacgcg ccgggcaaat atttctacgt ctggctggac   1740
gcaccgattg gctacatggg ttctttcaag aatctgtgcg acaagcgcgg cgacagcgta   1800
agcttcgatg aatactggaa gaaagactcc accgccgagc tgtaccactt catcggtaaa   1860
gatattgttt acttccacag cctgttctgg cctgccatgc tggaaggcag caacttccgc   1920
aagccgtcca acctgtttgt tcatggctat gtgacggtga acggcgcaaa gatgtccaag   1980
tctcgcggca cctttattaa agccagcacc tggctgaatc attttgacgc agacagcctg   2040
cgttactact acactgcgaa actctcttcg cgcattgatg atatcgatct caacctggaa   2100
gatttcgttc agcgtgtgaa tgccgatatc gttaacaaag tggttaacct ggcctcccgt   2160
aatgcgggct ttatcaacaa gcgttttgac ggcgtgctgg caagcgaact ggctgacccg   2220
cagttgtaca aaaccttcac tgatgccgct gaagtgattg gtgaagcgtg ggaaagccgt   2280
gaatttggta aagccgtgcg cgaaatcatg gcgctggctg atctggctaa ccgctatgtc   2340
gatgaacagg ctccgtgggt ggtggcgaaa caggaaggcc gcgatgccga cctgcaggca   2400
atttgctcaa tgggcatcaa cctgttccgc gtgctgatga cttacctgaa gccggtactg   2460
ccgaaactga ccgagcgtgc agaagcattc ctcaatacgg aactgacctg ggatggtatc   2520
cagcaaccgc tgctgggcca caaagtgaat ccgttcaagg cgctgtataa ccgcatcgat   2580
atgaggcagg ttgaagcact ggtggaagcc tctaaatgag aagtaaaagc cgctgccgcg   2640
ccggtaactg gcccgctggc agatgatccg attcaggaaa ccatcacctt tgacgacttc   2700
gctaaagttg acctgcgcgt ggcgctgatt gaaaacgcag agtttgttga aggttctgac   2760
aaactgctgc gcctgacgct ggatctcggc ggtgaaaaac gcaatgtctt ctccggtatt   2820
cgttctgctt acccggatcc gcaggcactg attggtcgtc acaccattat ggtggctaac   2880
ctggcaccac gtaaaatgcg cttcggtatc tctgaaggca tggtgatggc tgccggtcct   2940
ggcgggaaag atattttcct gctaagcccg gatgccggtg ctaaaccggg tcatcaggtg   3000
aaataatccc ccttcaaggc gctgcatcga cagccttttg ctttataaat tcctaaagtt   3060
gttttcttgc gattttgtct ctctctaacc cgcataaata ctggtagcat ctgcattcaa   3120
ctggataaaa ttacagggat gcagaatgag acactttatc tatcaggacg aaaaatcaca   3180
taaattcagg gcagttgagc aacagggaaa cgagttgcat atcagttggg gaaaagttgg   3240
caccaaaggc aaagccagat aaaaagtttt tcagatgctg cggcagcggc aaaagcggag   3300
cccgacctcg agggggggcc cggtacccgg ccggacgtct ctagagctag cttggcgaga   3360
```

```
ttttcaggag ctaaggaagc taaaatggag aaaaaaatca ctggatatac caccgttgat    3420
atatcccaat ggcatcgtaa agaacatttt gaggcatttc agtcagttgc tcaatgtacc    3480
tataaccaga ccgttcagct ggatattacg gccttttaa  agaccgtaaa gaaaaataag    3540
cacaagtttt atccggcctt tattcacatt cttgcccgcc tgatgaatgc tcatccggaa    3600
tttcgtatgg caatgaaaga cggtgagctg gtgatatggg atagtgttca cccttgttac    3660
accgttttcc atgagcaaac tgaaacgttt tcatcgctct ggagtgaata ccacgacgat    3720
ttccggcagt ttctacacat atattcgcaa gatgtggcgt gttacggtga aaacctggcc    3780
tatttcccta aagggtttat tgagaatatg ttttcgtct  cagccaatcc ctgggtgagt    3840
ttcaccagtt ttgatttaaa cgtggccaat atggacaact tcttcgcccc cgttttcacc    3900
atgggcaaat attatacgca aggcgacaag gtgctgatgc cgctggcgat tcaggttcat    3960
catgccgttt gtgatggctt ccatgtcggc agaatgctta atgaattaca acagtactgc    4020
gatgagtggc agggcgggc  gtaattttt  taaggcagtt attggtgccc ttaaacgcct    4080
ggggtaatga ctctctagct tgaggcatca aataaaacga aaggctcagt cgaaagactg    4140
ggcctttcgt tttatctgtt gtttgtcggt gaacgctctc ctgagtagga caaatccgcc    4200
ctctagatta cgtgcagtcg atgataagct gtcaaacatg agaattgtgc ctaatgagtg    4260
agctaactta cattaattgc gttgcgctca ctgcccgctt tccagtcggg aaacctgtcg    4320
tgccagctgc attaatgaat cggccaacgc gcggggagag gcggtttgcg tattgggcgc    4380
cagggtggtt tttcttttca ccagtgagac gggcaacagc tgattgccct tcaccgcctg    4440
gccctgagag agttgcagca agcggtccac gctggtttgc cccagcaggc gaaaatcctg    4500
tttgatggtg gttaacggcg ggatataaca tgagctgtct tcggtatcgt cgtatcccac    4560
taccgagata tccgcaccaa cgcgcagccc ggactcggta atggcgcgca ttgcgcccag    4620
cgccatctga tcgttggcaa ccagcatcgc agtgggaacg atgccctcat tcagcatttg    4680
catggtttgt tgaaaaccgg acatggcact ccagtcgcct tcccgttccg ctatcggctg    4740
aatttgattg cgagtgagat atttatgcca gccagccaga cgcagacgcg ccgagacaga    4800
acttaatggg cccgctaaca gcgcgatttg ctggtgaccc aatgcgacca gatgctccac    4860
gcccagtcgc gtaccgtctt catgggagaa aataatactg ttgatgggtg tctggtcaga    4920
gacatcaaga ataacgccg  gaacattagt gcaggcagct tccacagcaa tggcatcctg    4980
gtcatccagc ggatagttaa tgatcagccc actgacgcgt tgcgcgagaa gattgtgcac    5040
cgccgcttta caggcttcga cgccgcttcg ttctaccatc gacaccacca cgctggcacc    5100
cagttgatcg gcgcgagatt taatcgccgc gacaatttgc gacggcgcgt gcagggccag    5160 actgaggtg  gcaacgccaa tcagcaacga ctgtttgccc gccagttgtt gtgccacgcg    5220
gttgggaatg taattcagct ccgccatcgc cgcttccact ttttcccgcg ttttcgcaga    5280
aacgtggctg gcctggttca ccacgcggga aacggtctga taagagacac cggcatactc    5340
tgcgacatcg tataacgtta ctggtttcac attcaccacc ctgaattgac tctcttccgg    5400
gcgctatcat gccataccgc gaaaggtttt gcaccattcg atggtgtcgg aatttcgggc    5460
agcgttgggt cctggccacg ggtgcgcatg atctagagct gcctcgcgcg tttcggtgat    5520
gacggtgaaa acctctgaca catgcagctc ccggagacgg tcacagcttg tctgtaagcg    5580
gatgccggga gcagacaagc ccgtcagggc gcgtcagcgg tgttggcgg  gtgtcgggc     5640 gcagccatga cccagtcacg tagcgatagc ggagtgtata ctggcttaac tatgcggcat    5700
cagagcagat tgtactgaga gtgcaccata tgcggtgtga ataccgcac  agatgcgtaa    5760
```

```
ggagaaaata ccgcatcagg cgctcttccg cttcctcgct cactgactcg ctgcgctcgg    5820
tcgttcggct gcggcgagcg gtatcagctc actcaaaggc ggtaatacgg ttatccacag    5880
aatcagggga taacgcagga agaacatgt gagcaaaagg ccagcaaaag gccaggaacc    5940
gtaaaaaggc cgcgttgctg gcgttttttcc ataggctccg ccccctgac gagcatcaca    6000 aaaatcgacg ctcaagtcag aggtggcgaa acccgacagg actataaaga taccaggcgt    6060
ttccccctgg aagctccctc gtgcgctctc ctgttccgac cctgccgctt accggatacc    6120
tgtccgcctt tctcccttcg ggaagcgtgg cgctttctca gctcacgc tgtaggtatc    6180 tcagttcggt gtaggtcgtt cgctccaagc tgggctgtgt gcacgaaccc cccgttcagc    6240
ccgaccgctg cgccttatcc ggtaactatc gtcttgagtc caacccggta agacacgact    6300
tatcgccact ggcagcagcc actggtaaca ggattagcag agcgaggtat gtaggcggtg    6360
ctacagagtt cttgaagtgg tggcctaact acggctacac tagaaggaca gtatttggta    6420
tctgcgctct gctgaagcca gttaccttcg gaaaaagagt tggtagctct tgatccggca    6480
aacaaaccac cgctggtagc ggtggttttt ttgtttgcaa gcagcagatt acgcgcagaa    6540
aaaaaggatc tcaagaagat cctttgatct tttctacggg gtctgacgct cagtggaacg    6600
aaaactcacg ttaagggatt ttggtcatga gattatcaaa aaggatcttc acctagatcc    6660
ttttaaatta aaaatgaagt tttaaatcaa tctaaagtat atatgagtaa acttggtctg    6720
acagttacca atgcttaatc agtgaggcac ctatctcagc gatctgtcta tttcgttcat    6780
ccatagttgc ctgactcccc gtcgtgtaga taactacgat acgggagggc ttaccatctg    6840
gccccagtgc tgcaatgata ccgcgagacc cacgctcacc ggctccagat ttatcagcaa    6900
taaaccagcc agccggaagg gccgagcgca gaagtggtcc tgcaacttta tccgcctcca    6960
tccagtctat taattgttgc cgggaagcta gagtaagtag ttcgccagtt aatagtttgc    7020
gcaacgttgt tgccattgct acaggcatcg tggtgtcacg ctcgtcgttt ggtatggctt    7080
cattcagctc cggttcccaa cgatcaaggc gagttacatg atccccatg ttgtgcaaaa    7140 aagcggttag ctccttcggt cctccgatcg ttgtcagaag taagttggcc gcagtgttat    7200
cactcatggt tatggcagca ctgcataatt ctcttactgt catgccatcc gtaagatgct    7260
tttctgtgac tggtgagtac tcaaccaagt cattctgaga atagtgtatg cggcgaccga    7320
gttgctcttg cccggcgtca atacgggata ataccgcgcc acatagcaga actttaaaag    7380
tgctcatcat tggaaaacgt tcttcggggc gaaaactctc aaggatctta ccgctgttga    7440
gatccagttc gatgtaaccc actcgtgcac ccaactgatc ttcagcatct tttactttca    7500
ccagcgtttc tgggtgagca aaaacaggaa ggcaaaatgc cgcaaaaaag gaataaggg    7560 cgacacggaa atgttgaata ctcatactct tcctttttca atattattga agcatttatc    7620
agggttattg tctcatgagc ggatacatat ttgaatgtat ttagaaaaat aaacaaatag    7680
gggttccgcg cacatttccc cgaaaagtgc cacctgacgt ctaagaaacc attattatca    7740
tgacattaac ctataaaaat aggcgtatca cgaggccctt tcgtcttcac    7790
```

<210> SEQ ID NO 2
<211> LENGTH: 8294
<212> TYPE: DNA
<213> ORGANISM: Saccharomyces cerevisiae
<220> FEATURE:
<223> OTHER INFORMATION: Yeast phenylalanine aminoacyl synthetase gene

<400> SEQUENCE: 2

```
ctcgagaaat cataaaaaat ttatttgctt tgtgagcgga taacaattat aatagattca      60
```

```
attgtgagcg gataacaatt tcacacagaa ttcattaaag aggagaaatt aactatgaga    120
ggatcgcatc accatcacca tcacggatcc gtcgacctgc agccccgggt accggtagaa    180
aaaatgagta aaggagaaga acttttttact ggagttgtcc caattcttgt tgaattagat    240
ggtgatgtta atgggcacaa attttctgtc agtggagagg gtgaaggtga tgcaacatac    300
ggaaaactta cccttaaatt tatttgcact actggaaaac tacctgttcc atggccaaca    360
cttgtcacta cttttaccta tggtgttcaa tgcttttccc gttatccgga tcatatgaaa    420
cggcatgact ttttttaagag tgccatgccc gaaggttatg tacaggaacg cactatattt    480
tttaaagatg acgggaacta caagacgcgt gctgaagtca agttgaagg tgataccctt    540 gttaatcgta tcgagttaaa aggtattgat tttaaagaag atggaaacat tctcggacac    600
aaactcgagt acaactataa ctcacacaat gtatacatca tggcagacaa acaaaagaat    660
ggaatcaaag ctaactttaa aattcgccac aacattgaag atggatccgt tcaactagca    720
gaccattatc aacaaaatac tccaattggc gatggccctg tccttttacc agacaaccat    780
tacctgtcga cacaatctgc cctttcgaaa gatcccaacg aaaagcgtga ccacatggtc    840
cttcttgagt ttgtaactgc tgctgggatt acacatggca tggatgagct ctacaaactg    900
cagccaagct taattagctg aagcttggac tcctgttgat agatccagta atgacctcag    960
aactccatct ggatttgttc agaacgctcg gttgccgccg ggcgtttttt attggtgaga    1020
atccaagcta gcttggcgag attttcagga gctaaggaag ctaaaatgga gaaaaaaatc    1080
actggatata ccaccgttga tatatcccaa tggcatcgta aagaacattt tgaggcattt    1140
cagtcagttg ctcaatgtac ctataaccag accgttcagc tggcacgaca ggtttcccga    1200
ctggaaagcg ggcagtgagc gcaacgcaat taatgtgagt tagctcactc attaggcacc    1260
ccaggcttta cactttatgc ttccggctcg tatgttgtgt ggaattgtga gcggataaca    1320
atttcacaca ggaaacagct atgaccatga ttacgccaag cttgcatgcc tgcagttgac    1380
aattaatcat cggctcgtat aatggatcca attgtgagcg gaatcgattt tcacacagga    1440
aacagaccat gaatctagag atgtctgact tccaattaga aattctaaag aaactagatg    1500
aattggatga gatcaagtcc acactggcaa ctttccctca gcacggctct caagatgttc    1560
tttccgcttt gaactctttg aaagcccaca caagttaga gttttccaag gtcgacacgg    1620
ttacgtatga cttgaccaaa gaaggtgctc aaattttgaa tgaaggttcg tacgaaatta    1680
aactagtcaa gctcatccaa gagttgggtc aacttcaaat caaagatgtg atgtccaaac    1740 taggcccctca gttggtaag gtcggtcagg ctagagcttt caagaacggc tggatcgcca    1800
aaaacgcctc aaacgagctt gaactctccg caaaattgca aaataccgat ttaaatgagc    1860
ttactgatga aacgcaatct attctagcgc aaatcaagaa caactcgcat ctggatagca    1920
ttgacgccaa gattttgaac gacttgaaga aagaaagtt aattgctcaa ggtaaaatca    1980
cagatttcag tgtcaccaaa gggcagagt tctcgaccga cctcaccaaa ttggaaaccg    2040
atcttacctc cgacatggtc tccaccaatg catacaagga cttgaagttc aagccttaca    2100
atttcaattc tcaaggtgtg caaatatctt caggtgctct tcacccctta acaaagtca    2160 gagaggaatt tagacaaatt ttcttttcca tgggattcac agagatgccc tcgaaccaat    2220
acgtcgagac aggtttctgg aacttcgatg cccctttacgt cccacaacag catcctgctc    2280
gtgacctgca agacactttc tacatcaagg acccactaac cgctgagttg cccgatgaca    2340
agacatacat ggacaatatc aaagccgttc acgaacaggg gagattcggg tccatcggtt    2400
atcgttacaa ctggaagcca gaagaatgtc aaaaattggt cttgagaact cactccacag    2460
```

```
ccatctctgc cagaatgctg cacgatttgg ccaaagatcc aaagcccacc agattgtttt    2520
ctatcgaccg tgttttccgt aacgaagcag ttgacgccac ccatttggcc gaattccacc    2580
aggtggaagg tgttcttgcc gactacaaca ttactctggg tgacctgatc aagttcatgg    2640
aagagttttt cgaaagaatg ggtgtcaccg gtttgagatt caagcctacc tacaatcctt    2700
acaccgagcc atcaatggaa atcttttctt ggcacgaagg tttgcaaaaa tgggtcgaaa    2760
tcggtaactc tggtatgttc agaccagaaa tgctcgagtc catgggtcta ccaaaggatc    2820
taagagtcct tggttggggg ttatccttgg aaagacctac catgatcaaa tataaggttc    2880
aaaacatcag agaactgtta ggtcataaag tctctttgga ctttatcgaa accaatcctg    2940
ctgctagatt ggacgaagac ttgtacgaat aaggcaggaa tagattatgc ctaccgtctc    3000
cgtgaacaag cagcaattat ttgatcttct aggcaaagac tacacttccc aagagttcga    3060
cgaattatgt tttgaattcg gtatggaaat ggacgaagac accacagaag aggccttgaa    3120
aaccggggag gagccggaat tgaagcttga tatcagtgcc aatcgttacg atttgctttg    3180
tatcgaaggt atttcacagt cgctgaacga atacttggaa cgtaaagaaa gacctgacta    3240
taaattaagc aagccaacca ctaagttgat catcgacaaa tcaacggagc aaattagacc    3300
ttttgctacc gctgctgtat tgagaaatat caagcttaac gaaaaatctt acgcttcttt    3360
tattgccttg caagataaat tacatgccaa tctatgtaga aacagaagct tggttgccat    3420
gggtactcac gatttagatt caattgaagg tccattccat tacagagctc taccaccaaa    3480
ggacatcaag ttcgtaccat tgaatcaaac ccaagagttt actggtgaca aattgatcga    3540
gttttataaa tctccagaac agaaaaacaa catagggaga tacgttcaca ttattgagga    3600
ttctccagtc ttcccagtta ttatggacag caaagatcgt gtttgctccc tgccaccatt    3660
aatcaatagt gaacattcga agatctctgt gaacacccgt aacattttga ttgatataac    3720
cgccaccgat aagaccaaag ccgagatcgt tttgaacata ttaactacaa tgttctcacg    3780
ttattgtgac gaaccattca cggttgagcc tgtagaaatt gtctctgaac acaatggcca    3840
atcccgtttg gcgccaaact tcaacgatag aattatggat gtctccatta agtacatcaa    3900
ctcctgtctt ggcctagatc aatccgctga tgaaattgct cattgtctaa aaaagatgtc    3960
gttgcatgcc gttcaatcaa aggaagacaa ggacatcttg cacgttgaca ttccggtaac    4020
tagacctgat attttgcacg cttgtgatat aatggaagat gccgctgtcg gttatggttt    4080
caataatttg ccaaagggtg agaaattatc caatgccaac ttcattgcca aaccattacc    4140
aatcaacaag gtttctgata ttttcagagt tgcatcctct caagccacgt gggttgaggt    4200
tttaccattg accttatgtt cgcacgatga aaactttaaa tttctaagac aatccgacaa    4260
tgatgattta gctgtcaaat tggccaaccc aaagactttg gaataccaag ttgttagaac    4320
cactttattg cctggtatct taaagacagt caaggaaaac agaaaacatt ccttaccaat    4380
caaagtcttt gaaaccggtg acgttgtatt taaagacgac aaactagaaa ggaaggcgta    4440
caatgaacgt cactgggctg ccatctacgt gggtaagaat tctgggtttg aaatcattca    4500
agggttattg ggtaaaatca tgcaaacttt tagaacagag tggattgcag actacggtgc    4560
tgctgcttct ggcagaggtt actggattga agaagacgat tctgtgaaaa cctatttccc    4620
aggtagaggt gccaaggtca tgttcagatc caaagaaggc gctgagccaa agcaaatcgg    4680
ccacttgggt gtcttgcatc ctgaagtcat gatgaatttc gacgttccat tcgctgcatc    4740
ctttgtagag gttaatgccg aagtcttcct ataatgtaat gttctaacaa aaatttttac    4800
tgatttataa aacttatata gatagataga catatatata tatctatata tagaaacaca    4860
```

```
actaaagttt accatgtttt atatagggta ccgagctcga attcactggc cgtcgtttta   4920
caacgtcgtg actgggaaaa ccgcggttac gtgcagtcga tgataagctg tcaaacatga   4980
gaattgtgcc taatgagtga gctaacttac attaattgcg ttgcgctcac tgcccgcttt   5040
ccagtcggga aacctgtcgt gccagctgca ttaatgaatc ggccaacgcg cggggagagg   5100
cggtttgcgt attgggcgcc agggtggttt tcttttcac cagtgagacg ggcaacagct    5160
gattgccctt caccgcctgg ccctgagaga gttgcagcaa gcggtccacg ctggtttgcc   5220
ccagcaggcg aaaatcctgt ttgatggtgg ttaacggcgg gatataacat gagctgtctt   5280
cggtatcgtc gtatcccact accgagatat ccgcaccaac gcgcagcccg gactcggtaa   5340
tggcgcgcat tgcgcccagc gccatctgat cgttggcaac cagcatcgca gtgggaacga   5400
tgccctcatt cagcatttgc atggtttgtt gaaaaccgga catggcactc cagtcgcctt   5460
cccgttccgc tatcggctga atttgattgc gagtgagata tttatgccag ccagccagac   5520
gcagacgcgc cgagacagaa cttaatgggc ccgctaacag cgcgatttgc tggtgaccca   5580
atgcgaccag atgctccacg cccagtcgcg taccgtcttc atgggagaaa ataatactgt   5640
tgatgggtgt ctggtcagag acatcaagaa ataacgccgg aacattagtg caggcagctt   5700
ccacagcaat ggcatcctgg tcatccagcg atagttaat gatcagccca ctgacgcgtt    5760
gcgcgagaag attgtgcacc gccgctttac aggcttcgac gccgcttcgt tctaccatcg   5820
acaccaccac gctggcaccc agttgatcgg cgcgagattt aatcgccgcg acaatttgcg   5880
acggcgcgtg cagggccaga ctggaggtgg caacgccaat cagcaacgac tgtttgcccg   5940
ccagttgttg tgccacgcgg ttgggaatgt aattcagctc cgccatcgcc gcttccactt   6000
tttcccgcgt tttcgcagaa acgtggctgg cctggttcac cacgcgggaa acggtctgat   6060
aagagacacc ggcatactct gcgacatcgt ataacgttac tggtttcaca ttcaccaccc   6120
tgaattgact ctcttccggg cgctatcatg ccataccgcg aaaggttttg caccattcga   6180
tggtgtcgga atttcgggca gcgttgggtc ctggccacgg gtgcgcatga cttaagcggt   6240
gtgaaatacc gcacagatgc gtaaggagaa ataccgcat caggcgctct ccgcttcct    6300
cgctcactga ctcgctgcgc tcggtcgtc ggctgcggcg agcggtatca gctcactcaa    6360
aggcggtaat acggttatcc acagaatcag gggataacgc aggaaagaac atgtgagcaa   6420
aaggccagca aaaggccagg aaccgtaaaa aggccgcgtt gctggcgttt ttccataggc   6480
tccgcccccc tgacgagcat cacaaaaatc gacgctcaag tcagaggtgg cgaaacccga   6540
caggactata aagataccag gcgtttcccc ctggaagctc cctcgtgcgc tctcctgttc   6600
cgaccctgcc gcttaccgga tacctgtccg cctttctccc ttcgggaagc gtggcgcttt   6660
ctcaatgctc acgctgtagg tatctcagtt cggtgtaggt cgttcgctcc aagctgggct   6720
gtgtgcacga acccccgtt cagcccgacc gctgcgcctt atccggtaac tatcgtcttg    6780
agtccaaccc ggtaagacac gacttatcgc cactggcagc agccactggt aacaggatta   6840
gcagagcgag gtatgtaggc ggtgctacag agttcttgaa gtggtggcct aactacggct   6900
acactagaag gacagtattt ggtatctgcg ctctgctgaa gccagttacc ttcggaaaaa   6960
gagttggtag ctcttgatcc ggcaaacaaa ccaccgctgg tagcggtggt ttttttgttt    7020
gcaagcagca gattacgcgc agaaaaaaag gatctcaaga agatcctttg atcttttcta   7080
cggggtctga cgctcagtgg aacgaaaact cacgttaagg attttggtc atgagattat     7140
caaaaaggat cttcacctag atccttttaa attaaaaatg aagttttaaa tcaatctaaa   7200
gtatatatga gtaaacttgg tctgacagtt accaatgctt aatcagtgag gcacctatct   7260
```

```
                                          -continued
cagcgatctg tctatttcgt tcatccatag ctgcctgact ccccgtcgtg tagataacta     7320
cgatacggga gggcttacca tctggcccca gtgctgcaat gataccgcga gacccacgct     7380
caccggctcc agatttatca gcaataaacc agccagccgg aagggccgag cgcagaagtg     7440
gtcctgcaac tttatccgcc tccatccagt ctattaattg ttgccgggaa gctagagtaa     7500
gtagttcgcc agttaatagt ttgcgcaacg ttgttgccat gctacaggc atcgtggtgt      7560 cacgctcgtc gtttggtatg gcttcattca gctccggttc ccaacgatca aggcgagtta     7620
catgatcccc catgttgtgc aaaaaagcgg ttagctcctt cggtcctccg atcgttgtca     7680
gaagtaagtt ggccgcagtg ttatcactca tggttatggc agcactgcat aattctctta     7740
ctgtcatgcc atccgtaaga tgcttttctg tgactggtga gtactcaacc aagtcattct     7800
gagaatagtg tatgcggcga ccgagttgct cttgcccggc gtcaatacgg gataataccg     7860
cgccacatag cagaacttta aaagtgctca tcattggaaa acgttcttcg ggcgaaaac      7920 tctcaaggat cttaccgctg ttgagatcca gttcgatgta acccactcgt gcacccaact     7980
gatcttcagc atcttttact ttcaccagcg tttctgggtg agcaaaaaca ggaaggcaaa     8040
atgccgcaaa aaagggaata agggcgacac ggaaatgttg aatactcata ctcttccttt     8100
ttcaatatta ttgaagcatt tatcagggtt attgtctcat gagcggatac atatttgaat     8160
gtatttagaa aaataaacaa ataggggttc cgcgcacatt tccccgaaaa gtgccacctg     8220
acgtctaaga aaccattatt atcatgacat taacctataa aaataggcgt atcacgaggc     8280
cctttcgtct tcac                                                      8294

<210> SEQ ID NO 3
<211> LENGTH: 1512
<212> TYPE: DNA
<213> ORGANISM: Artificial Sequence
<220> FEATURE:
<223> OTHER INFORMATION: alpha-subunit of the yeast phenylalanine
      aminoacylsynthetase gene
<220> FEATURE:
<221> NAME/KEY: misc_feature
<222> LOCATION: 1234, 1235, 1236, 1243, 1244, 1245, 1252, 1253, 1254,
      1309, 1310 1311
<223> OTHER INFORMATION: n = A, T, C or G

<400> SEQUENCE: 3
atgtctgact ccaattaga aattctaaag aaactagatg aattggatga gatcaagtcc       60
acactggcaa cttccctca gcacggctct caagatgttc tttccgcttt gaactctttg      120
aaagcccaca caagttaga gttttccaag gtcgacacgg ttacgtatga cttgaccaaa      180
gaaggtgctc aaattttgaa tgaaggttcg tacgaaatta aactagtcaa gctcatccaa     240
gagttgggtc aacttcaaat caagatgtg atgtccaaac taggccctca agttggtaag     300
gtcggtcagg ctagagcttt caagaacggc tggatcgcca aaaacgcctc aaacgagctt     360
gaactctccg caaattgca aaataccgat ttaaatgagc ttactgatga acgcaatct      420 attctagcgc aaatcaagaa caactcgcat ctggatagca ttgacgccaa gattttgaac     480
gacttgaaga aagaaagtt aattgctcaa ggtaaaatca cagatttcag tgtcaccaaa     540
gggccagagt tctcgaccga cctcaccaaa ttggaaaccg atcttacctc cgacatggtc     600
tccaccaatg catacaagga cttgaagttc aagccttaca atttcaattc tcaaggtgtg     660
caaatatctt caggtgctct tcaccccta aacaaagtca gagaggaatt tagacaaatt     720 ttctttttcca tgggattcac agagatgcc tcgaaccaat acgtcgagac aggtttctgg     780
aacttcgatg ccctttacgt cccacaacag catcctgctc gtgacctgca agacactttc     840
```

```
tacatcaagg acccactaac cgctgagttg cccgatgaca agacatacat ggacaatatc      900
aaagccgttc acgaacaggg gagattcggg tccatcggtt atcgttacaa ctggaagcca      960
gaagaatgtc aaaaattggt cttgagaact cactccacag ccatctctgc cagaatgctg     1020
cacgatttgg ccaaagatcc aaagcccacc agattgtttt ctatcgaccg tgttttccgt     1080
aacgaagcag ttgacgccac ccatttggcc gaattccacc aggtggaagg tgttcttgcc     1140
gactacaaca ttactctggg tgacctgatc aagttcatgg aagagttttt cgaaagaatg     1200
ggtgtcaccg gtttgagatt caagcctacc tacnnncctt acnnngagcc annnatggaa     1260
atcttttctt ggcacgaagg tttgcaaaaa tgggtcgaaa tcggtaacnn nggtatgttc     1320
agaccagaaa tgctcgagtc catgggtcta ccaaaggatc taagagtcct tggttggggg     1380
ttatccttgg aaagacctac catgatcaaa tataaggttc aaaacatcag agaactgtta     1440
ggtcataaag tctctttgga ctttatcgaa accaatcctg ctgctagatt ggacgaagac     1500
ttgtacgaat aa                                                         1512

<210> SEQ ID NO 4
<211> LENGTH: 13
<212> TYPE: PRT
<213> ORGANISM: Artificial Sequence
<220> FEATURE:
<223> OTHER INFORMATION: Artificial derivative of dihydrofolate
      reductase

<400> SEQUENCE: 4

Asn Gly Asp Leu Pro Trp Pro Pro Leu Arg Asn Glu Lys
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Artificial derivative of dihydrofolate
      reductase

<400> SEQUENCE: 5

Asn Gly Asp Leu Pro Trp Pro Pro Leu Arg Asn Glu
  1               5                  10

<210> SEQ ID NO 6
<211> LENGTH: 8
<212> TYPE: PRT
<213> ORGANISM: Artificial Sequence
<220> FEATURE:
<223> OTHER INFORMATION: Artificial derivative of dihydrofolate
      reductase

<400> SEQUENCE: 6

Pro Trp Pro Pro Leu Arg Asn Glu
  1               5

<210> SEQ ID NO 7
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 7
cgattttcac acaggatcca gaccatgatt ctag                                   34

<210> SEQ ID NO 8
```

```
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
gacggccagt gaattcgagc tcggtac                                      27

<210> SEQ ID NO 9
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 9
ctacctacaa tccttacggc gagccatcaa tggaaatc                          38

<210> SEQ ID NO 10
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 10
gatttccatt gatggctcgc cgtaaggatt gtaggtag                          38

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 11
ccgctcagga acgagtagaa gtacttccaa agaatg                            36

<210> SEQ ID NO 12
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 12
cattctttgg aagtacttct actcgttcct gagcgg                            36

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 13
gcactgacca tggctgaaca acacgcacag                                   30

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 14
```

```
ggacttcgga tcctttctgt gggcgcatcg c                              31
```

<210> SEQ ID NO 15
<211> LENGTH: 12
<212> TYPE: PRT
<213> ORGANISM: Artificial Sequence
<220> FEATURE:
<223> OTHER INFORMATION: alpha-subunit of the yeast phenylalanine
      animoacylsynthetase gene

<400> SEQUENCE: 15

Asn Gly Asp Leu Pro Trp Pro Pro Leu Arg Asn Glu
 1               5                  10

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 16

```
gaacacagga cctccacatt tagagtatgg cgctctccc                      39
```

<210> SEQ ID NO 17
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 17

```
gggagagcgc catactctaa atgtggaggt cctgtgttc                      39
```

<210> SEQ ID NO 18
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 18

```
ctgggtaagc ttcgctaagg atctgccctg gtgcgaactc tg                  42
```

<210> SEQ ID NO 19
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 19

```
gattacggat tcctaatacg actcactata gcggacttag ctc                 43
```

<210> SEQ ID NO 20
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 20

```
cggaagcaga aagtgtaaag agcggggtgc ctaatgagtg                     40
```

<210> SEQ ID NO 21
<211> LENGTH: 40
<212> TYPE: DNA

<213> ORGANISM: Artificial Sequence
<220> FEATURE:
<223> OTHER INFORMATION: Oligonucleotide primer

<400> SEQUENCE: 21
cactcattag gcaccccgct ctttacactt tatgcttccg                                40

<210> SEQ ID NO 22
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 22
cttgtcacta ctctgaccta tgtgttcaa tgcttctccc gt                             42

<210> SEQ ID NO 23
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 23
acgggagaag cattgaacac cataggtcag agtagtgaca ag                            42

<210> SEQ ID NO 24
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 24
gtacaggaac gcactatatt cttcaaagat gacgggaac                                39

<210> SEQ ID NO 25
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 25
gttcccgtca tctttgaaga atatagtgcg ttcctgtac                                39

<210> SEQ ID NO 26
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 26
cacaatgtat acatcatggc agacaaacaa aagaatgga                                39

<210> SEQ ID NO 27
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 27
tccattcttt tgtttgtctg ccatgatgta tacattgtg                                39

<210> SEQ ID NO 28
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 28
gtgccacctg acgtctaaga aaccattatt atcatgacat taacc        45

<210> SEQ ID NO 29
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 29
gagtaaagga gaagaacttt ttactggagt tgtcccaatt c        41

<210> SEQ ID NO 30
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 30
gaattgggac aactccagta aaagttctt ctcctttact c        41

<210> SEQ ID NO 31
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 31
ggccaacact tgtcactact tttacctatg gtgttcaatg ctt        43

<210> SEQ ID NO 32
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 32
aagcattgaa caccataggt aaaagtagtg acaagtgttg gcc        43

<210> SEQ ID NO 33
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 33
catatgaaac ggcatgactt ttttaagagt gccatgcccg aag        43

<210> SEQ ID NO 34
<211> LENGTH: 43
<212> TYPE: DNA
<213> ORGANISM: Artificial Sequence
<220> FEATURE:
<223> OTHER INFORMATION: Oligonucleotide primer

```
<400> SEQUENCE: 34
cttcgggcat ggcactctta aaaaagtcat gccgtttcat atg          43

<210> SEQ ID NO 35
<211> LENGTH: 49
<212> TYPE: DNA
<213> ORGANISM: Artificial Sequence
<220> FEATURE:
<223> OTHER INFORMATION: Oligonucleotide primer

<400> SEQUENCE: 35
gttatgtaca ggaacgcact atattttca aagatgacgg gaactacaa     49

<210> SEQ ID NO 36
<211> LENGTH: 49
<212> TYPE: DNA
<213> ORGANISM: Artificial Sequence
<220> FEATURE:
<223> OTHER INFORMATION: Oligonucleotide primer

<400> SEQUENCE: 36
ttgtagttcc cgtcatcttt gaaaaatata gtgcgttcct gtacataac    49

<210> SEQ ID NO 37
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 37
acaaaagaat ggaatcaaag ctaactttaa aattcgccac aacattgaag atg    53

<210> SEQ ID NO 38
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 38
catcttcaat gttgtggcga attttaaagt tagctttgat tccattcttt tgt    53

<210> SEQ ID NO 39
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 39
cgccaagcta gcttggattc tcaccaataa aaaacgccc               39

<210> SEQ ID NO 40
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 40
tacctatggt gttcaatgct tttcccgtta tccggatcat atg          43

<210> SEQ ID NO 41
<211> LENGTH: 43
<212> TYPE: DNA
```

<213> ORGANISM: Artificial Sequence
<220> FEATURE:
<223> OTHER INFORMATION: Oligonucleotide primer

<400> SEQUENCE: 41
catatgatcc ggataacggg aaaagcattg aacaccatag gta                    43

<210> SEQ ID NO 42
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 42
gttatgtaca ggaacgcact atattttta aagatgacgg gaactacaag              50

<210> SEQ ID NO 43
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 43
cttgtagttc ccgtcatctt taaaaaatat agtgcgttcc tgtacataac             50

<210> SEQ ID NO 44
<211> LENGTH: 43
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 16, 17
<223> OTHER INFORMATION: n = A, T, C or G

<400> SEQUENCE: 44
gtcgaaatcg gtaacnnkgg tatgttcaga ccagaaatgc tcg                    43

<210> SEQ ID NO 45
<211> LENGTH: 43
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 27, 28
<223> OTHER INFORMATION: n = A, T, C or G

<400> SEQUENCE: 45
cgagcatttc tggtctgaac ataccmnngt taccgatttc gac                    43

<210> SEQ ID NO 46
<211> LENGTH: 47
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 14, 15, 23, 24, 32, 33
<223> OTHER INFORMATION: n = A, T, C or G

<400> SEQUENCE: 46
caagcctacc tacnnkcctt acnnkgagcc annkatggaa atctttt                47

-continued

<210> SEQ ID NO 47
<211> LENGTH: 47
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 15, 16, 24, 25, 33, 34
<223> OTHER INFORMATION: n = A, T, C or G

<400> SEQUENCE: 47
aaaagatttc catmnntggc tcmnngtaag gmnngtaggt aggcttg                    47

<210> SEQ ID NO 48
<211> LENGTH: 432
<212> TYPE: PRT
<213> ORGANISM: Thermus thermophilus

<400> SEQUENCE: 48

Met Ala Gly Thr Gly His Thr Pro Glu Glu Ala Leu Ala Leu Leu Lys
 1               5                  10                  15

Arg Gly Ala Glu Glu Ile Val Pro Glu Glu Leu Leu Ala Lys Leu
            20                  25                  30

Lys Glu Gly Arg Pro Leu Thr Val Lys Leu Gly Ala Asp Pro Thr Arg
        35                  40                  45

Pro Asp Leu His Leu Gly His Ala Val Val Leu Arg Lys Met Arg Gln
    50                  55                  60

Phe Gln Glu Leu Gly His Lys Val Val Leu Ile Ile Gly Asp Phe Thr
65                  70                  75                  80

Gly Met Ile Gly Asp Pro Ser Gly Arg Ser Lys Thr Arg Pro Pro Leu
                85                  90                  95

Thr Leu Glu Glu Thr Arg Glu Asn Ala Lys Thr Tyr Val Ala Gln Ala
            100                 105                 110

Gly Lys Ile Leu Arg Gln Glu Pro His Leu Phe Glu Leu Arg Tyr Asn
        115                 120                 125

Ser Glu Trp Leu Glu Gly Leu Thr Phe Lys Glu Val Val Arg Leu Thr
    130                 135                 140

Ser Leu Met Thr Val Ala Gln Met Leu Glu Arg Glu Asp Phe Lys Lys
145                 150                 155                 160

Arg Tyr Glu Ala Gly Ile Pro Ile Ser Leu His Glu Leu Leu Tyr Pro
                165                 170                 175

Phe Ala Gln Ala Tyr Asp Ser Val Ala Ile Arg Ala Asp Val Glu Met
            180                 185                 190

Gly Gly Thr Asp Gln Arg Phe Asn Leu Leu Val Gly Arg Glu Val Gln
        195                 200                 205

Arg Ala Tyr Gly Gln Ser Pro Gln Val Cys Phe Leu Met Pro Leu Leu
    210                 215                 220

Val Gly Leu Asp Gly Arg Glu Lys Met Ser Lys Ser Leu Asp Asn Tyr
225                 230                 235                 240

Ile Gly Leu Thr Glu Pro Pro Glu Ala Met Phe Lys Lys Leu Met Arg
                245                 250                 255

Val Pro Asp Pro Leu Leu Pro Ser Tyr Phe Arg Leu Leu Thr Asp Leu
            260                 265                 270

Glu Glu Glu Glu Ile Glu Ala Leu Leu Lys Ala Gly Pro Val Pro Ala
        275                 280                 285

His Arg Val Leu Ala Arg Leu Leu Thr Ala Ala Tyr Ala Leu Pro Gln
    290                 295                 300

```
Ile Pro Pro Arg Ile Asp Arg Ala Phe Tyr Glu Ser Leu Gly Tyr Ala
305                 310                 315                 320

Trp Glu Ala Phe Gly Arg Asp Lys Glu Ala Gly Pro Glu Glu Val Arg
            325                 330                 335

Arg Ala Glu Ala Arg Tyr Asp Glu Val Ala Lys Gly Gly Ile Pro Glu
        340                 345                 350

Glu Ile Pro Glu Val Thr Ile Pro Ala Ser Glu Leu Lys Glu Gly Arg
    355                 360                 365

Ile Trp Val Ala Arg Leu Phe Thr Leu Ala Gly Leu Thr Pro Ser Asn
370                 375                 380

Ala Glu Ala Arg Arg Leu Ile Gln Asn Arg Gly Leu Arg Leu Asp Gly
385                 390                 395                 400

Glu Val Leu Thr Asp Pro Met Leu Gln Val Asp Leu Ser Arg Pro Arg
                405                 410                 415

Ile Leu Gln Arg Gly Lys Asp Arg Phe Val Arg Val Arg Leu Ser Asp
            420                 425                 430

<210> SEQ ID NO 49
<211> LENGTH: 372
<212> TYPE: PRT
<213> ORGANISM: Homo sapiens

<400> SEQUENCE: 49

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255
```

```
Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Glu Val Ile Leu Glu His His
                355                 360                 365

His His His His
        370

<210> SEQ ID NO 50
<211> LENGTH: 424
<212> TYPE: PRT
<213> ORGANISM: Escherichia coli

<400> SEQUENCE: 50

Met Ala Ser Ser Asn Leu Ile Lys Gln Leu Gln Glu Arg Gly Leu Val
1               5                   10                  15

Ala Gln Val Thr Asp Glu Glu Ala Leu Ala Arg Leu Ala Gln Gly
                20                  25                  30

Pro Ile Ala Leu Tyr Cys Gly Phe Asp Pro Thr Ala Asp Ser Leu His
            35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255
```

-continued

Tyr Gln Phe Trp Ile Asn Thr Ala Asp Ala Asp Val Tyr Arg Phe Leu
              260                 265                 270

Lys Phe Phe Thr Phe Met Ser Ile Glu Glu Ile Asn Ala Leu Glu Glu
              275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
              325                 330                 335

Glu Ala Asp Phe Glu Gln Leu Ala Gln Asp Gly Val Pro Met Val Glu
              340                 345                 350

Met Glu Lys Gly Ala Asp Leu Met Gln Ala Leu Val Asp Ser Glu Leu
              355                 360                 365

Gln Pro Ser Arg Gly Gln Ala Arg Lys Thr Ile Ala Ser Asn Ala Ile
              370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
              405                 410                 415

Asn Tyr Cys Leu Ile Cys Trp Lys
              420

<210> SEQ ID NO 51
<211> LENGTH: 442
<212> TYPE: PRT
<213> ORGANISM: Drosophila melanogaster

<400> SEQUENCE: 51

Met Ser Gln Lys Asn Leu Leu Glu Leu Thr Asp Arg Gly Phe Phe His
1               5                   10                  15

Gly Ile Phe Pro Asp Thr Ala Ala Pro Arg Met Lys Gln Leu Phe Thr
              20                  25                  30

Arg Gly Gln Gln Ser Ile Tyr Ala Gly Phe Asp Pro Thr Ala Asp Ser
              35                  40                  45

Leu His Val Gly Asn Leu Leu Val Ile Met Gly Leu Ile His Cys Gln
        50                  55                  60

Arg Ala Gly His Arg Pro Ile Ala Leu Val Gly Gly Ala Thr Gly Leu
65                  70                  75                  80

Ile Gly Asp Pro Ser Gly Arg Lys Thr Glu Arg Asn Gln Leu Gly Glu
              85                  90                  95

Thr Val Ile Glu Thr Asn Leu Lys Ala Ile Glu Gln Gln Leu Arg Arg
              100                 105                 110

Val Phe Glu Asn His Glu Asn Cys Leu Trp Asp Ser Lys Lys Gln Lys
              115                 120                 125

Leu Pro Leu Ala Pro Leu Ile Ile Val Asn Asn Ala Asp Trp Tyr Ala
        130                 135                 140

Asp Leu Gln Leu Ile Asp Phe Val Ala Asn Met Gly Arg His Phe Arg
145                 150                 155                 160

Met Gly Ser Met Leu Ser Arg Ser Ser Val Gln Ser Arg Leu Glu Ser
              165                 170                 175

Glu Asp Gly Met Ser Phe Thr Glu Phe Thr Tyr Gln Ile Phe Gln Ala
              180                 185                 190

Tyr Asp Trp Leu His Leu Leu Arg Arg His Asn Cys Cys Phe Gln Met
              195                 200                 205

Gly Gly Ser Asp Gln Thr Gly Asn Leu Met Thr Gly His Glu Leu Ile
            210                 215                 220

Ser Arg Val Glu Arg Lys Arg Glu Val Phe Gly Leu Thr Leu Pro Leu
225                 230                 235                 240

Val Thr Thr Glu Glu Gly Asp Lys Phe Gly Lys Ser Ala Gly Asn Ala
                245                 250                 255

Val Trp Leu Asp Gly Asn Lys Thr Ser Pro Phe Ala Leu Tyr Gln Phe
            260                 265                 270

Phe Leu Arg Met Pro Asp Ser Glu Val Glu Lys Leu Leu Lys Leu Phe
            275                 280                 285

Thr Phe Ile Pro Leu Pro Gln Val Glu Gln Leu Met Arg Glu His Thr
            290                 295                 300

Lys Glu Pro Glu Lys Arg Lys Ala Gln Thr Leu Leu Ala Glu Asp Val
305                 310                 315                 320

Thr Leu Leu Val His Gly Glu Ser Gly Leu Lys Gln Ala Glu Arg Val
                325                 330                 335

Thr Asn Ala Leu Tyr Lys Gly Asn Val Glu Gly Leu Ala Glu Leu Asn
            340                 345                 350

Leu Ser Glu Ile Gln Gln Thr Phe Gln Gly Ala Thr Met Val Asn Leu
            355                 360                 365

Leu Thr Glu Pro Gly Met Ser Ile Leu Glu Leu Ala Met Lys Ala Lys
            370                 375                 380

Cys Phe Pro Thr Glu Thr Asp Ala Val Arg Ile Ile Asn Ala Gly Gly
385                 390                 395                 400

Phe Tyr Val Asn Gln Lys Arg Val Gln Asn Ile Ala Glu Val Leu Thr
                405                 410                 415

Thr Gly Val His Ile Leu Arg Asn Gly Ile Ser Leu Leu Arg Val Gly
            420                 425                 430

Lys Arg Asn Phe Tyr Ile Val Arg Trp Gln
            435                 440

<210> SEQ ID NO 52
<211> LENGTH: 492
<212> TYPE: PRT
<213> ORGANISM: Saccharomyces cerevisiae

<400> SEQUENCE: 52

Met Leu Glu Leu Arg Ser Cys Ser Asn Leu Val Asn Ser Ser Arg Arg
1               5                   10                  15

Leu Val Pro Leu Val Thr Tyr Ser Gly Leu Ser Ala Ile Thr Leu Pro
            20                  25                  30

Lys Ser Arg Phe Tyr Ser Gln Pro Ser Ala Leu Glu Val Gln Gly Thr
        35                  40                  45

Ser Asp Ser Arg Ser Asp Asn Ile Leu Asp Glu Leu Lys Gln Arg Gly
50                  55                  60

Leu Val Ser Gln Val Ser Gln Pro Glu Ser Phe Leu Arg Thr Lys Leu
65                  70                  75                  80

Asn Gly Asn Asp Lys Ile Lys Leu Tyr Cys Gly Val Asp Pro Thr Ala
                85                  90                  95

Gln Ser Leu His Leu Gly Asn Leu Val Pro Leu Met Val Leu Leu His
            100                 105                 110

Phe Tyr Val Lys Gly His Asp Ile Val Thr Val Ile Gly Gly Ala Thr
            115                 120                 125

Gly Lys Val Gly Asp Pro Ser Gly Arg Lys Thr Glu Arg Asp Val Met
130                 135                 140

```
Glu Asn Asp Ile Arg Gln Ser Asn Val Ala Ser Ile Ser Gln Gln Leu
145                 150                 155                 160

Gln Arg Phe Phe Lys Asn Gly Leu Glu Tyr Tyr Arg Asn Arg Cys Ala
                165                 170                 175

Leu Thr Glu Asp Val Pro Ser Gly Lys Tyr Thr Pro Arg Asn Asn Phe
            180                 185                 190

Asn Trp Trp Lys Asp Ile Lys Met Leu Asp Phe Leu Ala Asp Phe Gly
        195                 200                 205

Arg His Ile Arg Val Gln Ser Met Leu Ala Arg Asp Ser Ile Ser Ser
    210                 215                 220

Arg Leu Gln Thr Lys Asn Gly Leu Gly Phe Asn Glu Phe Thr Tyr Gln
225                 230                 235                 240

Val Leu Gln Ala Tyr Asp Phe Tyr His Leu Tyr Lys Glu Glu Asn Val
                245                 250                 255

Thr Ile Gln Val Gly Gly Asn Asp Gln Trp Gly Asn Ile Thr Ala Gly
            260                 265                 270

Ile Asp Leu Ile Asn Arg Ile Gln Pro Ile Lys Asn Lys Gly Leu Pro
        275                 280                 285

Phe Gly Ile Thr Val Pro Leu Leu Thr Thr Ala Thr Gly Glu Lys Phe
290                 295                 300

Gly Lys Ser Ala Gly Asn Ala Val Phe Ile Asp Pro Ser Ile Asn Thr
305                 310                 315                 320

Ala Tyr Asp Val Tyr Gln Phe Phe Tyr Asn Thr Leu Asp Ala Asp Val
                325                 330                 335

Pro Lys Phe Leu Lys Ile Phe Thr Phe Leu Asn Ser Ser Glu Ile Lys
            340                 345                 350

Lys Ile Val Glu Thr His Ile Lys Ser Pro Ser Leu Arg Tyr Gly Gln
        355                 360                 365

Thr Leu Leu Ala Lys Glu Val Thr Asp Met Leu Tyr Gly Val Gly Ser
    370                 375                 380

Gly Ser Asp Ser Glu Ala Leu Ser Asn Ile Ile Phe Gly Arg Tyr Asp
385                 390                 395                 400

Gly Thr Leu Ser Ala Ala Lys Leu Val Asp Leu Cys Lys Lys Ala Arg
                405                 410                 415

Ile Leu Gln Tyr Ala Asp Arg Glu Ile Asp Leu Ile Lys Leu Ile Cys
            420                 425                 430

Lys Leu Val Asn Cys Ser Val Ser Glu Ala Arg Arg Lys Leu Ser Gln
        435                 440                 445

Gly Ser Val Tyr Leu His His Ser Lys Ser Lys Val Asn Glu Asn Ile
    450                 455                 460

Ser Asn Leu Ala Pro Phe Leu Ile Asp Asp Arg Val Leu Ile Leu Arg
465                 470                 475                 480

Ile Gly Lys Gln Lys Cys Phe Ile Ile Glu Met Arg
                485                 490

<210> SEQ ID NO 53
<211> LENGTH: 445
<212> TYPE: PRT
<213> ORGANISM: Schizosaccharomyces pombe

<400> SEQUENCE: 53

Met Ser Arg Leu Leu Ala Cys Leu Lys Gln Leu Gln Ala Arg Ser Leu
1               5                   10                  15

Ile His Asn Thr Thr Leu Leu Gln Pro Ser Cys Asn Val Asn Ser Val
            20                  25                  30
```

```
Tyr Leu Gly Ala Asp Pro Thr Ala Ala Ser Leu His Val Gly Asn Leu
         35                  40                  45

Val Ala Leu Met Pro Leu Val His Phe Phe Leu Asn Gly Phe Pro Val
 50                  55                  60

Phe Thr Val Ile Gly Asp Ala Thr Ala Gln Leu Gly Asp Pro Ser Gly
 65                  70                  75                  80

Arg Ser Thr Ser Arg Lys Gln Met Ala Glu Thr Thr Arg Thr Ala Asn
                 85                  90                  95

Ser Asn Ser Ile His Asn Gln Leu Lys Asp Leu Ser Ser Ser Ile Leu
                100                 105                 110

Ser Tyr Ala Gln Asp Cys Asn Tyr Pro Phe Ser Gln Met Pro Ser Ser
            115                 120                 125

Ser Gln Trp Ser Ile Val Arg Asn Ser Ser Trp Tyr Glu Asn Leu Lys
        130                 135                 140

Leu Leu Lys Phe Leu Ser Ser Val Gly Pro His Val Arg Val Ser Gln
145                 150                 155                 160

Met Leu Ala Arg Asp Ser Val Thr Thr Arg Leu Gln Ser Pro Ser Gly
                165                 170                 175

Leu Ser Phe Ala Glu Leu Thr Tyr Gln Leu Leu Gln Ala Tyr Asp Tyr
            180                 185                 190

Ser Tyr Leu Tyr Glu Asn His Ser Val Asn Leu Gln Ile Gly Gly Ser
        195                 200                 205

Asp Gln Trp Gly Asn Ile Thr Ala Gly Thr Asp Leu Val Arg Arg Thr
        210                 215                 220

His Pro Asn Ala Asn Val Tyr Ala Leu Thr Thr Pro Leu Leu Thr Ser
225                 230                 235                 240

Ser Ser Gly Gln Lys Leu Gly Lys Ser Ala Gly Asn Ala Ile Trp Leu
                245                 250                 255

Asp Pro Lys Leu Thr Asp Ser Tyr Ser Leu Tyr Gln Tyr Phe Ile Ser
                260                 265                 270

Ala Pro Asp Asp Leu Ala Cys Lys Cys Leu Asp Met Leu Thr Leu Leu
            275                 280                 285

Pro Leu Glu Gln Leu Glu Gln Ile Lys Ala Glu His Glu Lys Asp Pro
        290                 295                 300

Ser Gln Arg Ile Val His Lys Tyr Leu Ala Ser Asn Val Val Arg Met
305                 310                 315                 320

Val His Gly Lys Lys Ala Leu Glu Leu Ala Gln Ile Gln Thr Lys Leu
                325                 330                 335

Leu His Gly Ala His Gln Ala Pro Phe Gly Phe Tyr Ser Glu Ala Pro
                340                 345                 350

Gln Gln Gly Asp Ser Phe Pro Ser Leu Pro Glu Ile Arg Ala Leu Phe
            355                 360                 365

Lys Asp Cys Lys Phe Tyr Arg Thr Ile Asp Ser Ser Ile Lys Asp Gln
        370                 375                 380

Pro Phe Ser Arg Leu Leu Arg Thr Leu Gln Ile Tyr Thr Ser Arg Lys
385                 390                 395                 400

Glu Ala Thr Glu His Ile Leu Ser Gly Ala Val Ser Leu Gly His Lys
                405                 410                 415

Pro Ile Leu Asp Ser Asn Tyr Lys Phe Pro Asp Asn Ser Leu Phe Val
            420                 425                 430

Leu Arg Ala Gly Lys Arg Thr Phe Val Leu Asp Ser Leu
        435                 440                 445
```

<210> SEQ ID NO 54
<211> LENGTH: 528
<212> TYPE: PRT
<213> ORGANISM: Xenopus laevis

<400> SEQUENCE: 54

```
Met Gly Asp Ser Leu Thr Leu Glu Gly Lys Ala Gln Leu Ile Thr Arg
  1               5                  10                  15
Asn Leu Gln Glu Leu Leu Gly Glu Asp Lys Met Lys Glu Ile Leu Lys
             20                  25                  30
Glu Arg Pro Leu Arg Ile Tyr Trp Gly Thr Ala Thr Thr Gly Lys Pro
         35                  40                  45
His Val Ala Tyr Phe Val Pro Met Ser Lys Ile Ala Asp Phe Leu Lys
     50                  55                  60
Ala Gly Cys Glu Val Thr Ile Leu Phe Ala Asp Leu His Ala Tyr Leu
 65                  70                  75                  80
Asp Asn Met Lys Ala Pro Trp Asp Leu Leu Glu Leu Arg Thr Arg Tyr
                 85                  90                  95
Tyr Glu Gln Val Ile Gln Ala Met Leu Gln Ser Ile Gly Val Pro Leu
            100                 105                 110
Glu Arg Leu Arg Phe Ile Arg Gly Thr Glu Phe Gln Leu Ser Lys Glu
        115                 120                 125
Tyr Thr Leu Asp Val Tyr Arg Leu Ser Ser Val Val Thr Gln His Asp
    130                 135                 140
Ala Lys Lys Ala Gly Ala Glu Val Val Lys Gln Val Glu His Pro Leu
145                 150                 155                 160
Leu Ser Gly Leu Leu Tyr Pro Gly Leu Gln Ala Leu Asp Glu Glu Tyr
                165                 170                 175
Leu Lys Val Asp Ala Gln Phe Gly Gly Val Asp Gln Arg Lys Ile Phe
            180                 185                 190
Thr Phe Ala Glu Lys Tyr Leu Pro Ala Leu Gly Tyr Ala Lys Arg Ile
        195                 200                 205
His Leu Met Asn Pro Met Val Pro Gly Leu Thr Gly Ala Lys Met Ser
    210                 215                 220
Ser Ser Glu Glu Glu Ser Lys Ile Asp Leu Leu Asp Ser Pro Ala Asp
225                 230                 235                 240
Val Lys Lys Lys Leu Lys Lys Ala Phe Cys Glu Pro Gly Asn Val Glu
                245                 250                 255
Asn Asn Gly Val Leu Ser Phe Val Arg His Val Leu Phe Pro Leu Lys
            260                 265                 270
Ser Glu Phe Val Val Leu Arg Asp Glu Lys Phe Gly Gly Asn Lys Thr
        275                 280                 285
Tyr Thr Asp Phe Glu Thr Leu Glu Lys Asp Phe Ala Glu Glu Leu Val
    290                 295                 300
His Pro Gly Asp Leu Lys Ala Ser Val Glu Lys Ala Leu Asn Lys Leu
305                 310                 315                 320
Leu His Pro Ile Arg Glu Lys Phe Asn Ser Pro Glu Met Lys Lys Leu
                325                 330                 335
Ser Asn Asp Ala Tyr Pro Asp Ala Ser Lys Gln Lys Ser Val Pro Lys
            340                 345                 350
Gly Ser Thr Lys Asn Ser Gly Thr Glu Glu Ile Asp Pro Ser Leu Leu
        355                 360                 365
Asp Leu Arg Val Gly Lys Ile Leu Ser Val Ser Gln His Pro Asp Ala
    370                 375                 380
Asp Ser Leu Tyr Val Glu Ser Val Asp Val Gly Glu Ala Asn Pro Arg
```

```
                385                 390                 395                 400
Cys Val Val Ser Gly Leu Val Gln Tyr Val Pro Ser Asp Gln Leu Leu
                    405                 410                 415

Gly Arg Ser Val Val Leu Leu Cys Asn Leu Lys Pro Gln Lys Met Arg
                420                 425                 430

Gly Ile Glu Ser Gln Gly Met Leu Leu Cys Ala Ser Thr Glu Gly Glu
                435                 440                 445

Gln Lys Gln Val Glu Pro Leu Asp Pro Pro Ser Gly Ser Ala Pro Gly
            450                 455                 460

Glu Arg Ile Tyr Ile Glu Gly Tyr Glu Asn Gly Glu Pro Glu Gly Glu
465                 470                 475                 480

Leu Lys Pro Lys Lys Val Phe Glu Lys Leu Gln Val Asp Phe Arg
                485                 490                 495

Ile Ser Asp Asp Leu Cys Ala Gln Trp Lys Gly Lys Asn Phe Leu Thr
                500                 505                 510

Lys Leu Gly Ser Val Thr Cys Lys Thr Leu Arg Gly Gly Ser Ile Gly
                515                 520                 525

<210> SEQ ID NO 55
<211> LENGTH: 402
<212> TYPE: PRT
<213> ORGANISM: Helicobacter pylori

<400> SEQUENCE: 55

Met Glu Gln Lys Ile Ala Ile Ala Leu Lys Glu Ile Ala Arg Gly Thr
1               5                   10                  15

Asn Glu Ile Ile Gly Leu Glu Tyr Ile Glu Lys Leu Val Arg Lys Tyr
                20                  25                  30

Tyr Glu Thr Asn Glu Arg Phe Ile Val Lys Ala Gly Phe Asp Pro Thr
            35                  40                  45

Ala Pro Asp Leu His Leu Gly His Thr Val Leu Ile Gln Lys Leu Ala
        50                  55                  60

Leu Leu Gln Gln Tyr Gly Ala Arg Val Lys Phe Leu Ile Gly Asp Phe
65                  70                  75                  80

Thr Ala Met Ile Gly Asp Pro Thr Gly Lys Asn Glu Thr Arg Lys Pro
                85                  90                  95

Leu Asn Arg Glu Gln Val Leu Glu Asn Ala Lys Thr Tyr Glu Glu Gln
                100                 105                 110

Ile Tyr Lys Ile Leu Asp Glu Lys His Thr Glu Val Cys Phe Asn Ser
            115                 120                 125

Thr Trp Leu Asp Ala Leu Gly Ala Lys Gly Met Ile Glu Leu Cys Ala
130                 135                 140

Lys Phe Ser Val Ala Arg Met Leu Glu Arg Asp Asp Phe Thr Lys Arg
145                 150                 155                 160

Tyr Lys Glu Asn Arg Pro Ile Ser Ile Val Glu Phe Leu Tyr Pro Leu
                165                 170                 175

Leu Gln Gly Tyr Asp Ser Val Ala Met Asp Ala Asp Ile Glu Leu Gly
            180                 185                 190

Gly Asn Asp Gln Lys Phe Asn Leu Leu Val Gly Arg Phe Leu Gln Arg
        195                 200                 205

Ala Tyr Gly Leu Asn Lys Glu Gln Ser Val Ile Thr Met Pro Leu Leu
    210                 215                 220

Glu Gly Leu Asp Gly Val Gln Lys Met Ser Lys Ser Leu Gly Asn Tyr
225                 230                 235                 240

Val Gly Ile Thr Glu Glu Pro Asn Ala Met Phe Gly Lys Ile Met Ser
```

```
                     245                 250                 255
Val Ser Asp Asp Leu Met Trp Arg Tyr Tyr Thr Leu Leu Ser Thr Lys
            260                 265                 270

Thr Leu Glu Glu Ile Glu Asp Leu Lys His Gly Ile Leu Asn Gln Thr
            275                 280                 285

Leu His Pro Lys Ala Val Lys Glu Asp Leu Ala Ser Glu Ile Val Ala
            290                 295                 300

Arg Tyr Tyr Asp Asn Asp Gln Ala Ile Lys Ala Lys Glu Gln Phe Ser
305                 310                 315                 320

Lys Val Phe Ser Ala Asn Leu Leu Pro Glu Ile Leu Ser Glu Ser Asp
            325                 330                 335

Phe Asp Glu Gly Val Gly Ile Leu Asp Val Leu Lys Gln Ile Gly Phe
            340                 345                 350

Cys Pro Ser Thr Ser Gln Ala Arg Arg Asp Ile Gln Gly Gly Val
            355                 360                 365

Lys Ile Asn Gln Glu Val Ile Lys Asn Glu Ser Tyr Arg Phe Val Lys
            370                 375                 380

Gly Asn Tyr Val Ile Gln Leu Gly Lys Lys Arg Phe Met Lys Leu Asn
385                 390                 395                 400

Ile Asn

<210> SEQ ID NO 56
<211> LENGTH: 447
<212> TYPE: PRT
<213> ORGANISM: Caenorhabditis elegans

<400> SEQUENCE: 56

Met Phe Asn Ser Lys Arg Ile Gly Asn Val Ala Leu Lys Thr Val Arg
 1               5                  10                  15

Ala Pro Arg Glu Ser Ser Phe Val Asp Tyr Ile Thr Asp Leu Asn Ala
            20                  25                  30

Arg Lys Gln Leu Gln His Ser Tyr Pro Thr Asp Leu Leu Ser Lys Cys
            35                  40                  45

Ser Glu Asp Leu Arg Gln Leu Pro Pro Tyr Val Tyr Ala Gly Phe Asp
            50                  55                  60

Pro Thr Ala Glu Ser Leu His Ile Gly Asn Leu Leu Ile Leu Val Asn
65                  70                  75                  80

Leu Ile Arg Ala Gln Gln Phe Gly Ile Arg Pro Ile Ala Leu Ile Gly
            85                  90                  95

Glu Phe Thr Ala Ser Ile Gly Asp Pro Ser Gly Lys Lys Ser Glu Arg
            100                 105                 110

Gly Leu Leu Ala Gly Asp Val Ile Met His Asn Ser Arg Lys Val Thr
            115                 120                 125

Asp Gln Ile Cys Lys Ile Phe Glu Asn Ala Pro Gly Ser Ser Glu Lys
130                 135                 140

Pro Ile Ile Val Asn Asn Asn Asp Trp Leu Gly Lys Ile Ser Leu Arg
145                 150                 155                 160

Asp Phe Leu Arg Glu Cys Lys Asn Met Gln Val Gly Lys Met Leu Arg
            165                 170                 175

Met Asn Thr Ile Lys Asn Arg Leu Glu Val Gly Leu Ser Tyr Thr Glu
            180                 185                 190

Phe Ser Tyr Gln Thr Met Gln Ala Phe Asp Trp Tyr Thr Leu Ser Glu
            195                 200                 205

Lys Tyr Gly Cys Arg Phe Gln Leu Gly Gly Tyr Asp Gln Leu Gly His
            210                 215                 220
```

```
Leu Asp Phe Gly Ala His Tyr Ile Lys Lys Met Met Asn Gln Ala Phe
225                 230                 235                 240

Ala Ala Gly Val Cys Phe Pro Ile Leu Thr Asp Ser Thr Gly Ala Lys
            245                 250                 255

Leu Gly Lys Ser Glu Gly Gly Ala Leu Trp Leu Asp Ala Thr Lys
        260                 265                 270

Thr Ser Pro Phe His Phe Tyr Gln Phe Phe Ala Gln Leu His Asp Asp
            275                 280                 285

Lys Ala Glu Glu Leu Leu Leu Phe Ser Leu Gln Asp Ile Glu His
290                 295                 300

Ile Arg Asp Val Leu Lys Asn His Arg Ser Asn Leu Gly Gln Trp Ile
305                 310                 315                 320

Ala Gln Arg Glu Leu Ala Ala Glu Ile Thr Arg Ile Val His Gly Lys
                325                 330                 335

Glu Gly Leu Glu Val Ala Met Arg Cys Thr Lys Ala Met Phe Gly Ala
            340                 345                 350

Lys Lys Ala Asp Leu Ser Gly Leu Ser Arg Ser Glu Val Leu Gln Leu
        355                 360                 365

Phe Arg Thr Thr Ile Asp Leu Lys Lys Glu Asn Val Ala Thr Met Gly
                370                 375                 380

Gln Leu Ala Asp Ala Ser Arg Leu Gly Ser Gly Lys Gly His Leu Leu
385                 390                 395                 400

Met Gln Gln Gly Ala Phe Ser Val Asn Gly Glu Lys Lys Arg Ser Pro
                405                 410                 415

Ser Glu Ser Ile Ala Asp Val Phe Leu Glu Asn Ala Ser Asp Leu Thr
                420                 425                 430

Leu Val Cys Trp Gly Lys Arg Gly Tyr Gln Leu Val Arg Trp Val
                435                 440                 445

<210> SEQ ID NO 57
<211> LENGTH: 412
<212> TYPE: PRT
<213> ORGANISM: Pseudomonas aeruginosa

<400> SEQUENCE: 57

Met Ser Val Pro Thr His Gln Gln Asp Leu Ile Ala Leu Leu Glu Glu
1               5                   10                  15

Arg Gly Phe Val His Gln Cys Thr Asp Arg Asp Gly Leu Ala Ala His
                20                  25                  30

Leu Ala Ala Gly Pro Ala Thr Ala Tyr Leu Gly Phe Asp Ala Thr Ala
            35                  40                  45

Asp Ser Leu His Val Gly His Leu Gln Gly Leu Met Leu Met Arg Trp
        50                  55                  60

Leu Gln Lys Ala Gly His Arg Pro Leu Leu Ile Gly Gly Ala Thr
65                  70                  75                  80

Thr Arg Ile Gly Asp Pro Ser Phe Arg Asp Ser Ser Arg Pro Ile Leu
                85                  90                  95

Thr Glu Ala Gln Ile Gln Ala Asn Ile Asp Gly Ile Ala Arg Val Phe
            100                 105                 110

Ser Arg Tyr Val Glu Leu His Asp Asp Ser Leu Val Asn Asn Ala Glu
        115                 120                 125

Trp Leu Asp Gly Val Gly Tyr Leu Glu Phe Leu Asp Arg Val Gly Arg
    130                 135                 140

His Phe Ser Ile Asn Arg Leu Leu Thr Phe Asp Ala Ile Arg Gln Arg
145                 150                 155                 160
```

Leu Asp Arg Glu His Ser Leu Ser Phe Leu Glu Phe Gly Tyr Thr Leu
................165.................170.................175

Leu Gln Ala Tyr Asp Phe Val Glu Leu Ser Arg Arg Gly Cys Thr
180.................185.................190

Leu Gln Leu Gly Gly Ala Asp Gln Trp Ala Asn Ile Ile Asn Gly Val
................195.................200.................205

Glu Leu Ser Arg Arg Gln Gly Gly Ala Gln Leu Phe Gly Leu Thr Met
210.................215.................220

Pro Leu Leu Ala Thr Ser Asp Gly Arg Lys Met Gly Lys Ser Ala Gln
225.................230.................235.................240

Gly Ala Val Trp Leu Asn Ala Glu Arg Leu Ala Pro Phe Asp Phe Trp
................245.................250.................255

Gln Phe Trp Arg Asn Cys Asp Asp Arg Asp Val Gly Arg Phe Leu Ala
................260.................265.................270

Leu Phe Ser Glu Leu Pro Met Asp Glu Val Arg Arg Leu Gly Ala Leu
................275.................280.................285

Gln Gly Ala Glu Leu Asn Glu Ala Lys Val Val Leu Ala Asn Ala Ala
290.................295.................300

Thr Ala Leu Ala His Gly Glu His Ala Ala Arg Ser Ala Ala Asp Ala
305.................310.................315.................320

Ala Arg Gly Val Phe Ala Asp Gly Thr Arg Asp Ser Gly Leu Pro Val
................325.................330.................335

Met Lys Leu Ser Arg Ala Arg Leu Ala Gln Gly Leu Ser Leu Thr Asp
................340.................345.................350

Leu Leu Leu Glu His Ala Ile Gln Pro Ser Arg Ser Ala Val Arg Arg
................355.................360.................365

Leu Ala Ala Gly Gly Leu Arg Leu Asp Gly Thr Pro Val Ser Asp
................370.................375.................380

Pro Asp Thr Pro Leu Ala Gly Glu Val Asp Gly Leu Arg Leu Ser Leu
385.................390.................395.................400

Gly Lys Lys Gln His Leu His Leu Arg Leu Glu Asp
................405.................410

<210> SEQ ID NO 58
<211> LENGTH: 399
<212> TYPE: PRT
<213> ORGANISM: Pseudomonas aeruginosa

<400> SEQUENCE: 58

Met Lys Ser Val Glu Glu Gln Leu Ala Leu Ile Gln Arg Gly Ala Asp
.1.................5.................10.................15

Glu Ile Leu Val Glu Ala Glu Leu Val Ala Lys Leu Lys Arg Gly Gln
................20.................25.................30

Pro Leu Arg Ile Lys Ala Gly Phe Asp Pro Thr Ala Pro Asp Leu His
................35.................40.................45

Leu Gly His Thr Val Leu Ile Asn Lys Leu Arg Gln Phe Gln Asp Leu
................50.................55.................60

Gly His Gln Val Ile Phe Leu Ile Gly Asp Phe Thr Gly Met Ile Gly
65.................70.................75.................80

Asp Pro Ser Gly Lys Ser Val Thr Arg Pro Leu Thr Arg Glu Gln
................85.................90.................95

Val Leu Glu Asn Ala Glu Thr Tyr Lys Ser Gln Val Phe Lys Ile Leu
................100.................105.................110

Asp Pro Ala Lys Thr Glu Val Ala Phe Asn Ser Thr Trp Met Asp Gln
................115.................120.................125

Leu Thr Pro Ala Asp Phe Ile Arg Leu Ala Ser Gln Tyr Thr Val Ala
            130                 135                 140

Arg Met Leu Glu Arg Asp Asp Phe Ser Lys Arg Tyr Ala Ser Asn Gln
145                 150                 155                 160

Pro Ile Ala Ile His Glu Phe Leu Tyr Pro Leu Val Gln Gly Tyr Asp
                165                 170                 175

Ser Val Ala Leu Lys Ala Asp Val Glu Leu Gly Gly Thr Asp Gln Lys
            180                 185                 190

Phe Asn Leu Leu Met Gly Arg Glu Leu Gln Arg Ala Tyr Gly Gln Glu
        195                 200                 205

Ala Gln Val Ile Leu Thr Met Pro Leu Leu Glu Gly Leu Asp Gly Val
    210                 215                 220

Lys Lys Met Ser Lys Ser Leu Gly Asn Tyr Ile Gly Ile Gln Glu Ala
225                 230                 235                 240

Pro Gly Val Met Tyr Ser Lys Leu Val Ser Ile Pro Asp Thr Leu Met
                245                 250                 255

Trp Arg Tyr Phe Glu Leu Leu Ser Phe Arg Ser Leu Asp Glu Ile Asp
            260                 265                 270

Ser Phe Arg Lys Asp Val Glu Ala Gly Ala Asn Pro Arg Asp Ile Lys
        275                 280                 285

Ile Lys Leu Ala Glu Glu Ile Val Ala Arg Phe His Gly Glu Glu Ala
    290                 295                 300

Ala Ala Ser Ala His Lys Ser Ala Gly Asn Arg Leu Lys Glu Gly Glu
305                 310                 315                 320

Leu Pro Glu Asp Leu Pro Glu Ile Glu Leu Ser Ser Pro Glu Asp Met
                325                 330                 335

Pro Val Ala Ser Val Leu Asn Lys Ala Gly Leu Val Lys Asn Ala Ala
            340                 345                 350

Ala Ala Arg Asp Leu Leu Gly Ala Gly Ser Val Lys Val Asp Gly Gln
        355                 360                 365

Val Val Asp Arg Thr Phe Met Leu Ala Leu Gly Glu Thr Arg Val Phe
    370                 375                 380

Gln Ala Gly Lys Lys Ala Phe Ala Arg Ile Thr Leu Lys Ala Glu
385                 390                 395

<210> SEQ ID NO 59
<211> LENGTH: 334
<212> TYPE: PRT
<213> ORGANISM: Escherichia coli

<400> SEQUENCE: 59

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110

```
Lys Ser Ala Arg Tyr Ala Glu Asn Ile Asn Ala Gly Leu Phe Asp Tyr
            115                 120                 125

Pro Val Leu Met Ala Ala Asp Ile Leu Leu Tyr Gln Thr Asn Leu Val
        130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asn Arg Asn Asn Val Ile Gly
        195                 200                 205

Leu Leu Glu Asp Pro Lys Ser Val Val Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
        275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330

<210> SEQ ID NO 60
<211> LENGTH: 326
<212> TYPE: PRT
<213> ORGANISM: Helicobacter pylori

<400> SEQUENCE: 60

Met His Lys Lys Arg Val Phe Ser Gly Ile Gln Pro Thr Gly Gln Ile
1               5                   10                  15

His Leu Gly Asn Tyr Leu Gly Ala Ile Lys His Trp Val Glu Met Gln
            20                  25                  30

Asp Glu Tyr Glu Asn Leu Phe Cys Val Val Asn Ser His Ala Ile Thr
        35                  40                  45

Leu Pro Ile Asp Pro Ala Phe Leu Lys Ser Gln Ser Tyr Glu Leu Val
    50                  55                  60

Lys Leu Leu Leu Ala Cys Gly Ile Asp Pro Lys Gln Ser Gly Leu Phe
65                  70                  75                  80

Ile Gln Ser Glu Val Asp Glu His Pro Ala Leu Ala Trp Leu Leu Asn
                85                  90                  95

Cys Gln Val Ser Met Gly Glu Met Gln Arg Met Thr Gln Phe Lys Asp
            100                 105                 110

Lys Ser Leu Lys Asn Pro Lys Ser Val Asn Val Gly Leu Phe Asn Tyr
        115                 120                 125

Pro Ile Leu Met Ala Ser Asp Ile Leu Leu Tyr Gln Ser Asp Leu Val
    130                 135                 140

Pro Val Gly Glu Asp Gln Lys Gln His Leu Glu Leu Thr Arg Asn Ile
145                 150                 155                 160
```

Ala Glu Lys Phe Asn Arg Asp Phe Gly Asn Cys Phe Lys Val Pro Glu
            165                 170                 175

Pro Leu Ile Ala Lys Val Gly Ala Arg Val Met Gly Leu Asp Asp Pro
        180                 185                 190

Lys Val Lys Met Ser Lys Ser His Gln Gly Ala Asn His Ala Ile Phe
    195                 200                 205

Leu Leu Asp Glu Pro Asp Ile Ile Val Lys Ile Lys Lys Ala Ala
210                 215                 220

Thr Asp Ser Met Gly Val Ile Ala Phe Asp Glu Lys Arg Glu Gly Ile
225                 230                 235                 240

Phe Asn Leu Leu Asn Ile Tyr Met Leu Leu Ser Asn Glu Ser Pro Glu
                245                 250                 255

Asn Ile Glu Glu Arg Phe Lys Asn Lys Gly Tyr Gly Asp Phe Lys Lys
            260                 265                 270

Glu Leu Ala Glu Val Met Ile Gln Ala Leu Lys Pro Ile Gln Glu Arg
        275                 280                 285

Tyr Lys Glu Ile Ser Asp Asp Glu Val Lys Ala Ile Leu Asn Gly Gly
    290                 295                 300

Ala Glu Lys Ala Arg Pro Leu Ala Arg Ala Thr Tyr Gln Lys Ala Lys
305                 310                 315                 320

Glu Leu Met Gly Leu Ile
                325

<210> SEQ ID NO 61
<211> LENGTH: 361
<212> TYPE: PRT
<213> ORGANISM: Schizosaccharomyces pombe

<400> SEQUENCE: 61

Met Ala Lys Leu Pro Lys Ile Thr Ser Leu Leu Pro His Ser Arg Val
1               5                   10                  15

Val Ser Gly Ile Gln Pro Thr Gly Ile Pro His Ile Gly Asn Tyr Leu
            20                  25                  30

Gly Ser Leu Lys Gln Trp Val Gln Leu Gln Glu Glu Ala Ala Arg Thr
        35                  40                  45

Pro Phe Ser Lys Cys Phe Phe Phe Val Ala Asp Leu His Ala Leu Thr
    50                  55                  60

Val Pro Gln Asp Pro Leu Lys Phe Arg Gln Ala Arg Leu Asp Met Leu
65                  70                  75                  80

Ala Ala Leu Leu Ala Ile Gly Ile Asn Pro Gln Lys Ser Thr Leu Phe
                85                  90                  95

Phe Gln Ser Asp Val Ala Gln His Ser Glu Leu Ala Trp Leu Leu Ala
            100                 105                 110

Cys Ser Thr Ser Met Gly Gln Leu Asn Arg Met Thr Gln Trp Lys Ser
        115                 120                 125

Lys Leu His Leu His Asp His Asp Leu Ser Phe Leu Asp Ala Ser
    130                 135                 140

Ala Thr Ser Ser Thr Arg Phe Asn Leu Gly Leu Phe Ser Tyr Pro Val
145                 150                 155                 160

Leu Gln Ala Ala Asp Ile Leu Leu Tyr Gly Ala Thr His Ile Pro Val
                165                 170                 175

Gly Lys Asp Gln Ser Gln His Val Glu Leu Thr Arg Ser Ile Ala Arg
            180                 185                 190

Ser Phe Asn Ser Ser Tyr Lys Glu Lys Ile Leu Thr Val Pro Asp Ile
        195                 200                 205

```
Ile Leu Asn Ser Ser Ser Ile Met Ala Leu Cys Gln Pro Glu Lys
    210                 215                 220

Lys Met Ser Lys Ser Asp Ile Asn Ser Lys Asn Tyr Ile Leu Leu Ser
225                 230                 235                 240

Asp Ser Thr Gly Glu Ile Arg Lys Lys Ile Ser Arg Ala Gln Thr Asp
                245                 250                 255

Asn Ile Lys Gly Ile Thr Tyr Gly Asp Ser Asn Arg Pro Gly Ile Asn
            260                 265                 270

Asn Leu Ile Asn Ile Phe Ala Ala Ile Ser Asp Ser Thr Pro Ser Asp
        275                 280                 285

Ile Ala Gln Ala Asn Ala Ser Cys Ser Asn Ala Glu Phe Lys Glu Lys
    290                 295                 300

Val Ser Ser Ala Ile Ile Arg Cys Leu Gln Pro Ile Ser Thr Ser Phe
305                 310                 315                 320

Asn Glu Trp Arg Gln Asn Arg Glu Leu Leu Arg Asp Ile Ala Lys Lys
                325                 330                 335

Gly Ala Glu Glu Ala Val Ala Glu Ala Ser Ser Cys Met His Lys Leu
            340                 345                 350

Lys Thr Leu Thr Gly Leu Ser Val Tyr
        355                 360

<210> SEQ ID NO 62
<211> LENGTH: 665
<212> TYPE: PRT
<213> ORGANISM: Drosophila melanogaster

<400> SEQUENCE: 62

Met Phe Arg Phe Gly Lys Leu His Arg Ser Leu Ser Lys Val Ala Lys
1               5                   10                  15

Lys Gly Gln Thr Ala Val Tyr Ser Gln Arg Arg Cys Ile Gln Ala Arg
            20                  25                  30

Ser Phe Leu Pro Gly Leu Ala Ser Arg Thr Ala Gly Thr Pro Ser Ala
        35                  40                  45

Thr Ala Gln Val Thr Gly Gly Asn Lys Gln His Val His Pro His Gly
    50                  55                  60

Asn Ser Val Asn Ser Gly His Glu Glu His Asn Thr Arg Trp Pro Arg
65                  70                  75                  80

Lys Val Phe Ser Gly Ile Gln Pro Thr Gly Ser Leu His Leu Gly Asn
                85                  90                  95

Tyr Leu Gly Ala Val Arg Lys Trp Val Gln Leu Gln Asn Ala Arg Asp
            100                 105                 110

Asp Val Thr Val Cys Ile Val Asp Leu His Ser Ile Thr Met Pro His
        115                 120                 125

Asn Pro Pro Leu Leu Arg Glu Asn Ile Phe Thr Met Ala Ala Thr Leu
    130                 135                 140

Leu Ala Cys Gly Ile Asp Pro Thr Lys Ser Thr Leu Phe Val Gln Ser
145                 150                 155                 160

Ala Val Ala Glu His Ala Glu Phe Asn Trp Ile Leu Ser Ser Leu Thr
                165                 170                 175

Thr Met Pro Arg Leu Ala Gln Leu Pro Gln Phe Arg Glu Lys Ser Arg
            180                 185                 190

Leu Leu Lys Asp Val Pro Leu Gly Leu Tyr Val Tyr Pro Val Leu Gln
        195                 200                 205

Ala Ala Asp Ile Met Leu Tyr Lys Ser Thr His Val Pro Val Gly Ala
    210                 215                 220
```

```
Asp Gln Ile Gln His Ile Gln Leu Ala Gln His Leu Ala Arg Ile Tyr
225                 230                 235                 240

Asn Gly Arg Tyr Gly Glu Thr Phe Pro Val Cys Thr Ala Ile Ile Glu
            245                 250                 255

Asp Gly Asp Ala Ser Arg Val Leu Ser Leu Arg Asp Pro Ser Lys Lys
        260                 265                 270

Met Ser Lys Ser Glu Ala Asn Pro Lys Ala Thr Ile Asn Leu Cys Asp
    275                 280                 285

Ser Pro Asp Leu Ile Thr Gln Lys Ile Lys Lys Ala Val Thr Asp Phe
290                 295                 300

Thr Ser Asp Ile Thr Tyr Asn Pro Gly Lys Arg Ala Gly Val Ser Asn
305                 310                 315                 320

Leu Val Asn Ile His Ala Gln Val Thr Gly Gln Ser Ile Lys Thr Val
                325                 330                 335

Val Asn Glu Ala Ala Thr Leu Asp Thr Ala Lys Tyr Lys Asp Arg Val
            340                 345                 350

Ala Glu Ala Val Val Glu His Leu Arg Pro Ile Arg Glu Gln Ile His
        355                 360                 365

His His Met Thr Lys Arg Asn Glu Met Ile Tyr Leu Leu Glu Val Gly
    370                 375                 380

Ala Glu Lys Ala Arg Gln Gln Ala Arg Gln Thr Leu Asn Asp Val Lys
385                 390                 395                 400

Gln Arg Leu Gly Leu Gly Thr Ser Ala Asn Ile Pro Ala Ala Val His
                405                 410                 415

Val Ala Pro Leu Leu Pro Ala Pro Asp Ile Ser Lys Thr Ser Ala Ser
            420                 425                 430

Arg Arg Met Ser Lys Asp Phe Asp Gly Asn Val His Glu Arg His Glu
        435                 440                 445

Arg Met Tyr Gly Phe Gly Asp Gln Pro Ser Gly Gly Ala Gly Gln Ser
    450                 455                 460

Ala Thr Gly Glu Val Ala Asp Met Pro Gln Ala Val Val Pro Arg Val
465                 470                 475                 480

Ile Arg Arg Ala Pro Ile Val Pro Thr Gln Ser Met Arg Val Glu Lys
                485                 490                 495

Gln Leu Gly Ser Thr Arg Thr Arg His Val Phe Gln Met Asp Thr Cys
            500                 505                 510

Asn Ala Pro His Ile Gly Phe Lys Pro Pro Gly Phe Ser Ala Ser
        515                 520                 525

Met Val Thr Gly Ala Leu Ala Lys Asn Lys Arg Ala Thr Val Lys Pro
    530                 535                 540

Val Thr Gly Asn Leu Gly Phe Gly Gln Gln Ser Gln Gly Gly Ser Tyr
545                 550                 555                 560

Lys His Ser Gln Asn Val Asn Pro Ser Ala Val Ser Thr Ile Ala Arg
                565                 570                 575

Glu Val Asn Ala Ala Lys Lys Gln Glu Phe Thr Cys Asn Pro Ala Leu
            580                 585                 590

Tyr Gly Ser Ala Leu Glu Ser Leu Ser Asn Ser Ser Arg Ser Ser Glu
        595                 600                 605

Lys Thr Asn Ser Thr Ala Gly Asp Ser Glu Phe Ile Ile Val Ala Ser
    610                 615                 620

Glu Glu Glu Gly Gln Ala Ala Ser Ser Glu Gln Arg Glu Glu Ala
625                 630                 635                 640

Glu Glu Glu Glu Ser Gly Glu Arg Glu Arg Glu Lys Gly Glu Arg Asn
```

```
                    645                 650                 655
Ala Thr Glu Ala Thr Lys Val Glu Ile
            660                 665

<210> SEQ ID NO 63
<211> LENGTH: 360
<212> TYPE: PRT
<213> ORGANISM: Homo sapiens

<400> SEQUENCE: 63

Met Ala Leu His Ser Met Arg Lys Ala Arg Glu Arg Trp Ser Phe Ile
 1               5                  10                  15

Arg Ala Leu His Lys Gly Ser Ala Ala Pro Ala Leu Gln Lys Asp
                20                  25                  30

Ser Lys Lys Arg Val Phe Ser Gly Ile Gln Pro Thr Gly Ile Leu His
             35                  40                  45

Leu Gly Asn Tyr Leu Gly Ala Ile Glu Ser Trp Val Arg Leu Gln Asp
         50                  55                  60

Glu Tyr Asp Ser Val Leu Tyr Ser Ile Val Asp Leu His Ser Ile Thr
 65                  70                  75                  80

Val Pro Gln Asp Pro Ala Val Leu Arg Gln Ser Ile Leu Asp Met Thr
                 85                  90                  95

Ala Val Leu Leu Ala Cys Gly Ile Asn Pro Glu Lys Ser Ile Leu Phe
            100                 105                 110

Gln Gln Ser Gln Val Ser Glu His Thr Gln Leu Ser Trp Ile Leu Ser
        115                 120                 125

Cys Met Val Arg Leu Pro Arg Leu Gln His Leu His Gln Trp Lys Ala
    130                 135                 140

Lys Thr Thr Lys Gln Lys His Asp Gly Thr Val Gly Leu Leu Thr Tyr
145                 150                 155                 160

Pro Val Leu Gln Ala Ala Asp Ile Leu Leu Tyr Lys Ser Thr His Val
                165                 170                 175

Pro Val Gly Glu Asp Gln Val Gln His Met Glu Leu Val Gln Asp Leu
            180                 185                 190

Ala Gln Gly Phe Asn Lys Lys Tyr Gly Glu Phe Phe Pro Val Pro Glu
        195                 200                 205

Ser Ile Leu Thr Ser Met Lys Lys Val Lys Ser Leu Arg Asp Pro Ser
    210                 215                 220

Ala Lys Met Ser Lys Ser Asp Pro Asp Lys Leu Ala Thr Val Arg Ile
225                 230                 235                 240

Thr Asp Ser Pro Glu Glu Ile Val Gln Lys Phe Arg Lys Ala Val Thr
                245                 250                 255

Asp Phe Thr Ser Glu Val Thr Tyr Asp Pro Ala Gly Arg Ala Gly Val
            260                 265                 270

Ser Asn Ile Val Ala Val His Ala Ala Val Thr Gly Leu Ser Val Glu
        275                 280                 285

Glu Val Val Arg Arg Ser Ala Gly Met Asn Thr Ala Arg Tyr Lys Leu
    290                 295                 300

Ala Val Ala Asp Ala Val Ile Glu Lys Phe Ala Pro Ile Lys Arg Glu
305                 310                 315                 320

Ile Glu Lys Leu Lys Leu Asp Lys Asp His Leu Glu Val Leu Gln
                325                 330                 335

Ile Gly Ser Ala Lys Ala Lys Glu Leu Ala Tyr Thr Val Cys Gln Glu
            340                 345                 350

Val Lys Lys Leu Val Gly Phe Leu
```

<210> SEQ ID NO 64
<211> LENGTH: 379
<212> TYPE: PRT
<213> ORGANISM: Saccharomyces cerevisiae

<400> SEQUENCE: 64

Met Ser Asn Lys Gln Ala Val Leu Lys Leu Ile Ser Lys Arg Trp Ile
1               5                   10                  15

Ser Thr Val Gln Arg Ala Asp Phe Lys Leu Asn Ser Glu Ala Leu His
            20                  25                  30

Ser Asn Ala Thr Val Phe Ser Met Ile Gln Pro Thr Gly Cys Phe His
        35                  40                  45

Leu Gly Asn Tyr Leu Gly Ala Thr Arg Val Trp Thr Asp Leu Cys Glu
    50                  55                  60

Leu Lys Gln Pro Gly Gln Glu Leu Ile Phe Gly Val Ala Asp Leu His
65                  70                  75                  80

Ala Ile Thr Val Pro Lys Pro Asp Gly Glu Met Phe Arg Lys Phe Arg
                85                  90                  95

His Glu Ala Val Ala Ser Ile Leu Ala Val Gly Val Asp Pro Glu Lys
            100                 105                 110

Ala Ser Val Ile Tyr Gln Ser Ala Ile Pro Gln His Ser Glu Leu His
        115                 120                 125

Trp Leu Leu Ser Thr Leu Ala Ser Met Gly Leu Leu Asn Arg Met Thr
    130                 135                 140

Gln Trp Lys Ser Lys Ser Asn Ile Lys Gln Ser Thr Asn Gly Asp Tyr
145                 150                 155                 160

Leu Val Asn Asp Ser Asp Val Gly Lys Val Arg Leu Gly Leu Phe Ser
                165                 170                 175

Tyr Pro Val Leu Gln Ala Ala Asp Ile Leu Leu Tyr Lys Ser Thr His
            180                 185                 190

Val Pro Val Gly Asp Asp Gln Ser Gln His Leu Glu Leu Thr Arg His
        195                 200                 205

Leu Ala Glu Lys Phe Asn Lys Met Tyr Lys Lys Asn Phe Phe Pro Lys
    210                 215                 220

Pro Val Thr Met Leu Ala Gln Thr Lys Lys Val Leu Ser Leu Ser Thr
225                 230                 235                 240

Pro Glu Lys Lys Met Ser Lys Ser Asp Pro Asn His Asp Ser Val Ile
                245                 250                 255

Phe Leu Asn Asp Glu Pro Lys Ala Ile Gln Lys Lys Ile Arg Lys Ala
            260                 265                 270

Leu Thr Asp Ser Ile Ser Asp Arg Phe Tyr Tyr Asp Pro Val Glu Arg
        275                 280                 285

Pro Gly Val Ser Asn Leu Ile Asn Ile Val Ser Gly Ile Gln Arg Lys
    290                 295                 300

Ser Ile Glu Asp Val Val Glu Asp Val Ser Arg Phe Asn Asn Tyr Arg
305                 310                 315                 320

Asp Phe Lys Asp Tyr Val Ser Glu Val Ile Glu Glu Leu Lys Gly
                325                 330                 335

Pro Arg Thr Glu Phe Glu Lys Tyr Ile Asn Glu Pro Thr Tyr Leu His
            340                 345                 350

Ser Val Val Glu Ser Gly Met Arg Lys Ala Arg Glu Lys Ala Ala Lys
        355                 360                 365

Asn Leu Ala Asp Ile His Lys Ile Met Gly Phe

```
                370                 375
```

<210> SEQ ID NO 65
<211> LENGTH: 475
<212> TYPE: PRT
<213> ORGANISM: Xenopus laevis

<400> SEQUENCE: 65

```
Met Ser Asp Ser Gly Thr Ser Thr Ser Gly Ser Leu Leu Pro Met Asp
 1               5                  10                  15

Leu Tyr Asn Gln Val Thr Ala Gln Gly Asp Lys Ile Arg Val Leu Lys
            20                  25                  30

Ser Glu Lys Ser Pro Lys Glu Glu Ile Asp Ala Ala Val Lys Leu Leu
        35                  40                  45

Leu Ala Leu Lys Val Asp Tyr Lys Asn Val Thr Gly Gln Asp Tyr Lys
    50                  55                  60

Pro Gly Val Pro Pro Ala Asp Asp Met Pro Thr Asn Arg Asn Gly Pro
65                  70                  75                  80

Ser Thr Pro Asn Asp Gly Asp Phe Val Asp Pro Trp Thr Val Gln
                85                  90                  95

Thr Gly Ser Ala Lys Gly Val Asp Tyr Asp Lys Leu Ile Val Arg Phe
            100                 105                 110

Gly Ser Ser Lys Ile Asp Gln Ala Leu Ile Asp Arg Ile Glu Arg Val
        115                 120                 125

Thr Gly Gln Lys Ala His His Phe Leu Arg Arg Gly Ile Phe Phe Ser
    130                 135                 140

His Arg Asp Met His Gln Val Leu Asp Ala Tyr Glu Lys Lys Lys Pro
145                 150                 155                 160

Phe Tyr Leu Tyr Thr Gly Arg Gly Pro Ser Ser Glu Ala Met His Val
                165                 170                 175

Gly His Leu Ile Pro Phe Ile Phe Thr Lys Trp Leu Gln Glu Val Phe
            180                 185                 190

Asn Val Pro Leu Val Val Gln Leu Thr Asp Asp Glu Lys Tyr Leu Trp
        195                 200                 205

Lys Asp Leu Thr Leu Glu Lys Ala Tyr Gln Tyr Ala Thr Glu Asn Ala
    210                 215                 220

Lys Asp Ile Ile Ala Cys Gly Phe Asp Val Asn Lys Thr Phe Ile Phe
225                 230                 235                 240

Ser Asp Leu Glu Tyr Met Gly Lys Ser Ser Gly Phe Tyr Gln Asn Val
                245                 250                 255

Val Lys Val Gln Lys His Val Thr Phe Asn Gln Val Lys Gly Ile Phe
            260                 265                 270

Gly Phe Thr Asp Ser Asp Cys Ile Gly Lys Ile Ser Phe Pro Ala Ile
        275                 280                 285

Gln Ala Ala Pro Ser Phe Ser Ser Ser Phe Pro Glu Ile Phe Lys Gly
    290                 295                 300

Arg Lys Asp Ile Gln Cys Leu Ile Pro Cys Ala Ile Asp Gln Asp Pro
305                 310                 315                 320

Tyr Phe Arg Met Thr Arg Asp Val Ala Pro Arg Ile Asn Tyr Pro Lys
                325                 330                 335

Pro Ala Leu Met His Ser Thr Phe Phe Pro Ala Leu Gln Gly Ala Gln
            340                 345                 350

Thr Lys Met Ser Ala Ser Asp Pro Asn Ser Ser Ile Phe Leu Thr Asp
        355                 360                 365

Thr Ala Lys Gln Ile Lys Ser Lys Ile Asn Lys His Ala Phe Ser Gly
```

```
              370                 375                 380
Gly Lys Asp Thr Ile Glu Glu His Arg Gln Phe Gly Gly Asn Trp Glu
385                 390                 395                 400

Val Asp Val Ser Tyr Met Tyr Leu Thr Phe Phe Leu Glu Asp Asp Glu
                405                 410                 415

Arg Leu Glu Gln Ile Lys Gln Asp Tyr Ser Ser Gly Ala Leu Leu Thr
            420                 425                 430

Gly Asp Leu Lys Lys Ile Leu Thr Glu Thr Leu Gln Pro Met Ile Ser
        435                 440                 445

Ala His Gln Glu Arg Arg Lys His Ile Thr Glu Glu Thr Val Lys Gln
    450                 455                 460

Phe Met Met Pro Arg Lys Leu Ala Phe Asp Phe
465                 470                 475

<210> SEQ ID NO 66
<211> LENGTH: 417
<212> TYPE: PRT
<213> ORGANISM: Caenorhabditis elegans

<400> SEQUENCE: 66

Met Ala Ala Pro Ala Glu Gln Val Ala Ala Glu Ile Glu Asn Leu Lys
 1               5                  10                  15

Val Asn Gly Gly Ala Ala Gly Gly Val Gln Glu Asp Glu Glu Asp
            20                  25                  30

Arg Val Thr Pro Trp Glu Val Thr Thr Thr Lys Ala Thr Gly Ile Asp
        35                  40                  45

Tyr Asp Lys Leu Ile Val Lys Phe Gly Cys Arg Lys Leu Asp Glu Glu
    50                  55                  60

Ile Ile Ala Arg Phe Glu Arg Val Thr Gly His Lys Ala Ser Pro Met
65                  70                  75                  80

Leu Arg Arg Gly Met Phe Phe Ala His Arg Asp Leu Thr Ala Ile Leu
                85                  90                  95

Asp Arg Lys Glu Gln Gly Lys Pro Phe Tyr Leu Tyr Thr Gly Arg Gly
            100                 105                 110

Ala Ser Ser Gly Ser Leu His Leu Gly His Leu Val Pro Phe Ile Phe
        115                 120                 125

Thr Lys Trp Leu Gln Glu Val Phe Asp Val Pro Leu Val Ile Gln Met
    130                 135                 140

Thr Asp Asp Glu Lys Phe Leu Trp Lys Asp Met Lys Val Asp Glu Ala
145                 150                 155                 160

Lys Lys Met Ala Arg Glu Asn Met Lys Asp Ile Ile Ser Val Gly Phe
                165                 170                 175

Asp Pro Thr Lys Thr Phe Ile Phe Asn Asn Phe Asp Tyr Met Cys Pro
            180                 185                 190

Pro Phe Tyr Glu Asn Ile Val Lys Ile Trp Lys Val Val Asn Thr Asn
        195                 200                 205

Gln Ala Arg Ala Ile Phe Gly Phe Thr Pro Glu Asp Cys Leu Gly Lys
    210                 215                 220

Ala Ala Phe Pro Ala Val Glu Ala Pro Cys Phe Ala Ser Ser Phe
225                 230                 235                 240

Pro Gln Ile Phe Gly Lys Arg Asn Asp Ile Pro Cys Leu Ile Pro Cys
                245                 250                 255

Ala Ile Asp Gln Asp Pro Phe Phe Arg Met Thr Arg Asp Val Ala Pro
            260                 265                 270

Arg Leu Lys Ala Ser Lys Pro Ser Leu Ile Phe Ser Thr Phe Leu Pro
```

```
                275                 280                 285
Ala Leu Thr Gly Ala Gln Thr Lys Met Ser Ala Ser Glu Pro Asn Thr
290                 295                 300
Cys Ile Phe Leu Ser Asp Thr Ala Lys Gln Ile Lys Asn Lys Ile Asn
305                 310                 315                 320
Lys Tyr Ala Phe Ser Gly Gln Gln Thr Val Gln Glu His Arg Glu
                325                 330                 335
Lys Gly Gly Asn Cys Asp Val Asp Ile Ser Tyr Gln Phe Leu Arg Phe
                340                 345                 350
Phe Leu Asp Asp Asp Glu Lys Leu Ala Glu Ile Arg Glu Asn Tyr Thr
                355                 360                 365
Lys Gly Glu Met Leu Ser Gly Glu Leu Lys Ala Leu Ala Thr Gln Lys
                370                 375                 380
Val Gln Glu Ile Val Leu Glu Met Gln Glu Arg Arg Lys Leu Val Thr
385                 390                 395                 400
Asp Glu Thr Val Glu Glu Phe Val Lys Val Arg Pro Leu Ala Tyr Lys
                405                 410                 415
Tyr

<210> SEQ ID NO 67
<211> LENGTH: 336
<212> TYPE: PRT
<213> ORGANISM: Salmonella enterica subsp. enterica serovar Typhi8

<400> SEQUENCE: 67

Met Asn Thr Leu Pro Ile Ile Leu Thr Gly Asp Arg Pro Thr Gly Ser
1               5                   10                  15
Leu His Leu Gly His Tyr Val Gly Ser Leu Arg Gln Arg Val Ala Leu
                20                  25                  30
Gln Gln Asp His Gln Gln Tyr Val Leu Ile Ala Asp Leu Gln Gly Leu
                35                  40                  45
Thr Asp Asn Gly Ser Asn Pro Gln Lys Ile Arg Asp Asn Ile Pro Gln
50                  55                  60
Val Leu Ala Asp Tyr Leu Ala Val Gly Ile Asp Pro Ala Leu Thr Thr
65                  70                  75                  80
Ile Cys Leu Gln Ser Ala Leu Pro Ala Leu Ala Glu Leu Thr Val Leu
                85                  90                  95
Tyr Met Asn Ile Val Thr Val Ala Arg Val Glu Arg Asn Pro Thr Val
                100                 105                 110
Lys Asn Glu Ile Ala Gln Lys Gly Phe Thr Arg Ser Leu Pro Val Gly
                115                 120                 125
Phe Met Ala Tyr Pro Ile Ser Gln Ala Ala Asp Ile Thr Ala Phe Lys
130                 135                 140
Ala Glu Met Val Pro Val Gly Asp Asp Gln Leu Pro Met Ile Glu Gln
145                 150                 155                 160
Thr Asn Glu Ile Val His Lys Met Asn Ser Leu Phe Ser Ser Pro Val
                165                 170                 175
Leu Arg Pro Cys Gln Ala Leu Leu Ser Asp Thr Gly Arg Leu Pro Gly
                180                 185                 190
Ile Asp Gly Ser Ala Lys Met Ser Lys Ser Leu Val Asn Thr Leu Leu
                195                 200                 205
Leu Ser Ala Ser Glu Glu Thr Ile His Arg Ala Val Ser Ala Met Tyr
                210                 215                 220
Thr Asp Pro Asn His Leu Lys Ile Ser Asp Pro Gly Lys Ile Glu Gly
225                 230                 235                 240
```

```
Asn Val Val Phe Thr Trp Leu Asp Ala Phe His Pro Asp Lys Ala Lys
                245                 250                 255

Val Ala Ala Met Lys Ala His Tyr Gln Gln Gly Gly Leu Gly Asp Arg
            260                 265                 270

Val Cys Lys Asn Glu Leu Glu Thr Cys Leu Gln Glu Leu Ile Ala Pro
        275                 280                 285

Ile Arg Glu Arg Arg Ala Thr Phe Ile Ala Asp Lys Gly Met Leu Met
    290                 295                 300

Glu Leu Leu Lys Lys Gly Ser Glu Arg Ala His Glu Val Thr Gln Lys
305                 310                 315                 320

Thr Leu Gln Glu Val Lys Arg Gly Leu Gly Leu Pro Thr Leu Phe Gln
                325                 330                 335

<210> SEQ ID NO 68
<211> LENGTH: 448
<212> TYPE: PRT
<213> ORGANISM: Pseudomonas aeruginosa

<400> SEQUENCE: 68

Met Thr Thr Arg Ile Leu Thr Gly Ile Thr Pro Thr Gly Thr Pro His
1               5                   10                  15

Leu Gly Asn Tyr Ala Gly Ala Ile Arg Pro Ala Ile Leu Ala Ser Arg
                20                  25                  30

Arg Ser Asp Val Asp Ser Phe Tyr Phe Leu Ala Asp Tyr His Ala Leu
            35                  40                  45

Ile Lys Cys Asp Asp Pro Ala Arg Ile Gln Arg Ser Arg Leu Glu Ile
    50                  55                  60

Ala Ala Thr Trp Leu Ala Gly Gly Leu Asp Val Glu Arg Ala Thr Phe
65                  70                  75                  80

Tyr Arg Gln Ser Asp Ile Pro Glu Ile Pro Glu Leu Thr Trp Leu Leu
                85                  90                  95

Thr Cys Val Ser Ala Lys Gly Leu Leu Asn Arg Ala His Ala Tyr Lys
                100                 105                 110

Ala Ala Val Asp Arg Asn Val Glu Ala Gly Glu Asp Pro Asp Ala Gly
            115                 120                 125

Val Thr Met Gly Leu Tyr Ser Tyr Pro Val Leu Met Ala Ala Asp Ile
    130                 135                 140

Leu Met Phe Asn Ala His Lys Ile Pro Val Gly Arg Asp Gln Val Gln
145                 150                 155                 160

His Val Glu Met Ala Arg Asp Ile Gly Gln Arg Phe Asn His Leu Phe
                165                 170                 175

Gly Asn Gly Arg Glu Phe Phe Val Leu Pro Glu Ala Val Ile Glu Glu
                180                 185                 190

Asn Val Ala Thr Leu Pro Gly Leu Asp Gly Arg Lys Met Ser Lys Ser
            195                 200                 205

Tyr Asp Asn Thr Ile Pro Leu Phe Ser Pro Ser Arg Gln Leu Lys Asp
    210                 215                 220

Ala Ile Ala Arg Ile Val Thr Asp Ser Arg Ala Pro Gly Glu Pro Lys
225                 230                 235                 240

Asp Pro Asp Ser Ser His Leu Phe Leu Leu Tyr Ser Ala Phe Ala Ser
                245                 250                 255

Ala Glu Gln Val Ala Ala Phe Arg Gln Glu Leu Leu Glu Gly Leu Ala
            260                 265                 270

Trp Gly Glu Ala Lys Gln Arg Leu Phe Gln Leu Leu Asp Asn Glu Leu
    275                 280                 285
```

```
Gly Glu Ala Arg Glu Arg Tyr Gln Ala Leu Ile Ala Lys Pro Asp Asp
    290                 295                 300

Ile Glu Asp Ile Leu Leu Ala Gly Ala Ala Lys Ala Arg Arg Ile Ala
305                 310                 315                 320

Thr Pro Phe Ile Ala Glu Leu Arg Glu Ala Val Gly Leu Arg Ser Leu
                325                 330                 335

Arg Glu Pro Leu Lys Ser Ala Glu Ser Gly Lys Lys Lys Ala Ala Lys
                340                 345                 350

Ala Ala Arg Leu Val Ser Phe Arg Asp Asp Gly Ser Phe Arg Phe
                355                 360                 365

Arg Leu Leu Asp Ala Ala Gly Glu Gln Leu Leu Ser Arg Ala Phe
    370                 375                 380

Ala Asp Gly Lys Ala Ala Gly Ala Val Ser Lys Arg Leu Leu Ala Gly
385                 390                 395                 400

Glu Thr Ala Asp Leu Arg Ala Glu Gly Asn Ala Phe Gly Leu Trp Leu
                405                 410                 415

Asp Gly Glu Ala Val Ala Gln Ser Pro Ala Phe Ala Asp Ala Ala
                420                 425                 430

Arg Asp Ala Ala Ile Glu Arg Thr Arg Glu Ala Leu Ala Pro Gln Glu
    435                 440                 445
```

<210> SEQ ID NO 69
<211> LENGTH: 350
<212> TYPE: PRT
<213> ORGANISM: Thermus thermophilus

<400> SEQUENCE: 69

```
Met Leu Glu Glu Ala Leu Ala Ala Ile Gln Asn Ala Arg Asp Leu Glu
 1               5                  10                  15

Glu Leu Lys Ala Leu Lys Ala Arg Tyr Leu Gly Lys Lys Gly Leu Leu
                20                  25                  30

Thr Gln Glu Met Lys Gly Leu Ser Ala Leu Pro Leu Glu Glu Arg Arg
            35                  40                  45

Lys Arg Gly Gln Glu Leu Asn Ala Ile Lys Ala Ala Leu Glu Ala Ala
    50                  55                  60

Leu Glu Ala Arg Glu Lys Ala Leu Glu Ala Ala Leu Lys Glu Ala
65                  70                  75                  80

Leu Glu Arg Glu Arg Val Asp Val Ser Leu Pro Gly Ala Ser Leu Phe
                85                  90                  95

Ser Gly Gly Leu His Pro Ile Thr Leu Met Glu Arg Glu Leu Val Glu
                100                 105                 110

Ile Phe Arg Ala Leu Gly Tyr Gln Ala Val Glu Gly Pro Glu Val Glu
            115                 120                 125

Ser Glu Phe Phe Asn Phe Asp Ala Leu Asn Ile Pro Glu His His Pro
    130                 135                 140

Ala Arg Asp Met Trp Asp Thr Phe Trp Leu Thr Gly Glu Gly Phe Arg
145                 150                 155                 160

Leu Glu Gly Pro Leu Gly Glu Glu Val Glu Gly Arg Leu Leu Leu Arg
                165                 170                 175

Thr His Thr Ser Pro Met Gln Val Arg Tyr Met Val Ala His Thr Pro
                180                 185                 190

Pro Phe Arg Ile Val Val Pro Gly Arg Val Phe Arg Phe Glu Gln Thr
            195                 200                 205

Asp Ala Thr His Glu Ala Val Phe His Gln Leu Glu Gly Leu Val Val
    210                 215                 220
```

```
Gly Glu Gly Ile Ala Met Ala His Leu Lys Gly Ala Ile Tyr Glu Leu
225                 230                 235                 240

Ala Gln Ala Leu Phe Gly Pro Asp Ser Lys Val Arg Phe Gln Pro Val
                245                 250                 255

Tyr Phe Pro Phe Val Glu Pro Gly Ala Gln Phe Ala Val Trp Trp Pro
            260                 265                 270

Glu Gly Gly Lys Trp Leu Glu Leu Gly Gly Ala Gly Met Val His Pro
        275                 280                 285

Lys Val Phe Gln Ala Val Asp Ala Tyr Arg Glu Arg Leu Gly Leu Pro
    290                 295                 300

Pro Ala Tyr Arg Gly Val Thr Gly Phe Ala Phe Gly Leu Gly Val Glu
305                 310                 315                 320

Arg Leu Ala Met Leu Arg Tyr Gly Ile Pro Asp Ile Arg Tyr Phe Phe
                325                 330                 335

Gly Gly Arg Leu Lys Phe Leu Glu Gln Phe Lys Gly Val Leu
                340                 345                 350

<210> SEQ ID NO 70
<211> LENGTH: 350
<212> TYPE: PRT
<213> ORGANISM: Thermus thermophilus

<400> SEQUENCE: 70

Met Leu Glu Glu Ala Leu Ala Ala Ile Gln Asn Ala Arg Asp Leu Glu
1               5                   10                  15

Glu Leu Lys Ala Leu Lys Ala Arg Tyr Leu Gly Lys Lys Gly Leu Leu
            20                  25                  30

Thr Gln Glu Met Lys Gly Leu Ser Ala Leu Pro Leu Glu Glu Arg Arg
        35                  40                  45

Lys Arg Gly Gln Glu Leu Asn Ala Ile Lys Ala Ala Leu Glu Ala Ala
    50                  55                  60

Leu Glu Ala Arg Glu Lys Ala Leu Glu Ala Ala Leu Lys Glu Ala
65                  70                  75                  80

Leu Glu Arg Glu Arg Val Asp Val Ser Leu Pro Gly Ala Ser Leu Phe
                85                  90                  95

Ser Gly Gly Leu His Pro Ile Thr Leu Met Glu Arg Glu Leu Val Glu
            100                 105                 110

Ile Phe Arg Ala Leu Gly Tyr Gln Ala Val Glu Gly Pro Glu Val Glu
        115                 120                 125

Ser Glu Phe Phe Asn Phe Asp Ala Leu Asn Ile Pro Glu His His Pro
    130                 135                 140

Ala Arg Asp Met Trp Asp Thr Phe Trp Leu Thr Gly Glu Gly Phe Arg
145                 150                 155                 160

Leu Glu Gly Pro Leu Gly Glu Glu Val Glu Gly Arg Leu Leu Leu Arg
                165                 170                 175

Thr His Thr Ser Pro Met Gln Val Arg Tyr Met Val Ala His Thr Pro
            180                 185                 190

Pro Phe Arg Ile Val Val Pro Gly Arg Val Phe Arg Phe Glu Gln Thr
        195                 200                 205

Asp Ala Thr His Glu Ala Val Phe His Gln Leu Glu Gly Leu Val Val
    210                 215                 220

Gly Glu Gly Ile Ala Met Ala His Leu Lys Gly Ala Ile Tyr Glu Leu
225                 230                 235                 240

Ala Gln Ala Leu Phe Gly Pro Asp Ser Lys Val Arg Phe Gln Pro Val
                245                 250                 255
```

Tyr Phe Pro Phe Val Glu Pro Gly Ala Gln Phe Ala Val Trp Trp Pro
                260                 265                 270

Glu Gly Gly Lys Trp Leu Glu Leu Gly Gly Ala Gly Met Val His Pro
            275                 280                 285

Lys Val Phe Gln Ala Val Asp Ala Tyr Arg Glu Arg Leu Gly Leu Pro
        290                 295                 300

Pro Ala Tyr Arg Gly Val Thr Gly Phe Ala Phe Gly Leu Gly Val Glu
305                 310                 315                 320

Arg Leu Ala Met Leu Arg Tyr Gly Ile Pro Asp Ile Arg Tyr Phe Phe
                325                 330                 335

Gly Gly Arg Leu Lys Phe Leu Glu Gln Phe Lys Gly Val Leu
            340                 345                 350

<210> SEQ ID NO 71
<211> LENGTH: 344
<212> TYPE: PRT
<213> ORGANISM: Bacillus subtilis

<400> SEQUENCE: 71

Met Glu Glu Lys Leu Lys Gln Leu Glu Gln Glu Ala Leu Glu Gln Val
1               5                   10                  15

Glu Ala Ala Ser Ser Leu Lys Val Val Asn Asp Ile Arg Val Gln Tyr
            20                  25                  30

Leu Gly Lys Lys Gly Pro Ile Thr Glu Val Leu Arg Gly Met Gly Lys
        35                  40                  45

Leu Ser Ala Glu Glu Arg Pro Lys Met Gly Ala Leu Ala Asn Glu Val
50                  55                  60

Arg Glu Arg Ile Ala Asn Ala Ile Ala Asp Lys Asn Glu Lys Leu Glu
65                  70                  75                  80

Glu Glu Glu Met Lys Gln Lys Leu Ala Gly Gln Thr Ile Asp Val Thr
                85                  90                  95

Leu Pro Gly Asn Pro Val Ala Val Gly Gly Arg His Pro Leu Thr Val
            100                 105                 110

Val Ile Glu Glu Ile Glu Asp Leu Phe Ile Gly Met Gly Tyr Thr Val
        115                 120                 125

Glu Glu Gly Pro Glu Val Glu Thr Asp Tyr Tyr Asn Phe Glu Ser Leu
130                 135                 140

Asn Leu Pro Lys Glu His Pro Ala Arg Asp Met Gln Asp Ser Phe Tyr
145                 150                 155                 160

Ile Thr Glu Glu Thr Leu Met Arg Thr Gln Thr Ser Pro Val Gln Thr
                165                 170                 175

Arg Thr Met Glu Lys His Glu Gly Lys Gly Pro Val Lys Ile Ile Cys
            180                 185                 190

Pro Gly Lys Val Tyr Arg Arg Asp Asn Asp Asp Ala Thr His Ser His
        195                 200                 205

Gln Phe Met Gln Ile Glu Gly Leu Val Val Asp Lys Asn Ile Ser Met
210                 215                 220

Ser Asp Leu Lys Gly Thr Leu Glu Leu Val Ala Lys Lys Met Phe Gly
225                 230                 235                 240

Gln Asp Arg Glu Ile Arg Leu Arg Pro Ser Phe Phe Pro Phe Thr Glu
                245                 250                 255

Pro Ser Val Glu Val Asp Val Thr Cys Phe Lys Cys Gly Gly Asn Gly
            260                 265                 270

Cys Ser Val Cys Lys Gly Thr Gly Trp Ile Glu Ile Leu Gly Ala Gly
        275                 280                 285

```
Met Val His Pro Asn Val Leu Lys Met Ala Gly Phe Asp Pro Lys Glu
    290                 295                 300

Tyr Gln Gly Phe Ala Phe Gly Met Gly Val Glu Arg Ile Ala Met Leu
305                 310                 315                 320

Lys Tyr Gly Ile Asp Asp Ile Arg His Phe Tyr Thr Asn Asp Val Arg
                325                 330                 335

Phe Ile Ser Gln Phe Lys Gln Ala
            340

<210> SEQ ID NO 72
<211> LENGTH: 328
<212> TYPE: PRT
<213> ORGANISM: Helicobacter pylori

<400> SEQUENCE: 72

Met His Thr Leu Ile Glu Arg Leu Glu Lys Val Thr Asn Ser Lys Glu
  1               5                  10                  15

Leu Glu Glu Ala Arg Leu Asn Ala Leu Gly Lys Lys Gly Val Phe Ala
             20                  25                  30

Asp Lys Phe Asn Gln Leu Lys His Leu Asn Gly Glu Glu Lys Asn Ala
         35                  40                  45

Phe Ala Lys Glu Ile His His Tyr Lys Gln Ala Phe Glu Lys Ala Phe
     50                  55                  60

Glu Trp Lys Lys Lys Ala Ile Ile Glu Leu Glu Leu Glu Glu Arg Leu
 65                  70                  75                  80

Lys Lys Glu Lys Ile Asp Val Ser Leu Phe Asn Ala Ile Lys Thr Ser
                 85                  90                  95

Ser Ser His Pro Leu Asn Tyr Thr Lys Asn Lys Ile Ile Glu Phe Phe
            100                 105                 110

Thr Pro Leu Gly Tyr Lys Leu Glu Ile Gly Ser Leu Val Glu Asp Asp
        115                 120                 125

Phe His Asn Phe Ser Ala Leu Asn Leu Pro Pro Tyr His Pro Ala Arg
    130                 135                 140

Asp Met Gln Asp Thr Phe Tyr Phe Lys Asp His Lys Leu Leu Arg Thr
145                 150                 155                 160

His Thr Ser Pro Val Gln Ile His Thr Met Gln Glu Gln Thr Pro Pro
                165                 170                 175

Ile Lys Met Ile Cys Leu Gly Glu Thr Phe Arg Arg Asp Tyr Asp Leu
            180                 185                 190

Thr His Thr Pro Met Phe His Gln Ile Glu Gly Leu Val Val Asp Gln
        195                 200                 205

Lys Gly Asn Ile Arg Phe Thr His Leu Lys Gly Val Ile Glu Asp Phe
    210                 215                 220

Leu His Tyr Phe Phe Gly Gly Val Lys Leu Arg Trp Arg Ser Ser Phe
225                 230                 235                 240

Phe Pro Phe Thr Glu Pro Ser Ala Glu Val Asp Ile Ser Cys Val Phe
                245                 250                 255

Cys Lys Gln Glu Gly Cys Arg Val Cys Ser His Thr Gly Trp Leu Glu
            260                 265                 270

Val Leu Gly Cys Gly Met Val Asn Asn Ala Val Phe Glu Ala Ile Gly
        275                 280                 285

Tyr Glu Asn Val Ser Gly Phe Ala Phe Gly Met Gly Ile Glu Arg Leu
    290                 295                 300

Ala Met Leu Thr Cys Gln Ile Asn Asp Leu Arg Ser Phe Phe Glu Thr
305                 310                 315                 320
```

```
Asp Leu Arg Val Leu Glu Ser Phe
            325

<210> SEQ ID NO 73
<211> LENGTH: 327
<212> TYPE: PRT
<213> ORGANISM: Escherichia coli

<400> SEQUENCE: 73

Met Ser His Leu Ala Glu Leu Val Ala Ser Ala Lys Ala Ala Ile Ser
1               5                   10                  15

Gln Ala Ser Asp Val Ala Ala Leu Asp Asn Val Arg Val Glu Tyr Leu
            20                  25                  30

Gly Lys Lys Gly His Leu Thr Leu Gln Met Thr Thr Leu Arg Glu Leu
        35                  40                  45

Pro Pro Glu Glu Arg Pro Ala Ala Gly Ala Val Ile Asn Glu Ala Lys
    50                  55                  60

Glu Gln Val Gln Gln Ala Leu Asn Ala Arg Lys Ala Glu Leu Glu Ser
65                  70                  75                  80

Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Gln Thr Ser Gly Val Gln Ile Arg
                165                 170                 175

Thr Met Lys Ala Gln Gln Pro Pro Ile Arg Ile Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

Gly Met Val His Pro Asn Val Leu Arg Asn Val Gly Ile Asp Pro Glu
        275                 280                 285

Val Tyr Ser Gly Phe Ala Phe Gly Met Gly Met Glu Arg Leu Thr Met
    290                 295                 300

Leu Arg Tyr Gly Val Thr Asp Leu Arg Ser Phe Phe Glu Asn Asp Leu
305                 310                 315                 320

Arg Phe Leu Lys Gln Phe Lys
            325

<210> SEQ ID NO 74
<211> LENGTH: 453
<212> TYPE: PRT
<213> ORGANISM: Drosophila melanogaster
```

<400> SEQUENCE: 74

```
Met Leu Leu Thr Leu Arg Val Gln Gly Ala Arg His Trp Leu Lys Ser
 1               5                  10                  15

Thr Arg Cys Leu Ala Ser Ser Ala Ala Pro Ala Lys Ser Pro Ser Ser
            20                  25                  30

Pro Pro Gln Leu Glu Val Ser Gly Ser Thr Tyr Ala Thr Asp Gly Trp
        35                  40                  45

Thr Asn Val Thr Pro Lys Ile Leu Ser Tyr Val Gly Ala Asn Lys His
 50                  55                  60

Leu Gln Thr Asp His Pro Leu Ser Ile Ile Arg Gln Arg Ile Val Asn
 65                  70                  75                  80

Tyr Phe Tyr Gly Ala Tyr Arg Asn Gln Arg Gly Asn Pro Leu Phe Ser
                85                  90                  95

Val Tyr Asp Gln Met Asn Pro Val Val Thr Val Gln Gln Asn Phe Asp
            100                 105                 110

Asn Leu Leu Ile Pro Ala Asp His Val Ser Arg Gln Lys Ser Asp Cys
        115                 120                 125

Tyr Tyr Ile Asn Gln Gln His Leu Leu Arg Ala His Thr Thr Ala His
130                 135                 140

Gln Val Glu Leu Ile Ser Gly Gly Leu Asp Asn Phe Leu Val Val Gly
145                 150                 155                 160

Glu Val Tyr Arg Arg Asp Glu Ile Asp Ser Thr His Tyr Pro Val Phe
                165                 170                 175

His Gln Ala Asp Ala Val Arg Leu Val Thr Lys Asp Lys Leu Phe Glu
            180                 185                 190

Arg Asn Pro Gly Leu Glu Leu Phe Glu Glu Thr Trp Ser Gly Thr Leu
        195                 200                 205

Ala Asp Pro Lys Leu Ile Leu Pro Ser Ser Lys Phe Met Asp Gln Thr
210                 215                 220

Lys Gln Pro Cys His Thr Leu Glu Ala Val Lys Leu Met Glu His Glu
225                 230                 235                 240

Met Lys His Val Leu Val Gly Leu Thr Lys Asp Leu Phe Gly Pro Arg
                245                 250                 255

Ile Lys Tyr Arg Trp Val Asp Thr Tyr Phe Pro Phe Thr Gln Pro Ser
            260                 265                 270

Trp Glu Leu Glu Ile Tyr Phe Lys Asp Asn Trp Leu Glu Val Leu Gly
        275                 280                 285

Cys Gly Ile Met Arg His Glu Ile Leu Gln Arg Ser Gly Val His Gln
290                 295                 300

Ser Ile Gly Tyr Ala Phe Gly Val Gly Leu Glu Arg Leu Ala Met Val
305                 310                 315                 320

Leu Phe Asp Ile Pro Asp Ile Arg Leu Phe Trp Ser Asn Asp Ser Gly
                325                 330                 335

Phe Leu Ser Gln Phe Ser Glu Lys Asp Leu His Asn Leu Pro Lys Tyr
            340                 345                 350

Lys Pro Ile Ser His Tyr Pro Gln Cys Thr Asn Asp Leu Ser Phe Trp
        355                 360                 365

Leu Pro Gln Asp Ile Glu Val Asp Ala Gly Phe Ser Pro Asn Asp Phe
370                 375                 380

Tyr Asp Leu Val Arg Ser Val Ala Gly Asp Met Val Glu Gln Ile Ser
385                 390                 395                 400

Leu Val Asp Lys Phe Lys His Pro Lys Thr Gly Lys Ser Ser Val Cys
                405                 410                 415
```

Phe Arg Ile Val Tyr Arg His Met Glu Arg Thr Leu Thr Gln Ala Glu
              420                 425                 430

Val Asn Glu Ile His Lys Gln Ile Ala Ser Ala Ser Val Asp Ser Phe
              435                 440                 445

Asn Val Gln Ile Arg
    450

<210> SEQ ID NO 75
<211> LENGTH: 339
<212> TYPE: PRT
<213> ORGANISM: Chilamydophila pneumoniae

<400> SEQUENCE: 75

Met Glu Met Lys Glu Glu Ile Glu Ala Val Lys Gln Gln Phe His Ser
 1               5                  10                  15

Glu Leu Asp Gln Val Asn Ser Ser Gln Ala Leu Ala Asp Leu Lys Val
             20                  25                  30

Arg Tyr Leu Gly Lys Gly Ile Phe Arg Ser Phe Ser Glu Lys Leu
         35                  40                  45

Lys Gln Cys Thr Asp Lys Ala Lys Leu Gly Ser Leu Ile Asn Asp Phe
 50                  55                  60

Lys Thr Tyr Val Glu Asp Leu Leu Gln Glu Lys Ser Leu Val Leu Leu
 65                  70                  75                  80

Ala Ser Glu Gln Ala Glu Ala Phe Ser Lys Glu Lys Ile Asp Ser Ser
                 85                  90                  95

Leu Pro Gly Asp Ser Gln Pro Ser Gly Gly Arg His Ile Leu Lys Ser
            100                 105                 110

Ile Leu Asp Asp Val Val Asp Ile Phe Val His Leu Gly Phe Cys Val
        115                 120                 125

Arg Glu Ala Pro Asn Ile Glu Ser Glu Ala Asn Asn Phe Thr Leu Leu
130                 135                 140

Asn Phe Thr Glu Asp His Pro Ala Arg Gln Met His Asp Thr Phe Tyr
145                 150                 155                 160

Leu Asn Ala Thr Thr Val Leu Arg Thr His Thr Ser Asn Val Gln Ala
                165                 170                 175

Arg Glu Leu Lys Lys Gln Gln Pro Pro Ile Lys Val Val Ala Pro Gly
            180                 185                 190

Leu Cys Phe Arg Asn Glu Asp Ile Ser Ala Arg Ser His Val Leu Phe
        195                 200                 205

His Gln Val Glu Ala Phe Tyr Val Asp His Asn Val Thr Phe Ser Asp
    210                 215                 220

Leu Thr Ala Ile Leu Ser Ala Phe Tyr His Ser Phe Phe Gln Arg Lys
225                 230                 235                 240

Thr Glu Leu Arg Phe Arg His Ser Tyr Phe Pro Phe Val Glu Pro Gly
                245                 250                 255

Ile Glu Val Asp Val Ser Cys Glu Cys Cys Gly Lys Gly Cys Ala Leu
            260                 265                 270

Cys Lys His Thr Gly Trp Leu Glu Val Ala Gly Ala Gly Met Ile His
        275                 280                 285

Pro Gln Val Leu Arg Asn Gly Asn Val Asp Pro Glu Ile Tyr Ser Gly
    290                 295                 300

Tyr Ala Val Gly Met Gly Ile Glu Arg Leu Ala Met Leu Lys Tyr Gly
305                 310                 315                 320

Val Ser Asp Ile Arg Leu Phe Ser Glu Asn Asp Leu Arg Phe Leu Gln
                325                 330                 335

Gln Phe Ser

<210> SEQ ID NO 76
<211> LENGTH: 451
<212> TYPE: PRT
<213> ORGANISM: Homo sapiens

<400> SEQUENCE: 76

Met Val Gly Ser Ala Leu Arg Arg Gly Ala His Ala Tyr Val Tyr Leu
1               5                   10                  15

Val Ser Lys Ala Ser His Ile Ser Arg Gly His Gln His Gln Ala Trp
            20                  25                  30

Gly Ser Arg Pro Pro Ala Ala Glu Cys Ala Thr Gln Arg Ala Pro Gly
        35                  40                  45

Ser Val Val Glu Leu Leu Gly Lys Ser Tyr Pro Gln Asp Asp His Ser
    50                  55                  60

Asn Leu Thr Arg Lys Val Leu Thr Arg Val Gly Arg Asn Leu His Asn
65                  70                  75                  80

Gln Gln His His Pro Leu Trp Leu Ile Lys Glu Arg Val Lys Glu His
                85                  90                  95

Phe Tyr Lys Gln Tyr Val Gly Arg Phe Gly Thr Pro Leu Phe Ser Val
            100                 105                 110

Tyr Asp Asn Leu Ser Pro Val Thr Thr Trp Gln Asn Phe Asp Ser
            115                 120                 125

Leu Leu Ile Pro Ala Asp His Pro Ser Arg Lys Lys Gly Asp Asn Tyr
        130                 135                 140

Tyr Leu Asn Arg Thr His Met Leu Arg Ala His Thr Ser Ala His Gln
145                 150                 155                 160

Trp Asp Leu Leu His Ala Gly Leu Asp Ala Phe Leu Val Val Gly Asp
                165                 170                 175

Val Tyr Arg Arg Asp Gln Ile Asp Ser Gln His Tyr Pro Ile Phe His
            180                 185                 190

Gln Leu Glu Ala Val Arg Leu Phe Ser Lys His Glu Leu Phe Ala Gly
        195                 200                 205

Ile Lys Asp Gly Glu Ser Leu Gln Leu Phe Glu Gln Ser Ser Arg Ser
    210                 215                 220

Ala His Lys Gln Glu Thr His Thr Met Glu Ala Val Lys Leu Val Glu
225                 230                 235                 240

Phe Asp Leu Lys Gln Thr Leu Thr Arg Leu Met Ala His Leu Phe Gly
                245                 250                 255

Asp Glu Leu Glu Ile Arg Trp Val Asp Cys Tyr Phe Pro Phe Thr His
            260                 265                 270

Pro Ser Phe Glu Met Glu Ile Asn Phe His Gly Glu Trp Leu Glu Val
        275                 280                 285

Leu Gly Cys Gly Val Met Glu Gln Gln Leu Val Asn Ser Ala Gly Ala
    290                 295                 300

Gln Asp Arg Ile Gly Trp Ala Phe Gly Leu Gly Leu Glu Arg Leu Ala
305                 310                 315                 320

Met Ile Leu Tyr Asp Ile Pro Asp Ile Arg Leu Phe Trp Cys Glu Asp
                325                 330                 335

Glu Arg Phe Leu Lys Gln Phe Cys Val Ser Asn Ile Asn Gln Lys Val
            340                 345                 350

Lys Phe Gln Pro Leu Ser Lys Tyr Pro Ala Val Ile Asn Asp Ile Ser
        355                 360                 365

```
Phe Trp Leu Pro Ser Glu Asn Tyr Ala Glu Asn Asp Phe Tyr Asp Leu
    370                 375                 380

Val Arg Thr Ile Gly Gly Asp Leu Val Glu Lys Val Asp Leu Ile Asp
385                 390                 395                 400

Lys Phe Val His Pro Lys Thr His Lys Thr Ser His Cys Tyr Arg Ile
                405                 410                 415

Thr Tyr Arg His Met Glu Arg Thr Leu Ser Gln Arg Glu Val Arg His
                420                 425                 430

Ile His Gln Ala Leu Gln Glu Ala Val Gln Leu Leu Gly Val Glu
        435                 440                 445

Gly Arg Phe
    450

<210> SEQ ID NO 77
<211> LENGTH: 341
<212> TYPE: PRT
<213> ORGANISM: Mycobacterium tuberculosis

<400> SEQUENCE: 77

Met Leu Ser Pro Glu Ala Leu Thr Thr Ala Val Asp Ala Ala Gln Gln
1               5                   10                  15

Ala Ile Ala Leu Ala Asp Thr Leu Asp Val Leu Ala Arg Val Lys Thr
            20                  25                  30

Glu His Leu Gly Asp Arg Ser Pro Leu Ala Leu Ala Arg Gln Ala Leu
        35                  40                  45

Ala Val Leu Pro Lys Glu Gln Arg Ala Glu Ala Gly Lys Arg Val Asn
    50                  55                  60

Ala Ala Arg Asn Ala Ala Gln Arg Ser Tyr Asp Glu Arg Leu Ala Thr
65                  70                  75                  80

Leu Arg Ala Glu Arg Asp Ala Ala Val Leu Val Ala Glu Gly Ile Asp
                85                  90                  95

Val Thr Leu Pro Ser Thr Arg Val Pro Ala Gly Ala Arg His Pro Ile
            100                 105                 110

Ile Met Leu Ala Glu His Val Ala Asp Thr Phe Ile Ala Met Gly Trp
        115                 120                 125

Glu Leu Ala Glu Gly Pro Glu Val Glu Thr Glu Gln Phe Asn Phe Asp
    130                 135                 140

Ala Leu Asn Phe Pro Ala Asp His Pro Ala Arg Gly Glu Gln Asp Thr
145                 150                 155                 160

Phe Tyr Ile Ala Pro Glu Asp Ser Arg Gln Leu Leu Arg Thr His Thr
                165                 170                 175

Ser Pro Val Gln Ile Arg Thr Leu Leu Ala Arg Glu Leu Pro Val Tyr
            180                 185                 190

Ile Ile Ser Ile Gly Arg Thr Phe Arg Thr Asp Glu Leu Asp Ala Thr
        195                 200                 205

His Thr Pro Ile Phe His Gln Val Glu Gly Leu Ala Val Asp Arg Gly
    210                 215                 220

Leu Ser Met Ala His Leu Arg Gly Thr Leu Asp Ala Phe Ala Arg Ala
225                 230                 235                 240

Glu Phe Gly Pro Ser Ala Arg Thr Arg Ile Arg Pro His Phe Phe Pro
                245                 250                 255

Phe Thr Glu Pro Ser Ala Glu Val Asp Val Trp Phe Ala Asn Lys Ile
            260                 265                 270

Gly Gly Ala Ala Trp Val Glu Trp Gly Gly Cys Gly Met Val His Pro
        275                 280                 285
```

```
Asn Val Leu Arg Ala Thr Gly Ile Asp Pro Asp Leu Tyr Ser Gly Phe
            290                 295                 300

Ala Phe Gly Met Gly Leu Glu Arg Thr Leu Gln Phe Arg Asn Gly Ile
305                 310                 315                 320

Pro Asp Met Arg Asp Met Val Glu Gly Asp Val Arg Phe Ser Leu Pro
                325                 330                 335

Phe Gly Val Gly Ala
            340

<210> SEQ ID NO 78
<211> LENGTH: 458
<212> TYPE: PRT
<213> ORGANISM: Caenorhabditis elegans

<400> SEQUENCE: 78

Met Arg Phe Leu Ser Thr Tyr Gln Thr Gly Ala Arg Arg Cys Cys Thr
1               5                   10                  15

Met Leu Phe Gln Lys Asn Ala Lys Ser Ile Arg Ala Thr Leu Met Ser
            20                  25                  30

Thr Thr Ala Ala Glu Glu Ser Arg Lys Ile Val Lys Glu Glu Val
        35                  40                  45

Phe Glu Leu Asp Gly Arg Lys Tyr Thr Pro Ala Leu Tyr Asn Leu
50                  55                  60

Ser Pro Gly Val Arg Arg Leu Leu Asp Arg Arg Ile Leu Gln Glu Ser
65                  70                  75                  80

Ser Asn Pro Leu Asn Leu Leu Lys Arg Arg Ile Val Asp Tyr Val His
            85                  90                  95

Gln Thr Tyr Arg Lys Pro Gly Asn Arg Ser Pro Leu Phe Thr Ile Cys
            100                 105                 110

Glu Ser Glu Pro Arg Val Val Thr Thr Tyr Gln Asn Phe Asp Ser Leu
            115                 120                 125

Leu Thr Pro Glu Asp His Val Ser Arg Arg Pro Ser Asp Thr Tyr Tyr
130                 135                 140

Val Asn His Glu His Cys Leu Arg Ala His Thr Ser Ala His Gln His
145                 150                 155                 160

Asn Leu Met Gln Ser Gly Leu Asp Ala Phe Leu Val Ile Gly Asp Val
            165                 170                 175

Tyr Arg Arg Asp Glu Val Asp Arg Thr His Tyr Pro Cys Phe His Gln
            180                 185                 190

Ile Glu Gly Val Arg Leu Tyr Ser Lys Asp Glu Leu Leu Gly Lys Lys
            195                 200                 205

Pro Asp Gly Lys Asn Val Ala Glu Leu Phe Ser Thr Ala Ala Ser Ala
210                 215                 220

Ala Thr Glu Arg Ser Pro Glu Lys Gln Glu Lys His Thr Leu Asp Ala
225                 230                 235                 240

Thr Lys Ala Ala Glu Ile Gln Leu Lys Gln Phe Leu Glu Asn Leu Cys
            245                 250                 255

Asp Glu Leu Phe Gly Lys Asp Ala Glu Lys Arg Trp Val Asp Ala Tyr
            260                 265                 270

Phe Pro Phe Thr His Pro Ser Trp Glu Leu Glu Val Phe Tyr Asn Gly
            275                 280                 285

Gln Trp Leu Glu Val Leu Gly Cys Gly Ile Met Glu Gln Lys Leu Leu
            290                 295                 300

Glu Ser Ala Gly Val Thr Asp Lys Ile Gly Trp Ala Phe Gly Ile Gly
305                 310                 315                 320
```

```
Leu Glu Arg Ile Ala Met Val Leu Tyr Gly Ile Pro Asp Ile Arg Leu
                325                 330                 335

Phe Trp Ser Lys Asp Thr Gly Phe Leu Ser Gln Phe Ala Gly Lys Met
            340                 345                 350

Pro Gly Glu Asp Val Lys Tyr Lys Gln Ile Ser Ala His Pro Gln Val
        355                 360                 365

Ile Phe Asp Ile Ser Phe Phe Leu Pro Ser Thr Val Gln Phe Asn Asp
    370                 375                 380

Met Thr Ser Asp Val Tyr Asp Thr Ile Arg Thr Val Gly Gly Glu Leu
385                 390                 395                 400

Val Glu Gln Val Lys Leu Thr Asp Glu Phe Glu Asn Lys Lys Lys Glu
                405                 410                 415

Lys Lys Ser Gln Thr Tyr Arg Ile Val Tyr Arg Ser His Glu Arg Ala
            420                 425                 430

Leu Thr Lys Glu Glu Val Asn Val Ile His Lys Gln Ile Glu Gln Ser
        435                 440                 445

Leu Ala Ser Ser Phe Gly Val Thr Leu Arg
    450                 455

<210> SEQ ID NO 79
<211> LENGTH: 469
<212> TYPE: PRT
<213> ORGANISM: Saccharomyces cerevisiae

<400> SEQUENCE: 79

Met Phe Leu Asn Arg Met Met Lys Thr Arg Thr Gly Leu Tyr Arg Leu
1               5                   10                  15

Tyr Ser Thr Leu Lys Val Pro His Val Glu Ile Asn Gly Ile Lys Tyr
                20                  25                  30

Lys Thr Asp Pro Gln Thr Thr Asn Val Thr Asp Ser Ile Ile Lys Leu
            35                  40                  45

Thr Asp Arg Ser Leu His Leu Lys Glu Ser His Pro Val Gly Ile Leu
        50                  55                  60

Arg Asp Leu Ile Glu Lys Lys Leu Asn Ser Val Asp Asn Thr Phe Lys
65                  70                  75                  80

Ile Phe Asn Asn Phe Lys Pro Val Val Thr Thr Met Glu Asn Phe Asp
                85                  90                  95

Ser Leu Gly Phe Pro Lys Asp His Pro Gly Arg Ser Lys Ser Asp Thr
                100                 105                 110

Tyr Tyr Ile Asn Glu Thr His Leu Leu Arg Thr His Thr Ser Ala His
            115                 120                 125

Glu Leu Glu Cys Phe Gln Lys Ile Arg Asn Asp Ser Asp Asn Ile Lys
        130                 135                 140

Ser Gly Phe Leu Ile Ser Ala Asp Val Tyr Arg Arg Asp Glu Ile Asp
145                 150                 155                 160

Lys Thr His Tyr Pro Val Phe His Gln Met Glu Gly Ala Thr Ile Trp
                165                 170                 175

Lys Arg Thr Lys Ala Asp Val Gly Val Lys Glu Pro Met Tyr Ile Glu
            180                 185                 190

Lys Ile Arg Glu Asp Ile Arg Gln Val Glu Asn Leu Leu Asn Lys Glu
        195                 200                 205

Asn Val Lys Ile Thr Val Asp Asp Thr Ile Pro Leu Lys Glu Asn
    210                 215                 220

Asn Pro Lys Gln Glu Tyr Met Ser Asp Leu Glu Val Asp Leu Cys Ser
225                 230                 235                 240
```

```
Gln His Leu Lys Arg Ser Ile Glu Leu Ile Val Ser Glu Val Phe Asn
            245                 250                 255

Lys Lys Ile Ser Ser Met Ile Lys Asn Lys Ala Asn Asn Thr Pro Lys
            260                 265                 270

Glu Leu Lys Val Arg Trp Ile Asn Ala Tyr Phe Pro Trp Thr Ala Pro
            275                 280                 285

Ser Trp Glu Ile Glu Val Trp Trp Gln Gly Glu Trp Leu Glu Leu Cys
            290                 295                 300

Gly Cys Gly Leu Ile Arg Gln Asp Val Leu Leu Arg Ala Gly Tyr Lys
305                 310                 315                 320

Pro Ser Glu Thr Ile Gly Trp Ala Phe Gly Leu Gly Leu Asp Arg Ile
            325                 330                 335

Ala Met Leu Leu Phe Glu Ile Pro Asp Ile Arg Leu Leu Trp Ser Arg
            340                 345                 350

Asp Glu Arg Phe Ser Arg Gln Phe Ser Lys Gly Leu Ile Thr Ser Phe
            355                 360                 365

Lys Pro Tyr Ser Lys His Pro Gly Ser Phe Arg Asp Val Ala Phe Trp
            370                 375                 380

Leu Pro Glu Asp Lys Pro Asp Ile His Gln Val His Glu Asn Asp Leu
385                 390                 395                 400

Met Glu Ile Ile Arg Asn Ile Ala Gly Asp Leu Val Glu Ser Val Lys
            405                 410                 415

Leu Val Asp Ser Phe Thr His Pro Lys Thr Gly Arg Lys Ser Met Cys
            420                 425                 430

Tyr Arg Ile Asn Tyr Gln Ser Met Asp Arg Asn Leu Thr Asn Ala Glu
            435                 440                 445

Val Asn Thr Leu Gln Asp Met Val Cys Ser Lys Leu Val Lys Glu Tyr
            450                 455                 460

Ser Val Glu Leu Arg
465

<210> SEQ ID NO 80
<211> LENGTH: 499
<212> TYPE: PRT
<213> ORGANISM: Schizosaccharomyces pombe

<400> SEQUENCE: 80

Met Ser Lys Leu Glu Ala Leu Gln Val Phe Leu Leu Glu Lys Leu Asn
 1               5                  10                  15

Glu Lys Asn Glu Ile Pro Asn Thr Ser His Leu Glu Phe Asp Gly Lys
            20                  25                  30

Lys Leu Gly Pro Gln Glu Ala Gln Ser Ala Ile Leu Ser Leu Ala Ala
            35                  40                  45

Lys Asn Met Ile Glu Phe Ser Arg His Glu Ile Glu Ile Tyr Asn Leu
 50                  55                  60

Thr Ala Glu Gly Glu Asn Ile Cys Ala Asn Gly Ser His Glu Ala Lys
 65                  70                  75                  80

Val Tyr Asn Glu Ile Cys Ala Ser Met Ser Gly Leu Asn Ile Gly Glu
            85                  90                  95

Leu Lys Lys Lys Leu Gly Asn Ser Ala Gly Ile Gly Gln Gly Arg Ala
            100                 105                 110

Phe Lys Leu Gly Trp Ile Lys Lys Asp Gly Asp Lys Leu Val Lys Asn
            115                 120                 125

Thr Asp Ser Ile Thr Asp Glu Thr Pro Lys Val Leu Ser Glu Ile Lys
            130                 135                 140
```

-continued

```
Glu His Gly Thr Ile Ser Asp Ser Lys Thr Leu Thr Asp Leu Lys Lys
145                 150                 155                 160

Arg Lys Leu Val Glu Arg Asn Lys Ile Met Tyr Phe Ser Leu Arg Lys
                165                 170                 175

Gly Pro Asn Phe Ser Leu Gln Ile Glu Lys Leu Asn Thr Asp Leu Thr
            180                 185                 190

Ala Glu Met Ile Thr Ser Arg Ser Trp Glu Ser Ala Lys Phe Lys Ser
        195                 200                 205

Tyr Asn Phe Ala Ala Glu Gly Ile Pro Pro Ala Gly Gly Cys Leu His
    210                 215                 220

Pro Leu Met Lys Val Arg Glu Glu Phe Arg Lys Phe Phe Glu Leu
225                 230                 235                 240

Gly Phe Glu Glu Met Pro Thr Asn Asn Phe Val Glu Ser Gly Phe Trp
                245                 250                 255

Asn Phe Asp Ala Leu Phe Val Pro Gln Gln His Ser Ala Arg Asp Ala
                260                 265                 270

Gln Asp Thr Phe Phe Leu Lys Val Pro Ala Ser Thr Asp Lys Leu Pro
            275                 280                 285

Asp Pro Glu Tyr Val Ala Arg Val Lys Ala Thr His Glu Asn Gly Gly
        290                 295                 300

Glu Thr Lys Gly Ile Gly Tyr Arg Ala Pro Phe Ser Leu Glu Glu Thr
305                 310                 315                 320

Arg Lys Leu Val Leu Arg Thr His Thr Thr Ala Val Ser Ala Asn Met
                325                 330                 335

Leu Tyr Lys Leu Ala Gln Asn Gly Phe His Pro Ala Lys Tyr Phe Ser
            340                 345                 350

Ile Asp Arg Val Phe Arg Asn Glu Thr Val Asp Ala Thr His Leu Ala
        355                 360                 365

Glu Phe His Gln Val Glu Gly Val Ile Cys Asp Arg Asn Ile Thr Leu
    370                 375                 380

Gly Asp Leu Ile Gly Phe Leu Glu Val Phe Phe Gly Lys Met Asn Val
385                 390                 395                 400

Lys Asn Leu Arg Phe Lys Pro Ala Tyr Asn Pro Tyr Thr Glu Pro Ser
                405                 410                 415

Leu Glu Val Phe Ser Tyr His Glu Lys Leu Gly Lys Trp Val Glu Val
            420                 425                 430

Gly Asn Ser Gly Met Phe Arg Pro Glu Met Leu Glu Pro Met Gly Leu
        435                 440                 445

Pro Lys Asp Val Arg Cys Leu Gly Phe Gly Leu Ser Leu Glu Arg Pro
    450                 455                 460

Thr Met Ile Lys Tyr Gly Val Ala Asp Ile Arg Gln Leu Ile Gly Pro
465                 470                 475                 480

Lys Val Asn Leu Asp Leu Ile Glu Ala Ser Pro Ala Val Arg Leu Asp
                485                 490                 495

Lys Glu Glu

<210> SEQ ID NO 81
<211> LENGTH: 338
<212> TYPE: PRT
<213> ORGANISM: Pseudomonas aeruginosa

<400> SEQUENCE: 81

Met Glu Asn Leu Asp Ala Leu Val Ser Gln Ala Leu Glu Ala Val Arg
1               5                   10                  15

His Thr Glu Asp Val Asn Ala Leu Glu Gln Ile Arg Val His Tyr Leu
```

```
                20                  25                  30
Gly Lys Lys Gly Glu Leu Thr Gln Val Met Lys Thr Leu Gly Asp Leu
            35                  40                  45

Pro Ala Glu Glu Arg Pro Lys Val Gly Ala Leu Ile Asn Val Ala Lys
            50                  55                  60

Glu Lys Val Gln Asp Val Leu Asn Ala Arg Lys Thr Glu Leu Glu Gly
 65                  70                  75                  80

Ala Ala Leu Ala Ala Arg Leu Ala Glu Arg Ile Asp Val Thr Leu
                85                  90                  95

Pro Gly Arg Gly Gln Leu Ser Gly Gly Leu His Pro Val Thr Arg Thr
                100                 105                 110

Leu Glu Arg Ile Glu Gln Cys Phe Ser Arg Ile Gly Tyr Glu Val Ala
                115                 120                 125

Glu Gly Pro Glu Val Glu Asp Asp Tyr His Asn Phe Glu Ala Leu Asn
                130                 135                 140

Ile Pro Gly His His Pro Ala Arg Ala Met His Asp Thr Phe Tyr Phe
145                 150                 155                 160

Asn Ala Asn Met Leu Leu Arg Thr His Thr Ser Pro Val Gln Val Arg
                165                 170                 175

Thr Met Glu Ser Gln Gln Pro Pro Ile Arg Ile Val Cys Pro Gly Arg
                180                 185                 190

Val Tyr Arg Cys Asp Ser Asp Leu Thr His Ser Pro Met Phe His Gln
                195                 200                 205

Val Glu Gly Leu Leu Val Asp Glu Gly Val Ser Phe Ala Asp Leu Lys
                210                 215                 220

Gly Thr Ile Glu Glu Phe Leu Arg Ala Phe Phe Glu Lys Gln Leu Glu
225                 230                 235                 240

Val Arg Phe Arg Pro Ser Phe Phe Pro Phe Thr Glu Pro Ser Ala Glu
                245                 250                 255

Val Asp Ile Gln Cys Val Ile Cys Ser Gly Asn Gly Cys Arg Val Cys
                260                 265                 270

Lys Gln Thr Gly Trp Leu Glu Val Met Gly Cys Gly Met Val His Pro
                275                 280                 285

Asn Val Leu Arg Met Ser Asn Ile Asp Pro Glu Lys Phe Gln Gly Phe
                290                 295                 300

Ala Phe Gly Met Gly Ala Glu Arg Leu Ala Met Leu Arg Tyr Gly Val
305                 310                 315                 320

Asn Asp Leu Arg Leu Phe Phe Asp Asn Asp Leu Arg Phe Leu Gly Gln
                325                 330                 335

Phe Arg

<210> SEQ ID NO 82
<211> LENGTH: 785
<212> TYPE: PRT
<213> ORGANISM: Thermus thermophilus

<400> SEQUENCE: 82

Met Arg Val Pro Phe Ser Trp Leu Lys Ala Tyr Val Pro Glu Leu Glu
 1                   5                  10                  15

Ser Pro Glu Val Leu Glu Glu Arg Leu Ala Gly Leu Gly Phe Glu Thr
                20                  25                  30

Asp Arg Ile Glu Arg Val Phe Pro Ile Pro Arg Gly Val Val Phe Ala
            35                  40                  45

Arg Val Leu Glu Ala His Pro Ile Pro Gly Thr Arg Leu Lys Arg Leu
            50                  55                  60
```

```
Val Leu Asp Ala Gly Arg Thr Val Glu Val Val Ser Gly Ala Glu Asn
 65                  70                  75                  80

Ala Arg Lys Gly Ile Gly Val Ala Leu Ala Leu Pro Gly Thr Glu Leu
                 85                  90                  95

Pro Gly Leu Gly Gln Lys Val Gly Glu Arg Val Ile Gln Gly Val Arg
            100                 105                 110

Ser Phe Gly Met Ala Leu Ser Pro Arg Glu Leu Gly Val Gly Glu Tyr
        115                 120                 125

Gly Gly Gly Leu Leu Glu Phe Pro Glu Asp Ala Leu Pro Pro Gly Thr
130                 135                 140

Pro Leu Ser Glu Ala Trp Pro Glu Glu Val Val Leu Asp Leu Glu Val
145                 150                 155                 160

Thr Pro Asn Arg Pro Asp Ala Leu Gly Leu Gly Leu Ala Arg Asp
                165                 170                 175

Leu His Ala Leu Gly Tyr Ala Leu Val Glu Pro Glu Ala Ala Leu Lys
            180                 185                 190

Ala Glu Ala Leu Pro Leu Pro Phe Ala Leu Lys Val Glu Asp Pro Glu
            195                 200                 205

Gly Ala Pro His Phe Thr Leu Gly Tyr Ala Phe Gly Leu Arg Val Ala
210                 215                 220

Pro Ser Pro Leu Trp Met Gln Arg Ala Leu Phe Ala Ala Gly Met Arg
225                 230                 235                 240

Pro Ile Asn Asn Val Val Asp Val Thr Asn Tyr Val Met Leu Glu Arg
                245                 250                 255

Ala Gln Pro Met His Ala Phe Asp Leu Arg Phe Val Gly Glu Gly Ile
            260                 265                 270

Ala Val Arg Arg Ala Arg Glu Gly Glu Arg Leu Lys Thr Leu Asp Gly
            275                 280                 285

Val Glu Arg Thr Leu His Pro Glu Asp Leu Val Ile Ala Gly Trp Arg
290                 295                 300

Gly Glu Glu Ser Phe Pro Leu Gly Leu Ala Gly Val Met Gly Gly Ala
305                 310                 315                 320

Glu Ser Glu Val Arg Glu Asp Thr Glu Ala Ile Ala Leu Glu Val Ala
                325                 330                 335

Cys Phe Asp Pro Val Ser Ile Arg Lys Thr Ala Arg Arg His Gly Leu
            340                 345                 350

Arg Thr Glu Ala Ser His Arg Phe Glu Arg Gly Val Asp Pro Leu Gly
            355                 360                 365

Gln Val Pro Ala Gln Arg Arg Ala Leu Ser Leu Leu Gln Ala Leu Ala
370                 375                 380

Gly Ala Arg Val Ala Glu Ala Leu Leu Glu Ala Gly Ser Pro Lys Pro
385                 390                 395                 400

Pro Glu Ala Ile Pro Phe Arg Pro Glu Tyr Ala Asn Arg Leu Leu Gly
                405                 410                 415

Thr Ser Tyr Pro Glu Ala Glu Gln Ile Ala Ile Leu Lys Arg Leu Gly
            420                 425                 430

Cys Arg Val Glu Gly Glu Gly Pro Thr Tyr Arg Val Thr Pro Pro Ser
            435                 440                 445

His Arg Leu Asp Leu Arg Leu Glu Glu Asp Leu Val Glu Glu Val Ala
450                 455                 460

Arg Ile Gln Gly Tyr Glu Thr Ile Pro Leu Ala Leu Pro Ala Phe Phe
465                 470                 475                 480

Pro Ala Pro Asp Asn Arg Gly Val Glu Ala Pro Tyr Arg Lys Glu Gln
```

```
                     485                 490                 495
Arg Leu Arg Glu Val Leu Ser Gly Leu Gly Phe Gln Glu Val Tyr Thr
                 500                 505                 510

Tyr Ser Phe Met Asp Pro Glu Asp Ala Arg Arg Phe Arg Leu Asp Pro
             515                 520                 525

Pro Arg Leu Leu Leu Asn Pro Leu Ala Pro Glu Lys Ala Ala Leu
         530                 535                 540

Arg Thr His Leu Phe Pro Gly Leu Val Arg Val Leu Lys Glu Asn Leu
545                 550                 555                 560

Asp Leu Asp Arg Pro Glu Arg Ala Leu Leu Phe Glu Val Gly Arg Val
                565                 570                 575

Phe Arg Glu Arg Glu Glu Thr His Leu Ala Gly Leu Leu Phe Gly Glu
             580                 585                 590

Gly Val Gly Leu Pro Trp Ala Lys Glu Arg Leu Ser Gly Tyr Phe Leu
         595                 600                 605

Leu Lys Gly Tyr Leu Glu Ala Leu Phe Ala Arg Leu Gly Leu Ala Phe
     610                 615                 620

Arg Val Glu Ala Gln Ala Phe Pro Phe Leu His Pro Gly Val Ser Gly
625                 630                 635                 640

Arg Val Leu Val Glu Gly Glu Val Gly Phe Leu Gly Ala Leu His
                645                 650                 655

Pro Glu Ile Ala Gln Glu Leu Glu Pro Pro Val His Leu Phe Glu
             660                 665                 670

Leu Arg Leu Pro Leu Pro Asp Lys Pro Leu Ala Phe Gln Asp Pro Ser
         675                 680                 685

Arg His Pro Ala Ala Phe Arg Asp Leu Ala Val Val Pro Ala Pro
     690                 695                 700

Thr Pro Tyr Gly Glu Val Glu Ala Leu Val Arg Glu Ala Ala Gly Pro
705                 710                 715                 720

Tyr Leu Glu Ser Leu Ala Leu Phe Asp Leu Tyr Gln Gly Pro Pro Leu
                725                 730                 735

Pro Glu Gly His Lys Ser Leu Ala Phe His Leu Arg Phe Arg His Pro
             740                 745                 750

Lys Arg Thr Leu Arg Asp Glu Glu Val Glu Glu Ala Val Ser Arg Val
         755                 760                 765

Ala Glu Ala Leu Arg Ala Arg Gly Phe Gly Leu Arg Gly Leu Asp Thr
     770                 775                 780

Pro
785

<210> SEQ ID NO 83
<211> LENGTH: 598
<212> TYPE: PRT
<213> ORGANISM: Arabidopsis thaliana

<400> SEQUENCE: 83

Met Pro Thr Ile Ser Val Gly Arg Asp Arg Leu Phe Ala Ala Leu Gly
 1               5                  10                  15

Glu Ser Tyr Thr Gln Glu Lys Phe Glu Leu Cys Phe Ser Phe Gly
                20                  25                  30

Ile Glu Leu Asp Asp Val Thr Thr Glu Lys Ala Ile Ile Arg Lys Glu
             35                  40                  45

Lys His Ile Asp Glu Glu Ala Asp Asp Glu Glu Ile Ile Tyr Lys
         50                  55                  60

Ile Glu Ile Pro Ala Asn Arg Pro Asp Leu Leu Cys Leu Glu Gly Leu
```

-continued

```
            65                  70                  75                  80
Ala Gln Ser Leu Arg Val Phe Ile Glu Lys Gln Glu Ile Pro Thr Tyr
                    85                  90                  95
Thr Leu Ala Asp Ile Ser Lys Asp Lys Ile Leu Gln Met Asn Val Lys
                100                 105                 110
Pro Glu Thr Ser Lys Ile Arg Pro Phe Val Val Cys Ala Val Leu Arg
                115                 120                 125
Gly Val Thr Phe Asp Glu Ala Arg Tyr Asn Ser Phe Ile Asp Leu Gln
            130                 135                 140
Asp Lys Leu His Gln Asn Ile Cys Arg Arg Ser Leu Val Ala Ile
145                 150                 155                 160
Gly Thr His Asp Leu Asp Thr Leu Gln Gly Pro Phe Thr Tyr Glu Ala
                165                 170                 175
Leu Pro Pro Thr Asp Ile Asn Phe Val Pro Leu Lys Gln Thr Lys Ser
                180                 185                 190
Phe Arg Ala Asp Glu Leu Ile Glu Phe Tyr Lys Ser Asp Met Lys Leu
                195                 200                 205
Lys Lys Phe Leu His Ile Ile Glu Asn Ser Pro Val Phe Pro Val Leu
    210                 215                 220
Tyr Asp Ser Lys Arg Thr Val Leu Ser Leu Pro Pro Ile Ile Asn Gly
225                 230                 235                 240
Ala His Ser Ala Ile Thr Leu Gln Thr Lys Asn Val Phe Ile Glu Cys
                245                 250                 255
Thr Ala Thr Asp Leu Thr Lys Ala Lys Ile Val Leu Asn Thr Met Val
                260                 265                 270
Thr Thr Phe Ser Glu Phe Cys Ala Arg Lys Phe Glu Ile Glu Pro Val
                275                 280                 285
Glu Val Thr Tyr Asp Asp Gly Lys Ser Tyr Ile Tyr Pro Asp Leu Ala
    290                 295                 300
Val Tyr Asp Met Glu Val Pro Leu Ser Phe Ile Thr Asp Ser Ile Gly
305                 310                 315                 320
Val Ser Leu Lys Val Glu Gln Val Thr Ser Leu Leu Thr Arg Met Gln
                325                 330                 335
Leu Gln Ala Glu Gln Ala Lys Ser Ser Asp Asn Gln Cys Ala Ile Lys
                340                 345                 350
Val His Val Pro Pro Ser Arg Ser Asp Val Leu His Pro Cys Asp Val
            355                 360                 365
Met Glu Asp Val Ala Ile Ala Tyr Gly Phe Asn Asn Ile Pro Thr Arg
    370                 375                 380
Lys Pro Ala Ser Ile Lys Pro Leu Thr Leu Asn Glu Leu Thr Asp Leu
385                 390                 395                 400
Leu Arg Ile Glu Ile Ala Met Cys Val Tyr Thr Glu Val Val Thr Trp
                405                 410                 415
Leu Leu Cys Ser His Lys Glu Asn Phe Ala Met Leu Asn Arg Glu Asp
                420                 425                 430
Val Asn Ser Ala Val Ile Val Gly Asn Pro Arg Ser Ala Asp Phe Glu
            435                 440                 445
Ala Met Arg Arg Ala Leu Met Pro Gly Leu Leu Lys Thr Val Gly His
    450                 455                 460
Asn Asn Lys Tyr Pro Lys Pro Ile Lys Ile Phe Glu Ile Ser Asp Val
465                 470                 475                 480
Val Met Leu Asp Glu Ser Lys Asp Val Gly Ala Ser Asn Arg Arg His
                485                 490                 495
```

-continued

```
Leu Ala Ala Leu Tyr Cys Gly Ala Thr Ser Gly Phe Glu Leu Ile His
                500                 505                 510

Gly Leu Val Asp Arg Ile Met Glu Val Met Ala Ile Pro Phe Leu Thr
            515                 520                 525

Ile His Glu Asn Asn Val Pro Ile Asn Glu Lys Asp Gly Tyr Tyr Val
530                 535                 540

Lys Leu Ser Gln Glu Pro Glu Phe Leu Pro Gly Arg Gln Ala Ser Ile
545                 550                 555                 560

Ile Val Arg Gly Lys His Ile Gly Asn Phe Gly Ile Val His Pro Glu
                565                 570                 575

Val Leu Asn Asn Phe Asp Ile Pro Asp Pro Cys Ser Tyr Leu Glu Leu
            580                 585                 590

Asp Ile Glu Ala Ile Leu
        595

<210> SEQ ID NO 84
<211> LENGTH: 589
<212> TYPE: PRT
<213> ORGANISM: Drosophila melanogaster

<400> SEQUENCE: 84

Met Pro Thr Ile Gly Val Lys Arg Asp Leu Leu Phe Glu Ala Leu Gly
1               5                   10                  15

Lys Thr Tyr Thr Asp Asp Glu Phe Gln Asp Leu Cys Phe Ala Phe Gly
            20                  25                  30

Leu Glu Leu Asp Glu Val Thr Thr Glu Lys Gln Met Leu Thr Lys Glu
        35                  40                  45

Gln Gly Asp Val Ala Ala Ala Asn Ala Ser Glu Glu Ile Ile Tyr
    50                  55                  60

Arg Ile Asp Ile Pro Ala Asn Arg Tyr Asp Leu Leu Cys Leu Glu Gly
65                  70                  75                  80

Leu Val Thr Gly Leu Leu Val Phe Gln Gly Lys Leu Lys Pro Pro Lys
                85                  90                  95

Phe Gln Phe Val Glu Leu Ala Lys Arg Gln Val Leu Lys Ile Asp Pro
            100                 105                 110

Ser Thr Ala Gln Ile Arg Pro Tyr Ala Val Ala Val Leu Arg Asn
        115                 120                 125

Val Thr Phe Thr Gln Ala Ser Tyr Asn Ser Phe Ile Asp Leu Gln Asp
    130                 135                 140

Lys Leu His Gln Asn Ile Cys Arg Lys Arg Thr Leu Val Ala Ile Gly
145                 150                 155                 160

Thr His Asp Leu Asp Thr Leu Gln Gly Pro Phe Ser Tyr Glu Ala Leu
                165                 170                 175

Ala Pro Asp Gln Ile Lys Phe Lys Pro Leu Asn Gln Thr Lys Glu Met
            180                 185                 190

Thr Gly Ser Glu Leu Met Asp Phe Tyr Ser Thr His Ala Gln Leu Lys
        195                 200                 205

Gln Tyr Leu Pro Ile Ile Arg Glu Ser Pro Val Tyr Pro Val Ile Tyr
    210                 215                 220

Asp Ala Asn Arg Val Val Leu Ser Leu Pro Pro Ile Ile Asn Gly Asp
225                 230                 235                 240

His Ser Lys Ile Thr Leu Lys Thr Lys Asn Val Phe Ile Glu Cys Thr
                245                 250                 255

Ala Thr Asp Arg Thr Lys Ala Lys Val Val Leu Asp Thr Ile Val Cys
            260                 265                 270
```

Leu Phe Ser Glu His Cys Ala Gln Lys Phe Thr Val Glu Pro Cys Asp
            275                 280                 285

Val Val Gln Pro Asp Gly Ser Val Ile Ser Tyr Pro Glu Leu Glu Val
        290                 295                 300

Arg Glu Glu Arg Ile Ser Val Lys Arg Ala Asn Ala Tyr Ile Gly Ile
305                 310                 315                 320

Asp Glu Pro Ala Glu Lys Leu Ala Asp Met Leu Thr Arg Met Tyr Leu
                325                 330                 335

Glu Ala Lys Val Asp Gly Asp Ser Leu Val Val Lys Ile Pro Pro Thr
            340                 345                 350

Arg His Asp Val Ile His Ala Cys Asp Ile Tyr Glu Asp Val Ala Ile
        355                 360                 365

Ala Tyr Gly Tyr Asn Asn Ile Lys Lys Ser Leu Pro Ala Phe Met Gln
370                 375                 380

Ile Ala Lys Gln Phe Pro Leu Asn Lys Leu Thr Glu Gln Leu Arg Glu
385                 390                 395                 400

Gln Val Ala Gln Ala Gly Phe Thr Glu Ala Leu Thr Phe Thr Leu Cys
                405                 410                 415

Ser Arg Asp Asp Ile Gly Arg Lys Leu Asn Lys Asn Ile Asp Ala Leu
            420                 425                 430

Pro Ala Val His Ile Gly Asn Pro Lys Thr Leu Glu Phe Gln Val Val
        435                 440                 445

Arg Thr Thr Leu Leu Pro Gly Leu Leu Lys Thr Leu Val Ala Asn Arg
450                 455                 460

Lys Met Pro Leu Pro Leu Lys Leu Phe Glu Ile Ser Asp Val Val Val
465                 470                 475                 480

Ala Asp Glu Ser Thr Glu Val Gly Ala Arg Asn Glu Arg Arg Val Cys
                485                 490                 495

Ala Val Asn Cys Asn Lys Thr Ala Gly Phe Glu Val Val His Gly Leu
            500                 505                 510

Leu Asp Arg Val Met Gln Leu Leu Ser Val Pro Trp Lys Ser Ala Ser
        515                 520                 525

Gly Thr Lys Gly Tyr Tyr Leu Gln Ala Thr Glu Asp Pro Ser Tyr Phe
530                 535                 540

Pro Gly Arg Cys Ala Asn Val Met Tyr Asp Gly Val Val Ile Gly Lys
545                 550                 555                 560

Ile Gly Val Leu His Pro Thr Val Leu Gln Ala Phe Glu Leu Thr Thr
                565                 570                 575

Pro Cys Ser Ala Val Glu Phe Thr Ile Glu Pro Phe Val
            580                 585

<210> SEQ ID NO 85
<211> LENGTH: 591
<212> TYPE: PRT
<213> ORGANISM: Caenorhabditis elegans

<400> SEQUENCE: 85

Met Pro Thr Val Gly Ile Lys Lys Val Ile Leu Asp Lys His Phe Lys
1                   5                   10                  15

Arg Val Tyr Ser Glu Lys Glu Phe Asp Glu Leu Cys Phe Glu Tyr Gly
                20                  25                  30

Leu Glu Leu Asp Glu Ile Thr Ser Glu Lys Ala Ala Val Glu Lys Glu
            35                  40                  45

Gln Gly Thr Arg Ala Ala Ser Asp Leu Asn Asp Gln Glu Val Tyr Lys
        50                  55                  60

```
Ile Asp Ile Pro Ala Asn Arg Tyr Asp Leu Leu Ser Val Glu Gly Leu
 65                  70                  75                  80

Ala Arg Ala Ile Arg Ile Phe Lys Gln Glu Ile Pro Ser Pro Ala Tyr
                 85                  90                  95

Lys Tyr Ala Asp Val Pro Lys Thr Gly Leu Gln Lys Ile Ile Val Lys
            100                 105                 110

Lys Glu Thr Ala Gln Val Arg Pro Phe Val Val Gly Ala Val Leu Arg
        115                 120                 125

Asp Ile Ser Phe Asp Ala Asp Ser Tyr Ala Ser Phe Ile Asp Leu Gln
130                 135                 140

Asp Lys Leu His Gln Asn Ile Cys Arg Lys Arg Thr Leu Val Ala Ile
145                 150                 155                 160

Gly Thr His Asp Leu Asp Thr Ile Gln Gly Pro Phe Glu Tyr Arg Ala
                165                 170                 175

Glu Ala Pro Lys Asp Ile Lys Phe Lys Pro Leu Asn Gln Thr Lys Glu
            180                 185                 190

Tyr Thr Ala Glu Glu Leu Met Thr Leu Tyr Ser Thr Asp Ser His Leu
        195                 200                 205

Lys Ala Tyr Leu Pro Ile Ile Gln Asn His Pro Val Tyr Pro Val Ile
210                 215                 220

Tyr Asp Lys Asn Gly Val Val Cys Ser Met Pro Pro Ile Ile Asn Gly
225                 230                 235                 240

Glu His Ser Lys Ile Thr Leu Asn Thr Lys Asn Val Phe Ile Glu Ala
                245                 250                 255

Thr Ala Thr Asp Lys Gln Lys Ala Phe Val Val Leu Asp Thr Ile Val
            260                 265                 270

Thr Leu Phe Ser Gln Tyr Cys Ala Lys Pro Phe Thr Ile Glu Gln Val
        275                 280                 285

Glu Val Val Tyr Glu Glu Thr Gly Val Lys Glu Leu Tyr Pro Leu Leu
290                 295                 300

Ser Tyr Arg Glu Met Thr Val Thr Thr Pro Glu Ile Asn Thr Lys Ile
305                 310                 315                 320

Gly Ile Asn Leu Lys Asp Glu Glu Met Ala Thr Leu Leu Asn Lys Met
                325                 330                 335

Ser Leu Lys Ala Glu Val Ala Ala Lys Glu Thr Leu Lys Ile Val Val
            340                 345                 350

Pro Pro Thr Arg His Asp Ile Leu His Ala Cys Asp Ile Ala Glu Asp
        355                 360                 365

Val Gly Val Ala Phe Gly Tyr Asn Asn Leu Ile Thr Lys Leu Pro Glu
370                 375                 380

Ser Asn Thr Val Ala Val Ala Phe Pro Ile Asn Lys Leu Cys Asp Asn
385                 390                 395                 400

Leu Arg Ile Glu Ile Ala Ala Ala Gly Trp Thr Glu Ala Leu Asn Phe
                405                 410                 415

Ala Leu Cys Ser Arg Asp Asp Ile Ser Ser Lys Leu Arg Gln Pro Asp
            420                 425                 430

Ala Leu Ser His Ala Val His Ile Gly Asn Pro Lys Thr Leu Glu Phe
        435                 440                 445

Gln Val Ala Arg Thr Ser Leu Leu Pro Gly Leu Leu Lys Thr Leu Ser
450                 455                 460

Ser Asn Arg Asp Met Pro Leu Pro Leu Lys Leu Phe Glu Leu Gln Asp
465                 470                 475                 480

Val Ile Val Lys Asp Ser Asn Thr Asp Val Gly Ala Arg Asn Glu Arg
                485                 490                 495
```

```
Arg Leu Ala Ala Val Tyr Tyr Asn Arg Ala Gly Phe Glu Ile Ile
                500                 505                 510

Gln Gly Phe Leu Asp Arg Ile Met Arg Met Leu Asn Val Asn Pro Ala
            515                 520                 525

Arg Asp Gly Thr Gly Tyr Tyr Ile Glu Ala Asp Glu Asn Ser Thr Tyr
530                 535                 540

Phe Pro Gly Arg Cys Ala Lys Ile Ile Gly Pro Lys Gly Val Val Leu
545                 550                 555                 560

Gly His Ile Gly Ala Leu His Pro Val Ile Thr Ser Phe Gly Leu
                565                 570                 575

Thr Leu Pro Cys Gly Ala Val Glu Ile Asn Val Glu Pro Phe Leu
            580                 585                 590

<210> SEQ ID NO 86
<211> LENGTH: 804
<212> TYPE: PRT
<213> ORGANISM: Bacillus subtilis

<400> SEQUENCE: 86

Met Phe Val Ser Tyr Lys Trp Leu Glu Asp Tyr Val Asp Leu Lys Gly
1               5                   10                  15

Met Asp Pro Ala Val Leu Ala Glu Lys Ile Thr Arg Ala Gly Ile Glu
                20                  25                  30

Val Glu Gly Ile Glu Tyr Lys Gly Glu Gly Ile Lys Gly Val Val Ile
            35                  40                  45

Gly His Val Leu Glu Arg Glu Gln His Pro Asn Ala Asp Lys Leu Asn
        50                  55                  60

Lys Cys Leu Val Asp Ile Gly Ala Glu Ala Pro Val Gln Ile Ile Cys
65                  70                  75                  80

Gly Ala Pro Asn Val Asp Lys Gly Gln Lys Val Ala Val Ala Thr Val
                85                  90                  95

Gly Ala Val Leu Pro Gly Asn Phe Lys Ile Lys Lys Ala Lys Leu Arg
            100                 105                 110

Gly Glu Glu Ser Asn Gly Met Ile Cys Ser Leu Gln Glu Leu Gly Ile
        115                 120                 125

Glu Ser Lys Leu Val Ala Lys Glu Tyr Ala Glu Gly Ile Phe Val Phe
130                 135                 140

Pro Asn Asp Ala Glu Thr Gly Ser Asp Ala Leu Ala Ala Leu Gln Leu
145                 150                 155                 160

Asp Asp Ala Ile Leu Glu Leu Gly Leu Thr Pro Asn Arg Ala Asp Ala
                165                 170                 175

Met Asn Met Leu Gly Val Ala Tyr Glu Val Ala Ala Ile Leu Asp Thr
            180                 185                 190

Glu Val Lys Leu Pro Gln Thr Asp Tyr Pro Ala Ala Ser Glu Gln Ala
        195                 200                 205

Ser Asp Tyr Ile Ser Val Lys Ile Glu Asp Gln Glu Ala Asn Pro Leu
210                 215                 220

Tyr Thr Ala Lys Ile Ile Lys Asn Val Thr Ile Ala Pro Ser Pro Leu
225                 230                 235                 240

Trp Met Gln Thr Lys Leu Met Asn Ala Gly Ile Arg Pro His Asn Asn
                245                 250                 255

Val Val Asp Ile Thr Asn Phe Val Leu Leu Glu Tyr Gly Gln Pro Leu
            260                 265                 270

His Ala Phe Asp Tyr Asp Arg Phe Gly Ser Lys Glu Val Val Val Arg
        275                 280                 285
```

```
Lys Ala Ala Glu Asn Glu Met Ile Val Thr Leu Asp Asp Gln Glu Arg
    290                 295                 300
Lys Leu Ser Ala Asp His Leu Val Ile Thr Asn Gly Thr Lys Ala Gln
305                 310                 315                 320
Ala Val Ala Gly Val Met Gly Gly Ala Glu Ser Glu Val Gln Glu Asp
                325                 330                 335
Thr Lys Thr Ile Leu Leu Glu Ala Ala Tyr Phe Asn Gly Gln Lys Val
                340                 345                 350
Arg Lys Ala Ser Lys Asp Leu Gly Leu Arg Ser Glu Ser Ser Val Arg
            355                 360                 365
Phe Glu Lys Gly Ile Asp Pro Ala Arg Val Arg Leu Ala Ala Glu Arg
    370                 375                 380
Ala Ala Gln Leu Ile His Leu Tyr Ala Gly Gly Glu Val Leu Ala Gly
385                 390                 395                 400
Thr Val Glu Glu Asp His Leu Thr Ile Glu Ala Asn Asn Ile His Val
                405                 410                 415
Ser Ala Asp Lys Val Ser Ser Val Leu Gly Leu Thr Ile Ser Lys Glu
            420                 425                 430
Glu Leu Ile Ser Ile Tyr Lys Arg Leu Gly Phe Thr Val Gly Glu Ala
    435                 440                 445
Asp Asp Leu Leu Val Val Thr Val Pro Ser Arg Arg Gly Asp Ile Thr
450                 455                 460
Ile Glu Glu Asp Leu Ile Glu Ala Ala Arg Leu Tyr Gly Tyr Asp
465                 470                 475                 480
Asn Ile Pro Ser Thr Leu Pro Glu Thr Ala Gly Thr Thr Gly Gly Leu
                485                 490                 495
Thr Pro Tyr Gln Ala Lys Arg Arg Lys Val Arg Arg Phe Leu Glu Gly
                500                 505                 510
Ala Gly Leu Ser Gln Ala Ile Thr Tyr Ser Leu Thr Asn Glu Lys Lys
            515                 520                 525
Ala Thr Ala Phe Ala Ile Glu Lys Ser Leu Asn Thr Val Leu Ala Leu
    530                 535                 540
Pro Met Ser Glu Glu Arg Ser Ile Leu Arg His Ser Leu Val Pro Asn
545                 550                 555                 560
Leu Leu Asp Ser Val Ser Tyr Asn Leu Ala Arg Gln Thr Asp Ser Val
                565                 570                 575
Ala Leu Tyr Glu Val Gly Ser Val Phe Leu Thr Lys Glu Glu Asp Thr
            580                 585                 590
Lys Pro Val Glu Thr Glu Arg Val Ala Gly Ala Val Thr Gly Leu Trp
    595                 600                 605
Arg Lys Gln Leu Trp Gln Gly Glu Lys Pro Val Asp Phe Val
    610                 615                 620
Val Lys Gly Ile Val Glu Gly Leu Leu Asp Lys Leu Asn Val Leu Asp
625                 630                 635                 640
Ser Ile Glu Phe Val Gln Ser Glu Arg Lys Gln Leu His Pro Gly Arg
                645                 650                 655
Thr Ala Asn Ile Leu Leu Asn Gly Ser Leu Ile Gly Phe Ile Gly Gln
            660                 665                 670
Val His Pro Ser Leu Glu Lys Glu Leu Asp Ile Lys Glu Thr Tyr Val
    675                 680                 685
Phe Glu Leu Asp Leu His Ala Leu Leu Ala Ala Glu Thr Ala Pro Leu
    690                 695                 700
Val Tyr Thr Ala Ile Pro Lys Tyr Pro Ser Val Thr Arg Asp Ile Ala
```

```
                        705                 710                 715                 720
Leu Val Thr Asp Lys Thr Val Thr Ser Gly Gln Leu Glu Ser Val Ile
                    725                 730                 735

Lys Glu Ala Gly Gly Lys Leu Leu Lys Glu Val Thr Val Phe Asp Val
                740                 745                 750

Tyr Glu Gly Glu His Met Glu Glu Gly Lys Lys Ser Val Ala Phe Ser
            755                 760                 765

Leu Gln Tyr Val Asn Pro Glu Gln Thr Leu Thr Glu Glu Val Thr
        770                 775                 780

Lys Ala His Ser Lys Val Leu Lys Ala Leu Glu Asp Thr Tyr Gln Ala
785                 790                 795                 800

Val Leu Arg Gly

<210> SEQ ID NO 87
<211> LENGTH: 595
<212> TYPE: PRT
<213> ORGANISM: Saccharomyces cerevisiae

<400> SEQUENCE: 87

Met Pro Thr Val Ser Val Asn Lys Gln Gln Leu Phe Asp Leu Leu Gly
  1               5                  10                  15

Lys Asn Tyr Thr Ser Gln Glu Phe Asp Glu Leu Cys Phe Glu Phe Gly
                 20                  25                  30

Met Glu Met Asp Glu Asp Thr Thr Glu Glu Ala Leu Lys Thr Gly Glu
            35                  40                  45

Glu Pro Glu Leu Lys Leu Asp Ile Ser Ala Asn Arg Tyr Asp Leu Leu
     50                  55                  60

Cys Ile Glu Gly Ile Ser Gln Ser Leu Asn Glu Tyr Leu Glu Arg Lys
 65                  70                  75                  80

Glu Arg Pro Asp Tyr Lys Leu Ser Lys Pro Thr Thr Lys Leu Ile Ile
                 85                  90                  95

Asp Lys Ser Thr Glu Gln Ile Arg Pro Phe Ala Thr Ala Ala Val Leu
            100                 105                 110

Arg Asn Ile Lys Leu Asn Glu Lys Ser Tyr Ala Ser Phe Ile Ala Leu
        115                 120                 125

Gln Asp Lys Leu His Ala Asn Leu Cys Arg Asn Arg Ser Leu Val Ala
    130                 135                 140

Met Gly Thr His Asp Leu Asp Ser Ile Glu Gly Pro Phe His Tyr Arg
145                 150                 155                 160

Ala Leu Pro Pro Lys Asp Ile Lys Phe Val Pro Leu Asn Gln Thr Gln
                165                 170                 175

Glu Phe Thr Gly Asp Lys Leu Ile Glu Phe Tyr Lys Ser Pro Glu Gln
            180                 185                 190

Lys Asn Asn Ile Gly Arg Tyr Val His Ile Ile Glu Asp Ser Pro Val
        195                 200                 205

Phe Pro Val Ile Met Asp Ser Lys Asp Arg Val Cys Ser Leu Pro Pro
    210                 215                 220

Leu Ile Asn Ser Glu His Ser Lys Ile Ser Val Asn Thr Arg Asn Ile
225                 230                 235                 240

Leu Ile Asp Ile Thr Ala Thr Asp Lys Thr Lys Ala Glu Ile Val Leu
                245                 250                 255

Asn Ile Leu Thr Thr Met Phe Ser Arg Tyr Cys Asp Glu Pro Phe Thr
            260                 265                 270

Val Glu Pro Val Glu Ile Val Ser Glu His Asn Gly Gln Ser Arg Leu
        275                 280                 285
```

```
Ala Pro Asn Phe Asn Asp Arg Ile Met Asp Val Ser Ile Lys Tyr Ile
    290                 295                 300

Asn Ser Cys Leu Gly Leu Asp Gln Ser Ala Asp Glu Ile Ala His Cys
305                 310                 315                 320

Leu Lys Lys Met Ser Leu His Ala Val Gln Ser Lys Glu Asp Lys Asp
                325                 330                 335

Ile Leu His Val Asp Ile Pro Val Thr Arg Pro Asp Ile Leu His Ala
            340                 345                 350

Cys Asp Ile Met Glu Asp Ala Ala Val Gly Tyr Gly Phe Asn Asn Leu
        355                 360                 365

Pro Lys Gly Glu Lys Leu Ser Asn Ala Asn Phe Ile Ala Lys Pro Leu
    370                 375                 380

Pro Ile Asn Lys Val Ser Asp Ile Phe Arg Val Ala Ser Ser Gln Ala
385                 390                 395                 400

Thr Trp Val Glu Val Leu Pro Leu Thr Leu Cys Ser His Asp Glu Asn
                405                 410                 415

Phe Lys Phe Leu Arg Gln Ser Asp Asn Gly Asp Leu Ala Val Lys Leu
            420                 425                 430

Ala Asn Pro Lys Thr Leu Glu Tyr Gln Val Val Arg Thr Thr Leu Leu
        435                 440                 445

Pro Gly Ile Leu Lys Thr Val Lys Glu Asn Arg Lys His Ser Leu Pro
    450                 455                 460

Ile Lys Val Phe Glu Thr Gly Asp Val Val Phe Lys Asp Asp Lys Leu
465                 470                 475                 480

Glu Arg Lys Ala Tyr Asn Glu Arg His Trp Ala Ala Ile Tyr Val Gly
                485                 490                 495

Lys Asn Ser Gly Phe Glu Ile Ile Gln Gly Leu Leu Gly Lys Ile Met
            500                 505                 510

Gln Thr Phe Arg Thr Glu Trp Ile Ala Asp Tyr Gly Ala Ala Ala Ser
        515                 520                 525

Gly Arg Gly Tyr Trp Ile Glu Glu Asp Asp Ser Val Lys Thr Tyr Phe
    530                 535                 540

Pro Gly Arg Gly Ala Lys Val Met Phe Arg Ser Lys Glu Gly Ala Glu
545                 550                 555                 560

Pro Lys Gln Ile Gly His Leu Gly Val Leu His Pro Glu Val Met Met
                565                 570                 575

Asn Phe Asp Val Pro Phe Ala Ala Ser Phe Val Glu Val Asn Ala Glu
            580                 585                 590

Val Phe Leu
        595

<210> SEQ ID NO 88
<211> LENGTH: 792
<212> TYPE: PRT
<213> ORGANISM: Chlamydophila pneumoniae

<400> SEQUENCE: 88

Met Arg Ile Pro Ile Thr Leu Leu Gln Thr Tyr Phe Ser Glu Pro Leu
  1               5                  10                  15

Ser Thr Lys Glu Ile Leu Glu Ala Cys Asp His Ile Gly Ile Glu Ala
                20                  25                  30

Glu Ile Glu Asn Thr Thr Leu Tyr Ser Phe Ala Ser Val Ile Thr Ala
            35                  40                  45

Lys Ile Leu His Thr Ile Pro His Pro Asn Ala Asp Lys Leu Arg Val
        50                  55                  60
```

```
Ala Thr Leu Thr Asp Gly Glu Lys Glu His Gln Val Val Cys Gly Ala
 65                  70                  75                  80

Pro Asn Cys Glu Ala Gly Leu Ile Val Ala Leu Ala Leu Pro Gly Ala
             85                  90                  95

Lys Leu Phe Asp Ser Glu Gly Gln Ala Tyr Thr Ile Lys Lys Ser Lys
            100                 105                 110

Leu Arg Gly Val Glu Ser Gln Gly Met Cys Cys Gly Ala Asp Glu Leu
        115                 120                 125

Gly Leu Asp Glu Leu Gln Ile Gln Glu Arg Ala Leu Leu Glu Leu Pro
        130                 135                 140

Glu Ala Thr Pro Leu Gly Glu Asp Leu Ala Thr Val Leu Gly Asn Thr
145                 150                 155                 160

Ser Leu Glu Ile Ser Leu Thr Pro Asn Leu Gly His Cys Ala Ser Phe
                165                 170                 175

Leu Gly Leu Ala Arg Glu Ile Cys His Val Thr Gln Ala Asn Leu Val
            180                 185                 190

Ile Pro Lys Glu Phe Ser Phe Glu Asn Leu Pro Thr Ala Leu Asp
        195                 200                 205

Met Gly Asn Asp Pro Asp Ile Cys Pro Phe Phe Ser Tyr Val Val Ile
    210                 215                 220

Thr Gly Ile Ser Ala Gln Pro Ser Pro Ile Lys Leu Gln Glu Ser Leu
225                 230                 235                 240

Gln Ala Leu Lys Gln Lys Pro Ile Asn Ala Ile Val Asp Ile Thr Asn
                245                 250                 255

Tyr Ile Met Leu Ser Leu Gly Gln Pro Leu His Ala Tyr Asp Ala Ser
            260                 265                 270

His Val Ala Leu Asp Ser Leu Arg Val Glu Lys Leu Ser Thr Pro Glu
        275                 280                 285

Ser Leu Thr Leu Leu Asn Gly Glu Thr Val Leu Leu Pro Ser Gly Val
        290                 295                 300

Pro Val Val Arg Asp Asp His Ser Leu Leu Gly Leu Gly Gly Val Met
305                 310                 315                 320

Gly Ala Lys Ala Pro Ser Phe Gln Glu Thr Thr Thr Thr Val Ile
                325                 330                 335

Lys Ala Ala Tyr Phe Leu Pro Glu Ala Leu Arg Ala Ser Gln Lys Leu
            340                 345                 350

Leu Pro Ile Pro Ser Glu Ser Ala Tyr Arg Phe Thr Arg Gly Ile Asp
        355                 360                 365

Pro Gln Asn Val Val Pro Ala Leu Gln Ala Ala Ile His Tyr Ile Leu
        370                 375                 380

Glu Ile Phe Pro Glu Ala Thr Ile Ser Pro Ile Tyr Ser Ser Gly Glu
385                 390                 395                 400

Ile Cys Arg Glu Leu Lys Glu Val Ala Leu Arg Pro Lys Thr Leu Gln
            405                 410                 415

Arg Ile Leu Gly Lys Ser Phe Ser Ile Glu Ile Leu Ser Gln Lys Leu
        420                 425                 430

Gln Ser Leu Gly Phe Ser Thr Thr Pro Gln Glu Thr Ser Leu Leu Val
        435                 440                 445

Lys Val Pro Ser Tyr Arg His Asp Ile Asn Glu Ile Asp Leu Val
        450                 455                 460

Glu Glu Ile Cys Arg Thr Glu Ser Trp Asn Ile Glu Thr Gln Asn Pro
465                 470                 475                 480

Val Ser Cys Tyr Thr Pro Ile Tyr Lys Leu Lys Arg Glu Thr Ala Gly
```

```
                    485                 490                 495
Phe Leu Ala Asn Ala Gly Leu Gln Glu Phe Phe Thr Pro Asp Leu Leu
                500                 505                 510

Asp Pro Glu Thr Val Ala Leu Thr Arg Lys Glu Lys Glu Glu Ile Ser
            515                 520                 525

Leu Gln Gly Ser Lys His Thr Thr Val Leu Arg Ser Ser Leu Leu Pro
        530                 535                 540

Gly Leu Leu Lys Ser Ala Ala Thr Asn Leu Asn Arg Gln Ala Pro Ser
545                 550                 555                 560

Val Gln Ala Phe Glu Ile Gly Thr Val Tyr Ala Lys His Gly Glu Gln
                565                 570                 575

Cys Gln Glu Thr Gln Thr Leu Ala Ile Leu Leu Thr Glu Asp Gly Glu
            580                 585                 590

Ser Arg Ser Trp Leu Pro Lys Pro Ser Leu Ser Phe Tyr Ser Leu Lys
        595                 600                 605

Gly Trp Val Glu Arg Leu Leu Tyr His His Leu Ser Ile Asp Ala
610                 615                 620

Leu Thr Leu Glu Ser Ser Ala Leu Cys Glu Phe His Pro Tyr Gln Gln
625                 630                 635                 640

Gly Val Leu Arg Ile His Lys Gln Ser Phe Ala Thr Leu Gly Gln Val
                645                 650                 655

His Pro Glu Leu Ala Lys Lys Ala Gln Ile Lys His Pro Val Phe Phe
            660                 665                 670

Ala Glu Leu Asn Leu Asp Leu Leu Cys Lys Met Leu Lys Lys Thr Thr
        675                 680                 685

Lys Leu Tyr Lys Pro Tyr Ala Ile Tyr Pro Ser Ser Phe Arg Asp Leu
690                 695                 700

Thr Leu Thr Val Pro Glu Asp Ile Pro Ala Asn Leu Leu Arg Gln Lys
705                 710                 715                 720

Leu Leu His Glu Gly Ser Lys Trp Leu Glu Ser Val Thr Ile Ile Ser
                725                 730                 735

Ile Tyr Gln Asp Lys Ser Leu Glu Thr Arg Asn Lys Asn Val Ser Leu
            740                 745                 750

Arg Leu Val Phe Gln Asp Tyr Glu Arg Thr Leu Ser Asn Gln Asp Ile
        755                 760                 765

Glu Glu Glu Tyr Cys Arg Leu Val Ala Leu Leu Asn Glu Leu Leu Thr
770                 775                 780

Asp Thr Lys Gly Thr Ile Asn Ser
785                 790

<210> SEQ ID NO 89
<211> LENGTH: 831
<212> TYPE: PRT
<213> ORGANISM: Mycobacterium tuberculosis

<400> SEQUENCE: 89

Met Arg Leu Pro Tyr Ser Trp Leu Arg Glu Val Val Ala Val Gly Ala
1               5                   10                  15

Ser Gly Trp Asp Val Thr Pro Gly Glu Leu Glu Gln Thr Leu Leu Arg
            20                  25                  30

Ile Gly His Glu Val Glu Val Ile Pro Leu Gly Pro Val Asp Gly
        35                  40                  45

Pro Val Thr Val Gly Arg Val Ala Asp Ile Glu Glu Leu Thr Gly Tyr
    50                  55                  60

Lys Lys Pro Ile Arg Ala Cys Ala Val Asp Ile Gly Asp Arg Gln Tyr
```

```
               65                  70                  75                  80
Arg Glu Ile Ile Cys Gly Ala Thr Asn Phe Ala Val Gly Asp Leu Val
                    85                  90                  95

Val Val Ala Leu Pro Gly Ala Thr Leu Pro Gly Gly Phe Thr Ile Ser
                100                 105                 110

Ala Arg Lys Ala Tyr Gly Arg Asn Ser Asp Gly Met Ile Cys Ser Ala
                115                 120                 125

Ala Glu Leu Asn Leu Gly Ala Asp His Ser Gly Ile Leu Val Leu Pro
                130                 135                 140

Pro Gly Ala Ala Glu Pro Gly Ala Asp Gly Ala Gly Val Leu Gly Leu
145                 150                 155                 160

Asp Asp Val Val Phe His Leu Ala Ile Thr Pro Asp Arg Gly Tyr Cys
                165                 170                 175

Met Ser Val Arg Gly Leu Ala Arg Glu Leu Ala Cys Ala Tyr Asp Leu
                180                 185                 190

Asp Phe Val Asp Pro Ala Ser Asn Ser Arg Val Pro Pro Leu Pro Ile
                195                 200                 205

Glu Gly Pro Ala Trp Pro Leu Thr Val Gln Pro Glu Thr Gly Val Arg
                210                 215                 220

Arg Phe Ala Leu Arg Pro Val Ile Gly Ile Asp Pro Ala Ala Val Ser
225                 230                 235                 240

Pro Trp Trp Leu Gln Arg Arg Leu Leu Leu Cys Gly Ile Arg Ala Thr
                245                 250                 255

Cys Pro Ala Val Asp Val Thr Asn Tyr Val Met Leu Glu Leu Gly His
                260                 265                 270

Pro Met His Ala His Asp Arg Asn Arg Ile Ser Gly Thr Leu Gly Val
                275                 280                 285

Arg Phe Ala Arg Ser Gly Glu Thr Ala Val Thr Leu Asp Gly Ile Glu
                290                 295                 300

Arg Lys Leu Asp Thr Ala Asp Val Leu Ile Val Asp Asp Ala Ala Thr
305                 310                 315                 320

Ala Ala Ile Gly Gly Val Met Gly Ala Ala Ser Thr Glu Val Arg Ala
                325                 330                 335

Asp Ser Thr Asp Val Leu Leu Glu Ala Ala Ile Trp Asp Pro Ala Ala
                340                 345                 350

Val Ser Arg Thr Gln Arg Arg Leu His Leu Pro Ser Glu Ala Ala Arg
                355                 360                 365

Arg Tyr Glu Arg Thr Val Asp Pro Ala Ile Ser Val Ala Ala Leu Asp
                370                 375                 380

Arg Cys Ala Arg Leu Leu Ala Asp Ile Ala Gly Gly Glu Val Ser Pro
385                 390                 395                 400

Thr Leu Thr Asp Trp Arg Gly Asp Pro Pro Cys Asp Asp Trp Ser Pro
                405                 410                 415

Pro Pro Ile Arg Met Gly Val Asp Val Pro Asp Arg Ile Ala Gly Val
                420                 425                 430

Ala Tyr Pro Gln Gly Thr Thr Ala Arg Arg Leu Ala Gln Ile Gly Ala
                435                 440                 445

Val Val Thr His Asp Gly Asp Thr Leu Thr Val Thr Pro Pro Ser Trp
                450                 455                 460

Arg Pro Asp Leu Arg Gln Pro Ala Asp Leu Val Glu Val Leu Arg
465                 470                 475                 480

Leu Glu Gly Leu Glu Val Ile Pro Ser Val Leu Pro Pro Ala Pro Ala
                485                 490                 495
```

```
Gly Arg Gly Leu Thr Ala Gly Gln Gln Arg Arg Thr Ile Gly Arg
            500                 505                 510

Ser Leu Ala Leu Ser Gly Tyr Val Glu Ile Leu Pro Thr Pro Phe Leu
        515                 520                 525

Pro Ala Gly Val Phe Asp Leu Trp Gly Leu Glu Ala Asp Asp Ser Arg
530                 535                 540

Arg Met Thr Thr Arg Val Leu Asn Pro Leu Glu Ala Asp Arg Pro Gln
545                 550                 555                 560

Leu Ala Thr Thr Leu Leu Pro Ala Leu Leu Glu Ala Leu Val Arg Asn
                565                 570                 575

Val Ser Arg Gly Leu Val Asp Val Ala Leu Phe Ala Ile Ala Gln Val
            580                 585                 590

Val Gln Pro Thr Glu Gln Thr Arg Gly Val Gly Leu Ile Pro Val Asp
        595                 600                 605

Arg Arg Pro Thr Asp Asp Glu Ile Ala Met Leu Asp Ala Ser Leu Pro
610                 615                 620

Arg Gln Pro Gln His Val Ala Ala Val Leu Ala Gly Leu Arg Glu Pro
625                 630                 635                 640

Arg Gly Pro Trp Gly Pro Gly Arg Pro Val Glu Ala Ala Asp Ala Phe
                645                 650                 655

Glu Ala Val Arg Ile Ile Ala Arg Ala Ser Arg Val Asp Val Thr Leu
            660                 665                 670

Arg Pro Ala Gln Tyr Leu Pro Trp His Pro Gly Arg Cys Ala Gln Val
        675                 680                 685

Phe Val Gly Glu Ser Ser Val Gly His Ala Gly Gln Leu His Pro Ala
690                 695                 700

Val Ile Glu Arg Ser Gly Leu Pro Lys Gly Thr Cys Ala Val Glu Leu
705                 710                 715                 720

Asn Leu Asp Ala Ile Pro Cys Ser Ala Pro Leu Pro Ala Pro Arg Val
                725                 730                 735

Ser Pro Tyr Pro Ala Val Phe Gln Asp Val Ser Leu Val Ala Ala
            740                 745                 750

Asp Ile Pro Ala Gln Ala Val Ala Asp Val Arg Ala Gly Ala Gly
        755                 760                 765

Asp Leu Leu Glu Asp Ile Ala Leu Phe Asp Val Phe Thr Gly Pro Gln
770                 775                 780

Ile Gly Glu His Arg Lys Ser Leu Thr Phe Ala Leu Arg Phe Arg Ala
785                 790                 795                 800

Pro Asp Arg Thr Leu Thr Glu Asp Ala Ser Ala Ala Arg Asp Ala
                805                 810                 815

Ala Val Gln Ser Ala Ala Glu Arg Val Gly Ala Val Leu Arg Gly
            820                 825                 830

<210> SEQ ID NO 90
<211> LENGTH: 764
<212> TYPE: PRT
<213> ORGANISM: Helicobacter pylori

<400> SEQUENCE: 90

Met Lys Leu Ser Ile Asn Asp Leu Asn Val Phe Val Asn Thr Pro Lys
1               5                   10                  15

Asp Ile Ala Lys Leu Cys Glu Asp Leu Ser Arg Leu Gly Leu Glu Val
                20                  25                  30

Glu Ser Cys Ile Pro Cys Ile Ala Pro Lys Asn Val Val Val Gly Lys
            35                  40                  45
```

```
Ile Leu Glu Lys Ala Pro His Lys Asn Ala Glu Lys Leu Ser Val Cys
 50                  55                  60

Gln Val Asp Val Gly Lys Glu Val Leu Gln Ile Val Cys Gly Ala Lys
 65                  70                  75                  80

Asn Val Ala Pro Asn Gln Phe Val Pro Val Ala Leu Asn Gly Ala Leu
                 85                  90                  95

Ile Gly Ser Thr Thr Ile Ala Lys Thr Glu Leu Arg Gly Val Glu Ser
            100                 105                 110

His Gly Met Ile Cys Ser Ser Ile Glu Leu Gly Phe Pro Lys Ile Asn
        115                 120                 125

Asp Gly Ile Leu Glu Leu Asp Glu Ser Val Gly Glu Leu Val Leu Gly
    130                 135                 140

Lys Glu Leu Asn Glu Tyr Ala Pro Phe Asn Thr His Val Leu Glu Ile
145                 150                 155                 160

Ser Leu Thr Pro Asn Arg Gly Asp Cys Leu Ser Val Leu Gly Ile Ala
                165                 170                 175

Arg Glu Ile Ser Ala Phe Tyr His Thr Pro Leu Lys Pro Ile Lys Ala
            180                 185                 190

Leu Asn Phe Thr Pro Lys Ser Gly Leu Ile Thr Leu Ser Ala Gly Glu
        195                 200                 205

Asn Ile Glu Ser His Leu Ala Tyr Tyr Leu Ile Cys Asn His Ser Leu
    210                 215                 220

Lys Thr Pro Leu Asn Ile Lys Leu Ser Leu Ala His Asn Asn Ala Leu
225                 230                 235                 240

Ser Glu Asn Asp Leu Asn Asn Phe Ile Glu Phe Ser Thr His Phe Ser
                245                 250                 255

Gly Val Ile Met Asn Ala Tyr Ser Leu Asn Thr Thr Pro Met Asp Leu
            260                 265                 270

Ser Val Lys Asn Asp Glu Asn Leu Glu Ser Val Tyr Ile Asn His
        275                 280                 285

Gln Lys Arg Ser Thr Ile Ala Ile Lys His Gln Val Gln Lys Asp Leu
    290                 295                 300

Ser Glu Cys Leu Leu Glu Ala Ser Tyr Thr Asp Pro Ile Ser Leu
305                 310                 315                 320

Ser Leu Lys Leu His Ala Leu Lys Asp Lys Thr Leu Gln Lys Asp Asn
                325                 330                 335

Ala Leu Ile Tyr Arg Ser Ala Arg Gly Ser Asn Pro Asn Leu Ser Asp
            340                 345                 350

Gly Leu Asn Phe Leu Ser Ala His Leu Lys Ala Thr Ile Leu Glu Ser
        355                 360                 365

Lys Gln Thr Glu His Ser Leu Lys Asp Arg Thr Leu Thr Phe Gln Leu
    370                 375                 380

Glu Asp Ile Thr Glu Ile Leu Gly Leu Ala Val Glu Lys Glu Lys Ile
385                 390                 395                 400

Gln Gly Ile Leu Lys Asn Leu Gly Phe Lys Val Ser Val Lys Glu Pro
                405                 410                 415

Asn Ser Lys Pro Gln Ile Leu Glu Val Ile Ala Pro Asn Phe Arg His
            420                 425                 430

Asp Ile Lys Thr Ile Gln Asp Ile Ala Glu Glu Ile Leu Arg Phe Val
        435                 440                 445

Gly Ile Asp Asn Leu Val Ser Lys Pro Leu His Cys Val Ser Ser Lys
    450                 455                 460

Asn Ser Asn Pro Asn Tyr Asp Thr His Arg Phe Phe Glu Asn Leu Lys
465                 470                 475                 480
```

```
His Lys Ala Leu Ala Cys Gly Phe Lys Glu Ile His Tyr Val Phe
                485                 490                 495

Tyr Ser Lys Glu Lys Gln Gln Lys Leu Gly Phe Glu Val Leu Glu Asp
            500                 505                 510

Pro Leu Glu Leu Gln Asn Pro Ile Thr Thr Glu Leu Asn Thr Leu Arg
        515                 520                 525

Thr Ser Leu Val Cys Gly Leu Leu Asp Ala Ser Leu Arg Asn Lys Asn
    530                 535                 540

Leu Gly Phe Lys Ser Ile Ala Leu Tyr Glu Lys Gly Ser Val Tyr Asn
545                 550                 555                 560

Ser Lys Arg Glu Glu Ile Gln Lys Leu Gly Phe Leu Ile Ser Gly Leu
                565                 570                 575

Gln Lys Lys Glu Ser Tyr Pro Asp Thr Lys Gly Lys Ala Trp Asp Phe
            580                 585                 590

Tyr Ser Phe Ala Glu Cys Val Ser Lys Val Ile Gly Asp Phe Ser Leu
        595                 600                 605

Glu Lys Leu Thr Thr Gln Thr Pro Ile Asn His Pro Tyr Gln Ser Ala
    610                 615                 620

Lys Ile Ile Gln Asn His Glu Ile Ile Gly Val Ile Ala Lys Ile His
625                 630                 635                 640

Pro Lys Val Ile Gln Glu Leu Asp Leu Phe Glu Ser Tyr Tyr Ala Glu
                645                 650                 655

Ile Asp Ala Phe Lys Leu Lys Arg Pro Ala Met Leu Leu Lys Pro Phe
            660                 665                 670

Ser Ile Tyr Pro Ser Ser Val Arg Asp Leu Thr Leu Ile Ile Asp Glu
        675                 680                 685

Asn Thr Ala Phe Ser Gly Ile Lys Lys Ala Leu Lys Asp Ala Gln Ile
    690                 695                 700

Pro Asn Leu Ser Glu Ile Leu Pro Leu Asp Ile Phe Lys Glu Ser Asn
705                 710                 715                 720

Asn Ser Ile Ala Leu Ser Val Arg Cys Val Ile His Ser Leu Glu Lys
                725                 730                 735

Thr Leu Asn Asp Glu Glu Val Asn Ser Ala Val Gln Lys Ala Leu Glu
            740                 745                 750

Ile Leu Glu Lys Glu Phe Asn Ala Arg Leu Lys Gly
        755                 760

<210> SEQ ID NO 91
<211> LENGTH: 792
<212> TYPE: PRT
<213> ORGANISM: Pseudomonas aeruginosa

<400> SEQUENCE: 91

Met Lys Phe Ser Glu Lys Trp Leu Arg Ser Trp Ala Asn Pro Gln Val
1               5                   10                  15

Ser His Asp Glu Leu Val Ala Arg Leu Ser Met Val Gly Leu Glu Val
            20                  25                  30

Asp Ala Asp Leu Pro Val Ala Gly Ala Phe Ser Gly Val Val Val Gly
        35                  40                  45

Glu Val Leu Ser Thr Glu Gln His Pro Asp Ala Asp Lys Leu Arg Val
    50                  55                  60

Cys Gln Val Ser Asn Gly Ser Glu Thr Phe Gln Val Val Cys Gly Ala
65                  70                  75                  80

Pro Asn Val Arg Ala Gly Leu Lys Ile Pro Phe Ala Met Ile Gly Ala
                85                  90                  95
```

Glu Leu Pro Asp Asp Phe Lys Ile Lys Lys Ala Lys Leu Arg Gly Val
            100                 105                 110

Glu Ser Phe Gly Met Leu Cys Ser Ala Lys Glu Leu Gln Ile Ser Glu
            115                 120                 125

Glu Asn Ala Gly Leu Leu Leu Pro Ala Asp Ala Pro Val Gly Gln
130                 135                 140

Asp Val Arg Thr Tyr Leu Glu Leu Ala Asp Tyr Thr Ile Glu Val Gly
145                 150                 155                 160

Leu Thr Pro Asn Arg Gly Asp Cys Leu Ser Leu Ala Gly Leu Ala Arg
                165                 170                 175

Glu Val Ser Ala Ile Tyr Asp Val Pro Leu Ala Pro Val Ala Val Asp
                180                 185                 190

Ala Val Ala Ala Gln His Asp Glu Thr Arg Pro Val Glu Leu Ala Ala
            195                 200                 205

Pro Ala Ala Cys Pro Arg Tyr Leu Gly Arg Val Ile Arg Asn Val Asp
210                 215                 220

Leu Ser Arg Pro Thr Pro Leu Trp Met Val Glu Arg Leu Arg Arg Ser
225                 230                 235                 240

Asp Ile Arg Ser Ile Asp Pro Val Val Asp Val Thr Asn Tyr Val Met
                245                 250                 255

Ile Glu Leu Gly Gln Pro Met His Ala Phe Asp Leu Ala Glu Ile Asn
            260                 265                 270

Gly Gly Val Arg Val Arg Met Ala Glu Asp Gly Glu Lys Leu Val Leu
            275                 280                 285

Leu Asp Gly Gln Glu Ile Thr Leu Arg Ala Asp Thr Leu Val Ile Ala
290                 295                 300

Asp His Gln Arg Ala Leu Ala Ile Ala Gly Val Met Gly Gly Glu His
305                 310                 315                 320

Ser Gly Val Ser Asp Ser Thr Arg Asp Leu Phe Leu Glu Ala Ala Phe
                325                 330                 335

Phe Asp Thr Ile Ala Leu Ala Gly Lys Ala Arg Ser Tyr Gly Leu His
            340                 345                 350

Thr Asp Ser Ser His Arg Phe Glu Arg Gly Val Asp Ser Gln Leu Ala
            355                 360                 365

Arg Lys Ala Met Glu Arg Ala Thr Arg Leu Ile Leu Asp Ile Val Gly
370                 375                 380

Gly Glu Pro Gly Pro Ile Val Glu Gln Val Ser Glu Ala His Leu Pro
385                 390                 395                 400

Lys Val Ala Pro Ile Thr Leu Arg Ala Glu Arg Val Thr Gln Met Leu
                405                 410                 415

Gly Met Pro Leu Asp Ala Ala Glu Ile Val Arg Leu Leu Gln Ala Leu
            420                 425                 430

Glu Leu Thr Val Val Ala Asp Gly Glu Gly Gln Trp Ser Val Gly Val
            435                 440                 445

Pro Ser His Arg Phe Asp Ile Ser Leu Glu Val Asp Leu Ile Glu Glu
450                 455                 460

Leu Ala Arg Leu Tyr Gly Tyr Asn Arg Leu Pro Val Arg Tyr Pro Gln
465                 470                 475                 480

Ala Arg Leu Ala Pro Asn Asn Lys Pro Glu Ala Arg Ala Ala Leu Pro
                485                 490                 495

Leu Leu Arg Arg Leu Leu Val Ala Arg Gly Tyr Gln Glu Ala Ile Thr
            500                 505                 510

Phe Ser Phe Ile Asp Pro Ala Leu Phe Glu Leu Phe Asp Pro Gly Thr

```
              515                 520                 525
Gln Pro Leu Thr Leu Ala Asn Pro Ile Ser Ala Asp Met Ala Ala Met
            530                 535                 540
Arg Ser Ser Leu Trp Pro Gly Leu Val Lys Ala Leu Gln His Asn Leu
545                 550                 555                 560
Asn Arg Gln Gln Ser Arg Val Arg Leu Phe Glu Ser Gly Leu Arg Phe
                565                 570                 575
Val Gly Gln Leu Glu Gly Leu Lys Gln Glu Ala Met Leu Ala Gly Ala
            580                 585                 590
Ile Cys Gly Lys Arg Leu Pro Glu Gly Trp Ala Asn Gly Arg Asp Gly
            595                 600                 605
Val Asp Phe Phe Asp Ala Lys Ala Asp Val Glu Ala Val Leu Ala Ser
            610                 615                 620
Ala Gly Ala Leu Gly Asp Phe Ser Phe Val Pro Gly Glu His Pro Ala
625                 630                 635                 640
Leu His Pro Gly Gln Thr Ala Arg Ile Glu Arg Glu Gly Arg Leu Val
                645                 650                 655
Gly Tyr Leu Gly Ala Leu His Pro Glu Leu Ala Lys Lys Leu Asp Leu
            660                 665                 670
Glu Gln Pro Val Phe Leu Phe Glu Leu Leu Ala Glu Val Val Asp
            675                 680                 685
Gly His Leu Pro Lys Phe Arg Glu Leu Ser Arg Phe Pro Glu Val Arg
            690                 695                 700
Arg Asp Leu Ala Leu Leu Val Asp Gln Asp Val Pro Ala Gln Asp Ile
705                 710                 715                 720
Leu Thr Gln Ile Arg Ala Ala Ala Gly Glu Trp Leu Thr Asp Leu Arg
                725                 730                 735
Leu Phe Asp Val Tyr His Gly Lys Gly Ile Asp Pro His Arg Lys Ser
                740                 745                 750
Leu Ala Val Gly Leu Thr Trp Gln His Pro Ser Arg Thr Leu Asn Asp
            755                 760                 765
Asp Glu Val Asn Ser Thr Thr Gln Asn Ile Val Thr Ser Leu Glu Glu
            770                 775                 780
Arg Phe Asn Ala Thr Leu Arg Lys
785                 790

<210> SEQ ID NO 92
<211> LENGTH: 551
<212> TYPE: PRT
<213> ORGANISM: Escherichia coli

<400> SEQUENCE: 92

Met Thr Gln Val Ala Lys Lys Ile Leu Val Thr Cys Ala Leu Pro Tyr
1               5                   10                  15
Ala Asn Gly Ser Ile His Leu Gly His Met Leu Glu His Ile Gln Ala
            20                  25                  30
Asp Val Trp Val Arg Tyr Gln Arg Met Arg Gly His Glu Val Asn Phe
        35                  40                  45
Ile Cys Ala Asp Asp Ala His Gly Thr Pro Ile Met Leu Lys Ala Gln
    50                  55                  60
Gln Leu Gly Ile Thr Pro Glu Gln Met Ile Gly Glu Met Ser Gln Glu
65                  70                  75                  80
His Gln Thr Asp Phe Ala Gly Phe Asn Ile Ser Tyr Asp Asn Tyr His
                85                  90                  95
Ser Thr His Ser Glu Glu Asn Arg Gln Leu Ser Glu Leu Ile Tyr Ser
```

```
                    100                 105                 110
Arg Leu Lys Glu Asn Gly Phe Ile Lys Asn Arg Thr Ile Ser Gln Leu
            115                 120                 125
Tyr Asp Pro Glu Lys Gly Met Phe Leu Pro Asp Arg Phe Val Lys Gly
        130                 135                 140
Thr Cys Pro Lys Cys Lys Ser Pro Asp Gln Tyr Gly Asp Asn Cys Glu
145                 150                 155                 160
Val Cys Gly Ala Thr Tyr Ser Pro Thr Glu Leu Ile Glu Pro Lys Ser
                165                 170                 175
Val Val Ser Gly Ala Thr Pro Val Met Arg Asp Ser Glu His Phe Phe
            180                 185                 190
Phe Asp Leu Pro Ser Phe Ser Glu Met Leu Gln Ala Trp Thr Arg Ser
        195                 200                 205
Gly Ala Leu Gln Glu Gln Val Ala Asn Lys Met Gln Glu Trp Phe Glu
    210                 215                 220
Ser Gly Leu Gln Gln Trp Asp Ile Ser Arg Asp Ala Pro Tyr Phe Gly
225                 230                 235                 240
Phe Glu Ile Pro Asn Ala Pro Gly Lys Tyr Phe Tyr Val Trp Leu Asp
                245                 250                 255
Ala Pro Ile Gly Tyr Met Gly Ser Phe Lys Asn Leu Cys Asp Lys Arg
            260                 265                 270
Gly Asp Ser Val Ser Phe Asp Glu Tyr Trp Lys Lys Asp Ser Thr Ala
        275                 280                 285
Glu Leu Tyr His Phe Ile Gly Lys Asp Ile Val Tyr Phe His Ser Leu
    290                 295                 300
Phe Trp Pro Ala Met Leu Glu Gly Ser Asn Phe Arg Lys Pro Ser Asn
305                 310                 315                 320
Leu Phe Val His Gly Tyr Val Thr Val Asn Gly Ala Lys Met Ser Lys
                325                 330                 335
Ser Arg Gly Thr Phe Ile Lys Ala Ser Thr Trp Leu Asn His Phe Asp
            340                 345                 350
Ala Asp Ser Leu Arg Tyr Tyr Tyr Thr Ala Lys Leu Ser Ser Arg Ile
        355                 360                 365
Asp Asp Ile Asp Leu Asn Leu Glu Asp Phe Val Gln Arg Val Asn Ala
370                 375                 380
Asp Ile Val Asn Lys Val Val Asn Leu Ala Ser Arg Asn Ala Gly Phe
385                 390                 395                 400
Ile Asn Lys Arg Phe Asp Gly Val Leu Ala Ser Glu Leu Ala Asp Pro
                405                 410                 415
Gln Leu Tyr Lys Thr Phe Thr Asp Ala Ala Glu Val Ile Gly Glu Ala
            420                 425                 430
Trp Glu Ser Arg Glu Phe Gly Lys Ala Val Arg Glu Ile Met Ala Leu
        435                 440                 445
Ala Asp Leu Ala Asn Arg Tyr Val Asp Glu Gln Ala Pro Trp Val Val
    450                 455                 460
Ala Lys Gln Glu Gly Arg Asp Ala Asp Leu Gln Ala Ile Cys Ser Met
465                 470                 475                 480
Gly Ile Asn Leu Phe Arg Val Leu Met Thr Tyr Leu Lys Pro Val Leu
                485                 490                 495
Pro Lys Leu Thr Glu Arg Ala Glu Ala Phe Leu Asn Thr Glu Leu Thr
            500                 505                 510
Trp Asp Gly Ile Gln Gln Pro Leu Leu Gly His Lys Val Asn Pro Phe
        515                 520                 525
```

```
Lys Ala Leu Tyr Asn Arg Ile Asp Met Arg Gln Val Glu Ala Leu Val
        530                 535                 540

Glu Ala Ser Lys Glu Glu Val
545                 550

<210> SEQ ID NO 93
<211> LENGTH: 594
<212> TYPE: PRT
<213> ORGANISM: Homo sapiens

<400> SEQUENCE: 93

Thr Met Leu Arg Thr Ser Val Leu Arg Leu Gly Arg Thr Gly Ala
  1               5                  10                  15

Ser Arg Leu Ser Leu Leu Glu Asp Phe Gly Pro Arg Tyr Tyr Ser Ser
                 20                  25                  30

Gly Ser Leu Ser Ala Gly Asp Asp Ala Cys Asp Val Arg Ala Tyr Phe
                 35                  40                  45

Thr Thr Pro Ile Phe Tyr Val Asn Ala Ala Pro His Ile Gly His Leu
         50                  55                  60

Tyr Ser Ala Leu Leu Ala Asp Ala Leu Cys Arg His Arg Arg Leu Arg
 65                  70                  75                  80

Gly Pro Ser Thr Ala Ala Thr Arg Phe Ser Thr Gly Thr Asp Glu His
                 85                  90                  95

Gly Leu Lys Ile Gln Gln Ala Ala Thr Ala Gly Leu Ala Pro Thr
                100                 105                 110

Glu Leu Cys Asp Arg Val Ser Glu Gln Phe Gln Gln Leu Phe Gln Glu
            115                 120                 125

Ala Gly Ile Ser Cys Thr Asp Phe Ile Arg Thr Thr Glu Ala Arg His
130                 135                 140

Arg Val Ala Val Gln His Phe Trp Gly Val Leu Lys Ser Arg Gly Leu
145                 150                 155                 160

Leu Tyr Lys Gly Val Tyr Glu Gly Trp Tyr Cys Ala Ser Asp Glu Cys
                165                 170                 175

Phe Leu Pro Glu Ala Lys Val Thr Gln Gln Pro Gly Pro Ser Gly Asp
            180                 185                 190

Ser Phe Pro Val Ser Leu Glu Ser Gly His Pro Val Ser Trp Thr Lys
        195                 200                 205

Glu Glu Asn Tyr Ile Phe Arg Leu Ser Gln Phe Arg Lys Pro Leu Gln
210                 215                 220

Arg Trp Leu Arg Gly Asn Pro Gln Ala Ile Thr Pro Glu Pro Phe His
225                 230                 235                 240

His Val Val Leu Gln Trp Leu Asp Glu Glu Leu Pro Asp Leu Ser Val
                245                 250                 255

Ser Arg Arg Ser Ser His Leu His Trp Gly Ile Pro Val Pro Gly Asp
            260                 265                 270

Asp Ser Gln Thr Ile Tyr Val Trp Leu Asp Ala Leu Val Asn Tyr Leu
        275                 280                 285

Thr Val Ile Gly Tyr Pro Asn Ala Glu Phe Lys Ser Trp Trp Pro Ala
290                 295                 300

Thr Ser His Ile Ile Gly Lys Asp Ile Leu Lys Phe His Ala Ile Tyr
305                 310                 315                 320

Trp Pro Ala Phe Leu Leu Gly Ala Gly Met Ser Pro Pro Gln Arg Ile
                325                 330                 335

Cys Val His Ser His Trp Thr Val Cys Gly Gln Lys Met Ser Lys Ser
            340                 345                 350
```

-continued

Leu Gly Asn Val Val Asp Pro Arg Thr Cys Leu Asn Arg Tyr Thr Val
            355                 360                 365

Asp Gly Phe Arg Tyr Phe Leu Leu Arg Gln Gly Val Pro Asn Trp Asp
        370                 375                 380

Cys Asp Tyr Tyr Asp Glu Lys Val Val Lys Leu Leu Asn Ser Glu Leu
385                 390                 395                 400

Ala Asp Ala Leu Gly Gly Leu Leu Asn Arg Cys Thr Ala Lys Arg Ile
                405                 410                 415

Asn Pro Ser Glu Thr Tyr Pro Ala Phe Cys Thr Thr Cys Phe Pro Ser
            420                 425                 430

Glu Pro Gly Leu Val Gly Pro Ser Val Arg Ala Gln Ala Glu Asp Tyr
        435                 440                 445

Ala Leu Val Ser Ala Val Ala Thr Leu Pro Lys Gln Val Ala Asp His
    450                 455                 460

Tyr Asp Asn Phe Arg Ile Tyr Lys Ala Leu Glu Ala Val Ser Ser Cys
465                 470                 475                 480

Val Arg Gln Thr Asn Gly Phe Val Gln Arg His Ala Pro Trp Lys Leu
                485                 490                 495

Asn Trp Glu Ser Pro Val Asp Ala Pro Trp Leu Gly Thr Val Leu His
            500                 505                 510

Val Ala Leu Glu Cys Leu Arg Val Phe Gly Thr Leu Leu Gln Pro Val
        515                 520                 525

Thr Pro Ser Leu Ala Asp Lys Leu Leu Ser Arg Leu Gly Val Ser Ala
    530                 535                 540

Ser Glu Arg Ser Leu Gly Glu Leu Tyr Phe Leu Pro Arg Phe Tyr Gly
545                 550                 555                 560

His Pro Cys Pro Phe Glu Gly Arg Arg Leu Gly Pro Glu Thr Gly Leu
                565                 570                 575

Leu Phe Pro Arg Leu Asp Gln Ser Arg Thr Trp Leu Val Lys Ala His
            580                 585                 590

Arg Thr

<210> SEQ ID NO 94
<211> LENGTH: 562
<212> TYPE: PRT
<213> ORGANISM: Xenopus laevis

<400> SEQUENCE: 94

Met Leu Arg Ser Leu Ala Leu Arg Thr Phe Ala Asn Ile Leu Gly Leu
  1               5                  10                  15

Ser Ser Arg Ser Gly Ser Thr Ala Ala Met Ser Arg Asn Ala Val Ala
            20                  25                  30

Ser Arg Pro His Leu Tyr Thr Thr Pro Ile Phe Tyr Val Asn Ala Ala
        35                  40                  45

Pro His Leu Gly His Val Tyr Ser Ala Leu Leu Ala Asp Val Gln His
    50                  55                  60

Arg Tyr Ser Ala Met Cys Gly Ile Glu Ser Lys Leu Ser Thr Gly Thr
65                  70                  75                  80

Asp Glu His Gly Met Lys Val Gln Gln Ala Ser Ala Leu Gly Leu
                85                  90                  95

Asp Pro Gln Thr Phe Cys Ser Val Ser Leu Gln Phe Arg Thr Ile
        100                 105                 110

Phe Asp Ala Leu Asp Ile Ser Tyr Thr Asp Phe Val Arg Thr Thr Glu
    115                 120                 125

Pro Arg His Ile Glu Ala Val Ser Arg Phe Trp Met Thr Leu Glu Glu

```
                130                 135                 140
Gln Gly Tyr Ile Tyr Lys Gly Thr Tyr Glu Gly Trp Tyr Cys Thr Ser
145                 150                 155                 160

Asp Glu Ala Phe Leu Ser Glu Gly Gln Thr Ala Glu His Thr Asp Phe
                165                 170                 175

Glu Gly Asn Lys Ile Arg Val Ser Leu Glu Ser Gly His Gln Val His
                180                 185                 190

Trp Val Ser Glu Glu Asn Tyr Met Phe Arg Leu Ser Ser Leu Arg Pro
                195                 200                 205

Ala Leu Leu Asn Trp Leu Gln Thr Glu Pro Val His Pro Ala Pro Phe
210                 215                 220

Leu Lys Leu Val His His Trp Leu Glu Glu Leu Pro Asp Leu Ser
225                 230                 235                 240

Val Ser Arg Gln Arg Ser Arg Leu Ser Trp Gly Ile Pro Val Pro Ser
                245                 250                 255

Asp Ser Ser His Val Ile Tyr Val Trp Leu Asp Ala Leu Val Asn Tyr
                260                 265                 270

Leu Thr Ala Ala Gly Tyr Pro Asn Pro Gln Leu Ala Pro Trp Gly Pro
                275                 280                 285

Ser Thr His Leu Leu Gly Lys Asp Ile Leu Arg Phe His Ala Ile Tyr
                290                 295                 300

Trp Pro Ala Phe Leu Ile Ala Ala Gly Leu Pro Pro Gln Lys Leu
305                 310                 315                 320

Leu Val His Ser His Trp Thr Ser Glu Gly Thr Lys Met Ser Lys Ser
                325                 330                 335

Leu Lys Asn Val Val Asp Pro Ser Asp Cys Ile Arg Arg Tyr Thr Thr
                340                 345                 350

Asp Gly Leu Arg Tyr Tyr Leu Leu Arg His Gly Ala Pro Glu Arg Asp
                355                 360                 365

Cys Asp Phe Thr His Arg Thr Ala Arg Met Leu Leu Asn Ser Glu Leu
                370                 375                 380

Ala Asp Ala Leu Gly Gly Leu Leu Asn Arg Cys Thr Ala Pro Ala Ile
385                 390                 395                 400

Asn Pro Met Gln His Phe Pro Lys Phe Gln Tyr Glu Asn Phe Pro Val
                405                 410                 415

Ala Ser Arg Asp Gln Val His Asp Leu Leu Gly Ala Leu Gln Glu Leu
                420                 425                 430

Pro Val Glu Val Asp Gln Trp Ile Lys Lys Phe Gln Val His Lys Ala
                435                 440                 445

Leu Glu Cys Ile Asp Ala Cys Val Arg Arg Ser Asn Ala Phe Phe Gln
450                 455                 460

Ser Gln Ala Pro Trp Lys Leu Gln Arg Gly Val Glu Lys Glu Ala Ala
465                 470                 475                 480

Leu Arg Asp Ser Val Ile Tyr Leu Thr Leu Glu Ala Leu Arg Leu Tyr
                485                 490                 495

Ala Thr Leu Leu His Pro Ala Val Pro Gly Leu Ala Thr Val Val Leu
                500                 505                 510

Asp Arg Leu Gly Val Pro His Lys Met Arg Thr Leu Lys Lys Asn Thr
                515                 520                 525

Phe Leu Ala Ala Thr Arg Gly Glu Ile Cys Tyr Phe Gln Ala Gln Thr
                530                 535                 540

Leu Gly Pro Asp Lys Gly Leu Leu Phe Pro Arg Leu Glu Lys Ser Glu
545                 550                 555                 560
```

Ala Phe

<210> SEQ ID NO 95
<211> LENGTH: 539
<212> TYPE: PRT
<213> ORGANISM: Schizosaccharomyces pombe

<400> SEQUENCE: 95

| | | | | | | | | | | | | | | |
|---|---|---|---|---|---|---|---|---|---|---|---|---|---|---|
| Met | Leu | Arg | Lys | Gly | Ile | Cys | Arg | Leu | Ile | His | Gln | Val | Ser | Glu | Ser |
| 1 | | | | 5 | | | | | 10 | | | | | 15 | |
| Ser | Lys | Lys | Pro | Tyr | Phe | Leu | Thr | Thr | Pro | Ile | Phe | Tyr | Val | Asn | Ala |
| | | | 20 | | | | | 25 | | | | | 30 | | |
| Ala | Pro | His | Leu | Gly | His | Leu | Tyr | Ser | Leu | Val | Leu | Thr | Asp | Ala | Ile |
| | | 35 | | | | | 40 | | | | | 45 | | | |
| Ala | Arg | Phe | Gln | Asn | Leu | Lys | Pro | Asp | Val | Ser | Val | Ile | Ser | Ser | Thr |
| | 50 | | | | | 55 | | | | | 60 | | | | |
| Gly | Thr | Asp | Glu | His | Gly | Leu | Lys | Val | Gln | Thr | Val | Ala | Gln | Thr | Glu |
| 65 | | | | | 70 | | | | | 75 | | | | | 80 |
| Gly | Val | Ser | Pro | Leu | Gln | Leu | Cys | Asp | Arg | Asn | Ser | Lys | Arg | Phe | Ala |
| | | | | 85 | | | | | 90 | | | | | 95 | |
| Asp | Leu | Ala | Val | Ala | Ala | Asn | Thr | Lys | Phe | Thr | His | Phe | Ile | Arg | Thr |
| | | | 100 | | | | | 105 | | | | | 110 | | |
| Thr | Asn | Pro | Lys | His | Gln | Ala | Ser | Val | Gln | Glu | Phe | Trp | Lys | Thr | Ile |
| | | 115 | | | | | 120 | | | | | 125 | | | |
| Gln | Lys | Ala | Gly | Met | Ile | Ser | Phe | Glu | Arg | His | Glu | Gly | Trp | Tyr | Cys |
| | 130 | | | | | 135 | | | | | 140 | | | | |
| Val | Ser | Asp | Glu | Thr | Phe | Tyr | Pro | Glu | Ser | Ala | Ile | Gln | Lys | Val | Val |
| 145 | | | | | 150 | | | | | 155 | | | | | 160 |
| Asp | Pro | Ala | Thr | Lys | Gln | Glu | Lys | Arg | Val | Ser | Met | Glu | Thr | Gly | Lys |
| | | | | 165 | | | | | 170 | | | | | 175 | |
| Glu | Val | Gln | Trp | Ser | Ser | Glu | Met | Asn | Tyr | His | Phe | Leu | Leu | Ser | Lys |
| | | | 180 | | | | | 185 | | | | | 190 | | |
| Phe | Gln | Ser | Arg | Leu | Ile | Glu | His | Tyr | Asn | Lys | Asn | Pro | Asn | Phe | Val |
| | | 195 | | | | | 200 | | | | | 205 | | | |
| Gln | Pro | Ser | Ile | Phe | His | Thr | Gln | Val | Leu | Glu | Glu | Leu | Lys | Thr | Gly |
| | 210 | | | | | 215 | | | | | 220 | | | | |
| Ile | Ser | Asp | Leu | Ser | Ile | Ser | Arg | Pro | Lys | Gln | Arg | Leu | Ser | Trp | Gly |
| 225 | | | | | 230 | | | | | 235 | | | | | 240 |
| Ile | Pro | Val | Pro | Gly | Asn | Ser | Gln | Gln | Thr | Ile | Tyr | Val | Trp | Leu | Asp |
| | | | | 245 | | | | | 250 | | | | | 255 | |
| Ala | Leu | Ile | Asn | Tyr | Ile | Ser | Val | Ile | Gly | Tyr | Pro | Trp | Leu | Asn | Glu |
| | | | 260 | | | | | 265 | | | | | 270 | | |
| Lys | Ser | Ser | Leu | Ser | Ala | Gly | Trp | Pro | Ala | Asn | Met | His | Val | Ile | Gly |
| | | 275 | | | | | 280 | | | | | 285 | | | |
| Lys | Asp | Ile | Ile | Arg | Phe | His | Cys | Ile | Tyr | Trp | Pro | Ala | Phe | Leu | Met |
| | 290 | | | | | 295 | | | | | 300 | | | | |
| Ala | Ala | Gly | Leu | Pro | Leu | Pro | Glu | Lys | Ile | Leu | Val | His | Ser | His | Trp |
| 305 | | | | | 310 | | | | | 315 | | | | | 320 |
| Thr | Met | Asn | Lys | Val | Lys | Met | Ser | Lys | Ser | Leu | Gly | Asn | Val | Val | Asp |
| | | | | 325 | | | | | 330 | | | | | 335 | |
| Pro | Phe | Trp | Leu | Ile | Glu | Lys | Tyr | Gly | Val | Asp | Thr | Ile | Arg | Tyr | Tyr |
| | | | 340 | | | | | 345 | | | | | 350 | | |
| Leu | Leu | Lys | Arg | Gly | Arg | Leu | Thr | Ser | Asp | Ser | Asn | Phe | Asp | Ile | Glu |
| | | 355 | | | | | 360 | | | | | 365 | | | |
| Glu | Leu | Glu | Lys | Asp | Glu | Glu | His | Asp | Leu | Arg | Arg | Ser | Leu | Gly | Val |

```
                    370                 375                 380
Leu Leu Ser Arg Leu Gln Ser Lys Lys Leu Phe Ile Ser Asn Glu Ile
385                 390                 395                 400

Gln Lys Gln Trp His Lys Lys Asp Asp Phe Thr Glu Tyr Glu Asp Ile
                405                 410                 415

Val His Glu Leu Ile Glu Leu Pro Val Val Cys Ala Gln Ser Ile Asp
                420                 425                 430

Gly Gly Cys Val Tyr Glu Val Ile Asn Leu Val Gln Ser Val Leu Arg
                435                 440                 445

Arg Val Thr Lys Leu Phe Gln Leu Lys Glu Pro Trp Lys Leu Ser Asp
450                 455                 460

Asp Ser Gln Glu Lys Ile Asp Thr Leu Met Leu Val Ala His Ser Leu
465                 470                 475                 480

Arg Ile Ser Gly Ile Leu Leu Gln Pro Ile Met Pro Thr Lys Ser Thr
                485                 490                 495

Glu Leu Leu Asp Gln Leu Gly Ile Pro Lys Asn Gln Arg Ser Leu Gln
                500                 505                 510

Asn Ala Thr Asn Val Phe Glu Pro Thr Glu Phe Thr Phe His Ser Gly
                515                 520                 525

Asn Asn Ser His Leu Phe Asp Lys Arg Thr Gln
530                 535

<210> SEQ ID NO 96
<211> LENGTH: 913
<212> TYPE: PRT
<213> ORGANISM: Danio rerio

<400> SEQUENCE: 96

Met Lys Leu Phe Ile Gly Glu Gly Asn Pro His Cys Leu Lys Val Leu
1               5                   10                  15

Ala Ala Leu Glu Leu Ser Gly Val Arg Cys Glu Thr Gln Leu Val Lys
                20                  25                  30

His Glu Glu Lys Val Val Pro Tyr Leu Thr His Pro Val Leu Pro Ile
                35                  40                  45

Leu Gln Leu Pro Ser Gly Gln His Leu Phe Ser Pro Asn Ser Ile Cys
50                  55                  60

Gln Tyr Leu Phe Asp Ile Ser Gly Gln Lys Ala Thr Asp Ala Thr Asn
65                  70                  75                  80

Gln Trp Leu Glu Trp Glu Ala Thr Asn Leu Gln Pro Ala Val Leu Gln
                85                  90                  95

Ser Leu Gln Leu Val Ala Leu Gln Gly Lys Arg Val Glu Ser Ala Ala
                100                 105                 110

Val Met Lys Glu Pro Leu Ser Trp Leu Glu Gln Ser Leu Ser Lys Arg
                115                 120                 125

Lys Thr Ser Phe Leu Thr Asp Glu Val Val Ser Val Ala Asp Val Val
130                 135                 140

Leu Trp Ala Ala Leu Tyr Pro Leu Leu Ser Asp Ser Ala Phe Glu Pro
145                 150                 155                 160

Gly Asp Leu Gln Ala Val Arg Gly Trp Phe Glu Arg Val Cys Ser Val
                165                 170                 175

Ser Ala Cys Gln Ser Ala Ala Leu Arg Val Leu Gln Gly Lys Gly Ala
                180                 185                 190

Glu Ala Leu Lys Ser Phe Leu Gln Lys Gln Pro Val Thr His Thr Pro
                195                 200                 205

Arg Arg Asp Ser Pro Ser Asn Ser Thr Glu Ala Glu Asp Ser Glu Arg
```

-continued

```
              210                 215                 220
Glu Leu Ser Pro Glu Ile Glu Ala Ala Gln Val Tyr Ser Glu
225                 230                 235                 240

Gly Leu Lys Asp Phe Thr Val Thr Glu Arg Lys His Pro Val Leu
                245                 250                 255

Pro Gln Glu Gly Lys Arg Asn Val Leu Ile Thr Ser Ala Leu Pro Tyr
                260                 265                 270

Val Asn Asn Val Pro His Leu Gly Asn Ile Ile Gly Cys Val Leu Ser
                275                 280                 285

Ala Asp Val Phe Ala Arg Tyr Gly Arg Leu Arg Gly Trp Asn Leu Leu
290                 295                 300

Tyr Ile Cys Gly Thr Asp Glu Tyr Gly Thr Ala Thr Glu Asn Lys Ala
305                 310                 315                 320

Arg Glu Glu Gly Leu Thr Pro Gln Gln Ile Cys Asp Lys Tyr His Cys
                325                 330                 335

Ile His Ala Ser Ile Tyr Gln Trp Phe Gln Ile Asp Phe Asp Phe Phe
                340                 345                 350

Gly Arg Thr Thr Thr Gln His Gln Thr Glu Ile Ala Gln Asp Ile Phe
                355                 360                 365

Trp Arg Leu His Glu Arg Gly Phe Leu Leu Glu Asp Thr Val Glu Gln
370                 375                 380

Leu Arg Cys Glu Gly Cys Gln Arg Phe Leu Ala Asp Arg Phe Val Glu
385                 390                 395                 400

Gly Glu Cys Pro His Cys Arg Tyr Pro Glu Ala Arg Gly Asp Gln Cys
                405                 410                 415

Asp Lys Cys Gly Arg Leu Ile Asn Ala Val Glu Leu Lys Asn Pro Gln
                420                 425                 430

Cys Lys Val Cys Lys Glu Thr Pro Val Ile Arg Ser Ser Lys His Leu
                435                 440                 445

Phe Leu Asn Leu Pro Lys Leu Glu Gln Asp Leu Glu Gln Trp Leu Gln
450                 455                 460

Thr Ser Thr Ala Ala Gly Asp Trp Thr Thr Asn Ala Arg His Ile Thr
465                 470                 475                 480

Arg Ser Trp Leu Arg Asp Gly Leu Lys Pro Arg Cys Ile Thr Arg Asp
                485                 490                 495

Leu Lys Trp Gly Thr Pro Val Pro His Pro Asp Tyr Lys Glu Lys Val
                500                 505                 510

Phe Tyr Val Trp Phe Asp Ala Pro Ile Gly Tyr Leu Ser Ile Thr Ala
                515                 520                 525

Asn Tyr Thr Asp Gln Trp Glu Arg Trp Trp Lys Asn Pro Gln Gln Val
530                 535                 540

Glu Leu Tyr Asn Phe Met Ala Lys Asp Asn Val Pro Phe His Ser Val
545                 550                 555                 560

Val Phe Pro Cys Ser Leu Leu Gly Ala Gln Asp Asn Tyr Thr Leu Val
                565                 570                 575

Asn Asn Leu Ile Ala Thr Glu Tyr Leu Asn Tyr Glu Asp Thr Lys Phe
                580                 585                 590

Ser Lys Ser Arg Gly Val Gly Val Phe Gly Asp Met Ala Lys Asp Thr
                595                 600                 605

Gly Ile Pro Ser Asp Val Trp Arg Phe Tyr Leu Leu Tyr Leu Arg Pro
                610                 615                 620

Glu Gly Gln Asp Ser Ala Phe Ser Trp Thr Asp Met Ala Leu Lys Asn
625                 630                 635                 640
```

```
Asn Ser Glu Leu Leu Asn Asn Leu Gly Asn Phe Ile Asn Arg Ala Gly
                645                 650                 655
Met Phe Val Ser Lys Phe Phe Glu Gly Cys Val Pro Glu Met Leu Leu
            660                 665                 670
Asn Asp Asp Lys Arg Leu Ile Ala Gln Val Cys Trp Glu Leu Lys
        675                 680                 685
Gln Tyr Ile Gln Leu Leu Asp Lys Val Arg Ile Arg Asp Ala Leu Lys
        690                 695                 700
Cys Ile Leu Asn Met Ser Arg His Gly Asn Gln Tyr Ile Gln Leu Asn
705                 710                 715                 720
Glu Pro Trp Lys Lys Ile Lys Gly Gly Ala Glu Asp Arg Cys Arg Ala
                725                 730                 735
Gly Thr Val Thr Gly Val Ser Val Asn Val Ala Cys Leu Leu Ala Ala
            740                 745                 750
Val Leu Glu Pro Phe Met Pro Thr Val Ser Leu Ser Ile Arg Ser Gln
        755                 760                 765
Leu Gln Ala Pro Glu Ser Ser Arg Ala Met Leu Ser Gly Pro Gly
        770                 775                 780
Ala Phe Ile Cys Thr Leu Pro Ala Gly His Arg Ile Gly Thr Val Ser
785                 790                 795                 800
Pro Leu Phe Gln Lys Leu Glu Asn Glu Gln Ile Glu Ala Leu Arg Lys
                805                 810                 815
Arg Phe Gly Gly Leu Gln Thr Pro Ser Asn Ser Val Ala Val Glu
            820                 825                 830
Ser Lys Pro Asn Ala Gly Ala Ala Gln His Thr Pro Ala Ser Val Thr
        835                 840                 845
Ala Asp Pro Glu Arg Ala Lys Gln Leu Thr Ala Leu Val Ala Glu Gln
        850                 855                 860
Gly Glu Lys Val Arg Ala Leu Lys Ala Gln Lys Ala Glu Lys Ser Ala
865                 870                 875                 880
Ile Gly Val Glu Val Ala Lys Leu Leu Asp Leu Lys Asn Gln Leu Cys
                885                 890                 895
Leu Ala Glu Gly Lys Thr Pro Glu Pro Pro Ala Gln Lys Thr Lys Lys
            900                 905                 910
Lys

<210> SEQ ID NO 97
<211> LENGTH: 650
<212> TYPE: PRT
<213> ORGANISM: helicobacter phlori

<400> SEQUENCE: 97

Met Gln Lys Ser Leu Ile Thr Thr Pro Ile Tyr Tyr Val Asn Asp Ile
1               5                   10                  15
Pro His Ile Gly His Ala Tyr Thr Thr Leu Ile Ala Asp Thr Leu Lys
            20                  25                  30
Lys Tyr Tyr Thr Leu Gln Gly Glu Glu Val Phe Phe Leu Thr Gly Thr
        35                  40                  45
Asp Glu His Gly Gln Lys Ile Glu Gln Ser Ala Arg Leu Arg Asn Gln
    50                  55                  60
Ser Pro Lys Ala Tyr Ala Asp Ser Ile Ser Thr Ile Phe Lys Asp Gln
65                  70                  75                  80
Trp Asp Phe Phe Asn Leu Asp Tyr Asp Gly Phe Ile Arg Thr Thr Asp
                85                  90                  95
Ser Glu His Gln Lys Cys Val Gln Asn Ala Phe Glu Ile Met Phe Glu
```

```
                   100              105              110
Lys Gly Asp Ile Tyr Lys Gly Ala Tyr Ser Gly Tyr Tyr Cys Val Ser
            115              120              125
Cys Glu Ser Tyr Cys Ala Ile Ser Lys Ala Asp Asn Thr Asn Asp Lys
            130              135              140
Val Leu Cys Pro Asp Cys Leu Arg Glu Thr Thr Leu Leu Glu Glu Glu
145              150              155              160
Ser Tyr Phe Phe Arg Leu Ser Ala Tyr Glu Lys Pro Leu Leu Asp Phe
                 165              170              175
Tyr Ala Lys Asn Pro Glu Ala Ile Leu Pro Val Tyr Arg Lys Asn Glu
            180              185              190
Val Thr Ser Phe Ile Glu Gln Gly Leu Leu Asp Leu Ser Ile Thr Arg
            195              200              205
Thr Ser Phe Glu Trp Gly Ile Pro Leu Pro Lys Lys Met Asn Asp Pro
            210              215              220
Lys His Val Val Tyr Val Trp Leu Asp Ala Leu Leu Asn Tyr Ala Ser
225              230              235              240
Ala Leu Gly Tyr Leu Asn Asp Leu Asp Asn Lys Met Ala His Phe Glu
                 245              250              255
Cys Ala Arg His Ile Val Gly Lys Asp Ile Leu Arg Phe His Ala Ile
                 260              265              270
Tyr Trp Pro Ala Phe Leu Met Ser Leu Asn Leu Pro Leu Phe Lys Gln
                 275              280              285
Leu Cys Val His Gly Trp Trp Thr Ile Glu Gly Val Lys Met Ser Lys
            290              295              300
Ser Leu Gly Asn Val Leu Asp Ala Gln Lys Ile Ala Met Glu Tyr Gly
305              310              315              320
Ile Glu Glu Leu Arg Tyr Phe Leu Leu Arg Glu Val Pro Phe Gly Gln
                 325              330              335
Asp Gly Asp Phe Ser Lys Lys Ala Leu Ile Glu Arg Ile Asn Ala Asn
                 340              345              350
Leu Asn Asn Asp Leu Gly Asn Leu Leu Asn Arg Leu Leu Gly Met Ala
            355              360              365
Lys Lys Tyr Phe Asn His Ser Leu Lys Ser Thr Lys Ile Thr Ala Tyr
            370              375              380
Tyr Ser Lys Glu Leu Glu Lys Val His Gln Ile Leu Asp Asn Ala Asn
385              390              395              400
Ser Phe Val Pro Lys Met Gln Leu His Lys Ala Leu Glu Glu Leu Phe
                 405              410              415
Asn Val Tyr Asp Phe Leu Asn Lys Leu Ile Ala Lys Glu Glu Pro Trp
                 420              425              430
Val Leu His Lys Asn Asn Glu Ser Glu Lys Leu Glu Ala Leu Leu Ser
            435              440              445
Leu Ile Ala Asn Ala Leu Leu Gln Ser Ser Phe Leu Leu Tyr Ala Phe
            450              455              460
Met Pro Lys Ser Ala Val Lys Leu Ala Asn Ala Phe Asn Thr Glu Ile
465              470              475              480
Thr Pro Asp Asn Tyr Glu Arg Phe Phe Lys Ala Lys Lys Leu Gln Asp
                 485              490              495
Met Ile Leu Gln Asp Thr Glu Pro Leu Phe Ser Lys Met Glu Lys Ile
            500              505              510
Glu Lys Thr Glu Lys Ala Gly Glu Ala Ser Pro Glu Lys Asn Glu Lys
            515              520              525
```

-continued

```
Glu Lys Lys Asp Ala Lys Glu Lys Ala Pro Leu Lys Gln Glu Asn Tyr
            530                 535                 540

Ile Gly Ile Glu Asp Phe Lys Lys Val Glu Ile Lys Val Gly Leu Ile
545                 550                 555                 560

Lys Glu Ala Gln Arg Ile Glu Lys Ser Asn Lys Leu Arg Leu Lys
                565                 570                 575

Val Asp Leu Gly Glu Gly Arg Leu Arg Gln Ile Ile Ser Gly Ile Ala
            580                 585                 590

Leu Asp Tyr Glu Pro Glu Ser Leu Val Gly Gln Met Val Cys Val Val
            595                 600                 605

Ala Asn Leu Lys Pro Ala Lys Leu Met Gly Glu Met Ser Glu Gly Met
            610                 615                 620

Ile Leu Ala Val Arg Asp Ser Asp Asn Leu Ala Leu Ile Ser Pro Thr
625                 630                 635                 640

Arg Glu Lys Ile Ala Gly Ser Leu Ile Ser
                645                 650

<210> SEQ ID NO 98
<211> LENGTH: 582
<212> TYPE: PRT
<213> ORGANISM: Drosophila melanogaster

<400> SEQUENCE: 98

Met Leu Ile Arg Arg Ile Lys Cys Leu Arg Tyr Leu Gly Thr Arg Tyr
1               5                   10                  15

Asn Ser Ser His Tyr Val Thr Thr Pro Ile Phe Tyr Val Asn Ala Ala
            20                  25                  30

Pro His Ile Gly His Leu Tyr Ser Ala Val Ile Ala Asp Ala His Cys
        35                  40                  45

Arg Tyr Gln Arg Leu Arg Tyr Pro Glu Gln Asp Val Arg Leu Cys Thr
    50                  55                  60

Gly Thr Asp Glu His Gly Thr Lys Ile Gln Gln Ala Ala Ser Leu His
65              70                  75                  80

Gly Val Pro Val Ala Lys Tyr Cys Asp Asp Ile Ser Gln Arg Tyr Arg
                85                  90                  95

Glu Val Phe Arg Ser Ala Ser Ile Gln Gln Asp Asp Phe Ile Arg Thr
            100                 105                 110

Thr Glu Asp Arg His Lys Arg Ala Val Ala Asn Phe Trp Arg Thr Leu
        115                 120                 125

His Thr Arg Gly His Ile Tyr Ser Ala Ala Tyr Ser Gly Trp Tyr Cys
    130                 135                 140

Val Ser Asp Glu Thr Phe Leu Thr Asp Ser Gln Leu Arg Leu Asp Glu
145                 150                 155                 160

Ala Thr Gly Thr Arg Tyr Ser Leu Glu Ser Gly His Pro Val Glu Trp
                165                 170                 175

Thr Glu Glu Thr Asn Tyr Met Phe Arg Leu Ser Gln Phe Gln Asp Asp
            180                 185                 190

Val Arg His Trp Val Lys Thr Glu Ala Arg Val Arg Pro Ala Lys Phe
        195                 200                 205

Glu Lys Ile Leu Leu Asp Thr Leu Ser Glu Pro Leu Pro Asp Val Ser
    210                 215                 220

Val Ser Arg Pro Ser Asn Arg Val His Trp Ala Ile Pro Val Pro Asp
225                 230                 235                 240

Asp Asp Ser Gln Thr Val Tyr Val Trp Leu Asp Ala Leu Val Asn Tyr
                245                 250                 255
```

```
Leu Ser Ser Val Gly Tyr Pro Asp Glu Lys Phe Ser Ala His Trp Pro
                260                 265                 270

Pro Ala Gln Gln Val Ile Gly Lys Asp Ile Leu Lys Phe His Gly Ile
                275                 280                 285

Tyr Trp Thr Ala Phe Leu Leu Ala Ala Gly Leu Glu Pro Pro Gly Gln
            290                 295                 300

Leu Tyr Val His Ser His Trp Thr Val Asp Gly Gln Lys Met Ser Lys
305                 310                 315                 320

Ser Lys His Asn Val Val Asp Pro Leu Gln Ala Ala Gln Gln Tyr Thr
                325                 330                 335

Met Glu Gly Leu Arg Tyr Phe Leu Leu Arg Glu Gly Val Ala His Ser
            340                 345                 350

Asp Gly Asn Tyr Ser His Val Lys Ala Gln Arg Ile Leu Asn Ser Glu
            355                 360                 365

Leu Ala Asp Thr Leu Gly Asn Leu Leu Ser Arg Ala Ser Ala Lys Ser
        370                 375                 380

Leu Asn Pro Gly Gln Ile Tyr Pro Ser Pro Ser Ala Glu His Leu Ala
385                 390                 395                 400

Asp Leu Leu Arg Ser Leu Asp Val Ala Lys Arg Leu Gln Asp Ser Leu
                405                 410                 415

Leu Gln Leu Ser Glu Arg Cys Glu Ser His Tyr Glu Cys Asn His Phe
            420                 425                 430

His Leu Val Ala Asp Thr Thr Met Ala Ala Leu His Ala Ala Asn Asn
        435                 440                 445

Phe Phe Glu Ser Ser Lys Pro Trp Thr Leu Lys Ala Gly Ala Pro Asp
450                 455                 460

Gly Asn Gln Ala Arg Leu Glu Thr Ile Ile Ala Met Thr Met Asp Ala
465                 470                 475                 480

Leu Arg Leu Ser Gly Ile Val Leu Gln Pro Ile Ile Pro Gln Leu Ala
            485                 490                 495

Asn Arg Leu Leu Asp Lys Leu Ser Val Pro Thr Ala Gln Arg Gly Trp
                500                 505                 510

Asn Tyr Leu Ala Glu Ser Phe Ala Thr Ser Pro Asn Ser Ser Asn Ser
            515                 520                 525

Pro Ala Gly Leu Gly Glu Ser Arg Gln Leu Asp Gly Gln Thr Ser Ala
        530                 535                 540

Leu Leu Phe Gln Arg Ile Leu Glu Glu Thr Ser Ala Lys Glu Val Lys
545                 550                 555                 560

Glu Gln Lys Pro Gln Pro Ala Lys Arg Ser Lys Ser Lys Lys Lys Glu
                565                 570                 575

Arg Arg Glu Thr Met Ser
            580

<210> SEQ ID NO 99
<211> LENGTH: 519
<212> TYPE: PRT
<213> ORGANISM: Mycobacterium tuberculosis

<400> SEQUENCE: 99

Met Lys Pro Tyr Tyr Val Thr Thr Ala Ile Ala Tyr Pro Asn Ala Ala
1               5                   10                  15

Pro His Val Gly His Ala Tyr Glu Tyr Ile Ala Thr Asp Ala Ile Ala
                20                  25                  30

Arg Phe Lys Arg Leu Asp Arg Tyr Asp Val Arg Phe Leu Thr Gly Thr
            35                  40                  45
```

-continued

```
Asp Glu His Gly Leu Lys Val Ala Gln Ala Ala Ala Ala Gly Val
    50                  55                  60

Pro Thr Ala Ala Leu Ala Arg Arg Asn Ser Asp Val Phe Gln Arg Met
65                  70                  75                  80

Gln Glu Ala Leu Asn Ile Ser Phe Asp Arg Phe Ile Arg Thr Thr Asp
                85                  90                  95

Ala Asp His His Glu Ala Ser Lys Glu Leu Trp Arg Arg Met Ser Ala
                100                 105                 110

Ala Gly Asp Ile Tyr Leu Asp Asn Tyr Ser Gly Trp Tyr Ser Val Arg
                115                 120                 125

Asp Glu Arg Phe Phe Val Glu Ser Glu Thr Gln Leu Val Asp Gly Thr
                130                 135                 140

Arg Leu Thr Val Glu Thr Gly Thr Pro Val Thr Trp Thr Glu Glu Gln
145                 150                 155                 160

Thr Tyr Phe Phe Arg Leu Ser Ala Tyr Thr Asp Lys Leu Leu Ala His
                165                 170                 175

Tyr His Ala Asn Pro Asp Phe Ile Ala Pro Glu Thr Arg Arg Asn Glu
                180                 185                 190

Val Ile Ser Phe Val Ser Gly Gly Leu Asp Asp Leu Ser Ile Ser Arg
                195                 200                 205

Thr Ser Phe Asp Trp Gly Val Gln Val Pro Glu His Pro Asp His Val
                210                 215                 220

Met Tyr Val Trp Val Asp Ala Leu Thr Asn Tyr Leu Thr Gly Ala Gly
225                 230                 235                 240

Phe Pro Asp Thr Asp Ser Glu Leu Phe Arg Arg Tyr Trp Pro Ala Asp
                245                 250                 255

Leu His Met Ile Gly Lys Asp Ile Ile Arg Phe His Ala Val Tyr Trp
                260                 265                 270

Pro Ala Phe Leu Met Ser Ala Gly Ile Glu Leu Pro Arg Arg Ile Phe
                275                 280                 285

Ala His Gly Phe Leu His Asn Arg Gly Glu Lys Met Ser Lys Ser Val
                290                 295                 300

Gly Asn Ile Val Asp Pro Val Ala Leu Ala Glu Ala Leu Gly Val Asp
305                 310                 315                 320

Gln Val Arg Tyr Phe Leu Leu Arg Glu Val Pro Phe Gly Gln Asp Gly
                325                 330                 335

Ser Tyr Ser Asp Glu Ala Ile Val Thr Arg Ile Asn Thr Asp Leu Ala
                340                 345                 350

Asn Glu Leu Gly Asn Leu Ala Gln Arg Ser Leu Ser Met Val Ala Lys
                355                 360                 365

Asn Leu Asp Gly Arg Val Pro Asn Pro Gly Glu Phe Ala Asp Ala Asp
                370                 375                 380

Ala Ala Leu Leu Ala Thr Ala Asp Gly Leu Leu Glu Arg Val Arg Gly
385                 390                 395                 400

His Phe Asp Ala Gln Ala Met His Leu Ala Leu Glu Ala Ile Trp Leu
                405                 410                 415

Met Leu Gly Asp Ala Asn Lys Tyr Phe Ser Val Gln Gln Pro Trp Val
                420                 425                 430

Leu Arg Lys Ser Glu Ser Glu Ala Asp Gln Ala Arg Phe Arg Thr Thr
                435                 440                 445

Leu Tyr Val Thr Cys Glu Val Val Arg Ile Ala Ala Leu Leu Ile Gln
                450                 455                 460

Pro Val Met Pro Glu Ser Ala Gly Lys Ile Leu Asp Leu Leu Gly Gln
465                 470                 475                 480
```

```
Ala Pro Asn Gln Arg Ser Phe Ala Ala Val Gly Val Arg Leu Thr Pro
                485                 490                 495

Gly Thr Ala Leu Pro Pro Thr Gly Val Phe Pro Arg Tyr Gln Pro
            500                 505                 510

Pro Gln Pro Pro Glu Gly Lys
        515

<210> SEQ ID NO 100
<211> LENGTH: 575
<212> TYPE: PRT
<213> ORGANISM: Saccharomyces cerevisiae

<400> SEQUENCE: 100

Met Gln Cys Arg Ser Ile Val His Arg Leu Tyr Ser Lys Val Ser His
 1               5                  10                  15

Val Thr Thr Pro Ile Phe Tyr Pro Asn Ala Lys Pro His Leu Gly His
            20                  25                  30

Leu Tyr Ser Ser Leu Leu Ser Asp Val Tyr His Arg Trp Gln Leu Phe
        35                  40                  45

Lys Gly Asn Leu Ser Phe Phe Thr Thr Gly Thr Asp Glu His Gly Leu
    50                  55                  60

Lys Ile Gln Cys Ala Ser Glu Ser Asn Gly Phe Asp Gln Pro Lys Lys
65                  70                  75                  80

Phe Val Asp Lys Leu Tyr Pro Glu Phe Val Gln Leu Asp Lys Ile Tyr
                85                  90                  95

Gly Ile Asn Tyr Thr Arg Phe Ile Arg Thr Thr Asp Pro Asp His Ile
            100                 105                 110

Glu Asn Val Met Lys Leu Trp Glu Leu Cys Leu Lys Asn Gly Tyr Ile
        115                 120                 125

Tyr Met Gly Glu His Lys Gly Trp Tyr Ser Ile Ser Asp Glu Thr Phe
    130                 135                 140

Tyr Pro Glu Ser Lys Val Ile Lys Asp Pro Lys Asn Asp Gly Lys Tyr
145                 150                 155                 160

Leu Asn Thr Glu Ser Lys Asn Glu Val Val Tyr Gln Ser Glu Thr Asn
                165                 170                 175

Tyr Phe Phe Arg Leu Ser Leu Phe Asn Lys Lys Ile Val Asp His Ile
            180                 185                 190

Arg Lys Asn Pro Asp Phe Ile Phe Pro Ala Ser Lys Arg Asp Gln Ile
        195                 200                 205

Leu Lys Glu Leu Glu Thr Gly Gly Thr Leu Pro Asp Leu Ser Ile Ser
    210                 215                 220

Arg Pro Ser Ala Arg Leu Lys Trp Gly Ile Pro Thr Pro Asn Asp Pro
225                 230                 235                 240

Ser Gln Lys Val Tyr Val Trp Phe Asp Ala Leu Cys Asn Tyr Leu Ser
                245                 250                 255

Ser Ile Gly Gly Ile Pro Ser Ile Leu Ser Asn Ala Thr Glu Val Val
            260                 265                 270

Ser Arg His Tyr Ser Asp Lys Ser Asn Val Lys Gly Gln Leu Leu Ile
        275                 280                 285

Pro Tyr Pro Lys Glu Val Gln Arg Asn Thr Ile His Val Ile Gly Lys
    290                 295                 300

Asp Ile Ala Lys Phe His Thr Val Tyr Trp Pro Ser Phe Leu Leu Ala
305                 310                 315                 320

Ala Gly Leu Pro Leu Pro Arg Gln Ile Val Val His Gly His Trp Leu
                325                 330                 335
```

Cys Asn Gly Met Lys Met Ser Lys Ser Leu Gly Asn Val Val Asp Pro
                340                 345                 350

Ile Asp Met Ala Arg Tyr Tyr Gly Ala Asp Ile Val Arg Trp Phe Leu
                355                 360                 365

Leu Glu Asn Ser Lys Leu Glu Glu Asp Gly Asp Phe Gln Glu Ala Lys
                370                 375                 380

Leu Tyr Glu Thr Arg Glu Leu Leu Val Ser Lys Trp Gly Asn Leu Ile
385                 390                 395                 400

Asn Arg Cys Cys Gly Ser Lys Phe Asn Ile Glu Arg Ala Val Met Lys
                405                 410                 415

Phe Ser Asp Lys Ala Asn Phe Gln Phe Gln Glu Ile Phe Gln Asn Glu
                420                 425                 430

Pro Ile Val Ser Glu Arg Ile Glu Asn Leu Ala Lys Leu Leu Asn Lys
                435                 440                 445

Ser Gln Glu Val Phe Asp Glu Lys Ile Ala Ile Phe Gln Tyr Pro Gln
450                 455                 460

Leu Leu Arg His Val Trp Ser Ile Ile Asn Asp Ala Asn Thr Leu Val
465                 470                 475                 480

Gln Asn Ser Lys Pro Trp Glu Arg Glu Leu Asp Gln Asp Asn Ile
                485                 490                 495

Ile Phe Leu Ala Met Glu Thr Ser Arg Ile Leu Ser Ile Leu Cys Gln
                500                 505                 510

Ser Ile Ile Pro Ser Leu Ser Gln Ser Phe Leu Asp Arg Ile Asp Val
                515                 520                 525

Ser Lys Glu Lys Arg Thr Ile Asn Tyr Ala Arg Leu Gly Ser Asp Lys
                530                 535                 540

Thr Tyr Gly Lys Gln Ser Asn Lys Lys Gly Arg Glu Val Pro Leu Lys
545                 550                 555                 560

Lys Ile Pro Phe Arg Leu Gln Glu Glu Gln Thr Asn Met Arg Ser
                565                 570                 575

<210> SEQ ID NO 101
<211> LENGTH: 917
<212> TYPE: PRT
<213> ORGANISM: Caenorhabditis elegans

<400> SEQUENCE: 101

Met Gly His Asp Leu Ala Asp Ile Lys Lys Ser Phe Glu Ala Ser Leu
1               5                   10                  15

Pro Gly Tyr Val Glu Lys Lys Asp Pro Lys Ser Ile Leu Pro Gln Pro
                20                  25                  30

Gly Lys Arg Asn Ile Leu Ile Thr Ala Ala Leu Pro Tyr Val Asn Asn
                35                  40                  45

Val Pro His Leu Gly Asn Ile Ile Gly Cys Val Leu Ser Ala Asp Val
            50                  55                  60

Phe Ala Arg Tyr Cys Asn Leu Arg Gly His Gln Thr Phe Tyr Val Gly
65                  70                  75                  80

Gly Thr Asp Glu Tyr Gly Thr Ala Thr Glu Thr Lys Ala Leu Gln Glu
                85                  90                  95

Gly Cys Thr Pro Arg Glu Leu Cys Asp Lys Tyr His Ala Ile His Lys
                100                 105                 110

Gly Ile Tyr Glu Trp Phe Gly Ile Asp Phe Ser His Phe Gly Arg Thr
            115                 120                 125

Thr Thr Asp His Gln Thr Glu Ile Cys Gln Asp Met Phe Leu Lys Leu
            130                 135                 140

```
His Lys Asn Gly Tyr Thr Ser Ser Gln Ser Val Asp Gln Leu Tyr Cys
145                 150                 155                 160

Asn Gln Cys Glu Lys Phe Leu Ala Asp Arg Phe Val Thr Gly Thr Cys
                165                 170                 175

Pro Met Cys Ala Tyr Asp Asp Ala Arg Gly Asp Gln Cys Asp Gly Cys
            180                 185                 190

Gly Lys Leu Ile Asn Ala Val Asp Leu Lys Asp Ala Lys Cys His Met
            195                 200                 205

Cys Lys Ala Thr Pro Glu Val Lys Gln Ser Thr His Ile Phe Leu Ser
210                 215                 220

Leu Asp Lys Leu Gln Gln Lys Thr Thr Glu His Leu Asp Arg Glu Leu
225                 230                 235                 240

Ala Lys Glu Asp Asn Arg Trp Ser Ser Asn Ala Val Gly Ile Thr Lys
                245                 250                 255

Ala Trp Met Lys Leu Gly Leu Asp Pro Arg Cys Ile Thr Arg Asp Leu
            260                 265                 270

Lys Trp Gly Thr Ala Val Pro Leu Asp Gly Phe Glu Lys Lys Val Phe
            275                 280                 285

Tyr Val Trp Phe Asp Ala Pro Ile Gly Tyr Leu Ser Ile Thr Lys Cys
290                 295                 300

Val Leu Gly Asp Asn Trp Thr Lys Trp Lys Asn Pro Glu Asn Val
305                 310                 315                 320

Glu Leu Phe Asn Phe Val Gly Lys Asp Asn Val Ala Phe His Ala Val
                325                 330                 335

Met Phe Pro Cys Ser Gln Leu Gly Ala Asn Asp Asn Tyr Thr Val Val
            340                 345                 350

Asn Asn Leu Cys Ala Thr Glu Tyr Leu Asn Tyr Glu Asp Thr Lys Phe
            355                 360                 365

Ser Lys Ser Arg Gly Thr Gly Ile Phe Gly Asp Ala Ala Gln Gly Thr
    370                 375                 380

Glu Ile Pro Ala Asp Ile Trp Arg Phe Tyr Leu Leu Tyr Met Arg Pro
385                 390                 395                 400

Glu Ser Gln Asp Thr Ala Phe Ser Trp Asp Asp Phe Val Leu Lys Val
                405                 410                 415

Asn Ser Glu Leu Leu Asn Asn Leu Gly Asn Phe Ile Asn Arg Ala Leu
            420                 425                 430

Ser Phe Val Ala Asn Ser Phe Gly Gly Val Val Pro Glu Met Asn Leu
            435                 440                 445

Thr Asn Asp Asp Ala Glu Val Leu Ser Glu Ile His Asn Glu Cys Met
450                 455                 460

Gln Trp Asp Lys Gln Phe Asp Gly Val His Leu Lys Asp Ala Val Lys
465                 470                 475                 480

Thr Ile Leu Asn Val Ser Arg Leu Gly Asn Gln Tyr Met Gln Ala Gln
                485                 490                 495

Thr Pro Trp Val Leu Met Lys Lys Asp Glu Glu Gly Lys Lys Arg Ala
            500                 505                 510

Gly Thr Ile Ile Gly Val Ala Ala Asn Ile Ala Tyr His Val Ser Val
            515                 520                 525

Leu Leu Tyr Pro Ile Met Pro Thr Ile Ser Ala Thr Ile Arg Glu Gln
            530                 535                 540

Cys Gly Leu Pro Ala Leu Pro Leu Phe Thr Pro Phe Pro Ile Cys Tyr
545                 550                 555                 560

Leu Lys Ala Gly His Lys Ile Gly Gln Pro Ser Pro Leu Phe Gln Lys
```

```
                565                 570                 575
Leu Asp Pro Ala Gln Ile Ala Glu Phe Lys Ala Lys Phe Gly Gly Ser
            580                 585                 590

Gln Asp Ala Gln Ser Ser Ala Pro Lys Thr Ala Glu Lys Pro Lys Gln
            595                 600                 605

Gln Lys Lys Gln Ala Pro Thr Lys Asp Lys Lys Gly Asp Lys Lys Met
            610                 615                 620

Ala Ser Thr Ala Ala Phe Val Glu Leu Glu Gly Ala Lys Val Ile
625                 630                 635                 640

Ser Gln Leu Ile Ala Gln Asn Leu Lys Lys Phe Asp Gln Ala Lys Ala
                645                 650                 655

Leu Phe Thr Arg Asn Gln Leu Gln Arg Leu Asp Gly Glu Asn Lys Gln
            660                 665                 670

Leu Thr Ile Asp Val Lys Thr Leu Gln His Gln Leu Ile Glu Leu Glu
            675                 680                 685

Thr Ala Ala Gly Ile Lys Gln Val Pro Lys Pro Val Val Ser Cys Thr
            690                 695                 700

Pro Thr Pro Thr Ser Thr Pro Ala Ser Gly Ile Ile Thr Glu Ala Pro
705                 710                 715                 720

Lys Lys Glu Ala Pro Ser Thr Pro Ala Pro Ser Glu Pro Lys Lys Ala
                725                 730                 735

Lys Glu Gln Lys Lys Gly Lys Gly Ala Ala Ala Pro Val Asp
            740                 745                 750

Asp Thr Ile Asp Val Gly Arg Leu Asp Met Arg Val Gly Arg Ile Ile
            755                 760                 765

Lys Cys Glu Lys His Pro Asp Ala Asp Ala Leu Tyr Val Glu Gln Ile
770                 775                 780

Asp Val Gly Glu Ser Ala Pro Arg Thr Val Val Ser Gly Leu Val Arg
785                 790                 795                 800

His Val Pro Leu Asp Gln Met Gln Asn Arg Leu Val Val Val Leu Cys
                805                 810                 815

Asn Leu Lys Pro Ala Lys Met Arg Gly Val Glu Ser Arg Ala Met Val
            820                 825                 830

Met Cys Ala Ser Ser Pro Asp Lys Val Glu Ile Met Glu Val Pro Ala
            835                 840                 845

Asp Ser Lys Pro Gly Thr Pro Val Val Cys Pro Pro Tyr Thr His Arg
850                 855                 860

Pro Asp Glu Gln Leu Asn Pro Lys Lys Ile Trp Glu Thr Val Ala
865                 870                 875                 880

Glu Asp Leu Lys Val Ser Ala Glu Gly Phe Ala Glu Trp Lys Gly Gln
                885                 890                 895

Pro Leu Leu Ile Gly Ser Glu Ser Lys Met Thr Ala Pro Thr Leu Arg
            900                 905                 910

Gly Val His Val Lys
            915

<210> SEQ ID NO 102
<211> LENGTH: 545
<212> TYPE: PRT
<213> ORGANISM: Streptococcus pneumoniae

<400> SEQUENCE: 102

Met Ser Ile Phe Ile Gly Gly Ala Trp Pro Tyr Ala Asn Gly Ser Leu
1               5                   10                  15

His Ile Gly His Ala Ala Ala Leu Leu Pro Gly Asp Ile Leu Ala Arg
```

```
                    20                  25                  30
Tyr Tyr Arg Gln Lys Gly Glu Glu Val Leu Tyr Val Ser Gly Ser Asp
         35                  40                  45
Cys Asn Gly Thr Pro Ile Ser Ile Arg Ala Lys Lys Glu Asn Lys Ser
         50                  55                  60
Val Lys Glu Ile Ala Asp Phe Tyr His Lys Glu Phe Lys Glu Thr Phe
65                   70                  75                  80
Glu Lys Leu Gly Phe Thr Tyr Asp Leu Tyr Ser Arg Thr Asp Ser Pro
                 85                  90                  95
Leu His His Glu Ile Val Gln Glu Leu Phe Leu Gln Leu Tyr Glu Lys
                100                 105                 110
Lys Phe Leu Tyr Thr Lys Lys Ile Lys Gln Leu Tyr Cys Thr Phe Asp
             115                 120                 125
Asn Gln Phe Leu Pro Asp Arg Phe Val Glu Gly Lys Cys Pro Asn Cys
         130                 135                 140
Gly Thr His Ser Arg Gly Asp Gln Cys Asp Asn Cys Ser Ala Ile Leu
145                 150                 155                 160
Asp Pro Ile Asp Leu Val Asp Lys Arg Cys Ser Ile Cys Ser Asn Glu
             165                 170                 175
Pro Glu Val Arg Glu Thr Glu His Phe Tyr Tyr Val Phe Ser Glu Phe
             180                 185                 190
Gln Asn Leu Leu Glu Thr Tyr Leu Asn Asp Ala Glu Glu Thr Val Arg
             195                 200                 205
Trp Arg Lys Asn Ala Ile Asn Leu Thr Lys Arg Tyr Leu Arg Glu Gly
         210                 215                 220
Leu Pro Asp Arg Ala Val Thr Arg Asp Leu Pro Asn Gly Ile Pro Val
225                 230                 235                 240
Pro Ile Asp Gly Phe Arg Asp Lys Lys Ile Tyr Val Trp Phe Glu Ala
                 245                 250                 255
Val Ala Gly Tyr Tyr Thr Ala Ser Val Asp Trp Ala Gly Lys Leu Gln
             260                 265                 270
Asn Asn Ile Thr Asp Phe Trp Asn Asn Arg Thr Lys Ser Tyr Tyr Val
         275                 280                 285
His Gly Lys Asp Asn Ile Pro Phe His Thr Ile Ile Trp Pro Ala Ile
         290                 295                 300
Leu Ser Gly Leu Glu Ile Glu Pro Leu Pro Glu Tyr Ile Ile Ser Ser
305                 310                 315                 320
Glu Tyr Leu Thr Leu Glu Asn Lys Lys Ile Ser Thr Ser Asn Asn Trp
                 325                 330                 335
Ala Ile Trp Leu Asn Asp Ile Ile Lys Lys Tyr Asp Ala Asp Ser Ile
                 340                 345                 350
Arg Tyr Phe Leu Thr Ile Asn Ala Pro Glu Met Lys Asp Ala Asn Phe
             355                 360                 365
Ser Trp Arg Glu Phe Ile Tyr Ser His Asn Ser Glu Leu Leu Gly Ser
             370                 375                 380
Tyr Gly Asn Phe Ile Asn Arg Thr Leu Lys Phe Ile Glu Lys Tyr Phe
385                 390                 395                 400
Glu Ser Glu Ile Pro Thr Lys Tyr Leu Glu Gly Glu Ile Leu Tyr Asn
                 405                 410                 415
Leu Lys Glu Leu Tyr Thr Thr Val Gly Asn Leu Val Glu Ser Gly His
             420                 425                 430
Met Lys Gln Ala Leu Glu Glu Ile Phe Glu Tyr Ile Arg Ser Ala Asn
             435                 440                 445
```

```
Lys Phe Tyr Asp Asp Met Lys Pro Trp Ala Leu Arg Glu Ser Asp Ile
        450                 455                 460

Glu Lys Cys Lys Glu Val Leu Ala Thr Cys Val Ile Ile Ile Leu Asn
465                 470                 475                 480

Leu Gly Gln Met Leu Asn Pro Phe Ile Pro Phe Ser Gly Lys Lys Ile
            485                 490                 495

Glu Asp Met Phe Lys Thr Lys Leu Asn Thr Trp Asn Tyr Ile Ser Asn
        500                 505                 510

Leu Pro Asn Lys Leu Ser Asp Val Ser Met Leu Phe Asp Arg Ile Asp
            515                 520                 525

Leu Lys Lys Ile Asp Glu Glu Val Leu Glu Leu Gln Gln Thr Ser Ser
530                 535                 540

Arg
545

<210> SEQ ID NO 103
<211> LENGTH: 677
<212> TYPE: PRT
<213> ORGANISM: Pseudomonas aeruginosa

<400> SEQUENCE: 103

Met Ser Glu Pro Arg Lys Ile Leu Val Thr Ser Ala Leu Pro Tyr Ala
1               5                   10                  15

Asn Gly Ser Ile His Leu Gly His Met Leu Glu Tyr Ile Gln Thr Asp
            20                  25                  30

Met Trp Val Arg Phe Gln Lys Met Arg Gly Asn Gln Ala Val Tyr Val
        35                  40                  45

Cys Ala Asp Asp Ala His Gly Ser Ala Ile Met Leu Arg Ala Glu Arg
    50                  55                  60

Glu Gly Ile Thr Ser Glu Gln Leu Ile Asp Ala Val Arg Ala Glu His
65                  70                  75                  80

Met Gly Asp Phe Ala Asp Phe Leu Val Asp Asp Asn Tyr His Ser
                85                  90                  95

Thr His Ser Glu Glu Asn Arg Glu Leu Ser Ser Ala Ile Tyr Leu Lys
            100                 105                 110

Leu Arg Asp Ala Gly His Ile Asp Thr Arg Pro Val Thr Gln Tyr Phe
        115                 120                 125

Asp Pro Glu Lys Gln Met Phe Leu Ala Asp Arg Phe Ile Lys Gly Thr
    130                 135                 140

Cys Pro Lys Cys Gly Thr Ala Asp Gln Tyr Gly Asp Asn Cys Glu Ala
145                 150                 155                 160

Cys Gly Ala Thr Tyr Ala Pro Thr Glu Leu Lys Asp Pro Lys Ser Ala
                165                 170                 175

Ile Ser Gly Ala Thr Pro Val Leu Lys Glu Ser Leu His Tyr Phe Phe
            180                 185                 190

Lys Leu Pro Asp Phe Glu Ala Met Leu Lys Gln Trp Thr Arg Ser Gly
        195                 200                 205

Ala Leu Gln Glu Ser Val Ala Asn Lys Leu Ala Glu Trp Leu Asp Ser
    210                 215                 220

Gly Leu Gln Gln Trp Asp Ile Ser Arg Asp Ala Pro Tyr Phe Gly Phe
225                 230                 235                 240

Glu Ile Pro Asp Ala Pro Gly Lys Tyr Phe Tyr Val Trp Leu Asp Ala
                245                 250                 255

Pro Ile Gly Tyr Met Ala Ser Phe Lys Asn Leu Cys Ala Arg Arg Pro
            260                 265                 270
```

```
Glu Leu Asp Phe Asp Ala Phe Trp Gly Lys Asp Ser Gly Ala Glu Leu
    275                 280                 285

Tyr His Phe Ile Gly Lys Asp Ile Val Asn Phe His Ala Leu Phe Trp
    290                 295                 300

Pro Ala Met Leu Glu Gly Ala Gly Tyr Arg Lys Pro Thr Ala Leu Asn
305                 310                 315                 320

Val His Gly Tyr Leu Thr Val Asn Gly Gln Lys Met Ser Lys Ser Arg
                325                 330                 335

Gly Thr Phe Val Lys Ala Arg Thr Tyr Leu Asp His Leu Asp Pro Glu
                340                 345                 350

Tyr Leu Arg Tyr Tyr Ala Ser Lys Leu Gly Arg Gly Val Glu Asp
        355                 360                 365

Leu Asp Leu Asn Leu Glu Asp Phe Val Gln Lys Val Asn Ser Asp Leu
    370                 375                 380

Val Gly Lys Val Val Asn Ile Ala Ser Arg Cys Ala Gly Phe Ile His
385                 390                 395                 400

Lys Gly Asn Ala Gly Val Leu Val Gly Ala Asp Pro Ala Pro Glu Leu
                405                 410                 415

Leu Ala Ala Phe Arg Glu Ala Ala Pro Gly Ile Ala Glu Ala Tyr Glu
                420                 425                 430

Ala Arg Asp Phe Asn Arg Ala Met Arg Glu Ile Met Ala Leu Ala Asp
                435                 440                 445

Arg Ala Asn Ala Trp Ile Ala Glu Gln Ala Pro Trp Ala Leu Ala Lys
    450                 455                 460

Gln Glu Gly Gln Gln Asp Lys Val Gln Ala Val Cys Gly Leu Gly Ile
465                 470                 475                 480

Asn Leu Phe Arg Gln Leu Val Ile Phe Leu Lys Pro Val Leu Pro Lys
                485                 490                 495

Leu Ala Ala Ala Ala Glu Ala Phe Leu Asn Val Ala Pro Leu Thr Trp
                500                 505                 510

Ala Asp His Gln Thr Leu Leu Ala Asn His Gln Leu Asn Pro Phe Gln
    515                 520                 525

Pro Leu Met Thr Arg Ile Glu Pro Ala Lys Val Glu Ala Met Ile Glu
    530                 535                 540

Ala Ser Lys Glu Asp Leu Ala Ala Ser Gln Pro Ala Gly Asn Gly
545                 550                 555                 560

Glu Leu Val Lys Glu Pro Ile Ala Ala Glu Ile Asp Phe Asp Ala Phe
                565                 570                 575

Ala Ala Val Asp Leu Arg Ile Ala Leu Ile Glu Lys Cys Glu Phe Val
                580                 585                 590

Glu Gly Ala Asp Lys Leu Leu Arg Leu Ser Leu Asp Ile Gly Asp Ala
    595                 600                 605

Lys Arg Asn Val Phe Ser Gly Ile Lys Ser Ala Tyr Pro Asp Pro Ser
    610                 615                 620

Ala Leu Glu Gly Arg Leu Thr Leu Tyr Val Ala Asn Leu Ala Pro Arg
625                 630                 635                 640

Lys Met Lys Phe Gly Val Ser Glu Gly Met Val Leu Ala Ala Gly Pro
                645                 650                 655

Gly Gly Glu Glu Ile Tyr Leu Leu Ser Pro Asp Ser Gly Ala Lys Pro
                660                 665                 670

Gly Gln Arg Val Lys
            675

<210> SEQ ID NO 104
```

```
<211> LENGTH: 618
<212> TYPE: PRT
<213> ORGANISM: Thermus thermophilus HB8

<400> SEQUENCE: 104

Met Glu Lys Val Phe Tyr Val Thr Thr Pro Ile Tyr Tyr Val Asn Ala
 1               5                  10                  15

Glu Pro His Leu Gly His Ala Tyr Thr Thr Val Ala Asp Phe Leu
            20                  25                  30

Ala Arg Trp His Arg Leu Asp Gly Tyr Arg Thr Phe Phe Leu Thr Gly
        35                  40                  45

Thr Asp Glu His Gly Glu Thr Val Tyr Arg Ala Ala Gln Ala Ala Gly
    50                  55                  60

Glu Asp Pro Lys Ala Phe Val Asp Arg Val Ser Gly Arg Phe Lys Arg
65                  70                  75                  80

Ala Trp Asp Leu Leu Gly Ile Ala Tyr Asp Asp Phe Ile Arg Thr Thr
                85                  90                  95

Glu Glu Arg His Lys Lys Val Val Gln Leu Val Leu Lys Lys Val Tyr
            100                 105                 110

Glu Ala Gly Asp Ile Tyr Gly Glu Tyr Glu Gly Leu Tyr Cys Val
        115                 120                 125

Ser Cys Glu Arg Phe Tyr Thr Glu Lys Glu Leu Val Glu Gly Leu Cys
130                 135                 140

Pro Ile His Gly Arg Pro Val Glu Arg Arg Lys Gly Gly Asn Tyr Phe
145                 150                 155                 160

Phe Arg Met Glu Lys Tyr Arg Pro Trp Leu Gln Glu Tyr Ile Gln Glu
                165                 170                 175

Asn Pro Asp Leu Ile Arg Pro Glu Gly Tyr Arg Asn Glu Val Leu Ala
            180                 185                 190

Met Leu Ala Glu Pro Ile Gly Asp Leu Ser Ile Ser Arg Pro Lys Ser
        195                 200                 205

Arg Val Pro Trp Gly Ile Pro Leu Pro Trp Asp Glu Asn His Val Thr
210                 215                 220

Tyr Val Trp Phe Asp Ala Leu Leu Asn Tyr Val Ser Ala Leu Asp Tyr
225                 230                 235                 240

Pro Glu Gly Glu Ala Tyr Arg Thr Phe Trp Pro His Ala Trp His Leu
                245                 250                 255

Ile Gly Lys Asp Ile Leu Lys Pro His Ala Val Phe Trp Pro Thr Met
            260                 265                 270

Leu Lys Ala Ala Gly Ile Pro Met Tyr Arg His Leu Asn Val Gly Gly
        275                 280                 285

Phe Leu Leu Gly Pro Asp Gly Arg Lys Met Ser Lys Thr Leu Gly Asn
    290                 295                 300

Val Val Asp Pro Phe Ala Leu Leu Glu Lys Tyr Gly Arg Asp Ala Leu
305                 310                 315                 320

Arg Tyr Tyr Leu Leu Arg Glu Ile Pro Tyr Gly Gln Asp Thr Pro Val
                325                 330                 335

Ser Glu Glu Ala Leu Arg Thr Arg Tyr Glu Ala Asp Leu Ala Asp Asp
            340                 345                 350

Leu Gly Asn Leu Val Gln Arg Thr Arg Ala Met Leu Phe Arg Phe Ala
        355                 360                 365

Glu Gly Arg Ile Pro Glu Pro Val Ala Gly Glu Leu Ala Glu Gly
    370                 375                 380

Thr Gly Leu Ala Gly Arg Leu Arg Pro Leu Val Arg Glu Leu Lys Phe
385                 390                 395                 400
```

His Val Ala Leu Glu Glu Ala Met Ala Tyr Val Lys Ala Leu Asn Arg
            405                 410                 415

Tyr Ile Asn Glu Lys Lys Pro Trp Glu Leu Phe Lys Lys Glu Pro Glu
            420                 425                 430

Glu Ala Arg Ala Val Leu Tyr Arg Val Val Glu Gly Leu Arg Ile Ala
            435                 440                 445

Ser Ile Leu Leu Thr Pro Ala Met Pro Asp Lys Met Ala Glu Leu Arg
            450                 455                 460

Arg Ala Leu Gly Leu Lys Glu Val Arg Leu Glu Glu Ala Glu Arg
465                 470                 475                 480

Trp Gly Leu Ala Glu Pro Arg Pro Ile Pro Glu Glu Ala Pro Val Leu
                485                 490                 495

Phe Pro Lys Lys Glu Ala Lys Val Glu Ala Lys Pro Lys Glu Glu Ala
                500                 505                 510

Trp Ile Gly Ile Glu Asp Phe Ala Lys Val Glu Leu Arg Val Ala Glu
            515                 520                 525

Val Leu Ala Ala Glu Lys His Pro Asn Ala Asp Arg Leu Leu Val Leu
530                 535                 540

Arg Leu Ser Leu Gly Asn Glu Glu Arg Thr Val Val Ser Gly Ile Ala
545                 550                 555                 560

Lys Trp Tyr Arg Pro Glu Glu Leu Val Gly Lys Val Val Leu Val
                565                 570                 575

Ala Asn Leu Lys Pro Ala Lys Leu Arg Gly Ile Glu Ser Gln Gly Met
                580                 585                 590

Ile Leu Ala Ala Gln Glu Gly Glu Ala Leu Ala Leu Val Thr Val Glu
            595                 600                 605

Gly Glu Val Pro Pro Gly Ala Val Val Lys
            610                 615

<210> SEQ ID NO 105
<211> LENGTH: 12
<212> TYPE: PRT
<213> ORGANISM: Thermus thermophilus

<400> SEQUENCE: 105

Arg Phe Gln Pro Val Tyr Phe Pro Phe Val Glu Pro
1               5                   10

<210> SEQ ID NO 106
<211> LENGTH: 16
<212> TYPE: PRT
<213> ORGANISM: Thermus thermophilus

<400> SEQUENCE: 106

Gly Phe Ala Phe Gly Leu Gly Val Glu Arg Leu Ala Met Leu Arg Tyr
1               5                   10                  15

<210> SEQ ID NO 107
<211> LENGTH: 12
<212> TYPE: PRT
<213> ORGANISM: Escherichia coli

<400> SEQUENCE: 107

Arg Phe Arg Pro Ser Thr Phe Pro Phe Thr Glu Pro
1               5                   10

<210> SEQ ID NO 108
<211> LENGTH: 16
<212> TYPE: PRT

<213> ORGANISM: Escherichia coli

<400> SEQUENCE: 108

Gly Phe Ala Phe Gly Met Gly Met Glu Arg Leu Thr Met Leu Arg Tyr
1               5                   10                  15

<210> SEQ ID NO 109
<211> LENGTH: 12
<212> TYPE: PRT
<213> ORGANISM: Saccharomyces cerevisiae

<400> SEQUENCE: 109

Arg Phe Lys Pro Thr Tyr Asn Pro Tyr Thr Glu Pro
1               5                   10

<210> SEQ ID NO 110
<211> LENGTH: 16
<212> TYPE: PRT
<213> ORGANISM: Saccharomyces cerevisiae

<400> SEQUENCE: 110

Val Leu Gly Met Gly Leu Ser Leu Glu Arg Pro Thr Met Ile Lys Tyr
1               5                   10                  15

<210> SEQ ID NO 111
<211> LENGTH: 37
<212> TYPE: PRT
<213> ORGANISM: Artificial sequence
<220> FEATURE:
<223> OTHER INFORMATION: Modified murine dihydrofolate reductase

<400> SEQUENCE: 111

Met Arg Gly Ser Gly Ile Met Val Arg Pro Leu Asn Ser Ile Val Ala
1               5                   10                  15

Val Ser Gln Asn Met Gly Ile Gly Lys Asn Gly Asp Leu Pro Trp Pro
                20                  25                  30

Pro Leu Arg Asn Glu
            35

<210> SEQ ID NO 112
<211> LENGTH: 14
<212> TYPE: PRT
<213> ORGANISM: Artificial Sequence
<220> FEATURE:
<223> OTHER INFORMATION: Modified murine dihydrofolate reductase

<400> SEQUENCE: 112

Tyr Phe Gln Arg Met Thr Thr Thr Ser Ser Val Glu Gly Lys
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Modified murine dihydrofolate reductase

<400> SEQUENCE: 113

Glu Leu Lys Glu Pro Pro Arg Gly Ala His Phe Leu Ala Lys
1               5                   10

<210> SEQ ID NO 114
<211> LENGTH: 16
<212> TYPE: PRT
<213> ORGANISM: Artificial Sequence
<220> FEATURE:

```
<223> OTHER INFORMATION: Modified murine dihydrofolate reductase

<400> SEQUENCE: 114

Leu Leu Pro Glu Tyr Pro Gly Val Leu Ser Glu Val Gln Glu Glu Lys
 1               5                  10                  15

<210> SEQ ID NO 115
<211> LENGTH: 164
<212> TYPE: PRT
<213> ORGANISM: Artificial Sequence
<220> FEATURE:
<223> OTHER INFORMATION: Modified murine dihydrofolate reductase

<400> SEQUENCE: 115

Lys Tyr Phe Gln Arg Met Thr Thr Thr Ser Ser Val Glu Gly Lys Gln
 1               5                  10                  15

Asn Leu Val Ile Met Gly Arg Lys Thr Trp Phe Ser Ile Pro Glu Lys
             20                  25                  30

Asn Arg Pro Leu Lys Asp Arg Ile Asn Ile Val Leu Ser Arg Glu Leu
         35                  40                  45

Lys Glu Pro Pro Arg Gly Ala His Phe Leu Ala Lys Ser Leu Asp Asp
     50                  55                  60

Ala Leu Arg Leu Ile Glu Gln Pro Glu Leu Ala Ser Lys Val Asp Met
65                  70                  75                  80

Val Trp Ile Val Gly Gly Ser Ser Val Tyr Gln Glu Ala Met Asn Gln
                 85                  90                  95

Pro Gly His Leu Arg Leu Phe Val Thr Arg Ile Met Gln Glu Phe Glu
            100                 105                 110

Ser Asp Thr Phe Phe Pro Glu Ile Asp Leu Gly Lys Tyr Lys Leu Leu
            115                 120                 125

Pro Glu Tyr Pro Gly Val Leu Ser Glu Val Gln Glu Glu Lys Gly Ile
        130                 135                 140

Lys Tyr Lys Phe Glu Val Tyr Glu Lys Lys Gly Ser Arg Ser His His
145                 150                 155                 160

His His His His
```